(12) United States Patent
Gill et al.

(10) Patent No.: US 7,497,854 B2
(45) Date of Patent: Mar. 3, 2009

(54) METHOD AND INSTRUMENT FOR EFFECTING ANASTOMOSIS OF RESPECTIVE TISSUES DEFINING TWO BODY LUMENS

(75) Inventors: Robert P. Gill, Mason, OH (US); Christopher J. Hess, Cincinnati, OH (US); William B. Weisenburgh, II, Maineville, OH (US); James W. Voegele, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 521 days.

(21) Appl. No.: 11/094,110

(22) Filed: Mar. 30, 2005

(65) Prior Publication Data

US 2005/0251171 A1    Nov. 10, 2005

Related U.S. Application Data

(60) Provisional application No. 60/569,195, filed on May 7, 2004, provisional application No. 60/582,302, filed on Jun. 23, 2004, provisional application No. 60/639,836, filed on Dec. 28, 2004.

(51) Int. Cl.
*A61M 27/00* (2006.01)
(52) U.S. Cl. .................................. 604/544; 604/540
(58) Field of Classification Search ................. 606/143, 606/139, 148–150, 151, 153–156; 604/540, 604/541, 544; 607/23; 600/37
See application file for complete search history.

(56) References Cited

U.S. PATENT DOCUMENTS

| | | | |
|---|---|---|---|
| 2,137,710 A | 11/1938 | Anderson | |
| 3,108,595 A | 10/1963 | Overment | |
| 4,007,743 A | 2/1977 | Blake | |
| 4,873,977 A | 10/1989 | Avant et al. | |

(Continued)

FOREIGN PATENT DOCUMENTS

WO    WO-04/000134 A2    12/2003

(Continued)

OTHER PUBLICATIONS

European Search Report, International Application No. PCT/US05/21755, May 21, 2005, pp. 1-4.

(Continued)

*Primary Examiner*—(Jackie) Tan-Uyen T. Ho
*Assistant Examiner*—Gregory A Anderson
(74) *Attorney, Agent, or Firm*—Frost Brown Todd LLC

(57) ABSTRACT

The method disclosed may be used following a prostatectomy may comprise inserting an instrument having a end effector into the bladder lumen via the urethra; using the end effector to urge the bladder wall to the pelvic floor and drive an anchor through the bladder wall into the pelvic floor, thereby connecting a balloon harness within the bladder to the pelvic floor; withdrawing the end effector; inserting and inflating a balloon catheter within the balloon harness, thereby pressing the bladder wall surrounding the bladder opening against the pelvic floor; maintaining the balloon catheter in place and draining the bladder during the time required for the tissues to effectively knit; and then deflating and withdrawing the balloon catheter and disconnecting and withdrawing the balloon harness. The instrument may comprise one or more tubes that support an end effector comprising a positioner and an anchor driver.

2 Claims, 123 Drawing Sheets

U.S. PATENT DOCUMENTS

| | | | |
|---|---|---|---|
| 4,884,572 A | 12/1989 | Bays et al. |
| 4,911,164 A | 3/1990 | Roth |
| 4,973,301 A | 11/1990 | Nissenkorn |
| 5,047,039 A | 9/1991 | Avant et al. |
| 5,151,105 A | 9/1992 | Kwan-Gett |
| 5,368,601 A | 11/1994 | Sauer et al. |
| 5,374,275 A | 12/1994 | Bradley et al. |
| 5,540,701 A | 7/1996 | Sharkey et al. |
| 5,545,171 A | 8/1996 | Sharkey et al. |
| 5,571,104 A | 11/1996 | Li |
| 5,591,179 A | 1/1997 | Edelstein |
| 5,676,670 A | 10/1997 | Kim |
| 5,690,676 A | 11/1997 | DiPoto et al. |
| 5,695,504 A | 12/1997 | Gifford, III et al. |
| 5,707,380 A | 1/1998 | Hinchliffe et al. |
| 5,817,113 A | 10/1998 | Gifford, III et al. |
| 5,849,004 A | 12/1998 | Bramlet |
| 5,868,762 A | 2/1999 | Cragg et al. |
| 5,954,732 A | 9/1999 | Hart et al. |
| 5,980,483 A | 11/1999 | Dimitri |
| 6,022,364 A | 2/2000 | Flumene et al. |
| 6,024,748 A | 2/2000 | Manzo et al. |
| 6,080,167 A | 6/2000 | Lyell |
| 6,083,170 A | 7/2000 | Ben-Haim |
| 6,117,144 A | 9/2000 | Nobles et al. |
| 6,146,407 A | 11/2000 | Krebs |
| 6,190,401 B1 | 2/2001 | Green et al. |
| 6,248,117 B1 | 6/2001 | Blatter |
| 6,254,570 B1 | 7/2001 | Rutner et al. |
| 6,264,633 B1 | 7/2001 | Knorig |
| 6,299,598 B1 | 10/2001 | Bander |
| 6,391,039 B1 | 5/2002 | Nicholas et al. |
| 6,440,146 B2 | 8/2002 | Nicholas et al. |
| 6,461,367 B1 | 10/2002 | Kirsch et al. |
| 6,508,822 B1 | 1/2003 | Peterson |
| 6,551,343 B1 | 4/2003 | Tormala et al. |
| 6,565,579 B2 | 5/2003 | Kirsch et al. |
| 6,599,311 B1 | 7/2003 | Biggs et al. |
| 6,666,873 B1 | 12/2003 | Cassell |
| 6,676,678 B2 | 1/2004 | Gifford, III et al. |
| 6,695,504 B2 | 2/2004 | Matsumoto |
| 6,726,697 B2 | 4/2004 | Nicholas et al. |
| 6,740,098 B2 | 5/2004 | Abrams et al. |
| 6,743,241 B2 | 6/2004 | Kerr |
| 6,855,126 B2 | 4/2005 | Takahashi et al. |
| 6,932,834 B2 | 8/2005 | Lizardi et al. |
| 6,942,674 B2 | 9/2005 | Belef et al. |
| 7,094,244 B2 | 8/2006 | Schreck |
| 7,131,973 B2 | 11/2006 | Hoffman |
| 7,294,216 B2 | 11/2007 | Whelan |
| 2002/0049453 A1 | 4/2002 | Nobles et al. |
| 2002/0177862 A1 | 11/2002 | Aranyi et al. |
| 2002/0193808 A1 | 12/2002 | Belef et al. |
| 2003/0032968 A1 | 2/2003 | Kirsch et al. |
| 2003/0229364 A1 | 12/2003 | Seiba |
| 2004/0087995 A1 | 5/2004 | Copa et al. |
| 2004/0220614 A1 | 11/2004 | Scalzo et al. |
| 2005/0070938 A1 | 3/2005 | Copa et al. |
| 2005/0131431 A1 | 6/2005 | Copa et al. |
| 2005/0228413 A1 | 10/2005 | Binmoeller et al. |
| 2005/0251167 A1 | 11/2005 | Voegele et al. |
| 2005/0251168 A1 | 11/2005 | Hess et al. |
| 2005/0251169 A1 | 11/2005 | Gill et al. |
| 2005/0251170 A1 | 11/2005 | Weisenburgh II et al. |
| 2005/0251171 A1 | 11/2005 | Gill et al. |
| 2005/0251172 A1 | 11/2005 | Voegele et al. |
| 2005/0251173 A1 | 11/2005 | Hess et al. |
| 2005/0251174 A1 | 11/2005 | Gill et al. |
| 2005/0251175 A1 | 11/2005 | Weisenburgh II et al. |
| 2006/0224166 A1 | 10/2006 | Weisenburgh II et al. |
| 2006/0224167 A1 | 10/2006 | Weisenburgh et al. |
| 2006/0224168 A1 | 10/2006 | Weisenburgh II et al. |
| 2006/0224169 A1 | 10/2006 | Weisenburgh II et al. |

FOREIGN PATENT DOCUMENTS

| | | |
|---|---|---|
| WO | WO-04/000135 A2 | 12/2003 |
| WO | WO-04/000136 A2 | 12/2003 |
| WO | WO-04/000137 A2 | 12/2003 |
| WO | WO-2004/098417 A1 | 11/2004 |
| WO | WO-2004/098418 A1 | 11/2004 |
| WO | WO 2006/009998 | 1/2006 |
| WO | WO 2007/056051 | 5/2007 |

OTHER PUBLICATIONS

PCT Search Report for International Application No. PCT/US06/42786, dated Aug. 24, 2006.
PCT Search Report for International Application No. PCT/US05/21755 dated Mar. 1, 2006.
PCT Search Report for International Application No. PCT/US06/42786 dated Aug. 24, 2007.
U.S. Appl. No. 60/582,302, filed Jun. 23, 2004, Gill et al.
U.S. Appl. No. 60/569,195, filed May 7, 2004, Gill et al.
U.S. Appl. No. 60/639,836, filed Dec. 28, 2004, Gill et al.

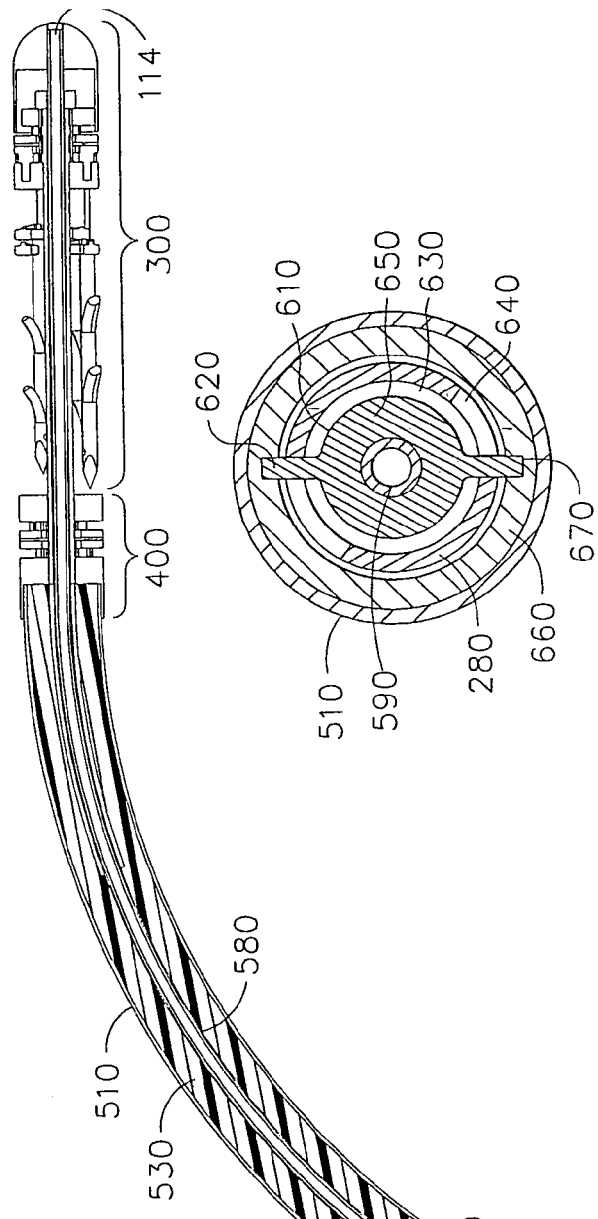
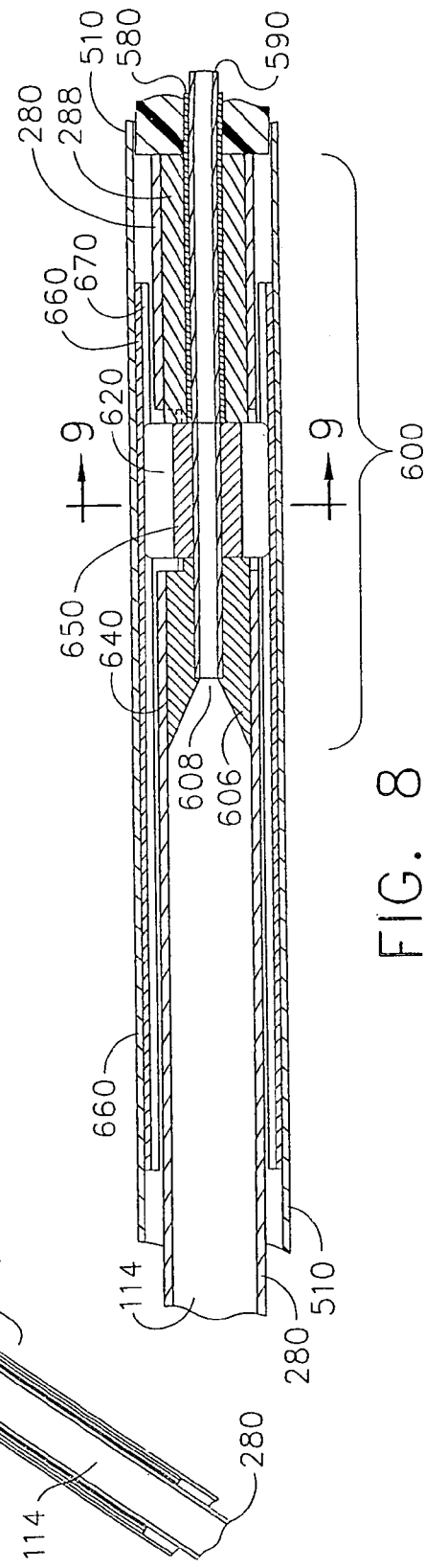
FIG. 7
FIG. 9
FIG. 8

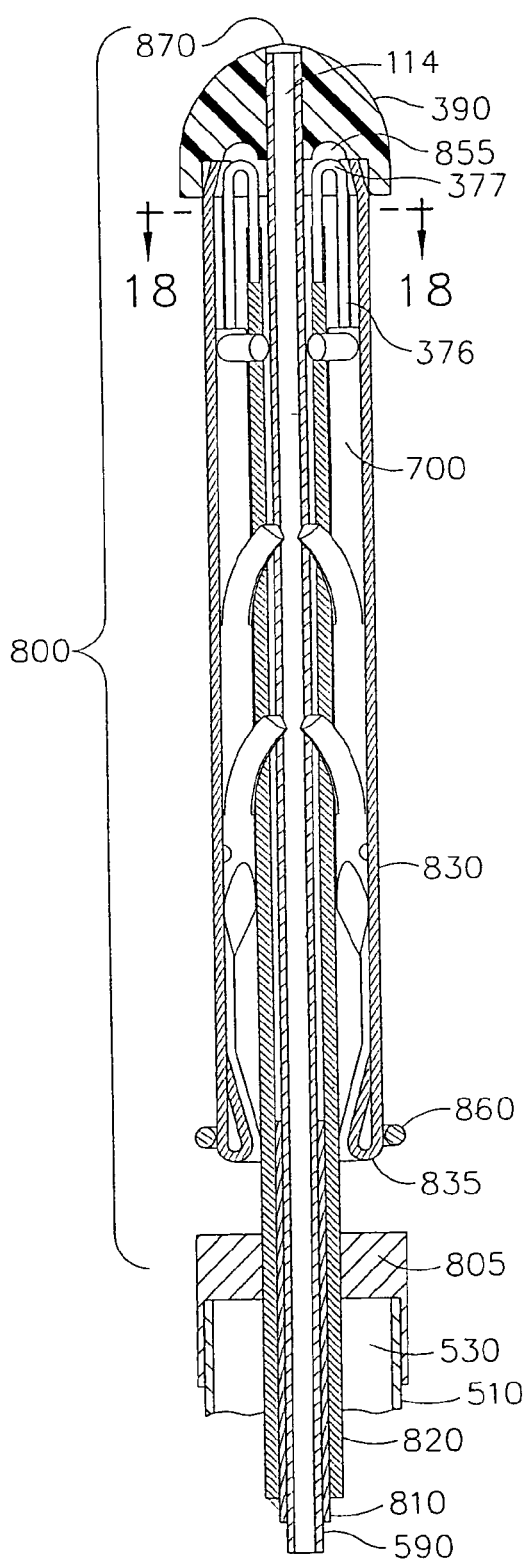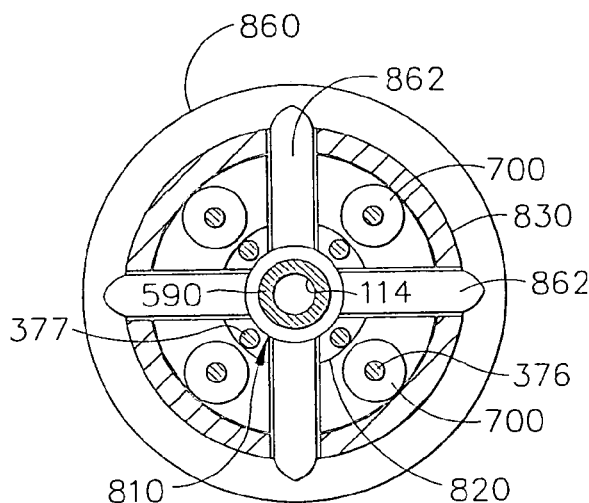
FIG. 17
FIG. 18

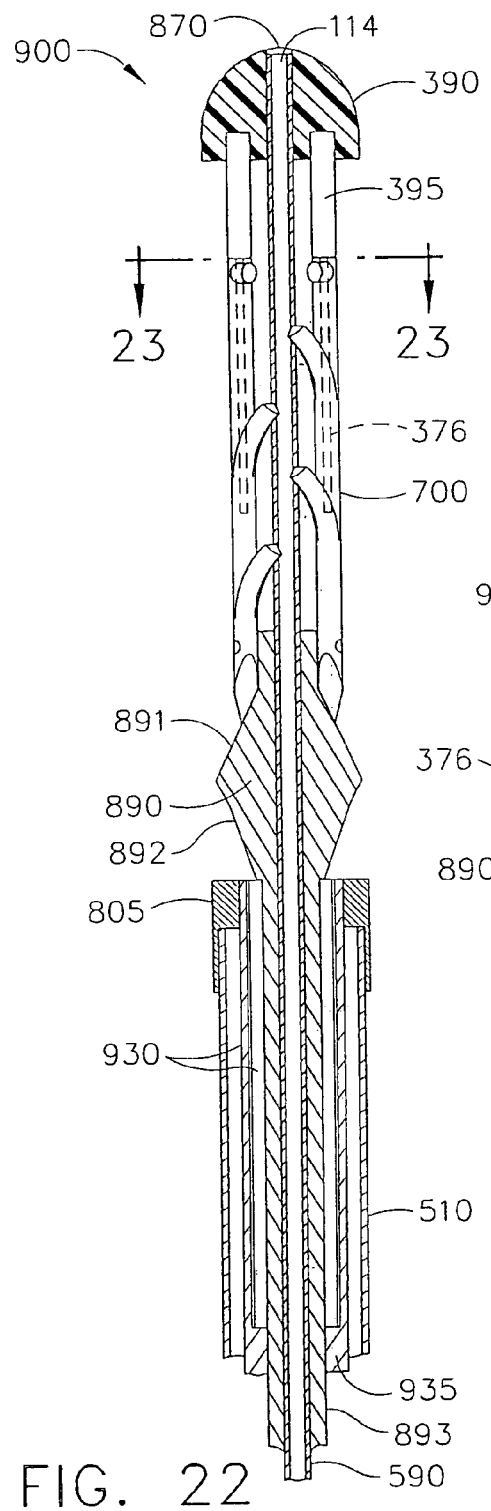
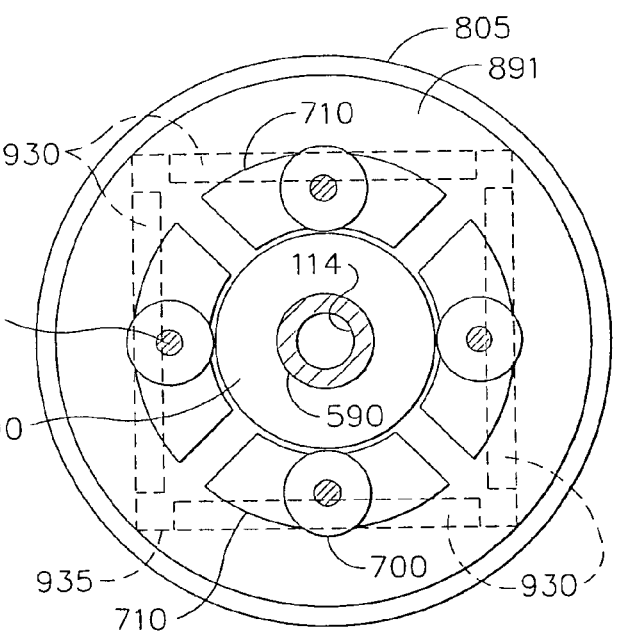
FIG. 22
FIG. 23

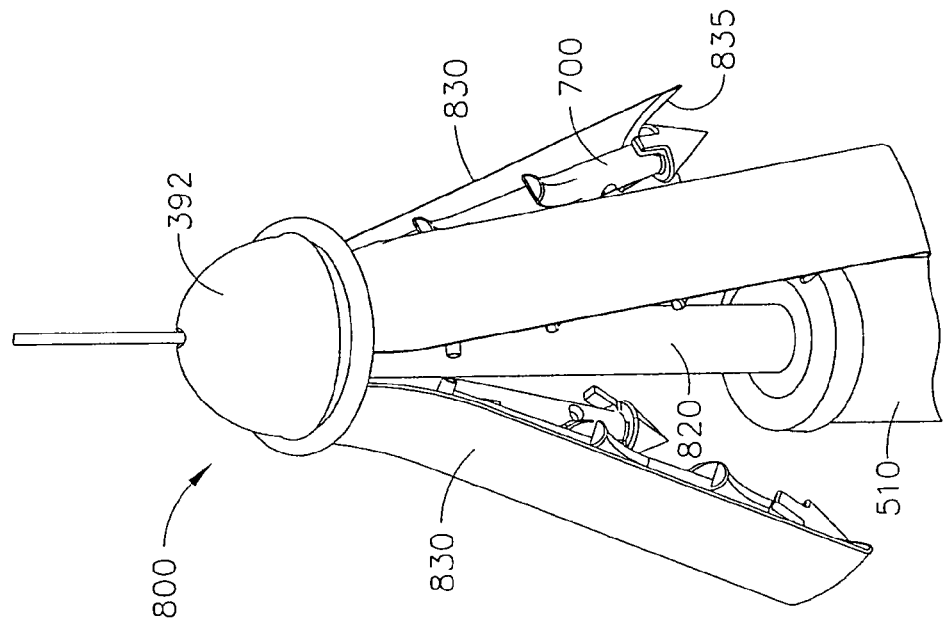
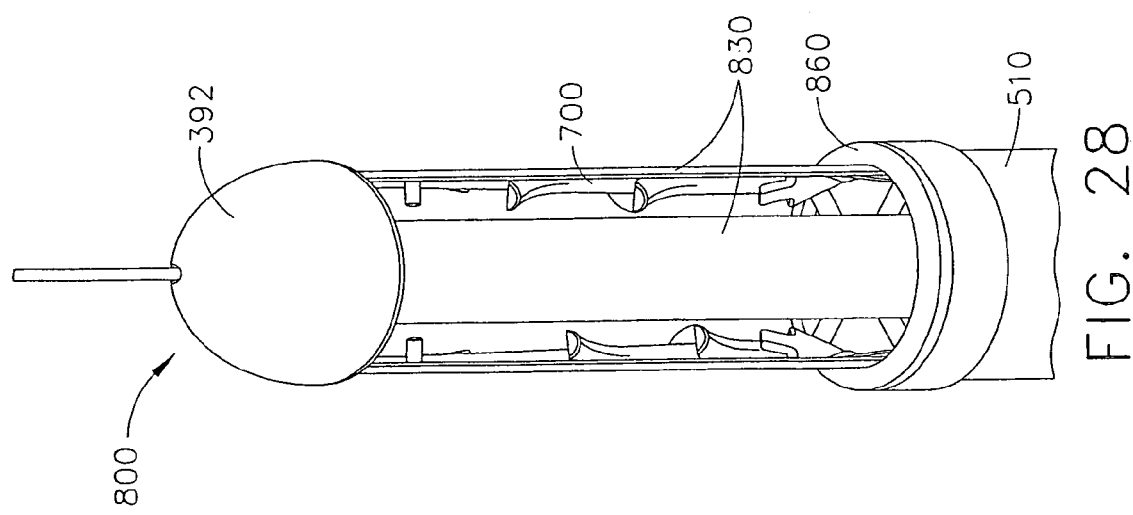

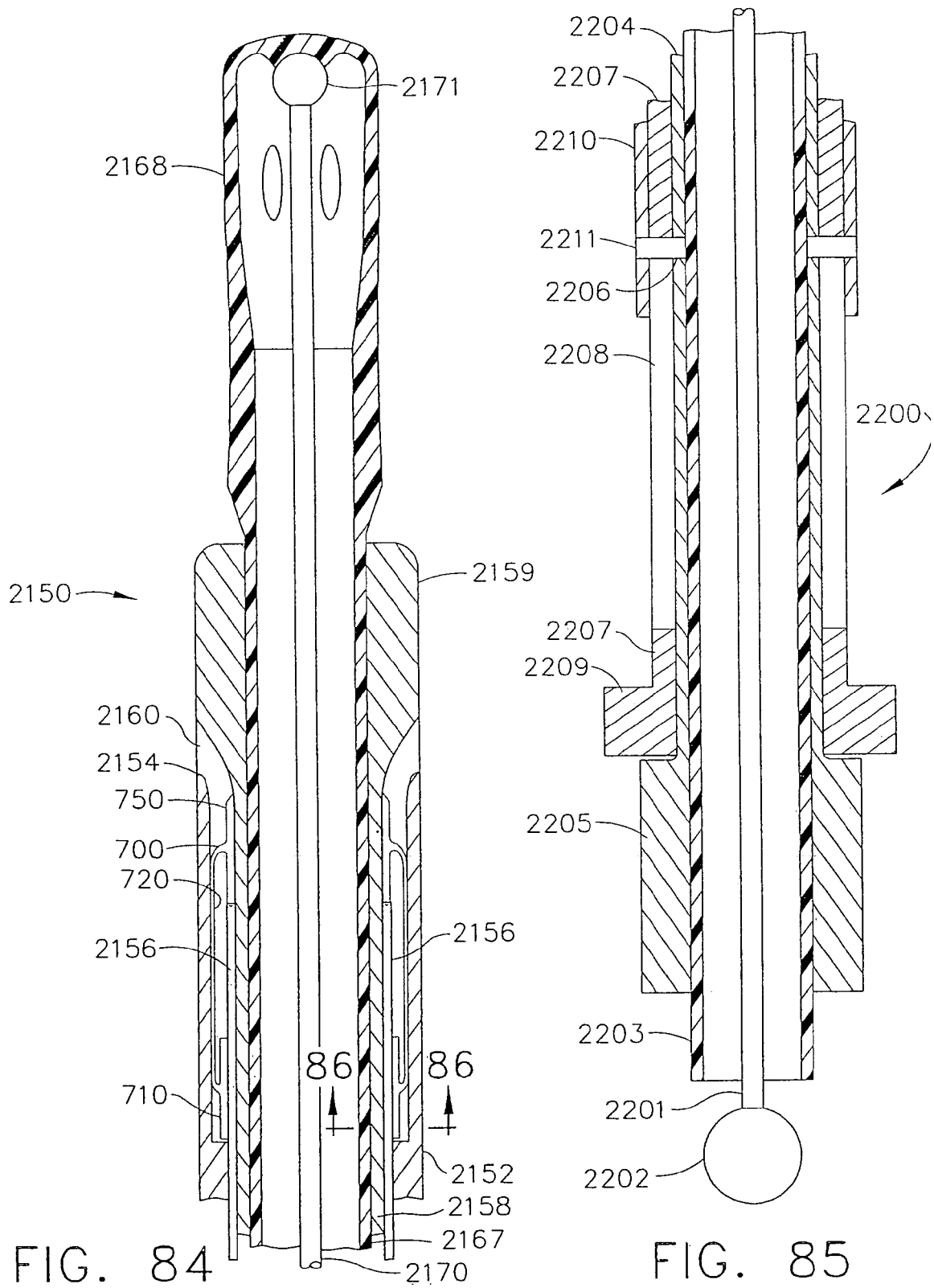

METHOD AND INSTRUMENT FOR EFFECTING ANASTOMOSIS OF RESPECTIVE TISSUES DEFINING TWO BODY LUMENS

RELATED APPLICATION

This application claims the benefit of the filing date(s) of one or more of U.S. provisional applications: METHODS AND DEVICE FOR ANASTOMOSIS, Ser. No. 60/569,195, filed May 7, 2004; METHODS AND DEVICE FOR ANASTOMOSIS, Ser. No. 60/582,302, filed Jun. 23, 2004, and METHOD AND INSTRUMENT FOR EFFECTING ANASTOMOSIS OF RESPECTIVE TISSUES DEFINING TWO BODY LUMENS, Ser. No. 60/639,836, filed Dec. 28, 2004.

This application relates to and incorporates by reference in their entirety, for any and all purposes, the following non-provisional applications, filed substantially contemporaneously herewith and having one or more inventors in common with the instant application:

INSTRUMENT FOR EFFECTING ANASTOMOSIS OF RESPECTIVE TISSUES DEFINING TWO BODY LUMENS, Ser. No. 11/093,802, filed Mar. 30, 2005;

METHOD AND INSTRUMENT FOR EFFECTING ANASTOMOSIS OF RESPECTIVE TISSUES DEFINING TWO BODY LUMENS, Ser. No. 11/094,110, filed Mar. 30, 2005;

INSTRUMENT FOR EFFECTING ANASTOMOSIS OF RESPECTIVE TISSUES DEFINING TWO BODY LUMENS, Ser. No. 11/093,694, filed Mar. 30, 2005;

ANCHORS FOR USE IN ATTACHMENT OF BLADDER TISSUES TO PELVIC FLOOR TISSUES FOLLOWING A PROSTATECTOMY, Ser. No. 11/094,624, filed Mar. 30, 2005;

INSTRUMENT FOR EFFECTING ANASTOMOSIS OF RESPECTIVE TISSUES DEFINING TWO BODY LUMENS, Ser. No. 11/094,624, filed Mar. 30, 2005;

INSTRUMENT FOR EFFECTING ANASTOMOSIS OF RESPECTIVE TISSUES DEFINING TWO BODY LUMENS, Ser. No. 11/093,646, filed Mar. 30, 2005;

DEVICE FOR ALTERNATELY HOLDING, OR EFFECTING RELATIVE LONGITUDINAL MOVEMENT, OF MEMBERS OF A MEDICAL INSTRUMENT, Ser. No. 11/094,119, filed Mar. 30, 2005; and METHOD AND INSTRUMENT FOR EFFECTING ANASTOMOSIS OF RESPECTIVE TISSUES DEFINING TWO BODY LUMENS, Ser. No. 11/094,110, filed Mar. 30, 200.

FIELD OF THE INVENTION

The present invention relates generally to the anastomosis of two hollow organs, a hollow organ and a vessel or two vessels, and is particularly directed to a method and embodiments of a device that accomplish the same in a minimally invasive manner. More particularly, the present invention also relates to an anastomosis instrument and method that may be used for the anastomosis of the bladder and urethra, especially after a patient's prostate has been removed in a prostatectomy.

BACKGROUND OF THE INVENTION

Prostate cancer is the second most common malignancy in males after cutaneous malignancies and is the second most common cause of cancer death among men in the United States. Prostate cancer is predominantly a disease of elderly men, and the absolute number of cases is expected to increase as worldwide life expectancy increases.

The retropubic approach to prostatectomy as a treatment for prostate cancer was introduced by Millin in 1947. The operation had distinct advantages over perineal prostatectomy in that urologists were more familiar with retropubic anatomy. The retropubic approach to radical prostatectomy also offers the advantage of the ability to perform an extraperitoneal pelvic lymph node dissection for staging purposes. During the past decade, modification in the technique of radical retropubic prostatectomy and the introduction of the anatomic nerve-sparing method resulted in a dramatic decrease in the two morbidities associated with the operation that cause the most concern—incontinence and impotence.

In a radical retropubic prostatectomy, the surgeon removes all or most of the patient's prostate. Because the urethra travels through the prostate, the upper part of the urethra is removed in the surgery. In order to restore proper urinary functions, the bladder and the urethra must be reconnected.

Providing this connection is particularly difficult due to the limited working space and the small size of the urethra. The size of the urethra makes it difficult to accurately place the suture thread through the wall of the urethra. Heretofore, surgeons would execute painstaking suturing operations with tiny, fine needles to reconnect the bladder to the urethra. It has been found that the use of sutures for this purpose has caused certain problems in recovery. These problems include necrosis of the sutured tissues, stricture of the urethra that impedes the flow of fluid through it, and a urethra-bladder connection that is not fluid-tight. In addition, when suturing the urethra to the bladder the surgeon can possibly inadvertently pierce the nearby neurovascular bundle, which can cause incontinence or impotence. The suturing process itself has also been found to be cumbersome, requiring the surgeon to grasp and stretch the bladder and urethra together before making the fine sutures. Sutures may also tear the urethra, resulting in further complications.

With radical retropubic prostatectomies becoming more common, faster and simpler ways to reconnect the bladder and urethra are in demand. It would be further advantageous to provide a means for the anastomosis of the urethra and bladder that does not require the use of potentially damaging sutures.

Additionally, there are other surgical procedures requiring the connection of vessels, hollow organs and tissues defining other body lumens. While some of these structures are large, and more easily manipulated by the surgeon, tissue structures defining other body lumens are smaller and more difficult to manipulate and hold in position while joining ends thereof after, for example, a transactional operation. Accordingly, a faster and simpler way to connect vessels, hollow organs and other tissues defining body lumens would be advantageous.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 7 is a longitudinal cross-sectional view of the tube assembly, positioner assembly and driver assembly of the instrument shown in FIG. 3;

FIG. 8 is an expanded longitudinal cross-sectional view of the bridge assembly portion of the tube assembly shown in FIG. 7;

FIG. 9 is an expanded transverse cross-sectional view of the bridge assembly shown in FIG. 8;

FIG. 17 is a longitudinal cross-sectional view of another embodiment of an anastomotic instrument in accordance with the present invention;

FIG. 18 is a transverse cross-sectional view of a driver assembly part of the anastomotic instrument shown in FIG. 17;

FIG. 22 is a longitudinal cross-sectional view of another alternate embodiment of an anastomotic instrument of the present invention;

FIG. 23 is a cross-sectional view of the driver assembly part of the anastomotic instrument shown in FIG. 22;

FIG. 28 is a perspective illustration of the alternate anastomotic instrument shown in FIG. 17, shown in a closed position;

FIG. 29 is a perspective illustration of the alternate anastomotic instrument shown in FIG. 17, shown in an opened position;

FIG. 84 is a longitudinal cross section of the distal end of the instrument shown in FIG. 83, shown in a retracted, pre-deployment position;

FIG. 85 is a longitudinal cross section of an embodiment of a handle assembly adapted for use at the proximal end of an anastomotic instrument of the present invention;

FIG. 119 is an enlarged perspective view of a fastener set that may be used with the instrument shown in FIG. 110, shown in the shape it may have prior to expansion and installation;

FIG. 120 is an enlarged perspective view of a fastener set that may be used with the instrument shown in FIG. 110, shown in the shape may have after expansion and installation;

FIG. 121 is an enlarged perspective view of an end cap of an actuator rod that may be used with the instrument shown in FIG. 110;

FIG. 122 is a longitudinal cross section of another embodiment of an anastomotic instrument of the present invention, in a pre-deployment, retracted position;

FIG. 123 is a longitudinal cross section of the instrument shown in FIG. 122, shown after insertion into and through a patient's urethra and into the bladder, following a prostatectomy;

FIG. 124 is a longitudinal cross section of the instrument shown in FIG. 122, shown after insertion into and through a patient's urethra and into the bladder, and after a positioner has been moved to a deployed position;

FIG. 125 is a longitudinal cross section of the instrument shown in FIG. 122, shown after insertion into and through a patient's urethra and into the bladder, after a positioner has been moved to a deployed position, and after the bladder wall has been urged into contact with the pelvic floor with the openings in the bladder and urethra aligned;

Figure 122:
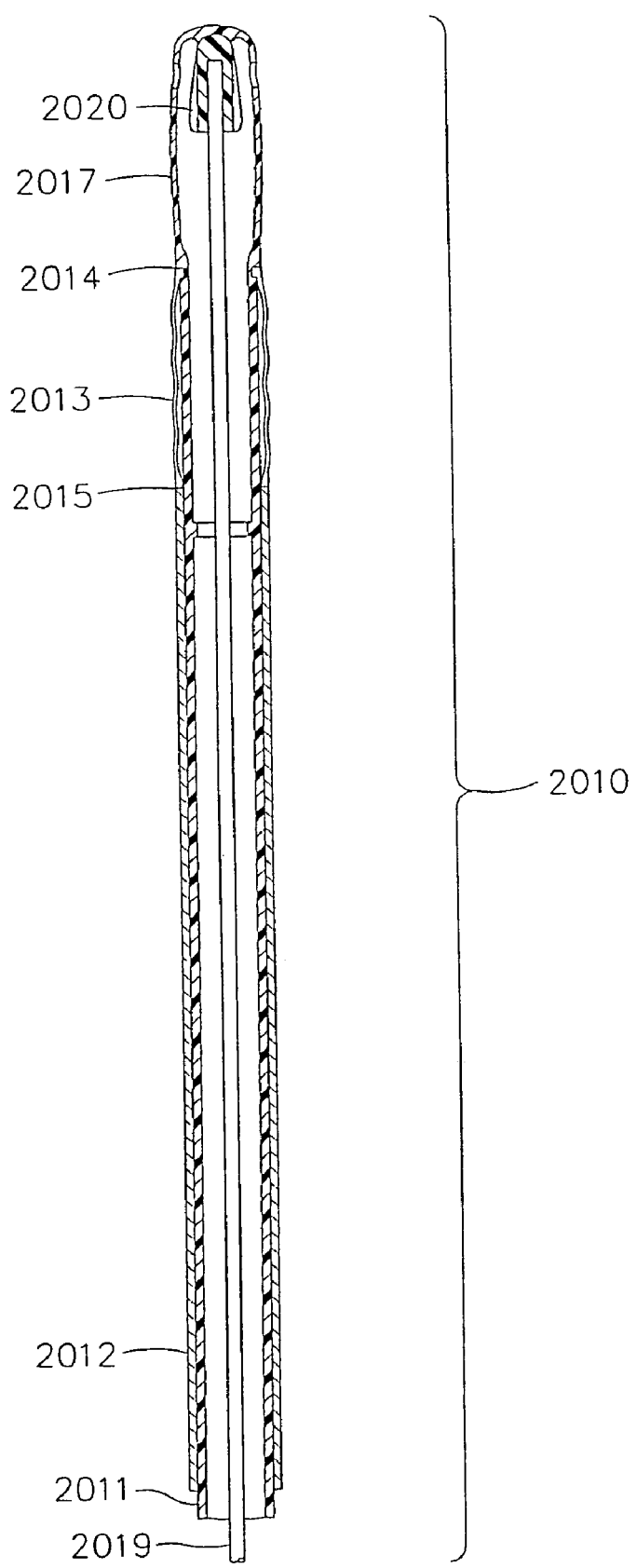
Figure 126:
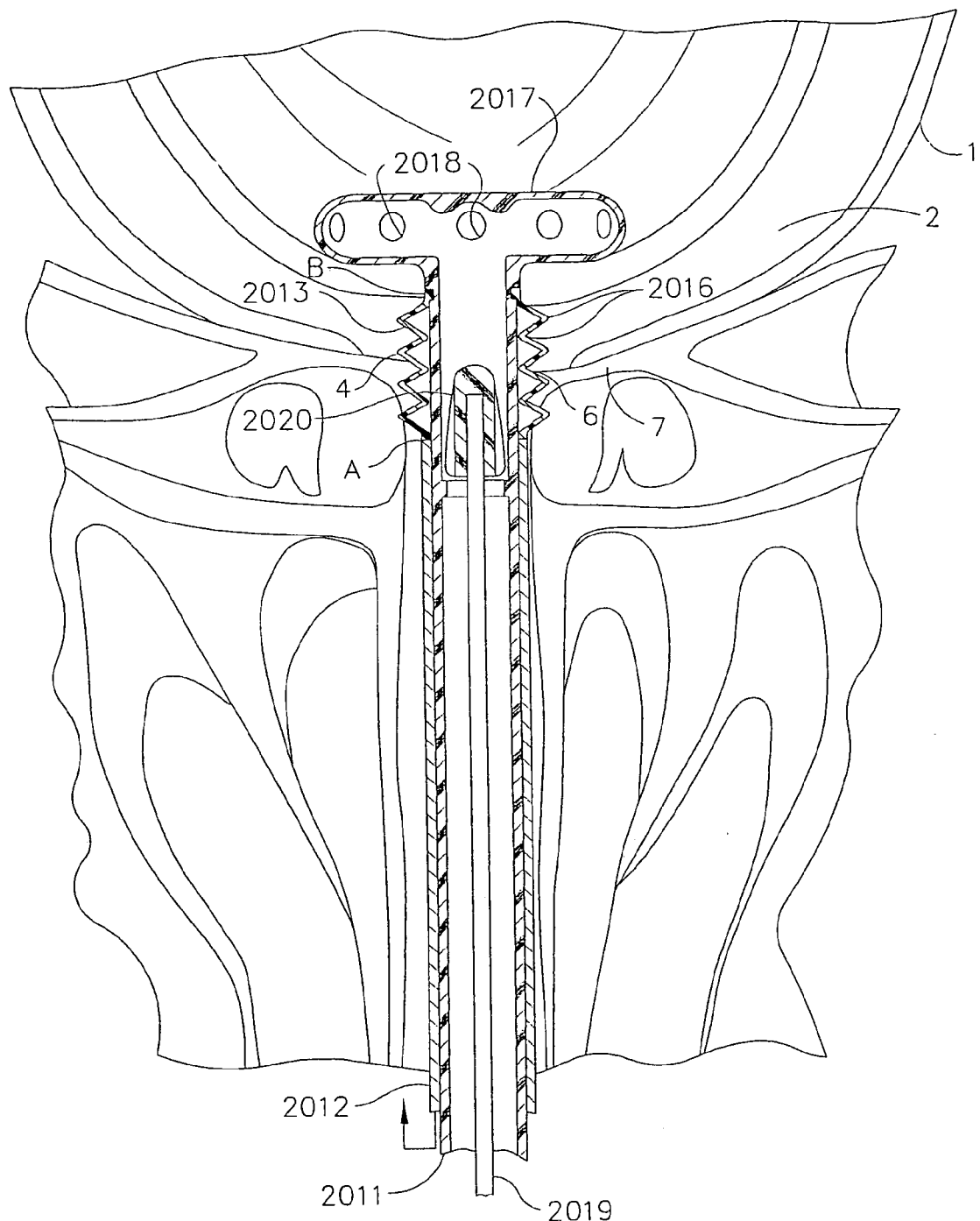
Figure 127:
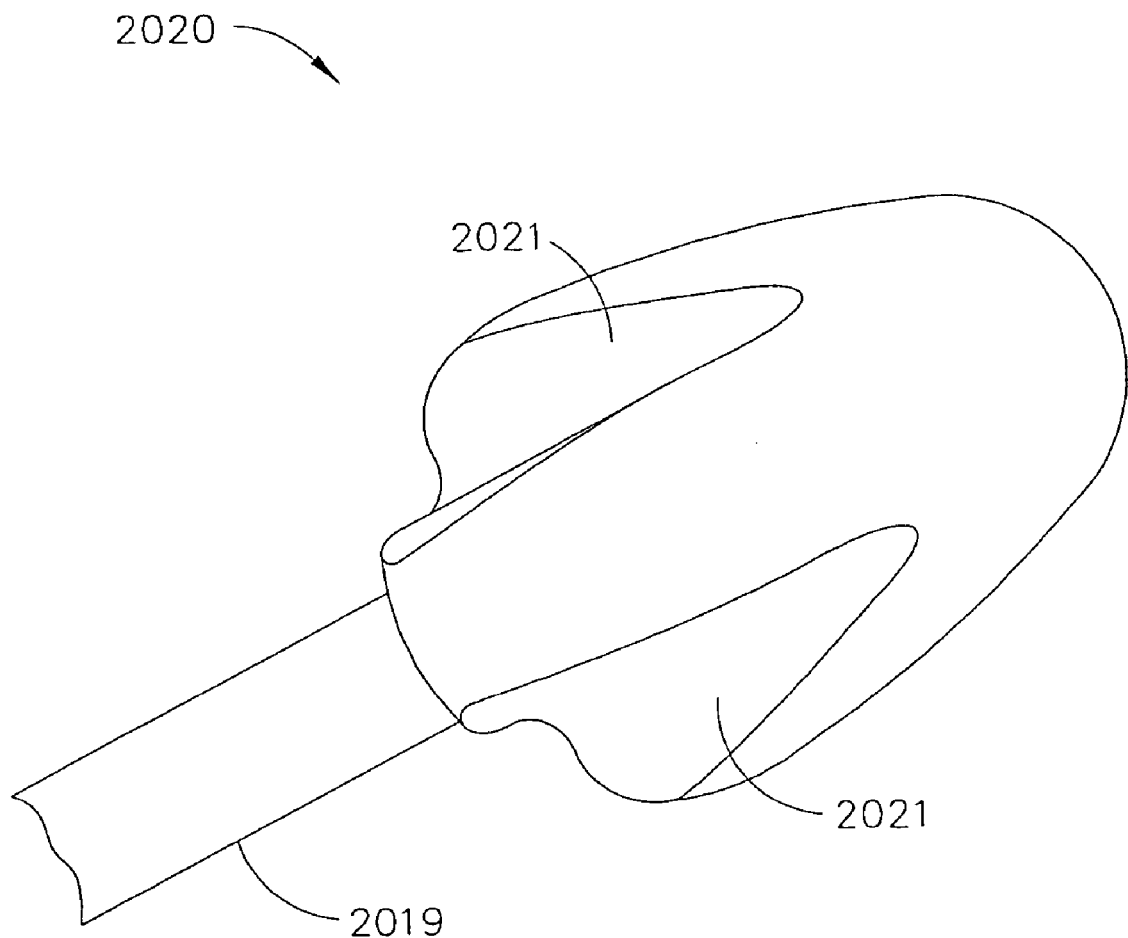
Figure 128:
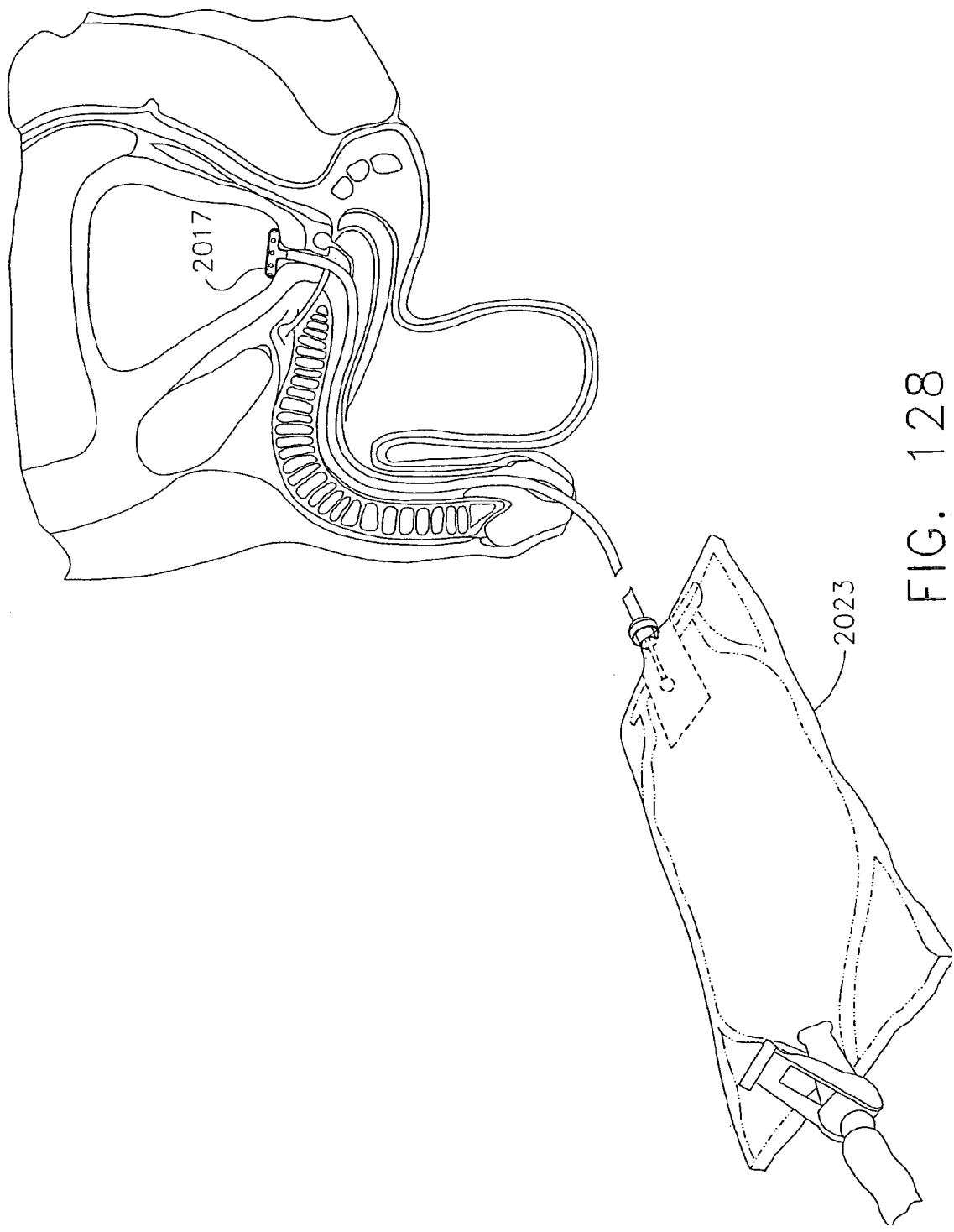
Figure 129:
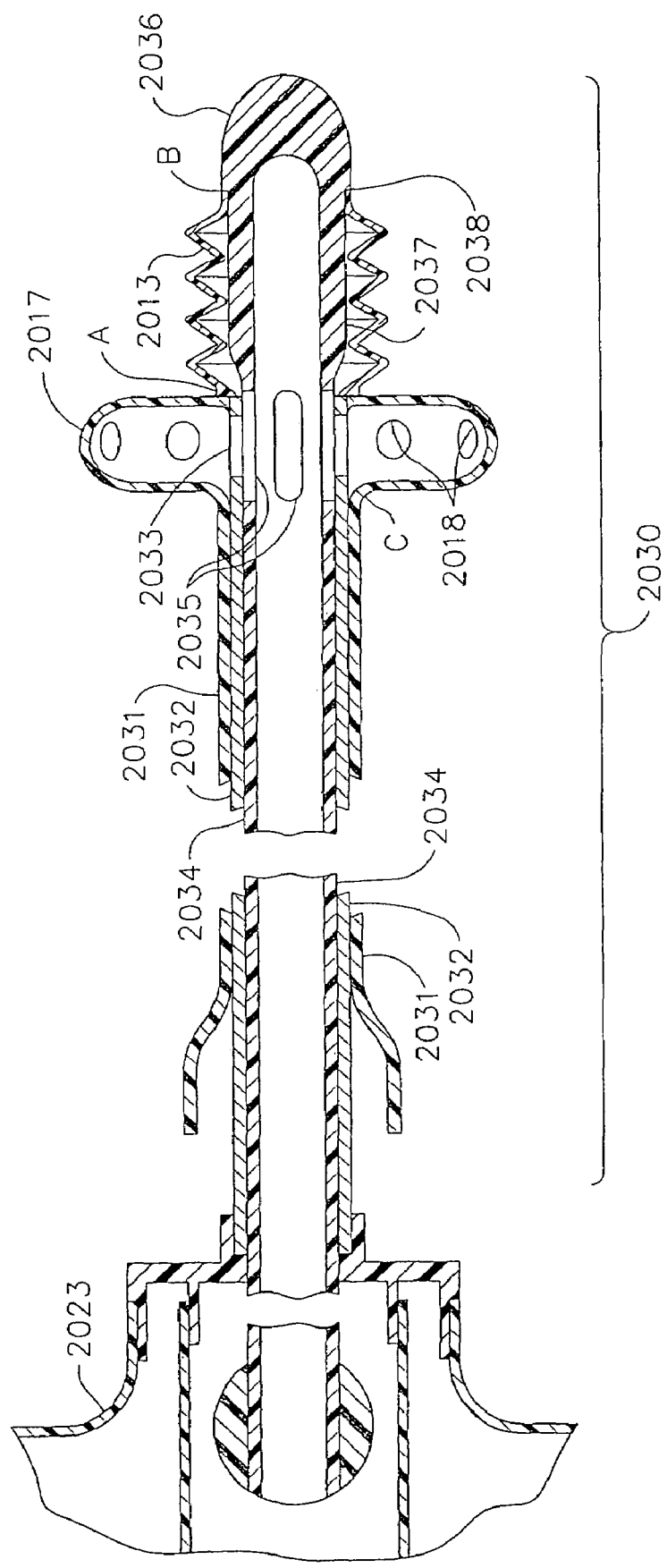
Figure 130:
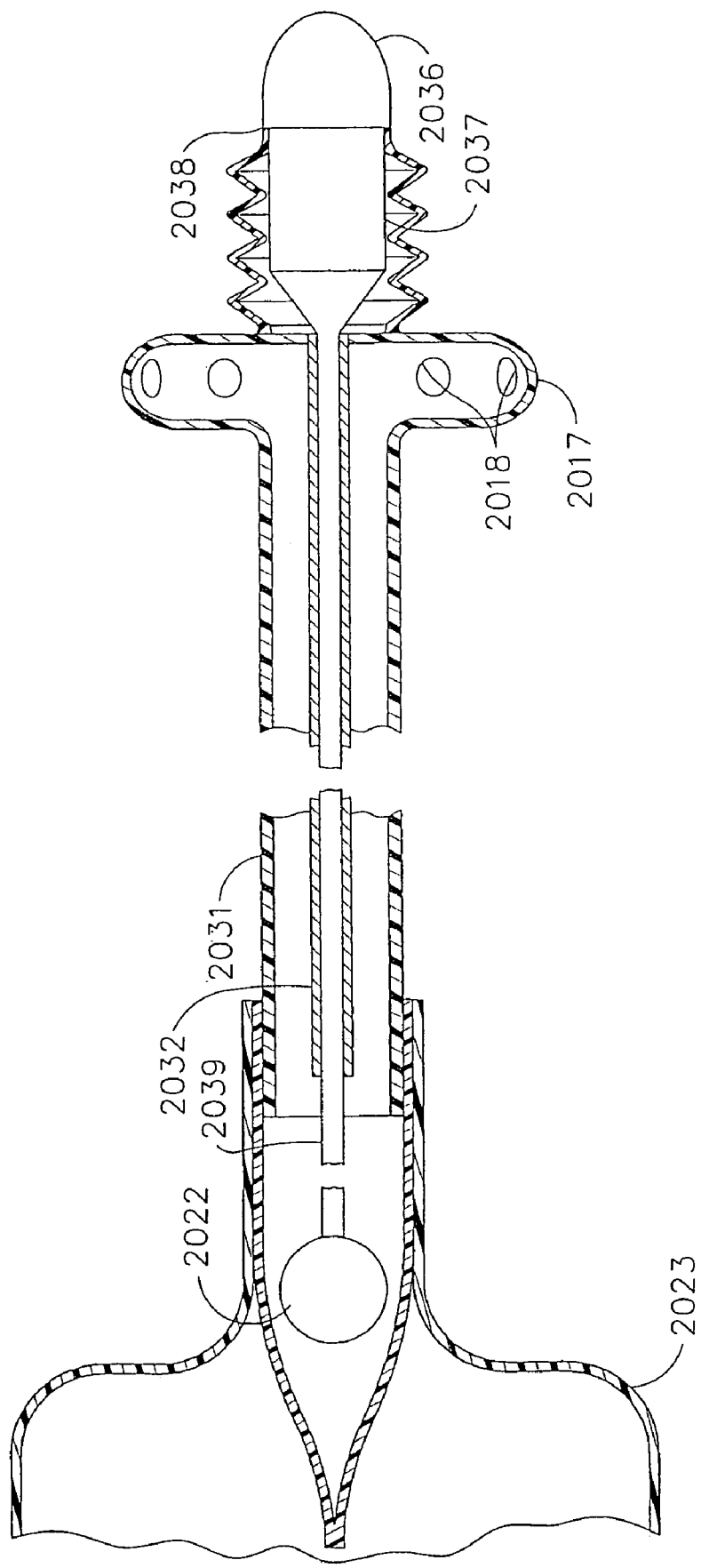
Figure 131:
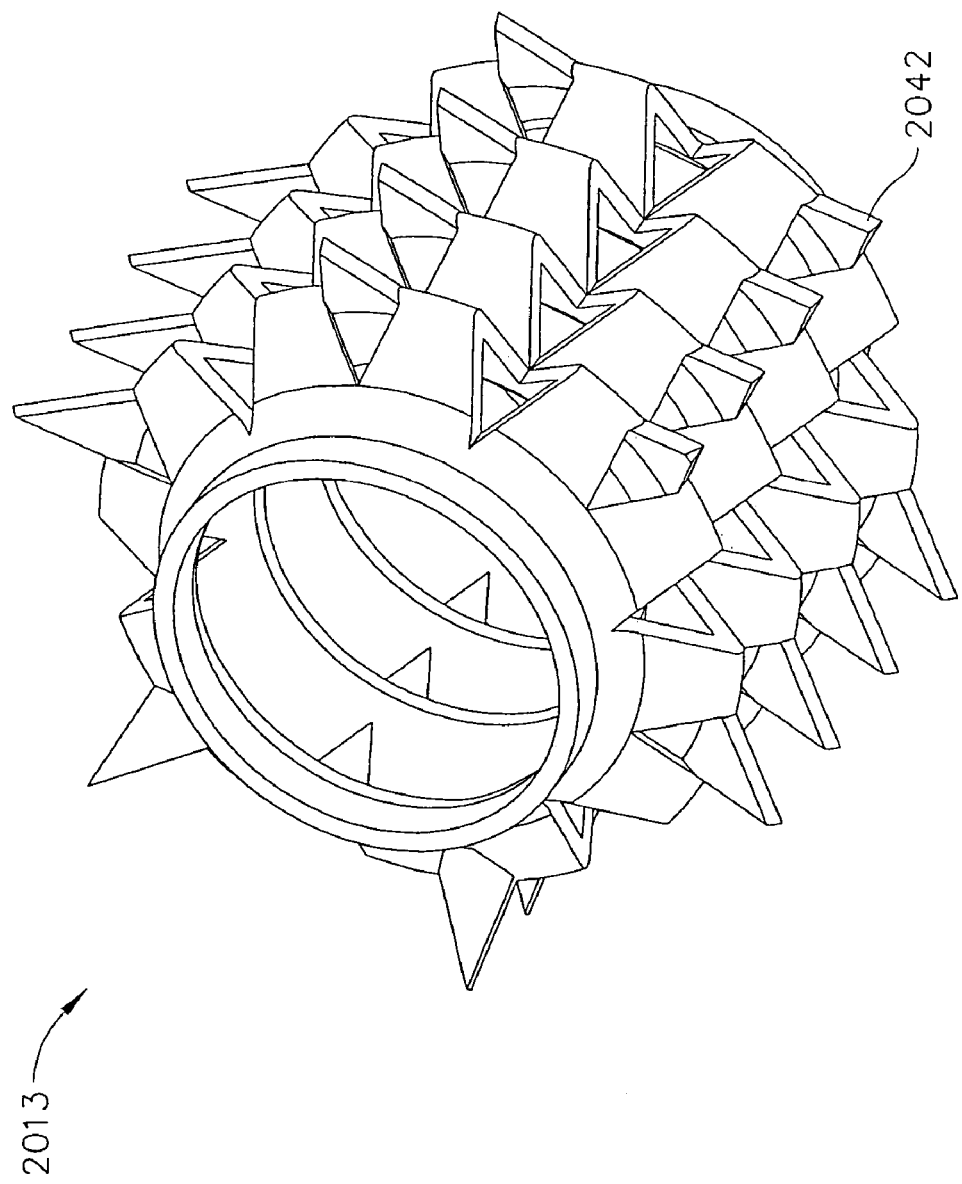
Figure 132:
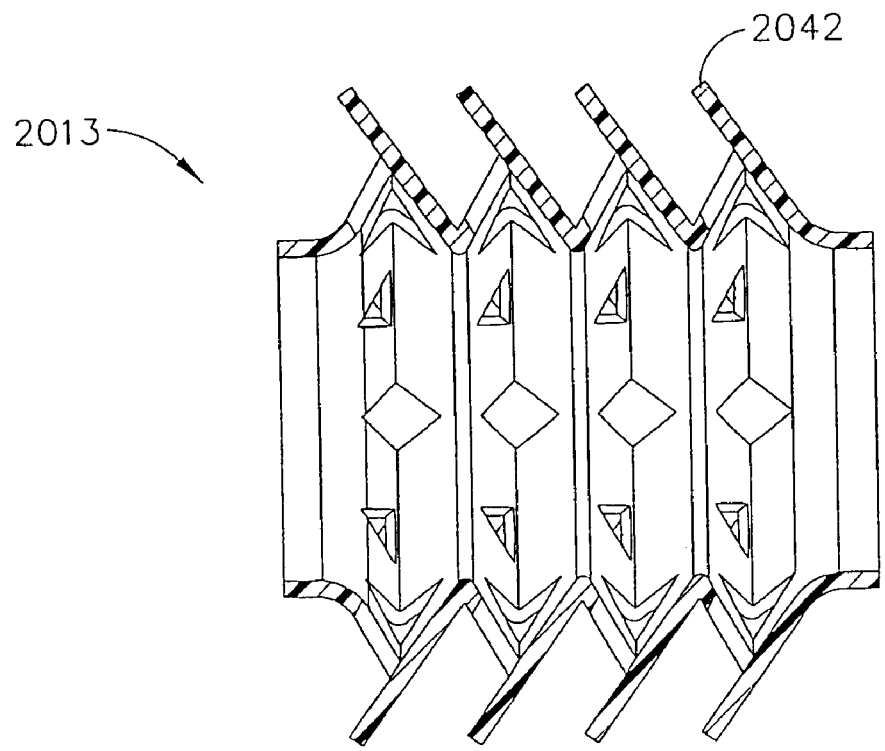
Figure 133:
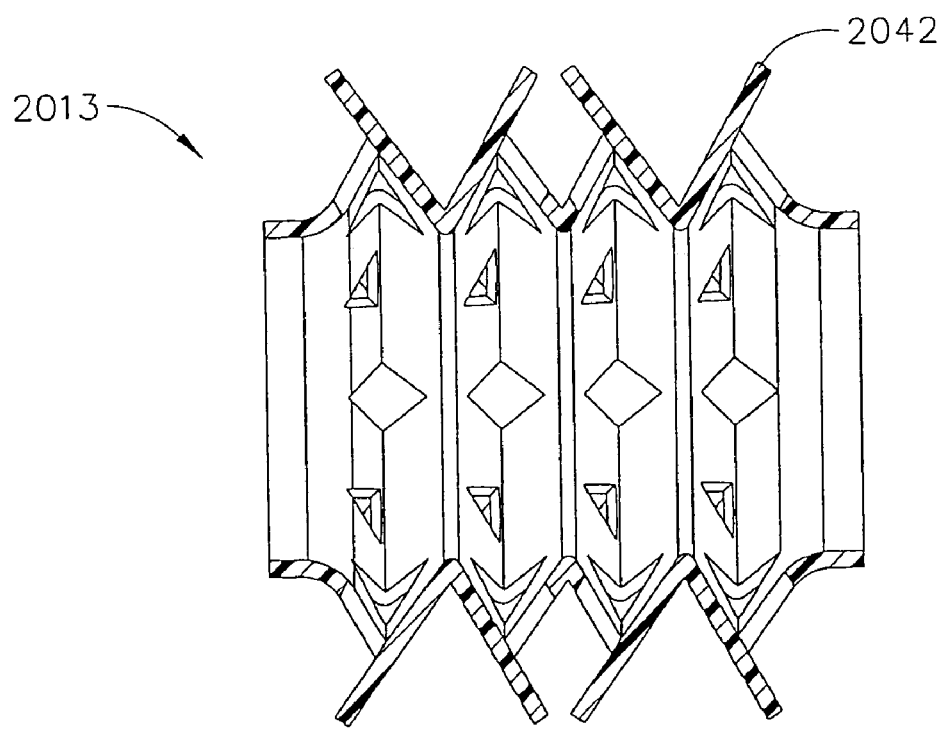
Figure 134:
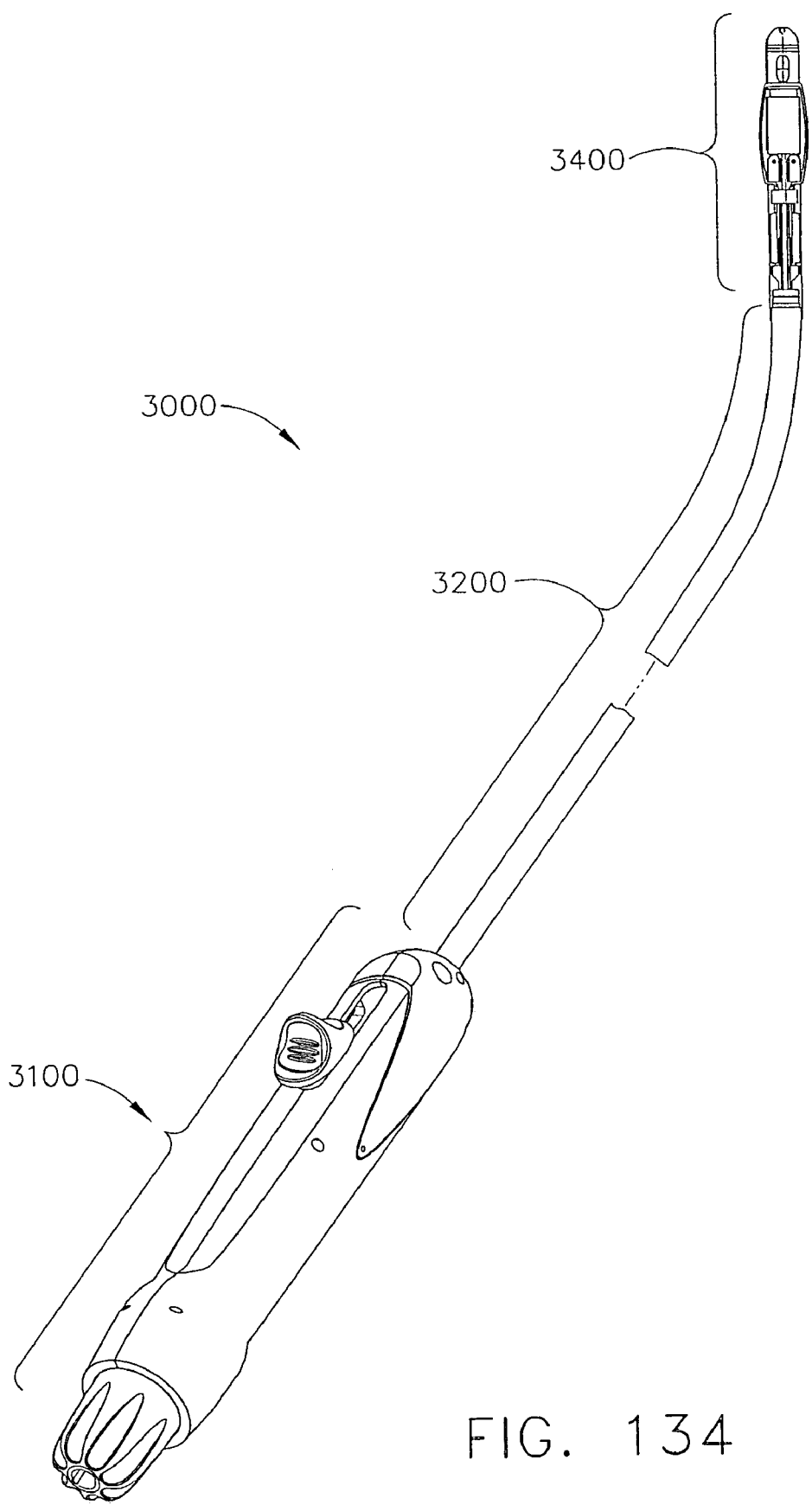
Figure 135:
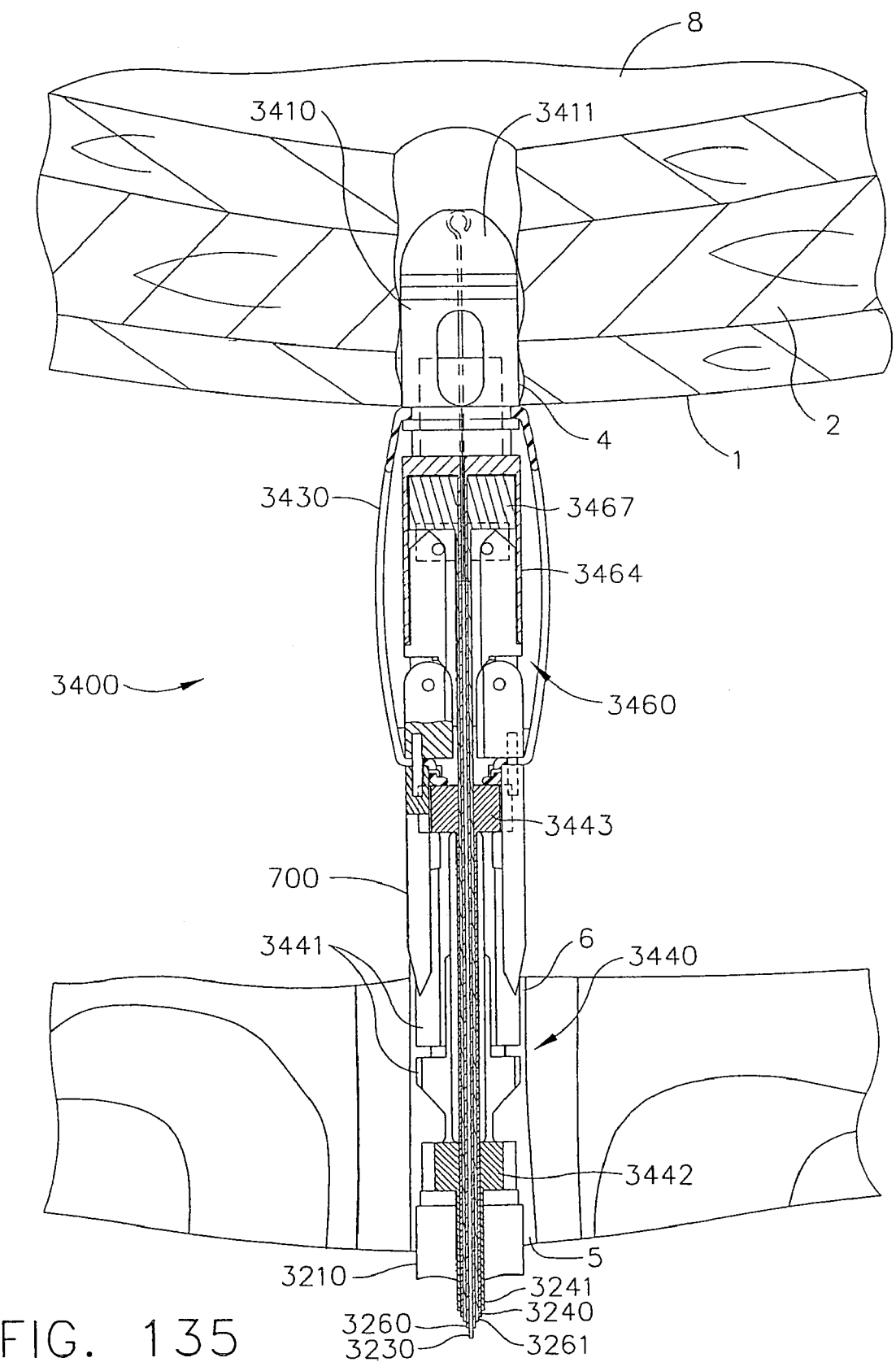
Figure 136:
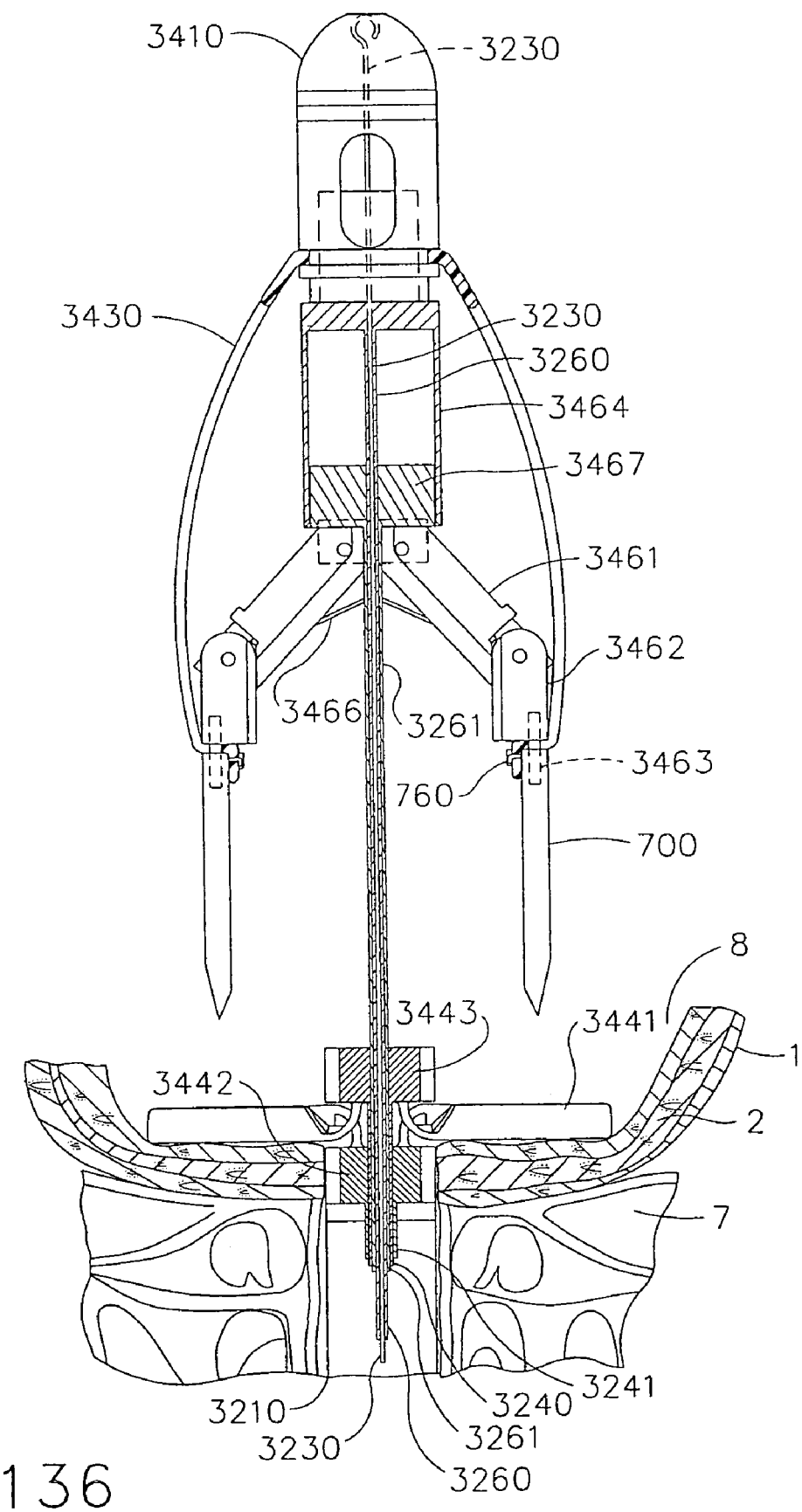
Figure 137:
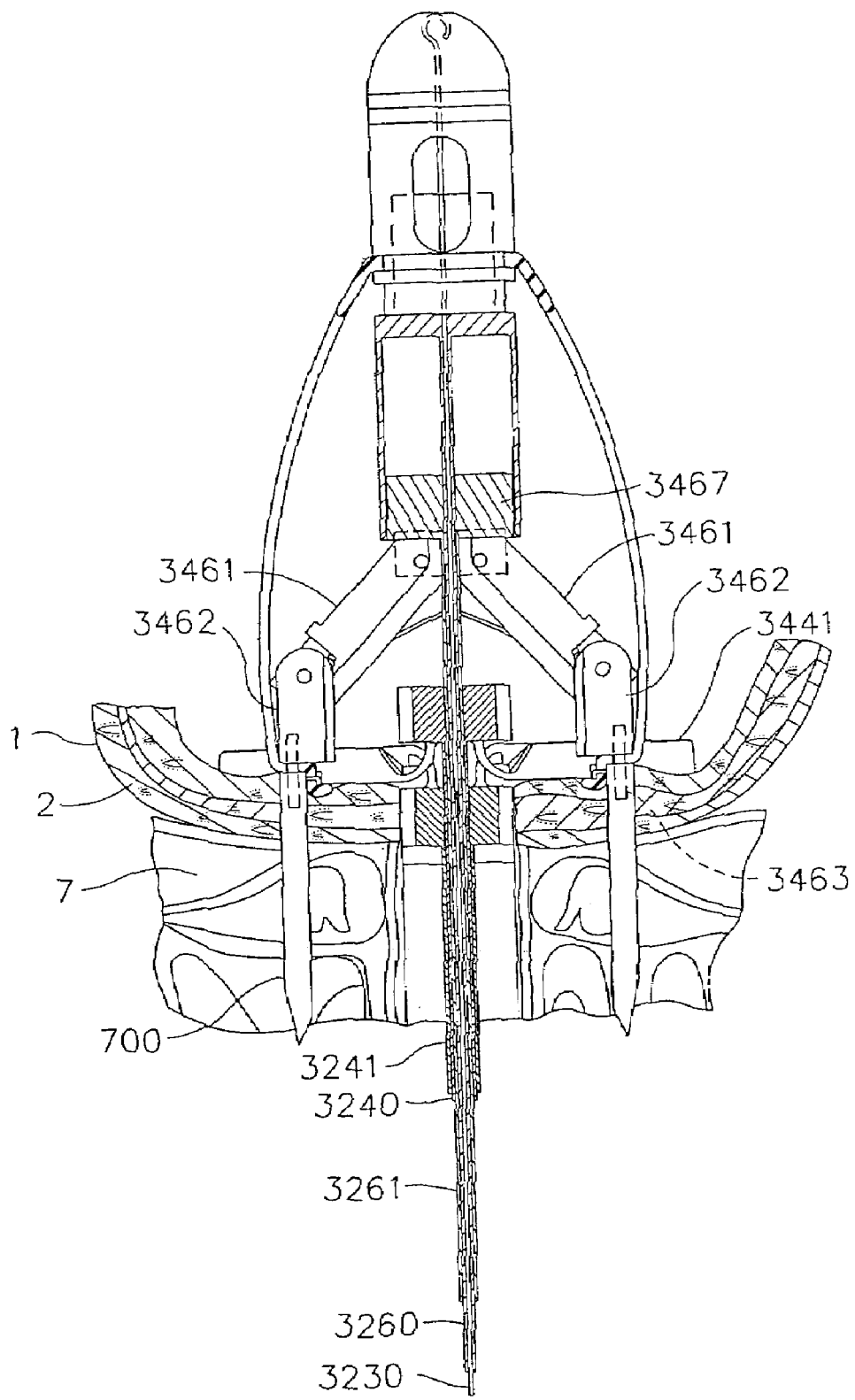
Figure 138:
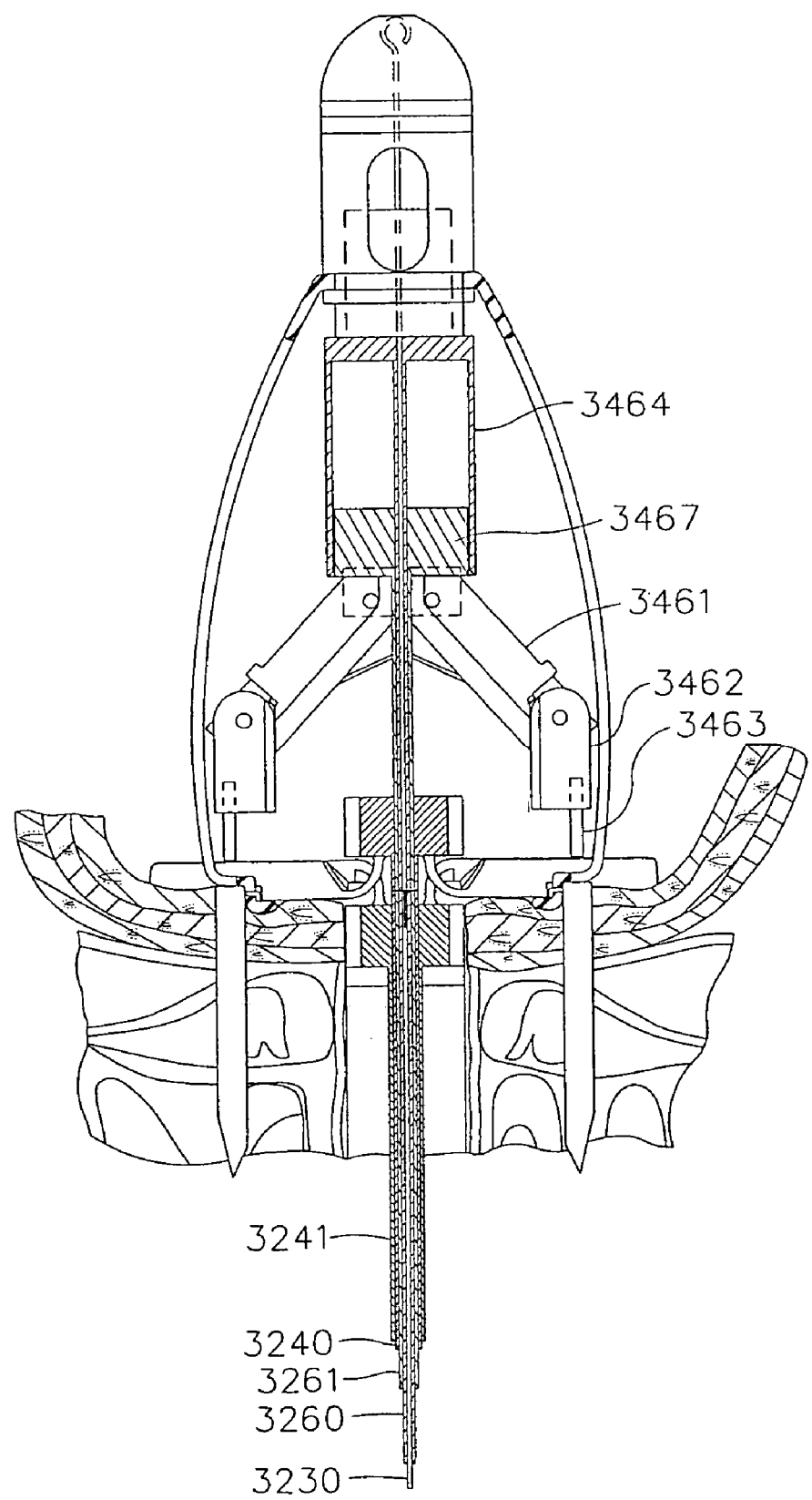
Figure 139:
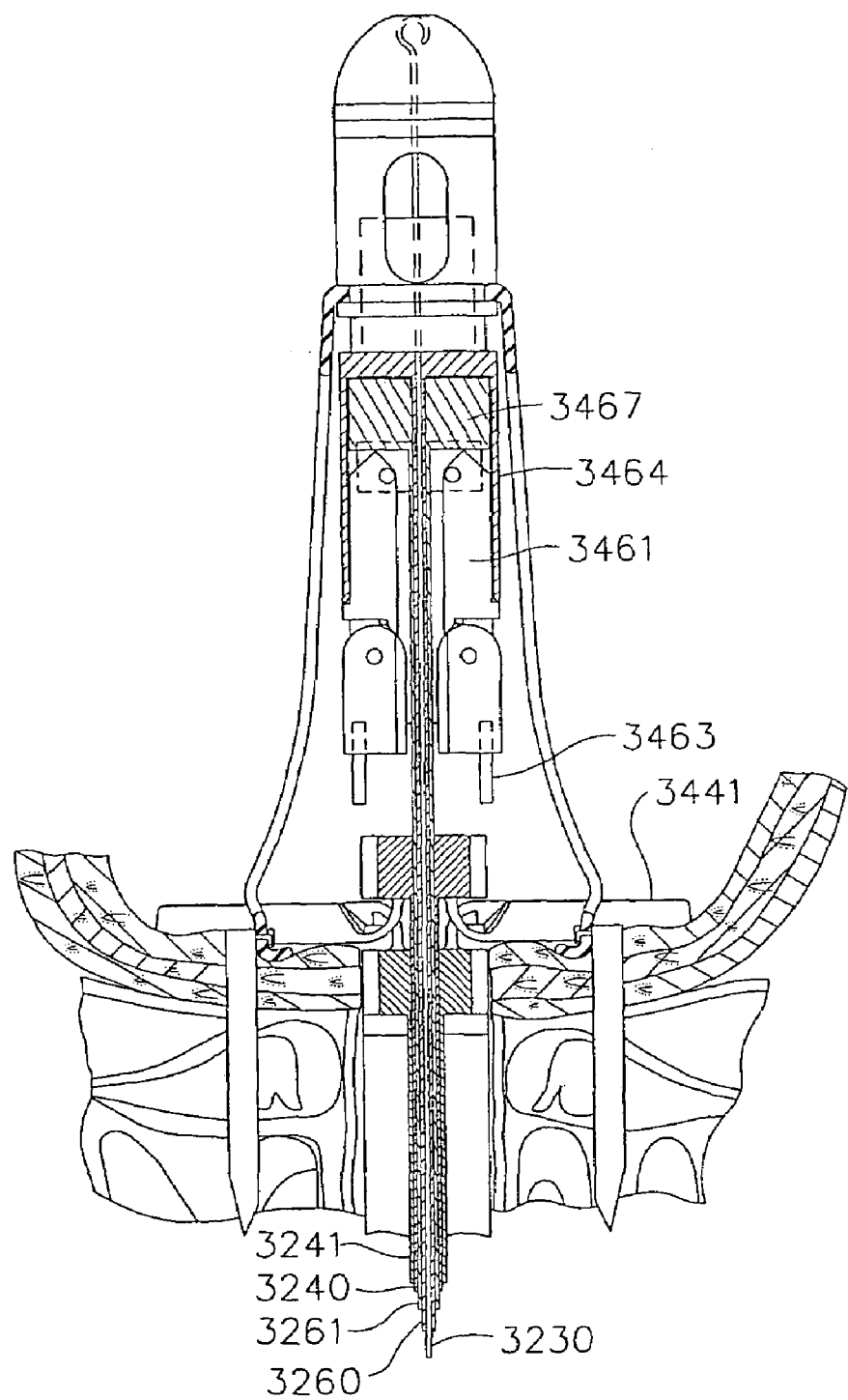
Figure 140:
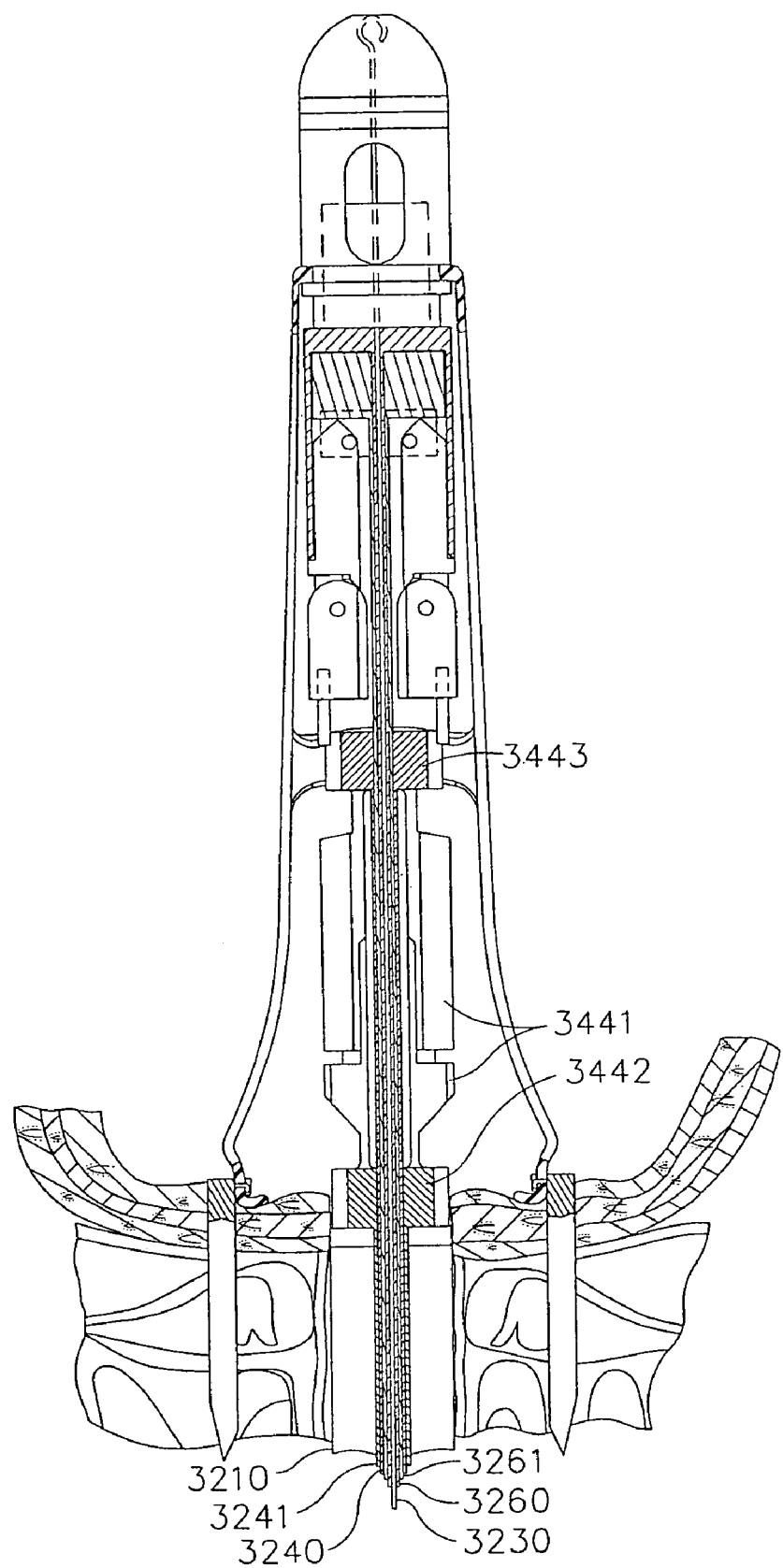
Figure 141:
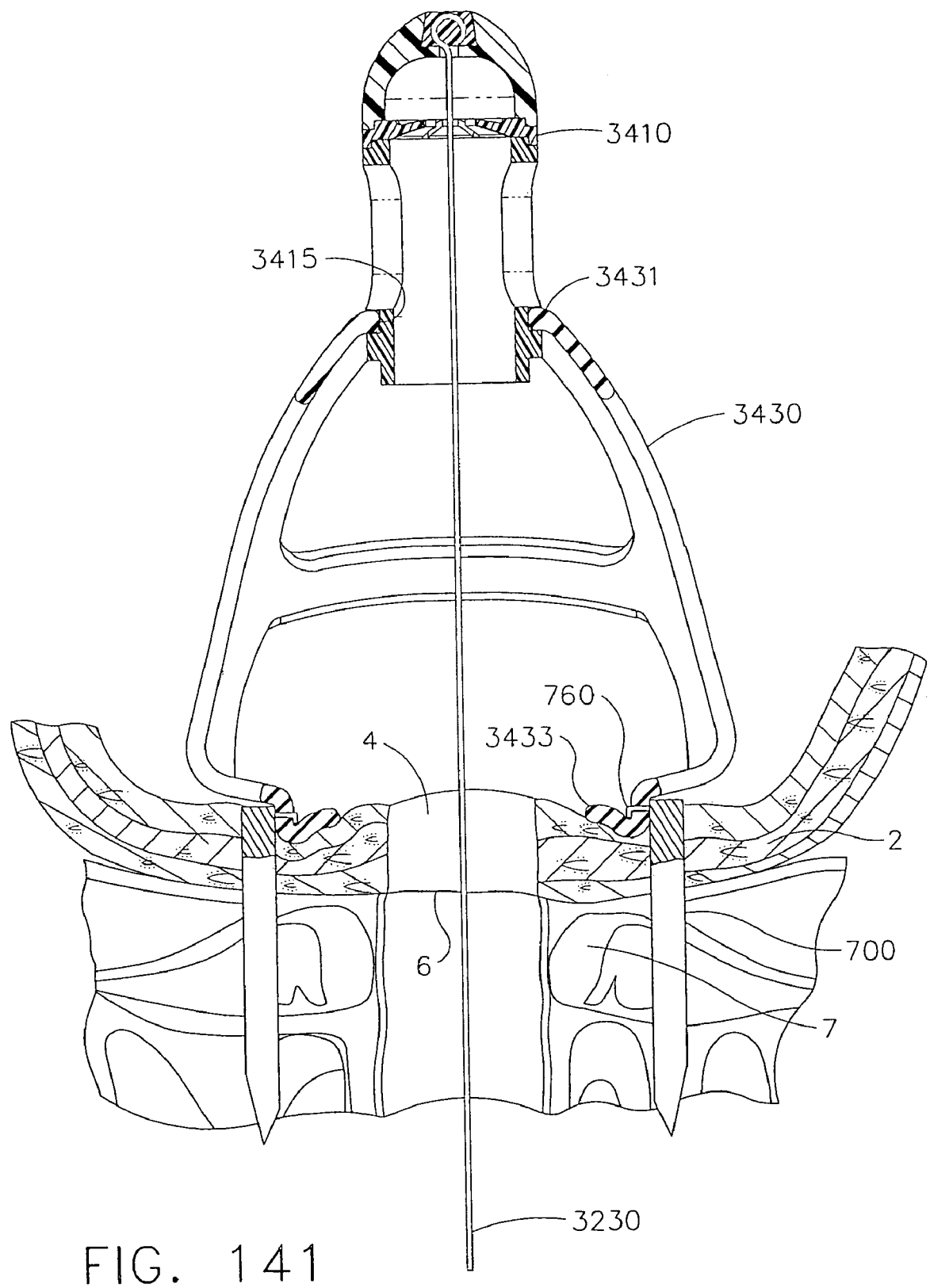
Figure 142:
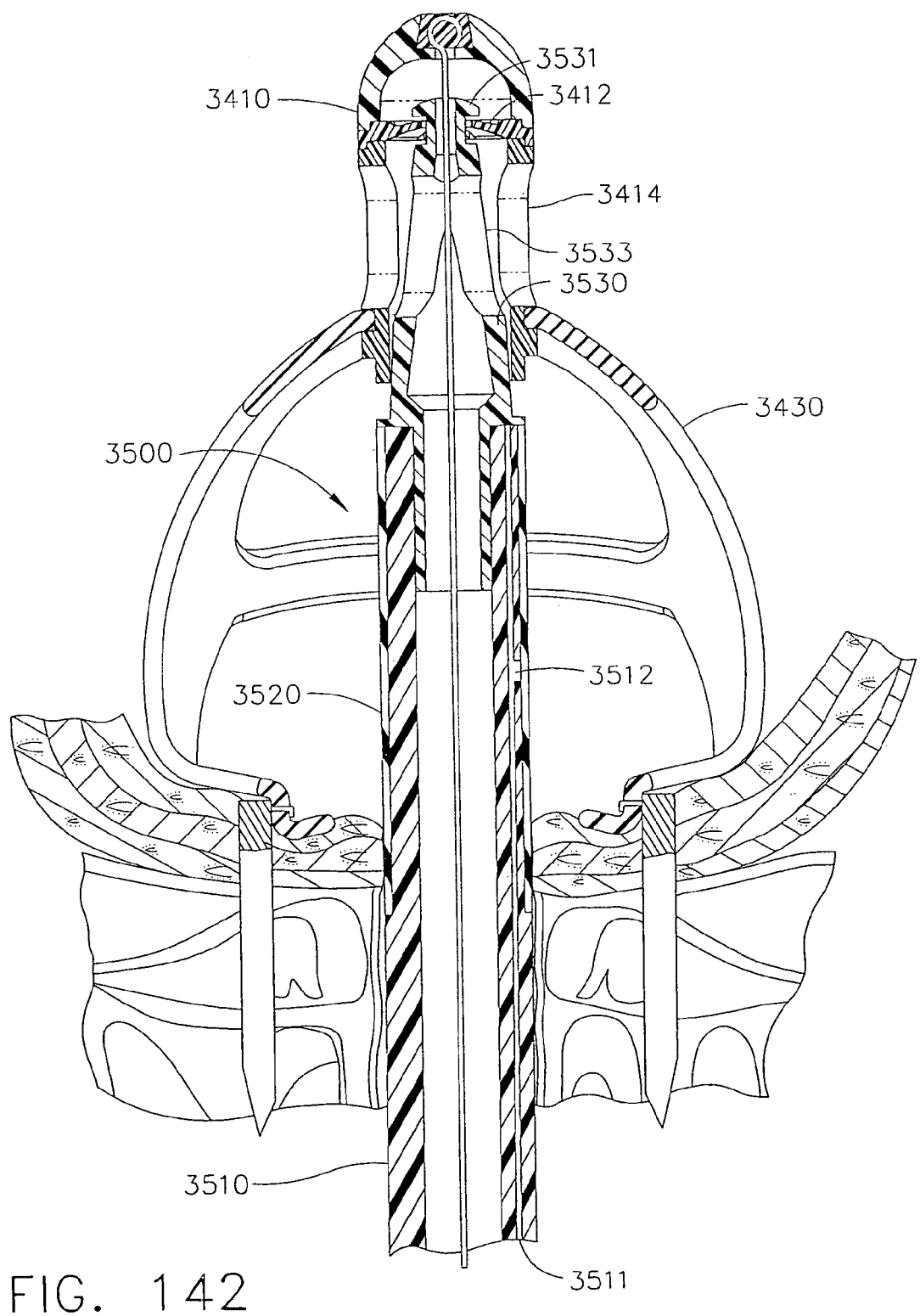
Figure 143:
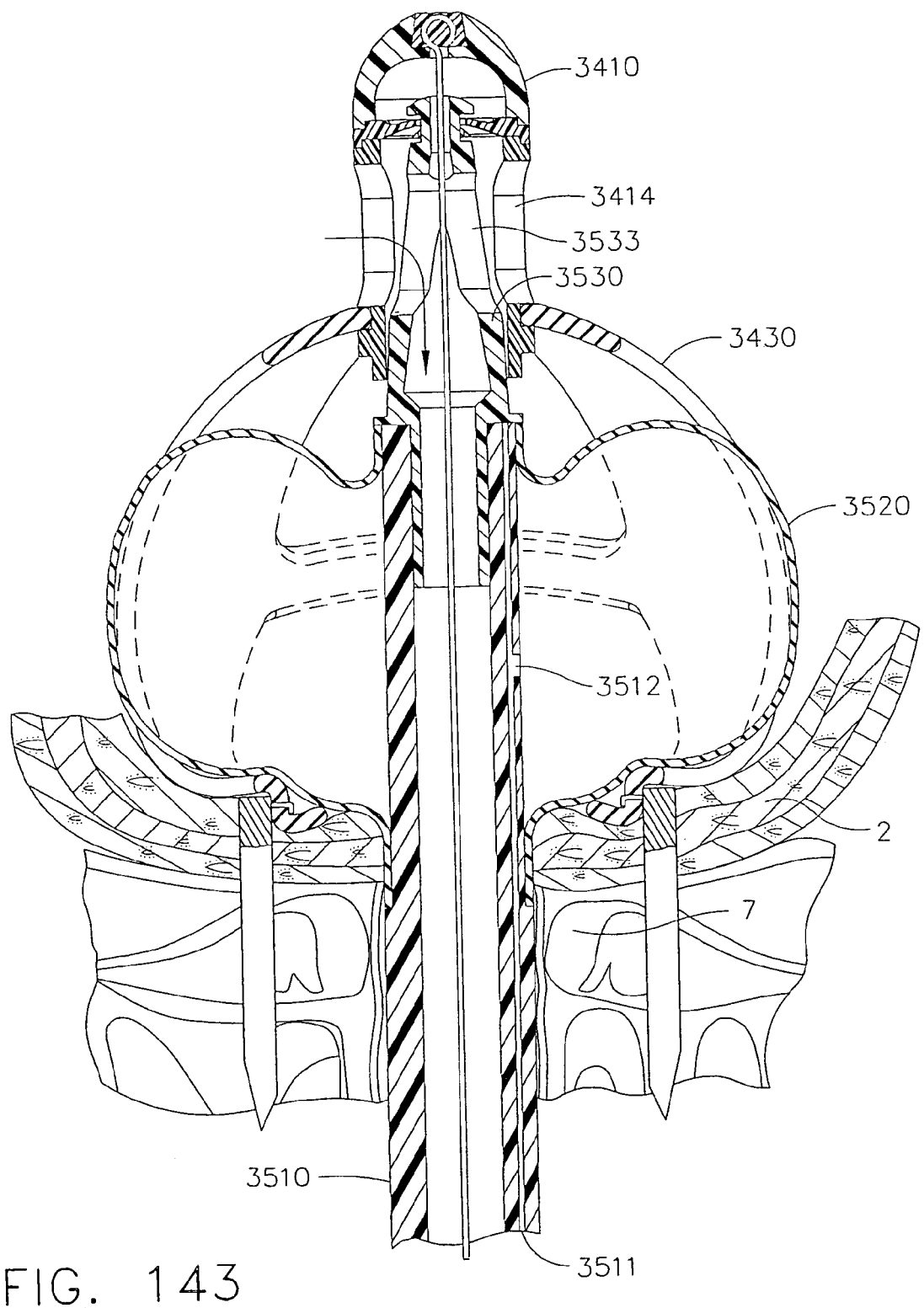
Figure 144:
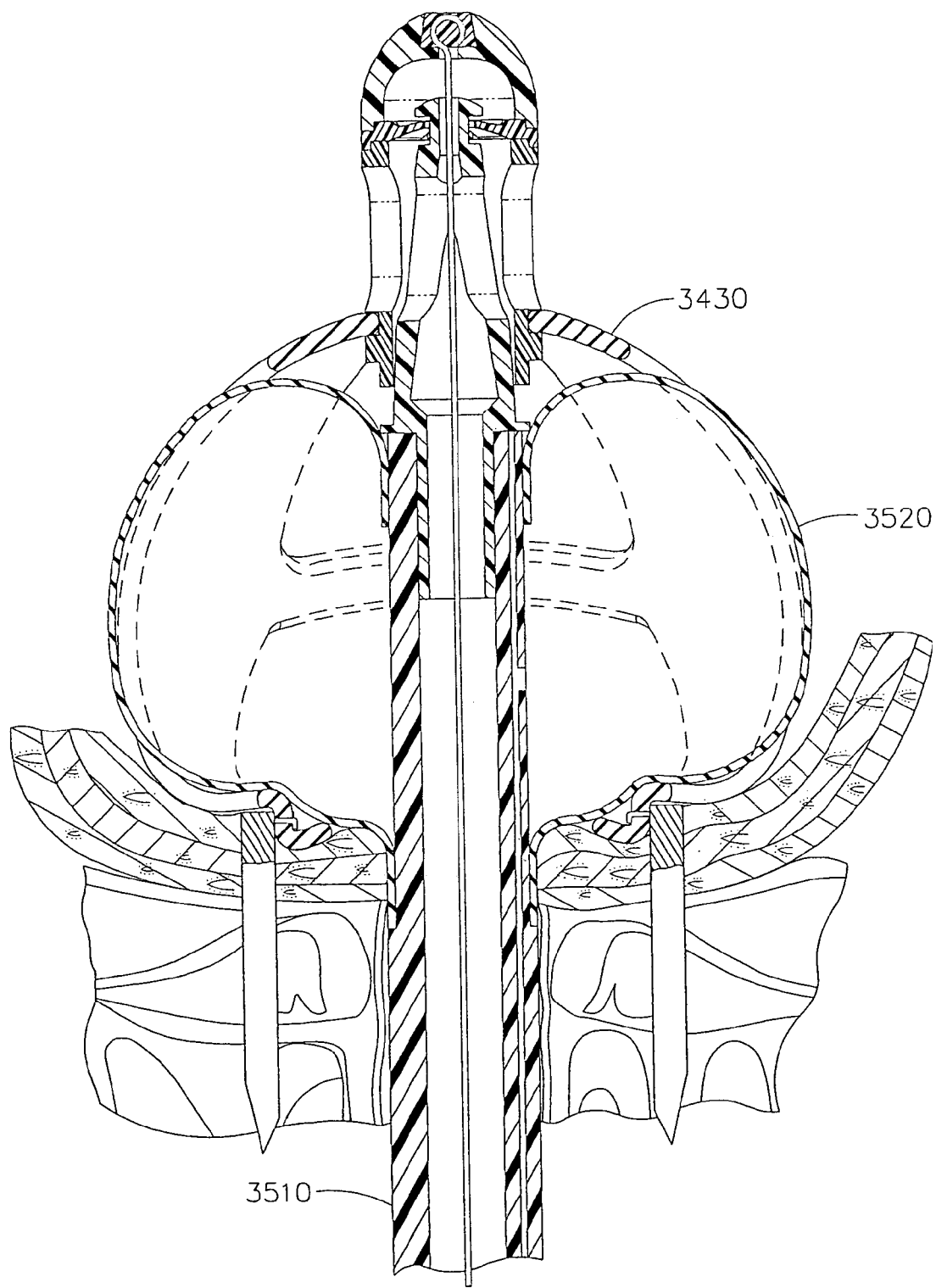
Figure 145:
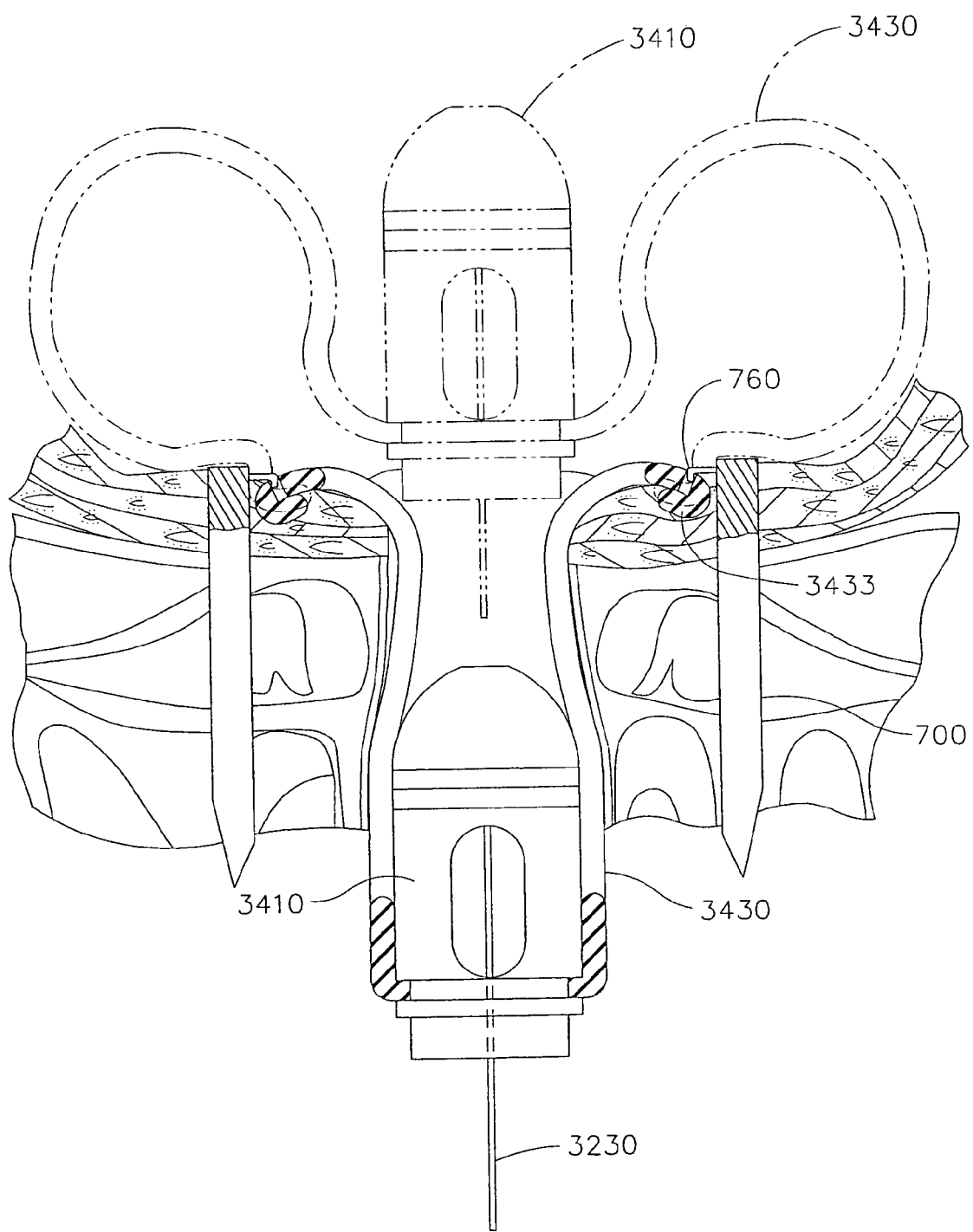
Figure 146:
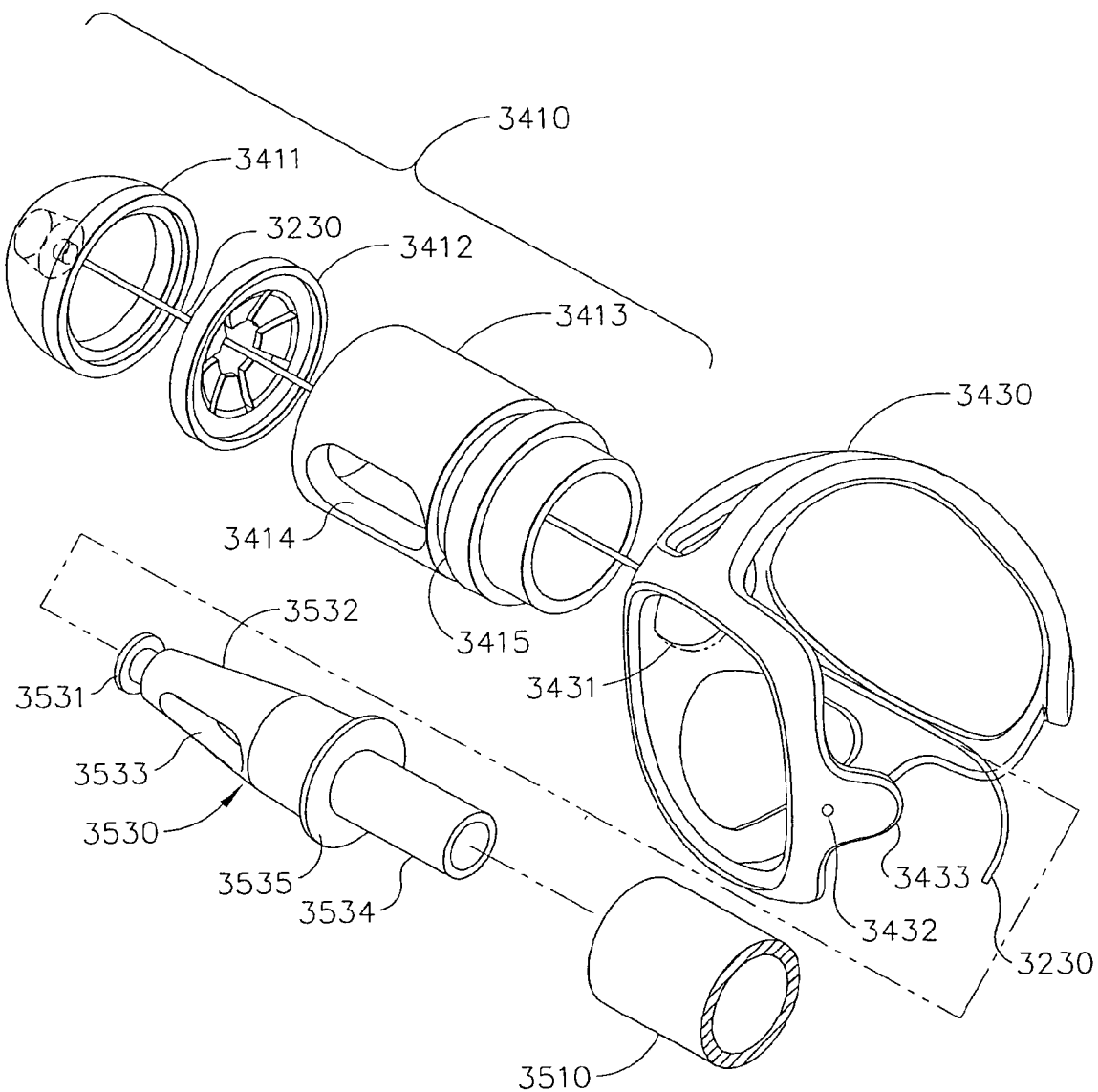
Figure 147:
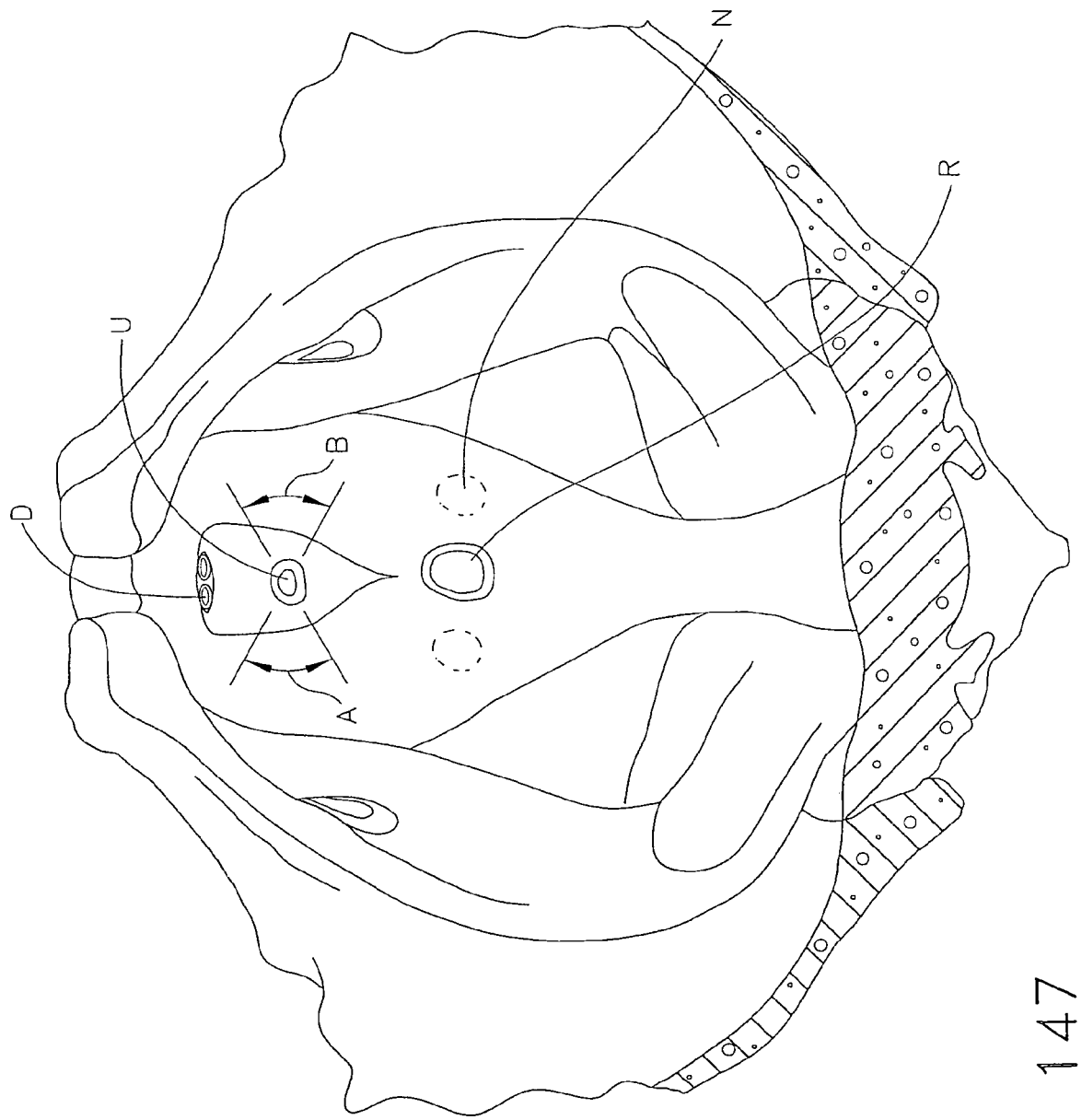

FIG. 126 is a longitudinal cross section of the instrument shown in FIG. 122, shown after insertion into and through a patient's urethra and into the bladder, after a positioner has been moved to a deployed position, after the bladder wall has been urged into contact with the pelvic floor with the openings in the bladder and urethra aligned, and after a lodging member has been moved to a deployed position;

FIG. 127 is an enlarged perspective view of an end cap of a positioner actuating rod, that may be used with the instrument shown in FIG. 122;

FIG. 128 is a schematic view of the instrument shown in FIG. 122, shown inserted into a patient with a positioner in a deployed position, with the instrument connected at its proximal end to a urine collection bag;

FIG. 129 is a longitudinal cross section of another embodiment of the instrument of the present invention, configured for an antegrade anastomosis procedure, shown in a deployed position;

FIG. 130 is a longitudinal cross section of another embodiment of the instrument of the present invention, configured for an antegrade anastomosis procedure, shown in a deployed position;

FIG. 131 is a perspective view of an embodiment of a lodging member having perforations and projections;

FIG. 132 is a longitudinal cross section of the lodging member shown in FIG. 131;

FIG. 133 is a longitudinal cross section of another embodiment of a lodging member having perforations and projections;

FIG. 134 is a perspective view of an anastomotic instrument having an actuator handle, a tube assembly and an end effector assembly in accordance with one embodiment of the present invention;

FIG. 135 is a longitudinal cross-sectional view of an end effector assembly of an anastomotic instrument in accordance with one embodiment of the present invention, shown inserted into and through a patient's urethra and into the bladder opening;

FIG. 136 is a longitudinal cross-sectional view of an end effector assembly of an anastomotic instrument in accordance with one embodiment of the present invention, shown inserted into and through a patient's urethra and into the bladder lumen, with a positioner assembly and an anchor driver assembly opened, and with the positioner assembly urging the bladder wall into contact with the pelvic floor;

FIG. 137 is a longitudinal cross-sectional view of an end effector assembly of an anastomotic instrument in accordance with one embodiment of the present invention, shown inserted into and through a patient's urethra and into the bladder lumen, with a positioner assembly opened, and after a driver assembly has driven anchors through the bladder wall and into the pelvic floor;

FIG. 138 is a longitudinal cross-sectional view of an end effector assembly of an anastomotic instrument in accordance with one embodiment of the present invention, shown inserted into and through a patient's urethra and into the bladder lumen, with a positioner assembly opened, after a driver assembly has driven anchors through the bladder wall and into the pelvic floor, and after driver pins have been withdrawn from the anchors;

FIG. 139 is a longitudinal cross-sectional view of an end effector assembly of an anastomotic instrument in accordance with one embodiment of the present invention, shown inserted into and through a patient's urethra and into the bladder lumen, with a positioner assembly opened, after a driver assembly has driven anchors through the bladder wall and into the pelvic floor, after driver pins have been withdrawn from anchors driven into the pelvic floor, and after the driver assembly has been closed;

FIG. 140 is a longitudinal cross-sectional view of an end effector assembly of an anastomotic instrument in accordance with one embodiment of the present invention, shown inserted into and through a patient's urethra and into the bladder lumen, with a positioner assembly opened, after a driver assembly has driven anchors through the bladder wall and into the pelvic floor, after driver pins have been withdrawn from anchors driven into the pelvic floor, and after the driver assembly and positioner assembly have been closed;

FIG. 141 is a longitudinal cross-sectional view of components of an end effector assembly of an anastomotic instrument in accordance with one embodiment of the present invention, shown inserted into and through a patient's urethra and into the bladder lumen, after installation of anchors, and after positioner and anchor driver assemblies have been withdrawn to leave behind an end cap assembly, anchors installed through the bladder wall and into the pelvic floor, and a balloon harness attached therebetween;

FIG. 142 is a longitudinal cross-sectional view of components of an end effector assembly of an anastomotic instrument in accordance with one embodiment of the present invention, shown inserted into and through a patient's urethra and into the bladder lumen, after installation of anchors, after positioner and anchor driver assemblies have been withdrawn to leave behind an end cap assembly, anchors installed through the bladder wall and into the pelvic floor, and a balloon harness attached therebetween, and after insertion of a balloon catheter assembly;

FIG. 143 is a longitudinal cross-sectional view of components of an end effector assembly of an anastomotic instrument in accordance with one embodiment of the present invention, shown inserted into and through a patient's urethra and into the bladder lumen, after installation of anchors, after positioner and anchor driver assemblies have been withdrawn to leave behind an end cap assembly, anchors installed through the bladder wall and into the pelvic floor, and a balloon harness attached therebetween, after insertion of a balloon catheter assembly, and after inflation of a balloon;

FIG. 144 is a longitudinal cross-sectional view of components of an end effector assembly of an anastomotic instrument in accordance with one embodiment of the present invention, shown inserted into and through a patient's urethra and into the bladder lumen, after installation of anchors, after positioner and anchor driver assemblies have been withdrawn to leave behind an end cap assembly, anchors installed through the bladder wall and into the pelvic floor, and a balloon harness attached therebetween, after insertion of a balloon catheter assembly, and after inflation of a balloon, shown one possible alternative embodiment;

FIG. 145 is a longitudinal cross-sectional view of components of an end effector assembly of an anastomotic instrument in accordance with one embodiment of the present invention, shown after the anastomosis procedure has been substantially completed, after withdrawal of a balloon catheter assembly, and in successive positions during withdrawal of an end cap assembly and balloon harness;

FIG. 146 is a perspective, exploded view of exemplary embodiments of an end cap assembly, balloon harness, and catheter end plug portion of a balloon catheter assembly; and FIG. 147 is a transverse (horizontal), superior (top) partial planar view of the human male pelvis and pelvic floor architecture, depicting preferred locations for installation of anchors.

Reference will now be made in detail to various alternative embodiments of the method and instrument of the invention, and various alternative components thereof, illustrated in the accompanying drawings.

DETAILED DESCRIPTION OF THE INVENTION

Before the present method and embodiments of an instrument are disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims.

Unless defined otherwise, all technical and scientific terms used herein have the same meaning as commonly understood to one of ordinary skill in the art to which this invention belongs. Although any method, instrument and materials similar or equivalent to those described herein may be used in the practice or testing of the invention, particular embodiments of a method, instrument and materials are now described.

It must be noted that, as used in this specification and the appended claims, the singular forms "a," "an," and "the" include plural referents unless the content clearly dictates otherwise.

In describing and claiming the present invention, the following terminology will be used in accordance with the definitions set out below.

As used herein, the term "anastomosis" means the surgical joining of respective tissues defining body lumens and other hollow body structures, especially the joining of hollow vessels, passageways or organs to create an intercommunication between them.

The term "patient," used herein, refers to any human or animal on which an anastomosis may be performed.

As used herein, the term "biocompatible" includes any material that is compatible with the living tissues and system (s) of a patient by not being substantially toxic or injurious and not causing immunological rejection. "Biocompatibility" includes the tendency of a material to be biocompatible.

As used herein, the term "bioabsorbable" includes the ability of a material to be dissolved and/or degraded, and absorbed, by the body.

As used herein, the term "shape memory" includes the tendency of a material, such as but not limited to a suitably prepared nickel-titanium alloy ("nitinol"), to return to a pre-formed shape, following deformation from such shape.

As used herein, the term "integral" means that two or more parts so described are affixed, fastened or joined together so as to move or function together as a substantially unitary part. "Integral" includes, but is not limited to, parts that are continuous in the sense that they are formed from the same continuous material, but also includes discontinuous parts that are joined, fastened or affixed together by any means so as become substantially immovably affixed to, and substantially unitary with, each other.

As used herein, the term "proximal" (or any form thereof), with respect to a component of an instrument, means that portion of the component that is generally nearest the surgeon, or nearest to the end of the instrument handled by the surgeon, when in use; and with respect to a direction of travel of a component of an instrument, means toward the end of the instrument generally nearest the surgeon, or handled by the surgeon, when in use.

As used herein, the term "distal" (or any form thereof), with respect to a component of an instrument, means that portion of the component that is generally farthest from the surgeon, or farthest from the end of the instrument handled by the surgeon, when in use; and with respect to a direction of travel of a component of an instrument, means away from the end of the instrument generally nearest the surgeon, or handled by the surgeon, when in use.

As used herein, the term "transverse" (or any form thereof), with respect to an axis, means extending in a line, plane or direction that is across such axis, i.e., not collinear or parallel therewith. "Transverse" as used herein is not to be limited to "perpendicular".

As used herein, the term "longitudinal axis", with respect to an instrument, means the exact or approximate central axis defined by said instrument along its greater dimension, i.e., along its length, from its distal end to its proximal end, and vice versa, and is not intended to be limited to imply a straight line, wherein, for example, an instrument includes a bend angle as described herein, it is intended that "longitudinal axis" as used herein follows such bend angle. Where used in association with an end effector, the term "longitudinal axis" means the exact or approximate central axis defined by said end effector extending along its greater dimension, i.e., along its length, from its distal end to its proximal end, and vice versa.

The method and instrument of the present invention utilizes a simple, effective mechanical arrangement for performing anastomosis of respective tissues defining two body lumens, for example, connecting the bladder to the urethra following a prostatectomy. By eliminating more painstaking, cumbersome suturing techniques, anastomosis techniques are improved. For use in the disclosed procedure, there are provided various embodiments of an improved instrument for bringing bladder wall tissues into contact with the pelvic floor tissues, with the openings in the bladder and urethra aligned, and for securing them in position so that they may knit and heal together.

By utilizing the disclosed techniques and an instrument of the present invention, the number of steps in the anastomosis procedure may be decreased, decreasing cost and reducing the required time for the procedure. The present invention may also eliminate complications associated with other anastomosis techniques that require hand suturing.

The present invention provides for a system that allows for, for example, connecting the bladder to the urethra using an instrument inserted through the urethra and into the bladder (in retrograde direction) without the need for access inside the bladder for manipulation and actuation of the instrument. Alternatively, the system and instrument may be configured such that it may be inserted into the bladder and then the urethra in an antegrade direction, through small incisions in the patient's abdomen and an upper surface of the bladder. Again, manipulation and actuation of the instrument may be performed by the surgeon from outside the patient's body.

Figure 1:
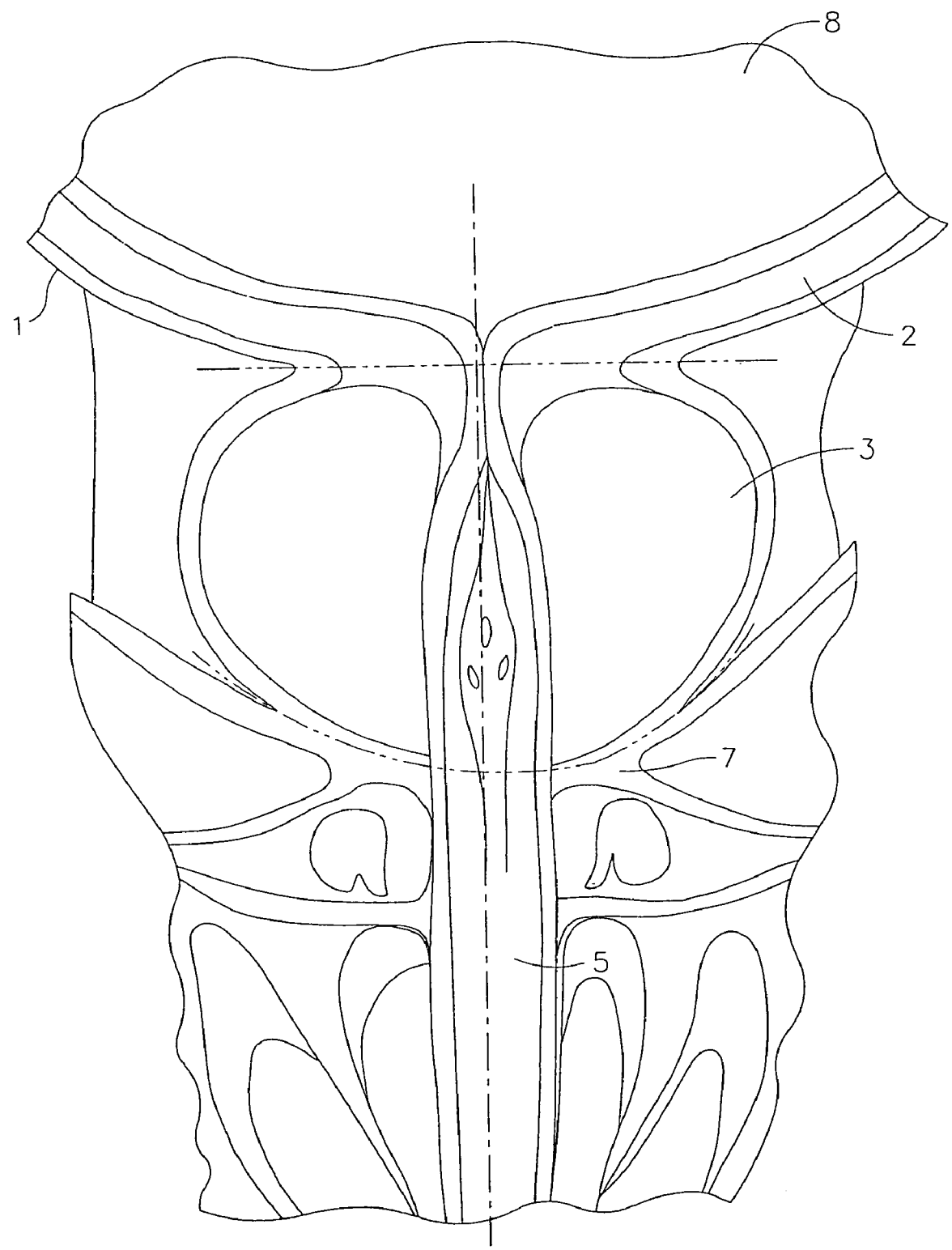
FIG. 1 is a partial, vertical sectional schematic depiction of the positional relationships of the human male bladder, prostate and urethra, and surrounding pelvic floor, prior to a prostatectomy.

Referring now to the drawings in detail, wherein like numerals indicate the same elements throughout the views, FIG. 1 schematically illustrates in vertical cross section the positioning of a human male bladder 1, bladder wall 2, prostate 3, pelvic floor 7 and urethra 5, prior to a prostatectomy. In a radical prostatectomy, the prostate 3, a lower portion of the bladder wall 2, and an upper portion of the urethra 5 are excised, removing the fluid connection between the bladder lumen 8 and the remaining portion of the urethra. The substantially horizontal broken lines in FIG. 1 schematically illustrate the lines along which the prostate and adjacent bladder and urethra tissues are excised.

Figure 2:
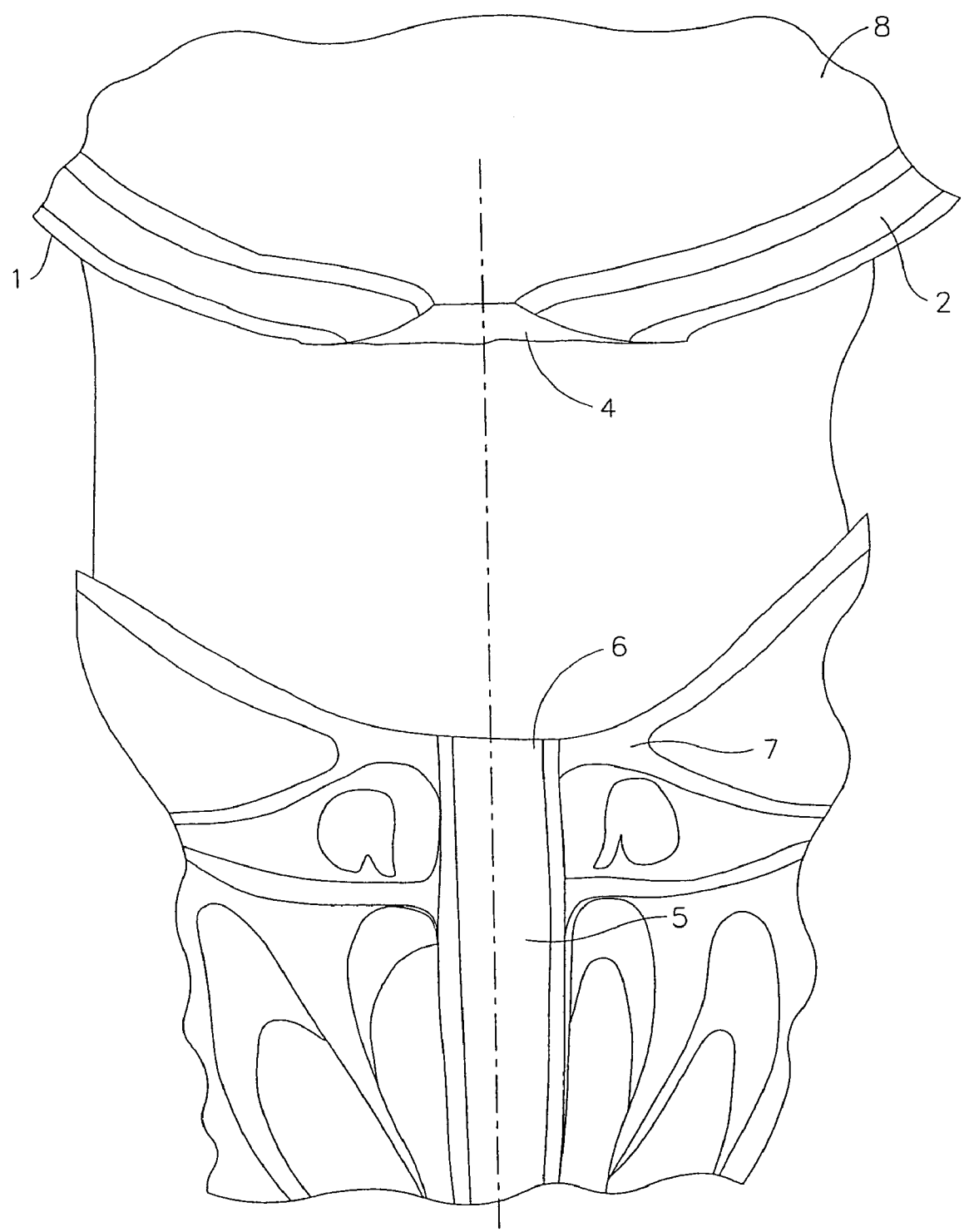
FIG. 2 is a partial, vertical sectional schematic depiction of the positional relationships of the human male bladder and urethra, and surrounding pelvic floor, following a prostatectomy.

FIG. 2 depicts an anatomical cross-section of the abdominal cavity following a radical prostatectomy wherein the excision of a portion of the bladder wall 2 results in a bladder opening 4 and the excision of the prostate results in a urethra opening 6 in urethra 5. Following this surgery, bladder opening 4 is typically reduced in size by means known in the art, such as a "tennis racket" suture technique.

Rotationally-Opened Embodiment

FIGS. 3-16 show an embodiment of an instrument 10 which may be used to perform an anastomosis procedure, for example, a procedure to effect anastomosis of a patient's bladder and urethra following a prostatectomy.

Figure 3:
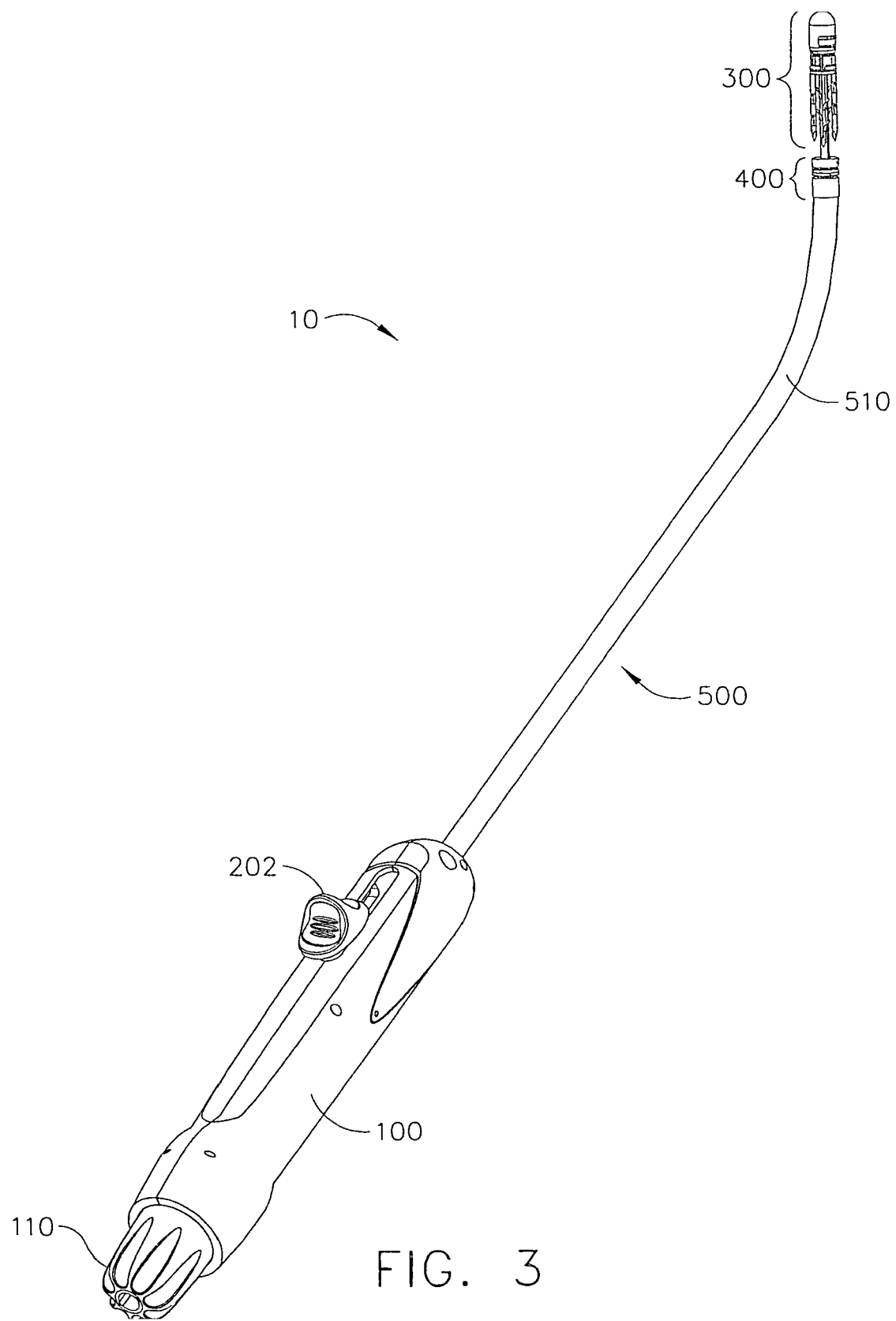
FIG. 3 is a perspective view of an anastomotic instrument having an actuator handle, a driver assembly and a positioner assembly in accordance with one embodiment of the present invention.

As shown configured for use in a retrograde manner in FIG. 3, one embodiment of the anastomotic applier instrument 10 in accordance with the invention may comprise an elongated tube assembly 500, a driver assembly 300 secured onto the distal end of the tube assembly 500, an optional positioner assembly 400 which may be used to bring the bladder wall and the pelvic floor tissues into close proximity or contact, and an actuator handle 100 for effecting opening of the positioner and driver assemblies and the driving and seating of anchors. In general, the instrument may be used for performing a vesico-urethral anastomosis after the prostate has been removed in a radical retropubic prostatectomy (see FIGS. 1 and 2). This connection is necessary to restore the patient's urinary functions after the prostatectomy.

Figure 4:
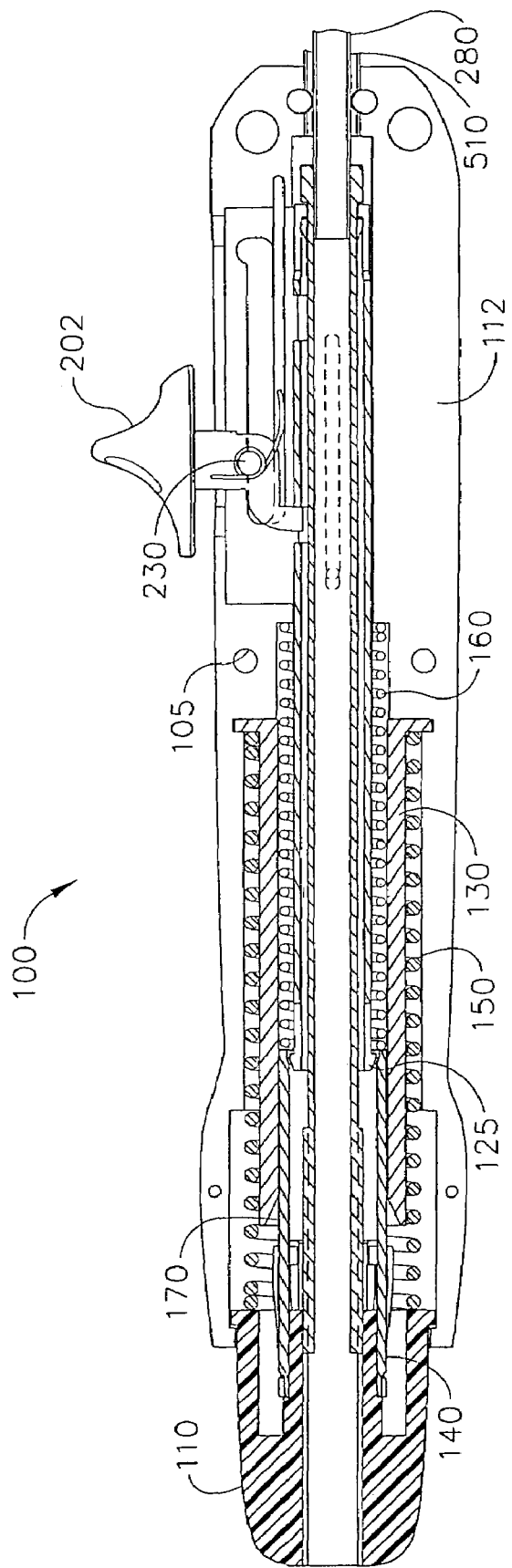
FIG. 4 is a longitudinal cross-sectional view of the actuator handle of the anastomotic instrument shown in FIG. 3.

FIG. 4 shows an embodiment of an actuator handle 100 of the anastomotic instrument shown in FIG. 3. Handle 100 is operatively connected to the proximal end of the elongated tube assembly 500, which transmits manipulating and actuating forces from the handle 100 to the positioner assembly 400 and driver assembly 300 at the distal end of the tube assembly 500. Two tubes, outer tube 510 and medial actuator tube 280, exit handle 100 at its distal end. Outer tube 510 is affixed by any suitable means to and is substantially integral with handle housing 112, and housing 112 and outer tube 510 are substantially stationary and skeletal with respect to the other, moving, parts of the handle 100 and tube assembly 500. Medial actuator tube 280 both rotates and moves longitudinally with respect to outer tube 510, in response to input from the surgeon as will be hereinafter described, and thereby transmits rotational and longitudinal actuating forces and movement through tube assembly 500.

In the embodiment shown in FIGS. 4-6, the handle 100 may comprise a housing 112 having actuating mechanisms disposed therein as will be hereinafter described. The housing 112 may include two or more parts, having alignment pins 105 and mating holes to facilitate assembly and make the parts integral after assembly.

Housing 112 contains actuating mechanisms to effect rotational and longitudinal actuating forces and movement in medial actuator tube 280. Referring to FIG. 5, knob 110 may be an actuating member for manipulation by a surgeon, and may be adapted to be pushed distally by the surgeon, and urged back proximally by knob return spring 150, with respect to housing 112. Knob 110 may also be adapted to be rotated by the surgeon with respect to housing 112 by the surgeon. Thus, knob 110 may be rotatable and movable longitudinally within housing 112, within the limits of longitudinal travel defined by knob track 116 in housing 112, as the ends thereof stop longitudinal movement of knob 110 by contact with knob rim 111. Knob 110 may also be hollow, having guidewire passage 114 therethrough. Within guidewire passage 114 of knob 110 may be one or more longitudinal spline grooves 115. Spline grooves 115 can slidably mate with one or more splines 185 of proximal rotation tube 180. Thus, it can be appreciated that knob 110 and proximal rotation tube 180 may be coupled with respect to rotational movement, but not coupled with respect to longitudinal movement and therefore, be longitudinally slidable with respect to one another. Thus configured, rotation of knob 110 can effect corresponding rotation of proximal rotation tube 180. In turn, proximal rotation tube 180 may be fixedly coupled to medial actuator tube 280. Thus, rotation of knob 110 can effect corresponding rotation of medial actuator tube 280, while longitudinal movement of knob 110 will not effect longitudinal movement of medial actuator tube 280.

Prior to the firing of the handle assembly as will be described below, knob 110 may be turned to effect corresponding rotational movement in medial actuator tube 280, so as to open driver assembly 300 and positioner assembly 400 as will be described below.

Figure 5:
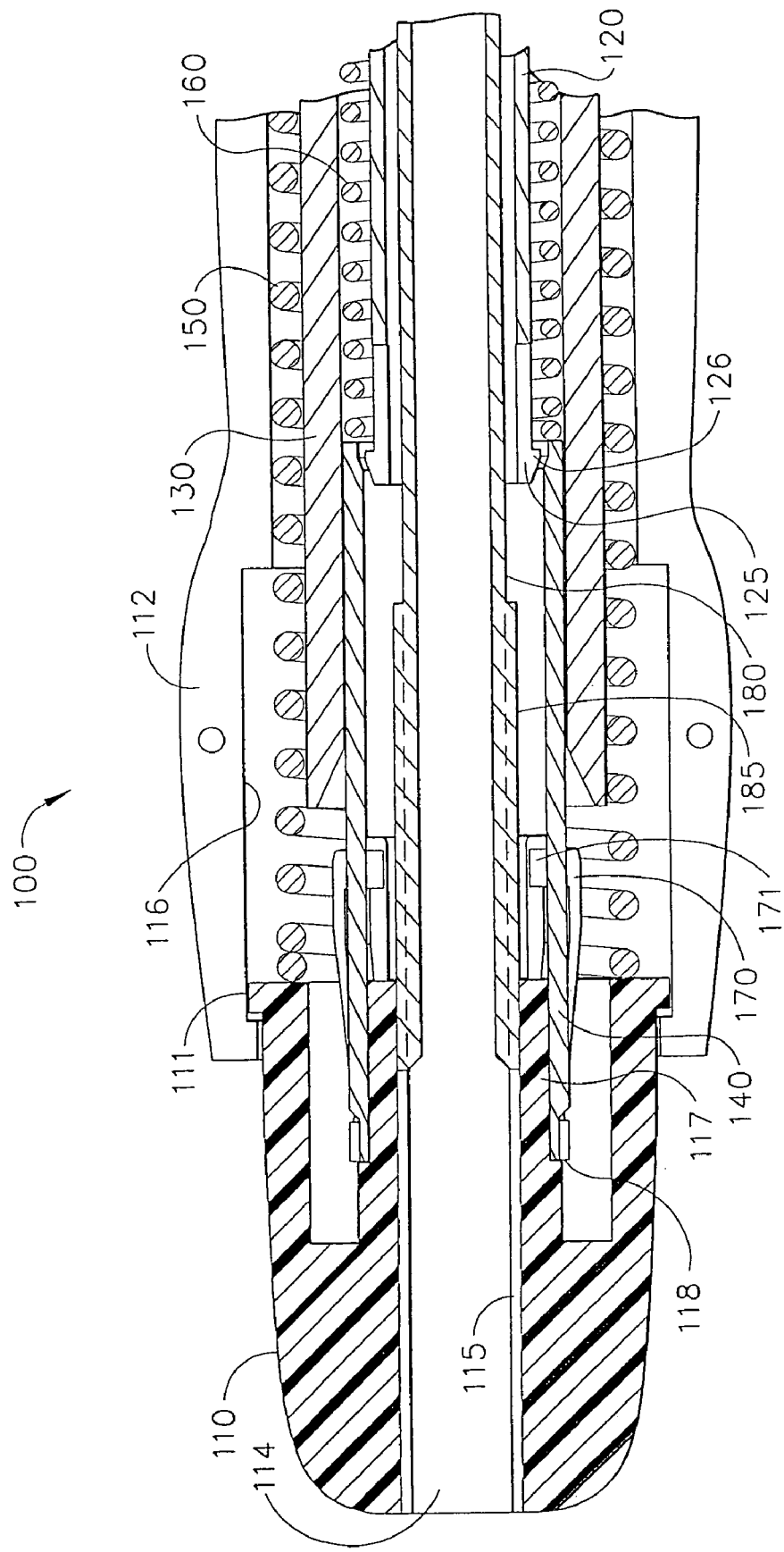
FIG. 5 is an expanded longitudinal cross-sectional view of the proximal end of the actuator handle of the anastomotic instrument shown in FIG. 3.
Figure 6:
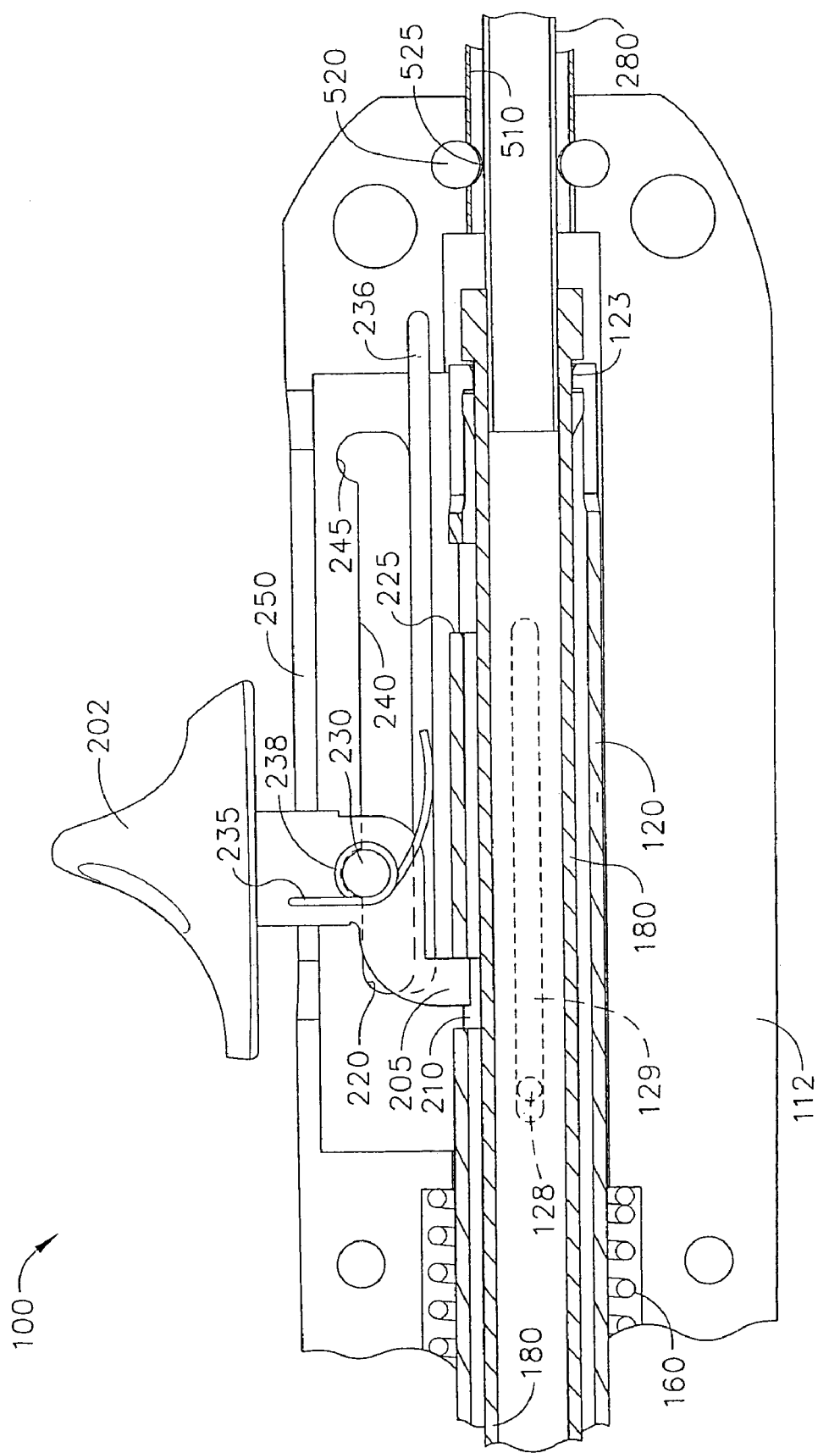
FIG. 6 is an expanded longitudinal cross-sectional view of the distal end of the actuator handle of the anastomotic instrument shown in FIG. 3.

FIGS. 5 and 6, depict handle 100 in an uncocked, pre-deployment position. As will be hereinafter described, one embodiment of an anchor driver assembly of the present invention (such as that shown in FIG. 3 at 300) requires longitudinal force and movement of a member in a proximal direction in order to drive anchors. This force and movement in a proximal direction may be effected by handle 100 via medial actuator tube 280. Medial actuator tube 280 may be drawn in a longitudinally proximal direction, i.e., rearwardly, into handle 100, through a mechanism that will now be described.

A driving spring 160 may be contained within housing 112, in compression, as shown in FIGS. 5 and 6. The proximal end of driving spring 160 contacts and acts against the distal end of a proximal linking tube 140, urging linking tube 140 to move in a proximal direction with respect to housing 112. The proximal end of linking tube 140 rotatably and slidably fits around an interior spindle 117 of knob 110 and rests against spindle shoulder 118.

In the position shown in FIGS. 5 and 6, driving tube 120 is in a forward, distal position inside housing 112. Driving tube 120 is connected at its distal end to proximal rotation tube 180 via lip 123, such that proximal rotation tube 180 is free to rotate within driving tube 120, but by the arrangement shown, driving tube 120 and proximal rotation tube 180 are configured to be linked and move as a unit in a longitudinal direction. Driving tube 120 may be prevented from rotating so as not to interfere with actuation of driving button pawl 205, by one or more pins 128 affixed in housing 112, engaged in driving tube pin slot 129. At the top of FIG. 6, it can be seen that driving button 202 may be integral with driving button pawl 205, and driving button 202 and correspondingly driving button pawl 205 are biased in a counterclockwise direction by spring 235, such that pawl 205 is biased downward into driving tube firing slot 210.

In order the ready the handle depicted in FIGS. 5 and 6 to effect a longitudinal proximal movement of medial actuator tube 280 (which movement may be used to drive anchors as will be hereinafter described), a surgeon may depress knob 110 in longitudinal, distal direction within housing 112 (to the right with respect to FIG. 5). As a result of contact between shoulder 118 and the proximal end of linking tube 140, this movement of knob 112 can move linking tube 140 a corresponding direction and distance, and also correspondingly, longitudinally compress and thereby charge driving spring 160. Linking tube 140 has affixed at its proximal end one or more driving tube engagers 170, which may be spring-biased inwardly and have latching ends 171 that protrude inwardly through slots in linking tube 140 as shown. Upon longitudinal movement of linking tube 140 in a distal direction as a result of depressing knob 110, latching ends 171 can moveably engage and latch upon latching shoulder 126 of driving tube 120, latching driving tube 120 to linking tube 140 such that the two will move as a unit in a rearward, proximal longitudinal direction, in response to force exerted on linking tube 140 by driving spring 160, once driving tube 120 is released as will be described below. Thus, when a surgeon depresses knob 110 in a distal longitudinal direction (to the right with respect to FIG. 5, driving spring 160 is charged and the handle is thereby cocked for driving anchors as will be hereinafter described. After cocking, knob 110 is urged to return to its proximal (rearward) position by knob return spring 150. Knob return spring 150 and driving spring 160 may be coaxially aligned and separated by a spring divider 130.

Driving tube 120 is released and permitted to be driven in a longitudinal proximal (rearward) direction with respect to housing 112 when the surgeon engages and urges driving button 202 forwardly (with respect to FIG. 6). This rotates driving button 202 and correspondingly, pawl 205 clockwise about pin 230, and lifts pawl driving tube firing slot 210. Driving tube 120 is thereby released to be driven rearwardly (to the left with respect to FIGS. 5 and 6) under the force exerted by driving spring 160, acting on linking tube 140, linked to driving tube 120 via driving tube engagers 170. As driving tube 120 is driven rearwardly, it correspondingly pulls medial actuator tube 280 rearwardly a corresponding distance, via lip 123. This actuation constitutes "firing" the handle 100 to pull medial actuator tube 280 in a longitudinal proximal (rearward) direction into handle 100, which may be used to drive anchors as will be described below.

After "firing" of handle 100, it may be desirable to effect additional longitudinal movement of medial actuator tube 280 so as to cause further seating of anchors, and afterward, to effect withdrawal of anchor driver pins from anchors as will be described below. Referring to FIG. 6, after firing, driving tube retraction slot 225 in driving tube 120 is moved to a position beneath driving button pawl 205, and pawl 205, at the urging of torsion spring 235 and/or pressure by the surgeon, moves into retraction slot 225. The surgeon may then exert proximal and downward pressure (with respect to FIG. 6) on driving button 202, which will both maintain pawl 205 in retraction slot 225, and also urge pin 230 down and out of rocker detent 238 in driving button slot 240, enabling the surgeon to urge driving tube 120 further proximally and thus further drive anchors a distance allowed by seating extension 220 in driving button slot 240, and/or further seat anchors into tissues, as will be described below. This arrangement may also transfer to the surgeon touch-perceptible feedback through driving button 202 as to how much pressure is being exerted to drive and seat anchors.

After driving and seating of anchors, the surgeon may then effect the withdrawal of anchor driver pins from anchors (as will be described below) by effecting a return of medial actuator tube to its original position as will now be described. The surgeon exerts downward and distally-directed pressure on driving button 202. Such downward pressure maintains pawl 205 in retraction slot 225 and keeps pin 230 out of rocker detent 238, while urging driving tube 120 distally (to the right with respect to FIG. 6). As driving tube 120 is urged distally, medial actuator tube 280 is urged distally a corresponding distance via driving tube lip 123 acting on proximal actuator tube 180, which is affixed to medial actuator tube 280. This returning motion is limited by the distal extent of driving button slot 240. When pin 230 reaches this extent, the surgeon's release of pressure on driving button 202 will permit pin 230 to be urged upwardly (with respect to FIG. 6) under the force exerted by torsion spring 235 into extension detent 245.

Following installation of anchors, knob 110 may be turned to effect corresponding rotational movement in medial actuator tube 280 so as to retract or close driver assembly 300 and positioner assembly 400 as will be described below.

It is contemplated that various pieces of the handle assembly may be an integral structure formed from several components, or these features may be an integrally molded from a material such as plastic so as to form a single integral structure. The handle assembly may be constructed from conventional materials for surgical instruments, for example a metal such as stainless steel or plastic. The instrument may be constructed primarily from conventional metal or plastic materials so that it is inexpensive to manufacture and can be disposable. The instrument may also be sold in a package that is presterilized for surgical use.

Housing 112, driving button 202, spring divider 130 and knob 110 may be formed of plastic or any suitable material having necessary properties of strength, stiffness and formability. It may be desirable for spline grooves 115 to be a suitable metal for improved hardness and wear resistance, such that spline grooves 115 would be part of a metal insert around which knob 110 is formed. Proximal actuator tube 180, linking tube 140 and driving tube engagers 170, driving tube 120, medial actuator tube 280 and outer tube 510 may be formed of stainless steel, plastic or any other suitable material having necessary properties of strength, hardness and stiffness. Springs 150, 160 and 235 may be formed of spring steel or any suitable material that would have suitable formability, shape memory, stiffness (spring constant) and strength properties. While proximal actuator tube 180, linking tube 140, driving tube 120, medial actuator tube 280 and outer tube 510 are depicted as having tube shapes, they may also have any shape suitable for transmitting longitudinal and rotational forces and movement to a distal end as required for an instrument of the present invention.

It will be apparent to persons skilled in the art that a variety of mechanisms might be configured and adapted to transmit longitudinal (advancement and retraction) and rotational forces and movement move from a proximal handle assembly to a distal end in order to effect the forces and movement necessary to actuate an instrument of the present invention. It will be apparent to persons skilled in the art that the mechanism that supplies the driving force supplied by driving spring 160 may also be other biasing or driving devices including but not limited to levers, gears, pressurized gases/fluids and any other mechanisms for selectively deploying linear driving forces known in the art.

Figure 52:
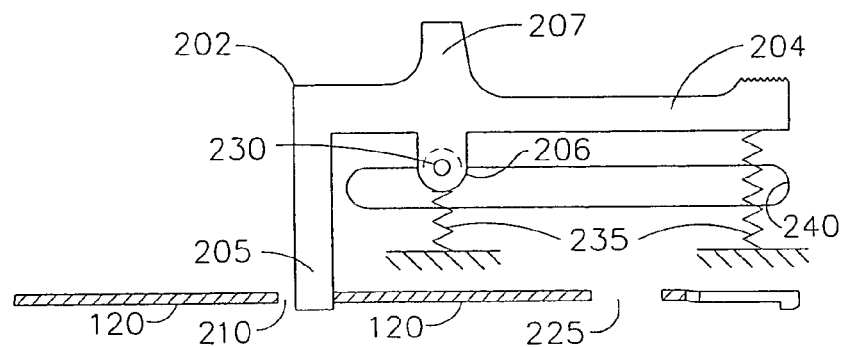
FIG. 52 is a schematic illustration of a driving button assembly shown in a cocked position.
Figure 53:
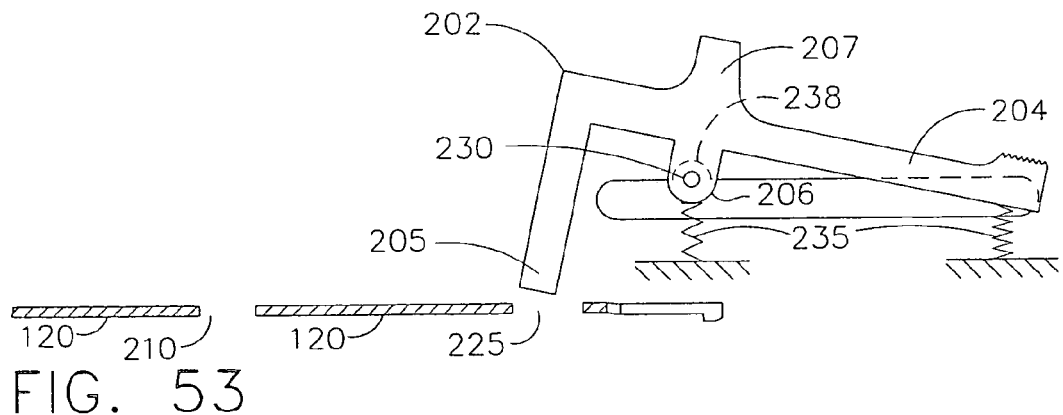
FIG. 53 is a schematic illustration of a driving button assembly shown in a released position.
Figure 54:
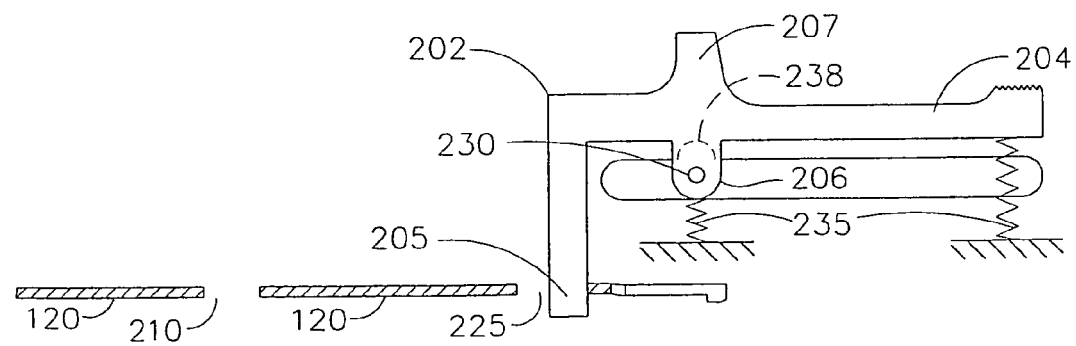
FIG. 54 is a schematic illustration of a driving button assembly shown in a forward seating position.

An alternative embodiment for the driving button assembly shown in FIG. 6 will now be described. Referring to FIGS. 52-54, driving button 202 is linked to the mechanism by driving button pin 230, captured by driving button pin boss 206. Driving button 202 includes driving button pawl 205, driving pin boss 206, driving trigger 204 and retraction member 207. Driving button 202 is angularly movable about driving button pin 230 which is captured by driving pin boss 206, and driving button pin 230 may slidably ride in a longitudinal direction with respect to the length of the instrument, in driving button groove 240, which includes rocker detent 238. One or more springs 235 are provided which act upon driving button 202 in two ways: First, to urge driving button 202 upward such that driving button pin 230 is urged upward, in orientation with respect to FIGS. 52-54, and such that driving pin 230 is urged into rocker detent 238, when driving trigger 204 is not being depressed; second, to urge driving button 202 in a counterclockwise direction, such that driving trigger 204 and driving button pawl 205 are urged in a counterclockwise direction, about driving button pin 230, with respect to FIGS. 52-54, thus maintaining driving button pawl 205 engaged with driving tube retention slot 210. It will be appreciated that a single torsion spring configured and acting upon driving button 202 in a manner such as shown in FIG. 6 (torsion spring 235) may be used to accomplish the desired result, but also, that other suitable spring or biasing mechanisms or configurations are possible. Driving button pawl 205 is adapted to engage, alternatively, driving tube retention slot 210, and driving tube retraction slot 225, of driving tube 120, in a manner similar to that shown for the driving button pawl 205 in FIG. 6.

Operation of the embodiment of driving button assembly shown in FIGS. 52-54 will now be described. When an instrument such as driver assembly 300 (FIG. 3) has been loaded with anchors and is in the retracted position ready for insertion and subsequent use, driving button assembly 200 will be in the position shown in FIG. 52. Driving button 202 is biased upwardly and in a counterclockwise direction about driving button pin 230 by one or more springs 235 so that driving button pin 230 is maintained engaged in rocker detent 238, and driving button pawl 205 is maintained engaged in driving tube retention slot 210, restraining driving tube 120 against spring bias acting upon driving tube 120 as more fully described above.

Figure 14:
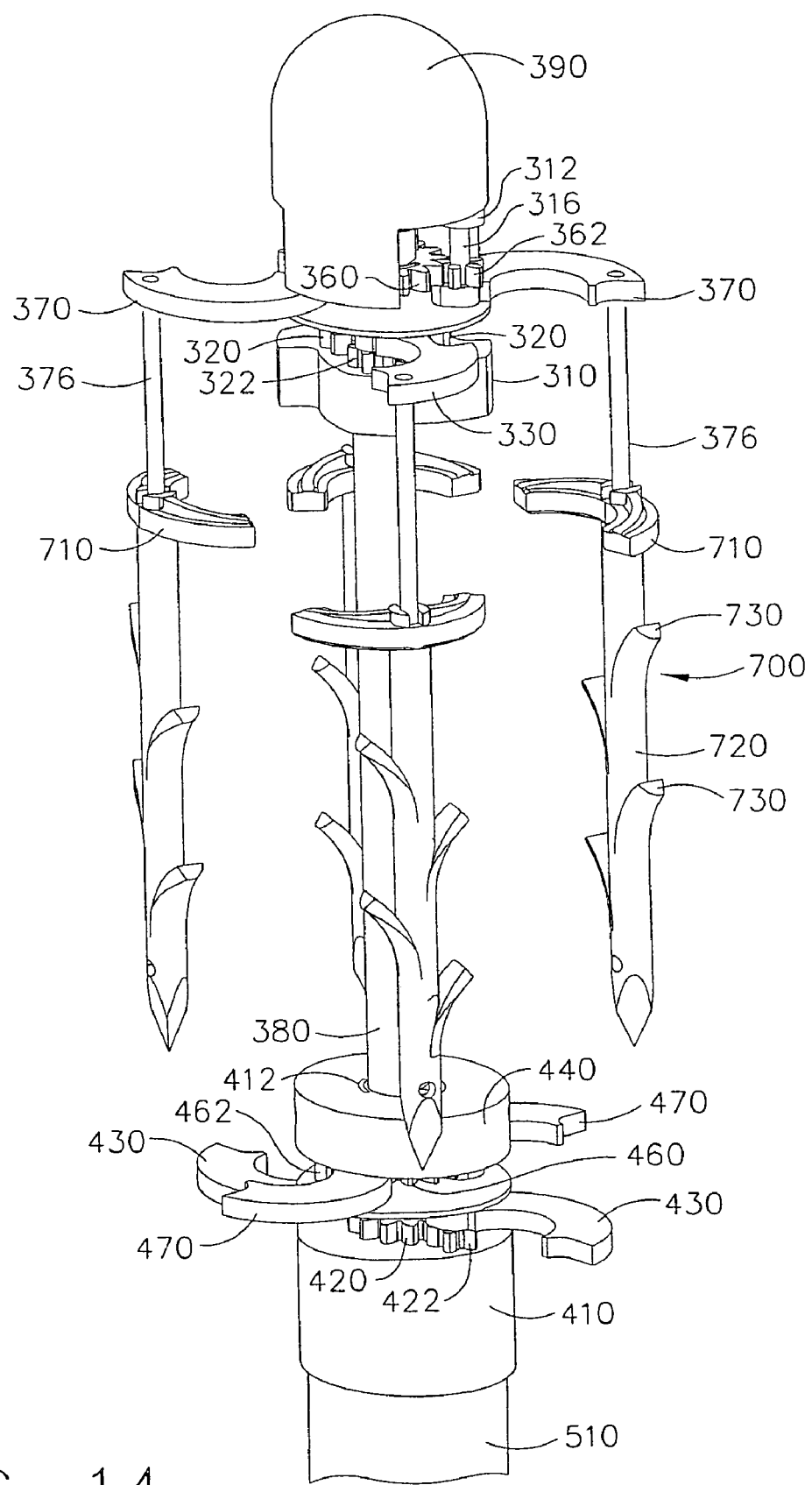
FIG. 14 is a perspective illustration of embodiments of the positioner and driver assemblies of the anastomotic instrument shown in FIG. 3 with the positioner and driver assemblies shown in open positions.
Figure 15:
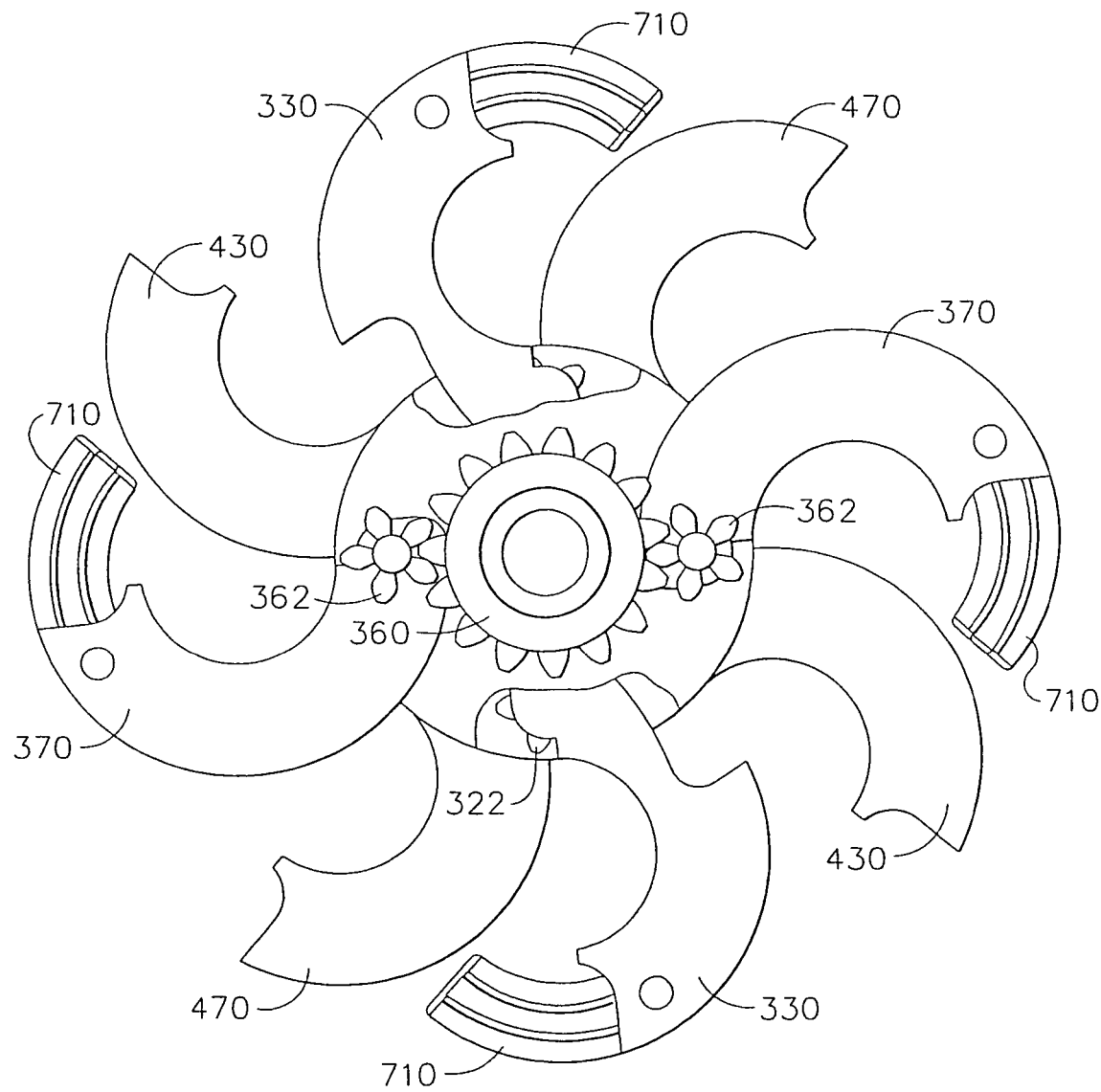
FIG. 15 is a cross-sectional overhead view of the positioner and driver assemblies of the anastomotic instrument shown in FIG. 14 showing the driver arms and positioner arms in open positions.
Figure 16:
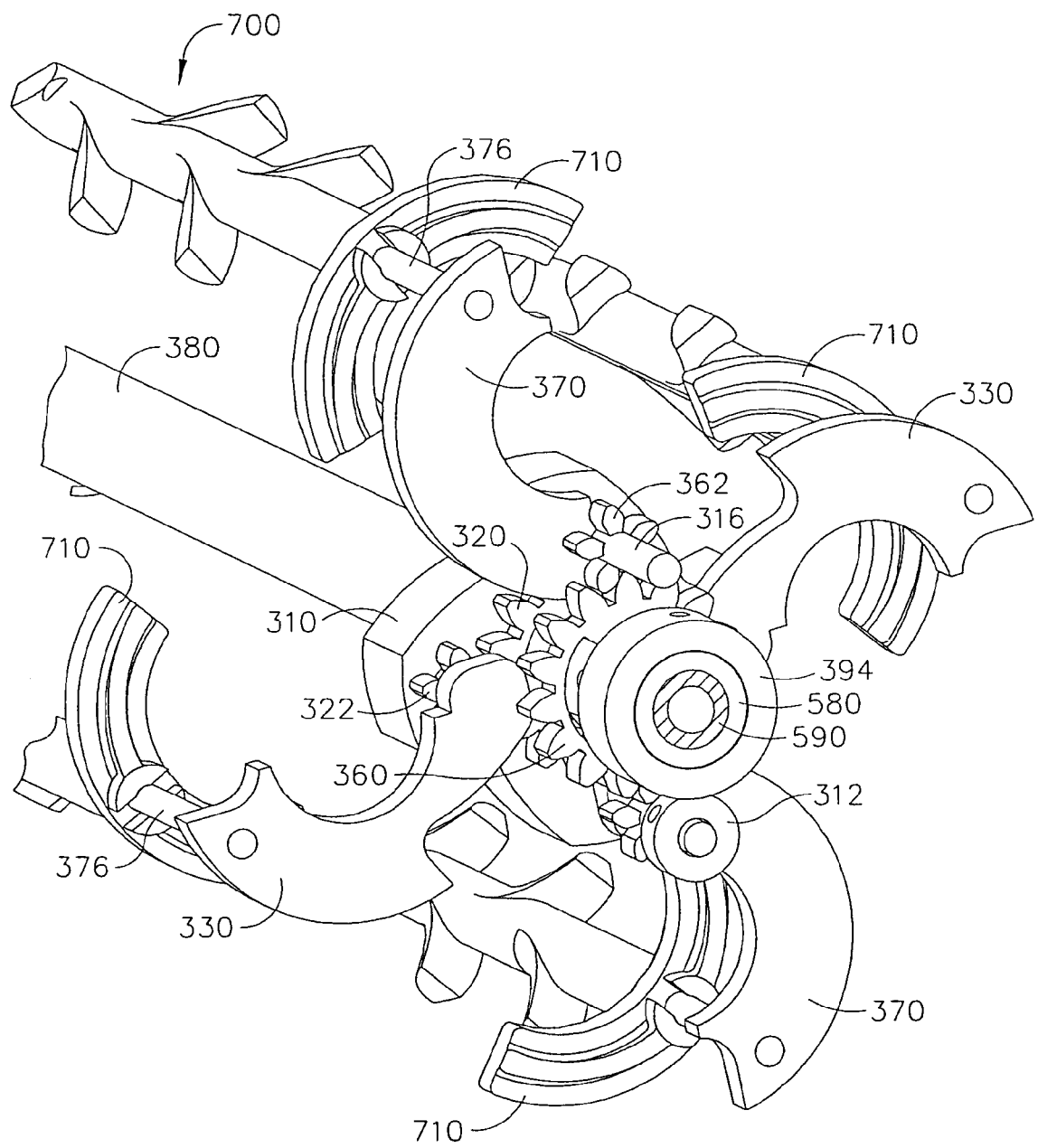
FIG. 16 is an expanded perspective view of the driver assembly of the anastomotic instrument shown in FIG. 14, showing driver arms, driver pins and anchors.

Once the applier has been inserted and opened to the position shown in FIG. 14, the driving tube 120 is released and driven by depressing driving trigger 204. FIG. 53 depicts a "snapshot" of the positioning of driving button 202 relative to driving tube 120, after driving trigger 204 is depressed to release driving tube 120 by disengaging driving button pawl from driving tube retention slot. With respect to FIG. 53, it can be seen that downward pressure on driving trigger 204 causes clockwise rotation of driving button 202 about driving button pin 230, causing driving button pawl 205 to move upwardly and disengage from driving tube retention slot 210. Disengagement of driving button pawl 205 from driving tube retention slot 210 releases driving tube 120, permitting it to move to the left (with respect to FIGS. 52-54) under urging of a spring as more fully described above. This drives driver pins and anchors as more fully described below.

FIG. 54 illustrates the positioning of driving button 202 relative to driving tube 120, when the mechanism is ready for retraction of the driver pins from the installed anchors. It will be appreciated from FIGS. 53 and 54 that continuing downward pressure exerted by the surgeon on driving trigger 204 urges driving button pawl 205 downward into driving tube retraction slot 225. At the same time, driving button pin boss 206 is urged downward, and correspondingly, driving button pin 230 is urged downward and out of rocker detent 238. When driving button 202 is in this position, shown in FIG. 54, the surgeon may then engage retraction member 207 to move driving button 202 to the right (with respect to FIG. 54), which correspondingly pulls driving tube 120 to the right by engagement of driving button pawl 205 with driving tube retraction slot 225. In this manner, the driver pins may be withdrawn from the now-installed anchors as more fully described below.

Referring back to FIGS. 3 and 7-9, it may be desirable that tube assembly 500 be curved and flexible to facilitate insertion into the patient. Accordingly, it may be desirable to manufacture certain components of tube assembly 500, including outer tube 510, medial actuator tube 280, distal rotation tube 580 and central tube 590, of materials that have suitable combined properties of biocompatibility, strength, stiffness, flexibility, elasticity and shape memory so as to provide a suitable balance of flexibility to facilitate insertion, with strength, rigidity and shape memory to facilitate manipulation to transfer longitudinal and rotational forces from the handle assembly 100 to the positioner assembly 400 and driver assembly 300. The inventors have found that suitably treated nitinol, known in the art for having such properties and used for endoscopic surgical instruments with similar requirements, is a suitable material. However, other materials such as styrene or other polymers may be satisfactory for some components.

FIGS. 7-10 are views of the portion of tube assembly including a bridge assembly 600. The tube assembly and bridge assembly provide for isolation and transmission of rotational and longitudinal advancement and retraction force and movement from medial actuator tube 280 to a positioner assembly 400 and driver assembly 300. In one embodiment, medial actuator tube 280 may rotate, and longitudinally advance and retract within and with respect to outer tube 510, and is operatively connected to a positioner assembly 400 and a driver assembly 300, via a bridge assembly 600. The bridge assembly 600 provides an operative connection of the medial actuator tube 280 so as to limit rotational movement, and transmit both limited rotational movement and longitudinal movement to distal rotation tube 580, and is adapted to allow an effective amount of rotational and longitudinal travel. The bridge assembly 600 also provides an operative connection of the medial actuator tube 280 to central tube 590 so as to translate longitudinal movement to central tube 590.

Figure 10:
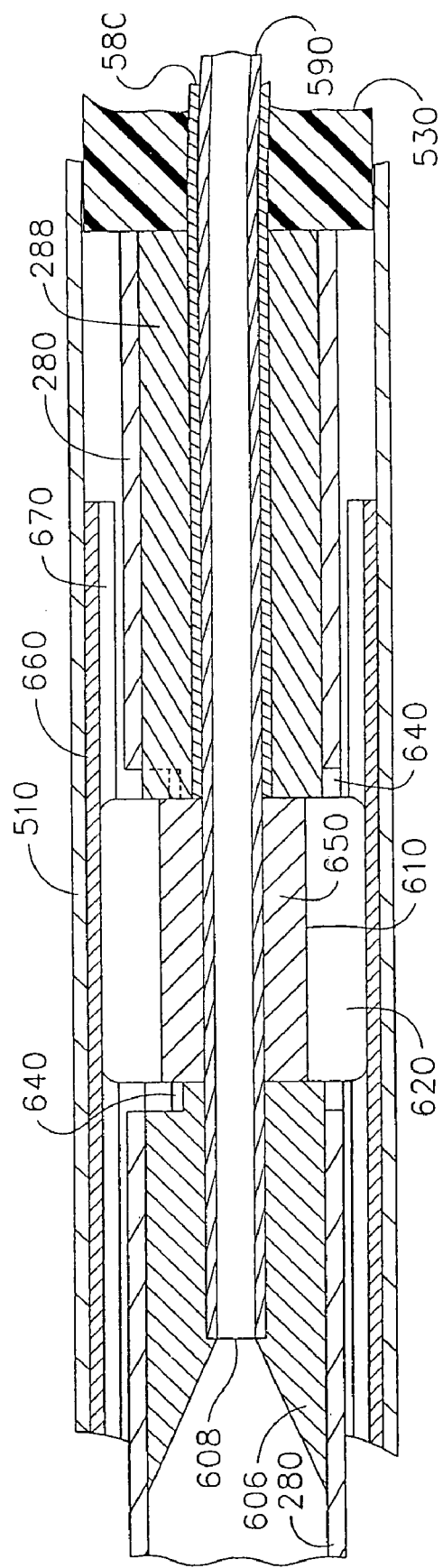
FIG. 10 is an expanded longitudinal cross-sectional view of the bridge assembly shown in FIG. 8.

Referring to FIGS. 9 and 10, medial actuator tube 280 has therein one or more bridge slots 640, and terminates within bridge assembly 600. Bridge 610 has a hub 650 located within medial actuator tube 280, and one or more vanes 620, which protrude through bridge slots 640 in medial actuator tube 280, and longitudinally ride within one or more longitudinal bridge tracks 670 cut or formed within a bridge guide 660. Bridge guide 660 is affixed within, and therefore integral with, outer tube 510. Thus, vanes 620 and therefore bridge 610 may slide longitudinally within bridge guide 660 and outer tube 510, but are prevented from rotating.

It can be appreciated from FIGS. 9 and 10 that the range of rotation of medial actuator tube 280 with respect to outer tube 510 is limited by the circumferential dimension of bridge slots 640 in medial actuator tube 280, and contact between the edges of bridge slots 640 and vanes 620. The circumferential dimension of bridge slots 640 in actuator tube 280 may be varied according to the range of rotation that may be required to actuate the instrument. Longitudinal bridge tracks 670 may be long enough to allow vanes 620 to slide longitudinally to the full range of longitudinal motion of medial rotation tube 280 that may be required to actuate the instrument.

Central tube 590 is affixed within bridge hub 650 and is integral therewith. Thus, longitudinal motion is translated from medial actuator tube 280 to bridge vanes 620 and correspondingly bridge hub 650 via interaction between bridge slots 640 and bridge vanes 620. Correspondingly, longitudinal motion of bridge hub 650 is translated to central tube 590 because bridge hub 650 and central tube 590 are integral. Thus, longitudinal motion of medial actuator tube 280 is translated to corresponding longitudinal motion of central tube 590.

At the same time, rotational motion of medial actuator tube 280 is not translated to central tube 590. As noted, central tube 590 is integral with bridge hub 650, and bridge hub 650 is prevented from rotating by the situation of bridge vanes 620 in bridge tracks 670, which are, in turn, integral with outer tube 510.

Referring to FIG. 10, distal rotation tube 580 is affixed and integral with rotation spacer 288, which, in turn, is affixed and integral with the distal end of medial actuator tube 280. Thus, both longitudinal movement and rotation of medial actuator tube 280 are translated directly to corresponding longitudinal movement and rotation of distal rotation tube 580. As previously noted, however, the range of rotational movement of medial actuator tube 280 is limited by the circumferential dimension of bridge slots 640, and thus, the range of rotational movement of distal rotation tube 580 is correspondingly limited.

Central tube 590 and distal rotation tube 580 are not affixed to one another and therefore distal rotation tube 580 may rotate with respect to central tube 590.

A funnel guide 606 may be affixed to the proximal end 608 of central tube 590, thereby providing for ease of feeding a guide wire upward through medial actuator tube 280 and into central tube 590. Funnel guide 606 would not be affixed to medial actuator tube 280, and would be longitudinally and rotationally movable therein.

Distal rotation tube 580 and central tube 590 may be located within and supported through a bend in the tube assembly by rotation tube stabilizer 530, a proximal end of which appears at the right of FIGS. 8 and 10, and the entirety of which appears in FIG. 7.

Referring now to FIG. 11-16, the tube assembly is operably coupled with positioner assembly 400. A proximal positioner mount 410 is affixed and integral with outer tube 510. Distal positioner mount 440 is affixed and made integral with proximal positioner mount 410 by positioner mount connector members 412. Thus, proximal positioner mount 410 and distal positioner mount 440, as made integral with outer tube 510, provide a stationary reference and mounting point for moving parts which will now be described.

Figure 11:
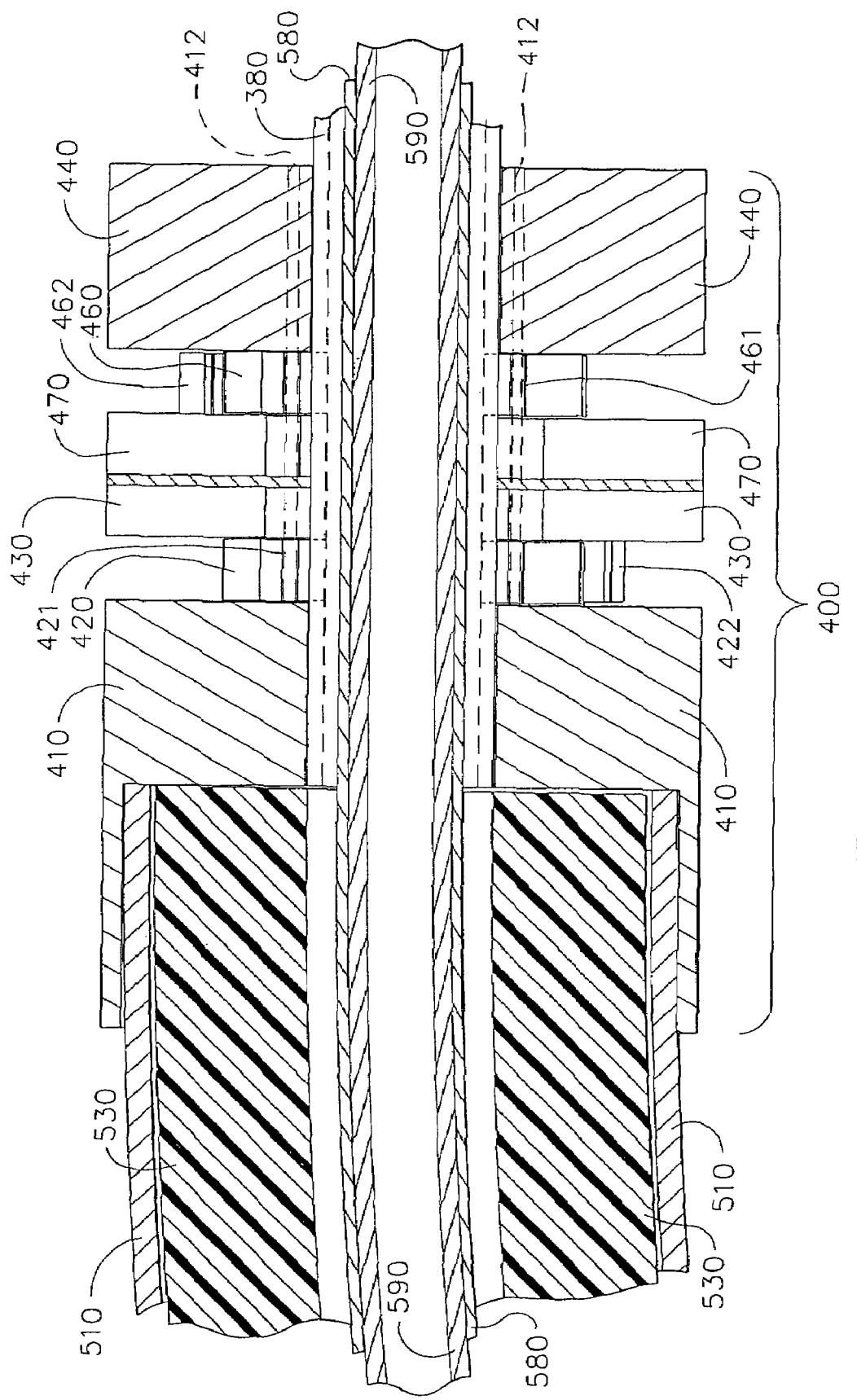
FIG. 11 is an expanded longitudinal cross-sectional view of a positioner assembly part of the anastomotic instrument shown in FIG. 3.
Figure 12:
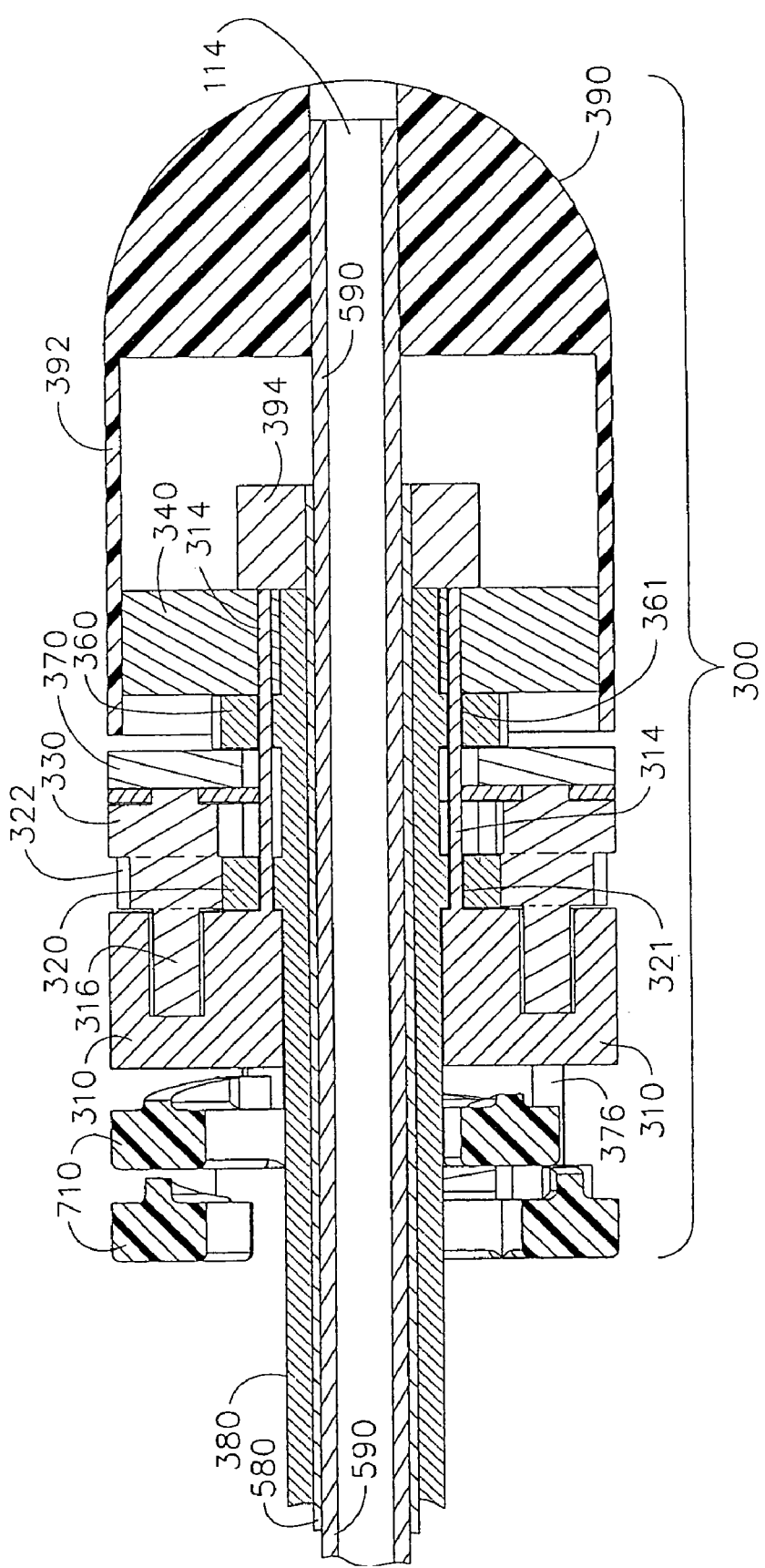
FIG. 12 is a longitudinal cross-sectional view of the driver assembly part of the anastomotic instrument shown in FIG. 3.

Referring to FIGS. 11 and 12, as noted and described above, central tube 590 may move longitudinally, but may not rotate, with respect to outer tube 510, and thus, may move longitudinally, but may not rotate, with respect to proximal positioner mount 410 and distal positioner mount 440. Central tube 590 is affixed and integral at its distal end with distal end cap 390. Distal driver mount 340 is affixed and integral with tabs 392 of distal end cap 390. Proximal driver mount 310 is affixed and made integral with distal driver mount 340 via driver mount connector members 314. Thus, distal end cap 390, distal positioner mount 340, driver mount connector members 314 and proximal driver mount 310 and central tube 590 are integral and move longitudinally as a unit with respect to outer tube 510, but may not rotate with respect to outer tube 510.

It can be seen from FIGS. 3-14 that guidewire passage 114 leads through the center of handle assembly 100, through tube assembly 500 (and within medial actuator tube 280), through central tube 590, through positioner assembly 400 and driver assembly 300 and out distal end cap 390.

As noted and described above, distal rotation tube 580 may rotate about central tube 590, in direct correspondence with rotation of medial actuator tube 280, within a range limited by the circumferential dimension of bridge slots 640 in medial actuator tube 280 (see FIGS. 9 and 10). Within driver assembly 300, distal rotation tube 580 terminates and is integrally affixed to distal rotation tube collar 394 and gear tube 380. Thus, rotation of distal rotation tube 580 causes directly corresponding rotation of gear tube 380. In FIGS. 11 and 12, it can be seen that gear tube 380 resides directly outside distal rotation tube 580 and extends proximally from distal driver mount 340 to proximal positioner mount 410. FIG. 11, it can be seen that clearance within rotation tube stabilizer 530 is present to permit proximal longitudinal movement of gear tube 380 thereinto.

Referring again to FIG. 12, and also FIG. 14, it can be seen that distal driver gear 360 and proximal driver gear 320 reside within driver assembly 300. Distal driver gear 360 and proximal driver gear 320 are coaxial and integrally affixed to gear tube 380. Arcuate slots 361 in distal driver gear 360 and arcuate slots 321 in proximal driver gear 320 accommodate passage of driver mount connector members 314 therethrough and also permit distal driver gear 360 and proximal driver gear 320 to rotate within a limit about the axis of gear tube 380 without interference from driver mount connector members 314.

Referring to FIG. 11, distal positioner gear 460 and proximal positioner gear 420 reside within positioner assembly 400. Distal positioner gear 460 and proximal positioner gear 420 are coaxial with, and longitudinally splined with, gear tube 380, such that distal positioner gear 460 and proximal positioner gear 420 are coupled with gear tube 380 with respect to rotation, but uncoupled with respect to relative longitudinal motion. Thus, gear tube 380 may move longitudinally within positioner assembly 400, without effecting corresponding longitudinal movement of positioner assembly 400 or any parts thereof. Arcuate slots 461 in distal driver gear 460 and arcuate slots 421 in proximal driver gear 420 accommodate passage of driver mount connector members 412 therethrough and also permit distal positioner gear 460 and proximal positioner gear 420 to rotate within a limit about the axis of gear tube 380 without interference from positioner mount connector members 412.

Thus, it can be appreciated from the description above that rotating medial actuator tube 280 correspondingly rotates distal rotation tube 580 and gear tube 380, finally, distal driver gear 360, proximal driver gear 320, distal positioner gear 460 and proximal positioner gear 420. It also may be seen that longitudinal movement of central tube 590 with respect to outer tube 510 causes corresponding longitudinal movement of driver assembly 300 with respect to outer tube 510, but not longitudinal movement of positioner assembly 400 with respect to outer tube 510.

Figure 13:
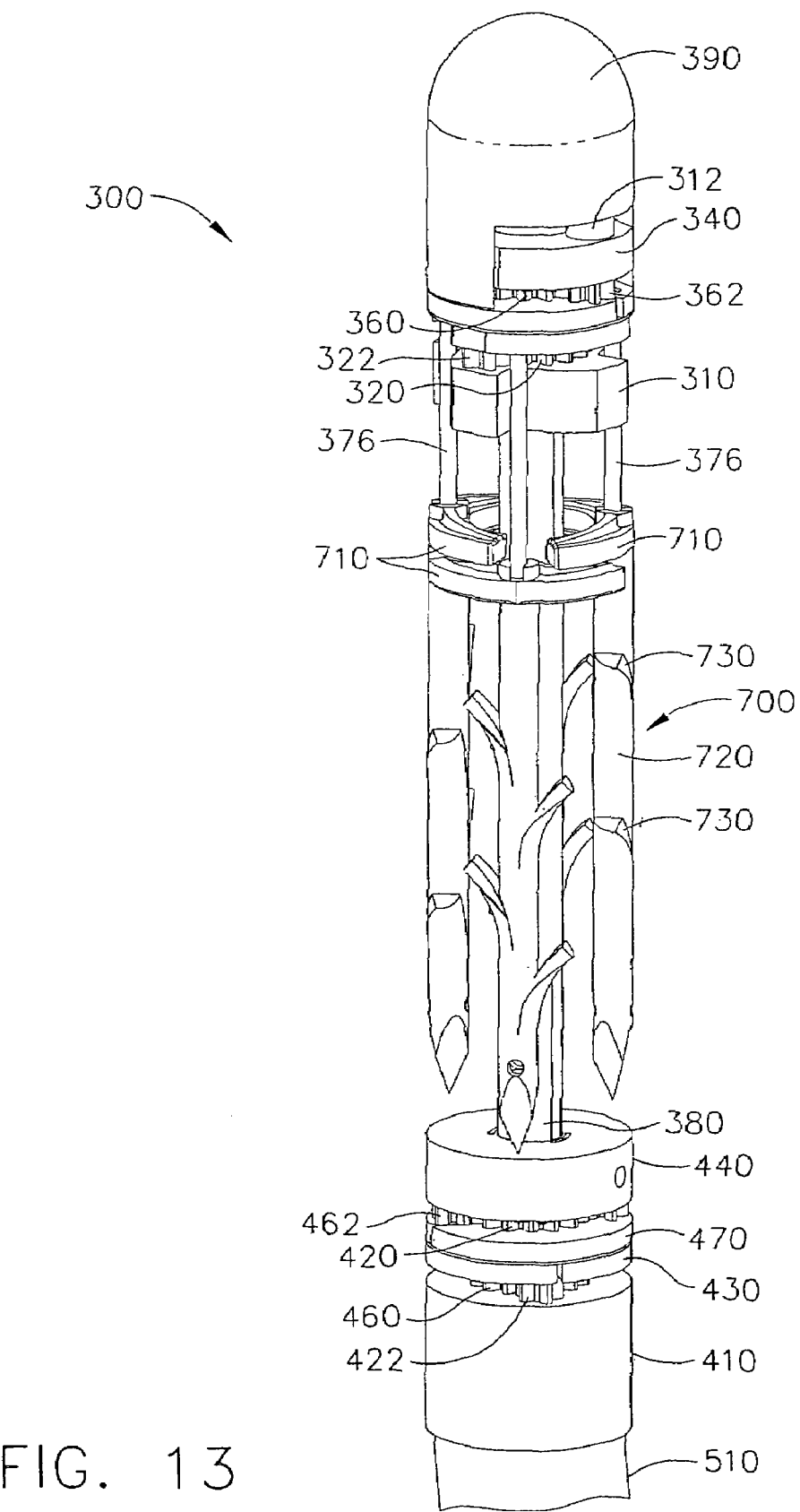
FIG. 13 is a perspective illustration of embodiments of the positioner and driver assemblies of the anastomotic instrument shown in FIG. 3.

Referring now to FIGS. 11, 13 and 14, distal positioner pinions 462 are integral with and may rotate about pinion shafts (not shown) which are rotatably supported in distal positioner mount 440. Distal positioner pinions 462 mesh with distal positioner gear 460, and may be driven thereby. Distal positioner pinions 462 are also integral with distal positioner arms 470. Similarly, proximal positioner pinions 422 are integral with and may rotate about pinion shafts (not shown) which are rotatably supported in proximal positioner mount 410. Proximal positioner pinions 422 mesh with proximal positioner gear 420, and may be driven thereby. Proximal positioner pinions 422 are also integral with proximal positioner arms 430.

Thus, referring to FIGS. 11, 13 and 14, it can be seen that rotation of distal rotation tube 580 correspondingly rotates gear tube 380, and thus, distal and proximal positioner gears 460 and 420, which, in turn, drive distal and proximal positioner pinions 462 and 422, causing positioner arms 470 and 430 to either swing outwardly (toward a position shown in FIG. 14) or inwardly (toward a position shown in FIG. 13). It will be appreciated that the position shown in FIG. 13 is the position in which positioner assembly 400 would be placed during insertion into and retraction from a patient. It will be further appreciated that the position shown in FIG. 14 is the position in which positioner assembly 400 is ready for use for bringing the bladder wall surrounding the bladder opening into contact with the pelvic floor, as will be further described below. Finally, it will be appreciated from the description set forth above (and referring also to FIGS. 8-10), that the limits of the rotational motion of gear tube 380 required, alternately, to extend or retract arms 470 and 430 of positioner assembly 400, are defined by the circumferential dimension of bridge slots 640 in medial rotation tube 280 and their interaction with bridge vanes 620.

Referring now to FIGS. 12-16, distal driver pinions 362 are integral with pinion shafts 316, which are rotatably supported in distal driver mount 340. Distal driver pinions 362 mesh with distal driver gear 360, and may be driven thereby. Distal driver pinions 362 are also integral with distal driver arms 370, which, in turn, are integral with driver pins 376. Similarly, proximal driver pinions 322 are integral with pinion shafts 316, which are rotatably supported in proximal driver mount 310. Proximal driver pinions 322 mesh with proximal driver gear 320, and may be driven thereby. Proximal driver pinions 322 are also integral with proximal driver arms 330, which, in turn, are integral with additional driver pins 376.

Thus, referring to FIGS. 12-16, it can be seen that rotation of distal rotation tube 580 correspondingly rotates gear tube 380, and thus, distal and proximal driver gears 360 and 320, which, in turn, drive distal and proximal driver pinions 362 and 322, causing driver arms 370 and 330 to either swing outwardly (toward a position shown in FIG. 14) or inwardly (toward a position shown in FIG. 13). It will be appreciated that the position shown in FIG. 13 is the position in which driver assembly 300 would be placed during insertion into and retraction from a patient. It will be further appreciated that the position shown in FIG. 14 is the position in which driver assembly 300 is ready for driving anchors, as will be further described below. Finally, from the description set forth above (and referring also to FIGS. 8-10), it will be appreciated that the limits of the rotational motion of gear tube 380 required, alternately, to extend or to retract arms 370 and 330 of driver assembly 300, are defined by the circumferential dimension of bridge slots 640 in medial rotation tube 280 and their interaction with bridge vanes 620.

Referring to FIG. 14, one or more driver pins 376 are affixed to driver arms 330 and 370. Each of the one or more driver pins 376 are adapted to retain anchors 700 having anchor heads 710, for example, by friction fit or other suitable means. Anchors 700 may have hollow bores within, opening at their heads 710, and extending substantially within their lengths, and driver pins 376 may extend within such bores substantially the entire lengths thereof, so that the distal ends of driver pins 376 drive anchors 700 at their forward ends, so as to prevent anchors 700 from buckling or veering off-direction as they might otherwise do if driven at their rearward ends proximate to heads 710.

Still referring to FIGS. 10-14, longitudinal force and movement may be translated to the driver arms 370 to, alternately, drive anchors 700 into tissues, and withdraw driver pins 376 from anchors 700 after they are installed into tissues, as follows. As previously noted and described, longitudinal force and movement is translated directly from medial actuator tube 280 to central tube 590 via bridge assembly 600. As noted, central tube 590 is integral with distal end cap 390, distal driver mount 340, driver mount connector member 314 and proximal driver mount 310. Because driver arms 330 and 370 are operably mounted within driver mounts 310 and 340, longitudinal force and movement exerted via medial actuator tube 280, translated to central tube 590, is also translated directly to longitudinal force and movement of driver arms 330 and 370 (and entire driver assembly 300), and thus to driver pins 376 and anchors 700. As can be appreciated from the description above, gear tube 380 will be moved longitudinally in correspondence with longitudinal movement of central tube 590 and driver assembly 300. As noted, gear tube 380 is permitted to longitudinally move relative to and through positioner assembly 400 by means of longitudinal splines coupling gear tube 380 with proximal and distal positioner gears 420 and 460, without effecting corresponding longitudinal movement thereto.

It will be appreciated that sufficient proximal longitudinal movement should be provided and translated to driver arms 330 and 370 and driver pins 376 by the mechanism described above so as to carry and drive anchors 700 past positioner assembly 400 and into the target tissues. The advancement/retraction longitudinal travel distance of the driver assembly 300 can be generally greater than the length of the anchors 700 in order to move the anchors past the positioner and fully seat the anchors into the target tissues. In the embodiment shown and described thus far, the position of the anchors when installed in the tissues may be substantially parallel with the longitudinal axis of the driver assembly 300, but the position of the anchors may also be at an angle therewith. Additionally, in the embodiment shown and described thus far, the anchors may enter the target tissues substantially perpendicular with them, as they are held by positioner assembly 400.

It is also contemplated that various integral components of the positioner and driver assemblies described above may be formed, molded or machined as a unitary, continuous structure. For example, driver arms 330 and 370 may be unitary and continuous with driver pins 376, rather than be assembled pieces.

Referring now to FIGS. 3 and 31-38, a surgeon may use the embodiment just described in a retrograde direction in the following manner. The driver assembly 300 may loaded with one or more anchors 700, as may be required, prior to use. The instrument may then be inserted into the urethra and advanced in a retrograde direction until the distal end of the instrument 10 is through the urethra 5 (FIG. 31), through the bladder opening 4, and the driver assembly 300 and positioner assembly 400 are inside the bladder lumen 8.

Figure 32:
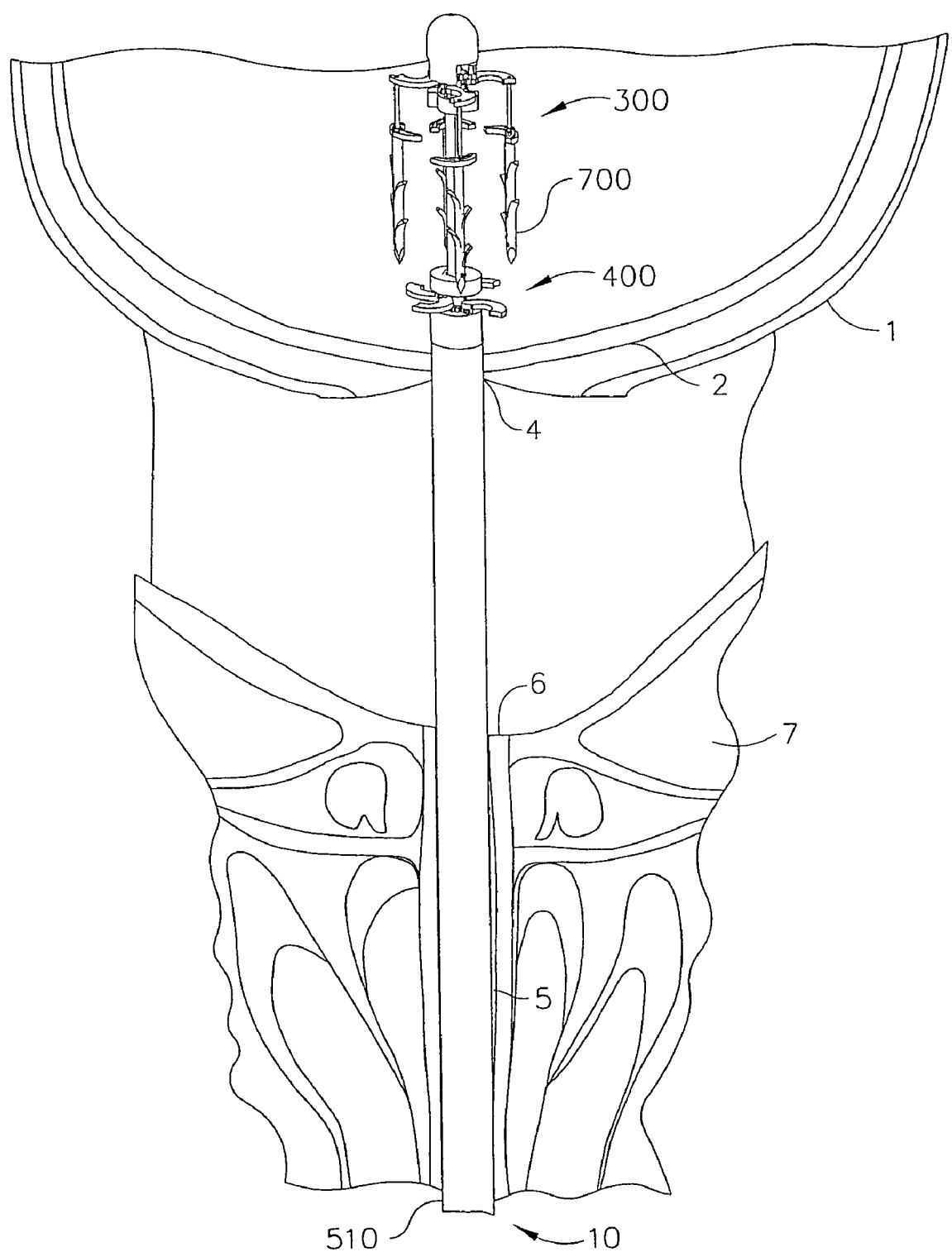
FIG. 32 is an illustration showing an anastomotic instrument fully inserted through a patient's urethra and into the bladder following a prostatectomy, with driver and positioner assemblies opened.
Figure 33:
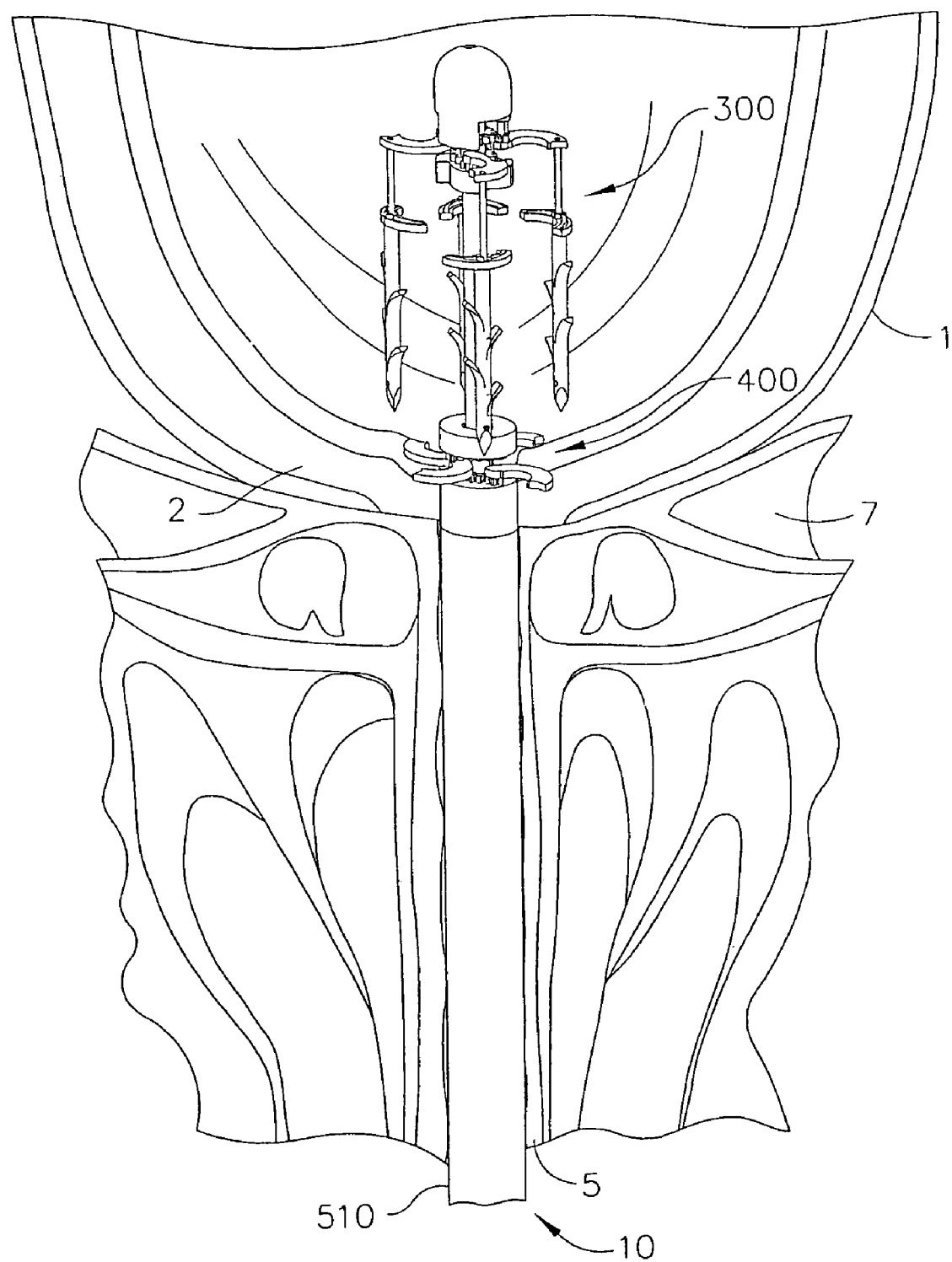
FIG. 33 is an illustration showing an anastomotic instrument fully inserted through a patient's urethra and into the bladder following a prostatectomy, with a positioner assembly urging the bladder wall into contact with the pelvic floor with the openings in the bladder and urethra aligned.
Figure 34:
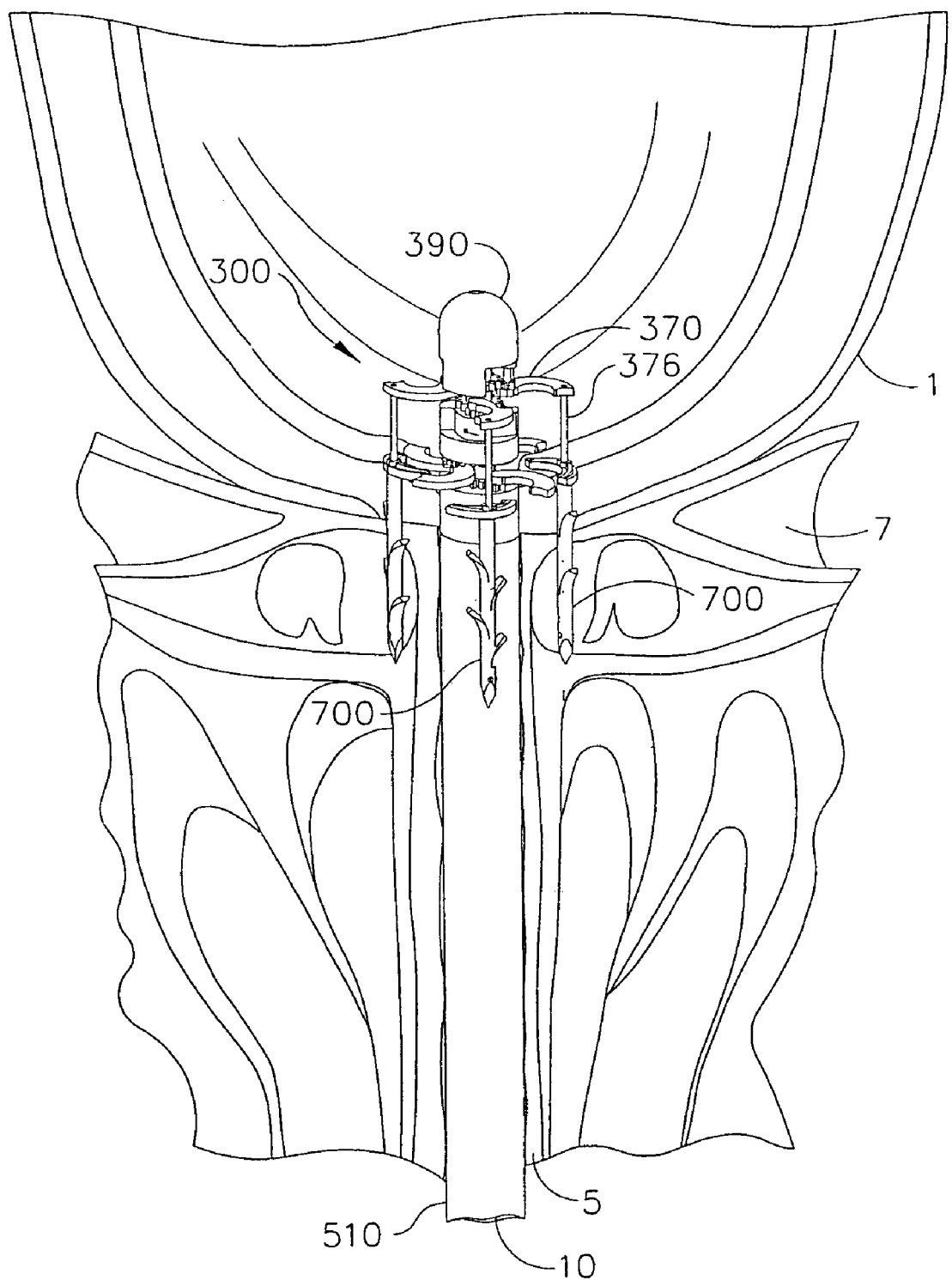
FIG. 34 is an illustration showing an anastomotic instrument fully inserted through a patient's urethra and into the bladder following a prostatectomy, and with a driver assembly actuated and anchors driven through the bladder wall and into the pelvic floor.
Figure 35:
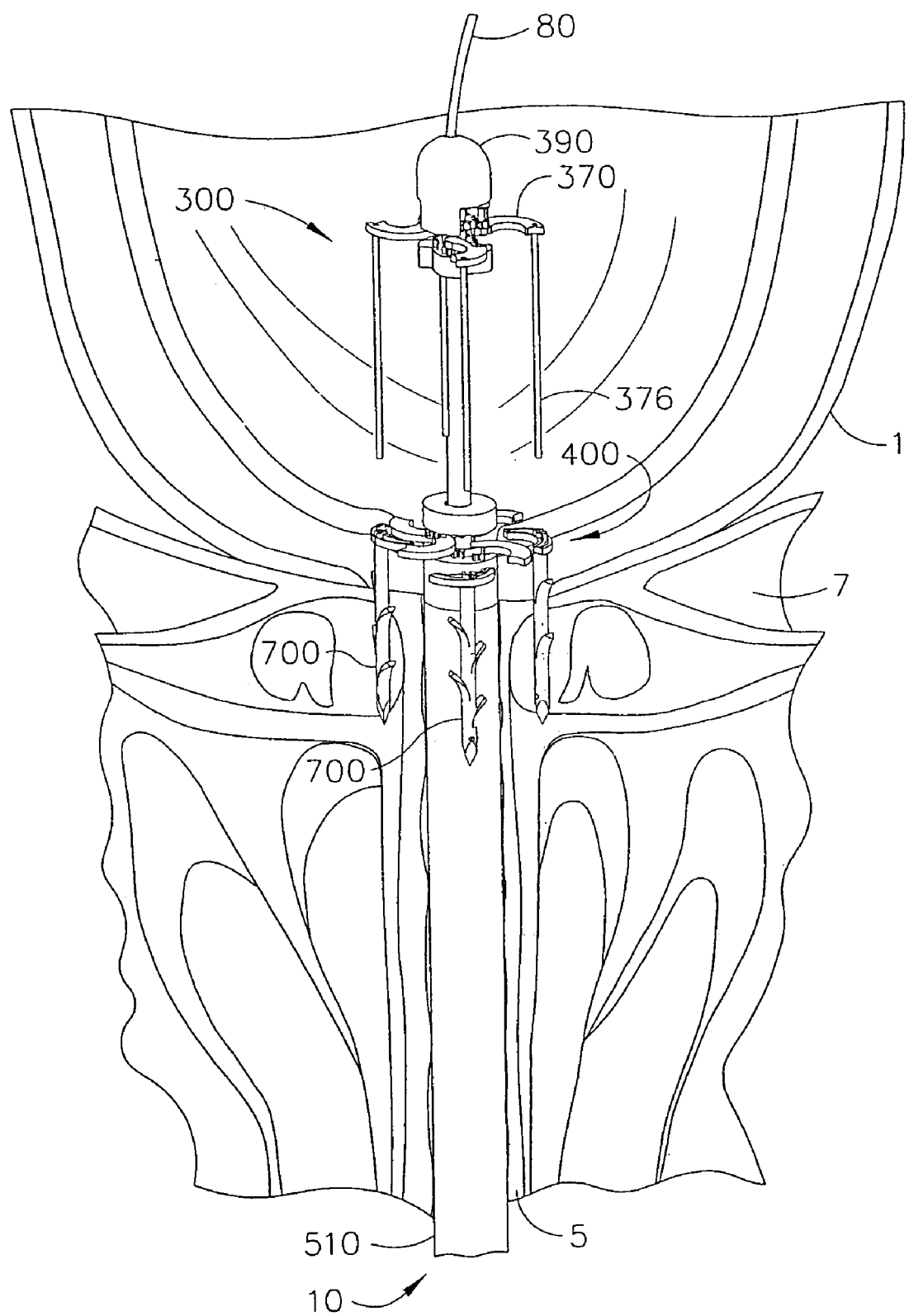
FIG. 35 is an illustration showing an anastomotic instrument inserted through the urethra and into the bladder, with a driver assembly and driver pins retracted and withdrawn from anchors, which are left installed through the bladder wall and into the pelvic floor.
Figure 36:
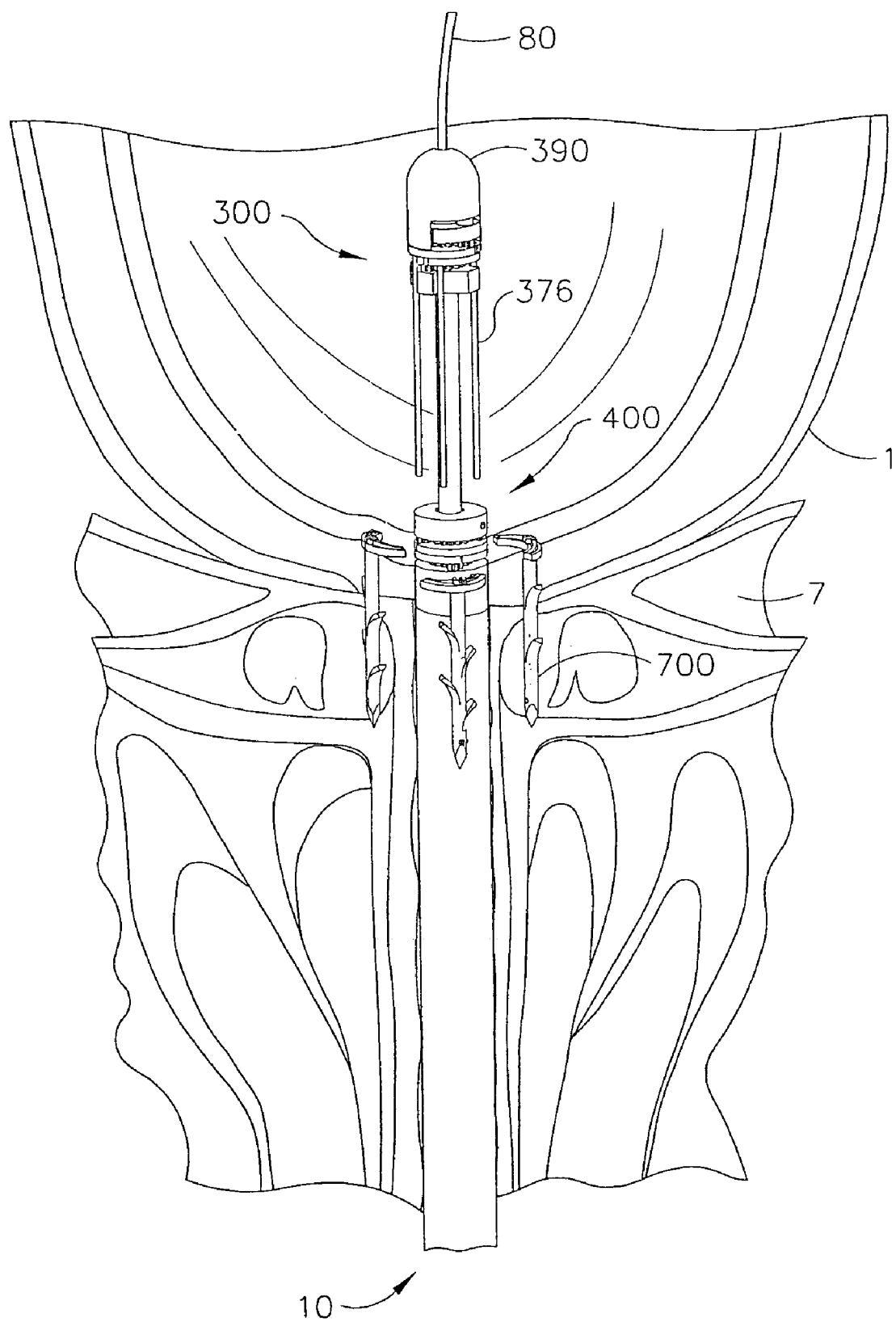
FIG. 36 is an illustration showing an anastomotic instrument fully inserted through a patient's urethra and into the bladder following a prostatectomy, with driver and positioner assemblies returned to initial retracted positions following installation of anchors.

After insertion into the bladder 1, instrument 10 may be initially actuated by rotating knob 110 to open the positioner and driver assemblies to the initial deployment position as shown in FIG. 32 (see also FIG. 14). The entire instrument may then be retracted by pulling handle 100 in a proximal direction downwardly through the urethra 5, bringing the opened positioner assembly into contact with the bladder wall 2 surrounding the bladder opening 4, and urging bladder wall 2 surrounding bladder opening 4 into contact with pelvic floor 7 surrounding urethra opening 6, with the respective openings 4 and 6 aligned, as shown in FIG. 33. Once in position, the instrument may then be prepared for further actuation by cocking the handle mechanism by depressing knob 110 as described above. Next, it may be further actuated to drive anchors 700 by depressing driving button 202, which will actuate the mechanism in handle assembly 100 previously described so as to pull driver assembly 300 in a proximal direction with respect to positioner assembly 400, driving anchors 700 into and through the bladder wall 2 and into the underlying pelvic floor 7, in positions surrounding the aligned openings 4 and 6, to positions shown in FIG. 34. As noted above, using driving button 202, the surgeon may then desire to further actuate the handle assembly 100 to further seat anchors 700 into the tissues. Next, still using driving button 202 as described above, the surgeon may push driver assembly 300 in a distal direction, withdrawing driver pins 376 from the installed anchors 700, to the position shown in FIG. 35. Finally, knob 110 may be rotated again to re-close driver assembly 300 and positioner assembly 400 to the position shown in FIG. 36. In the closed position, the instrument 10 can then be withdrawn back out of the urethra 5. Optionally, prior to withdrawal of the instrument from the urethra, a guide wire 80 may be inserted through the instrument (via a guide wire passage) and into the bladder lumen, and left behind for use described below after withdrawal of the instrument, see FIGS. 36 and 37.

Figure 38:
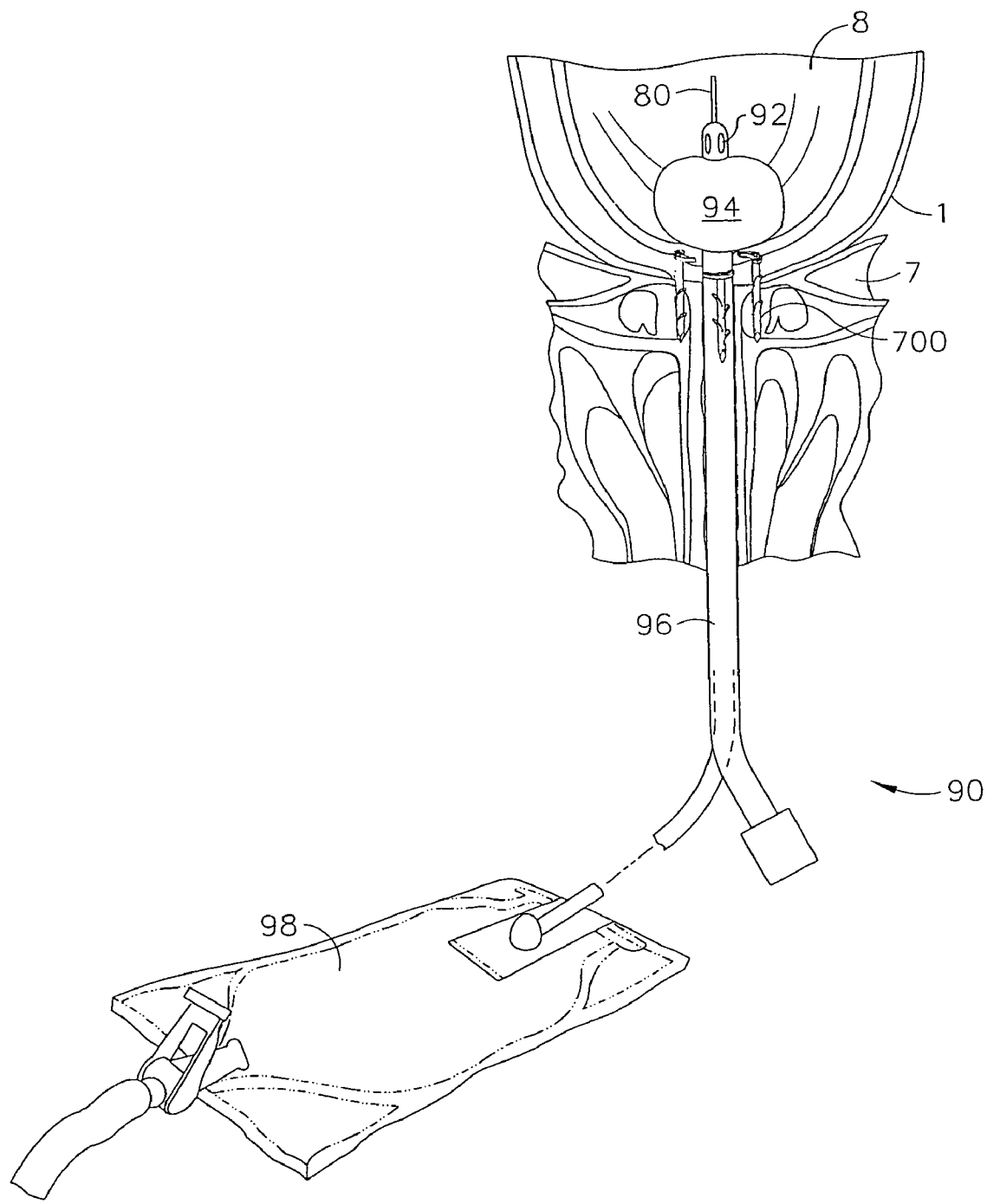
FIG. 38 is a schematic illustration showing the bladder and urethra after installation of anchors and removal of an anastomotic instrument used to effect such installation, and showing a balloon catheter system inserted into the bladder through the urethra and leading to a urine collection bag.
Figure 39:
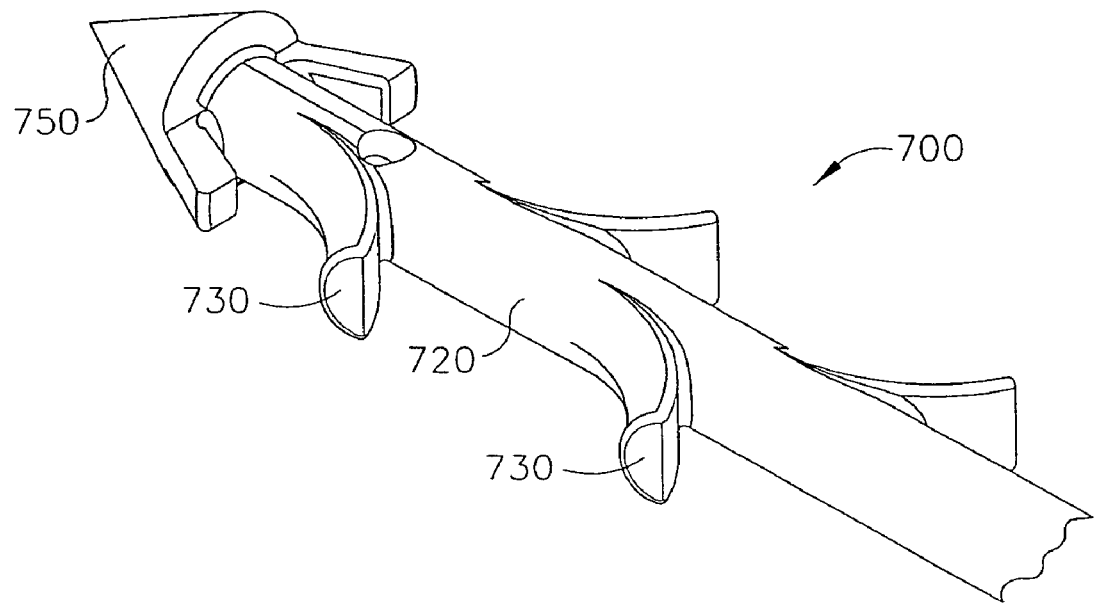
FIG. 39 is a perspective illustration of an embodiment of an anchor.
Figure 40:
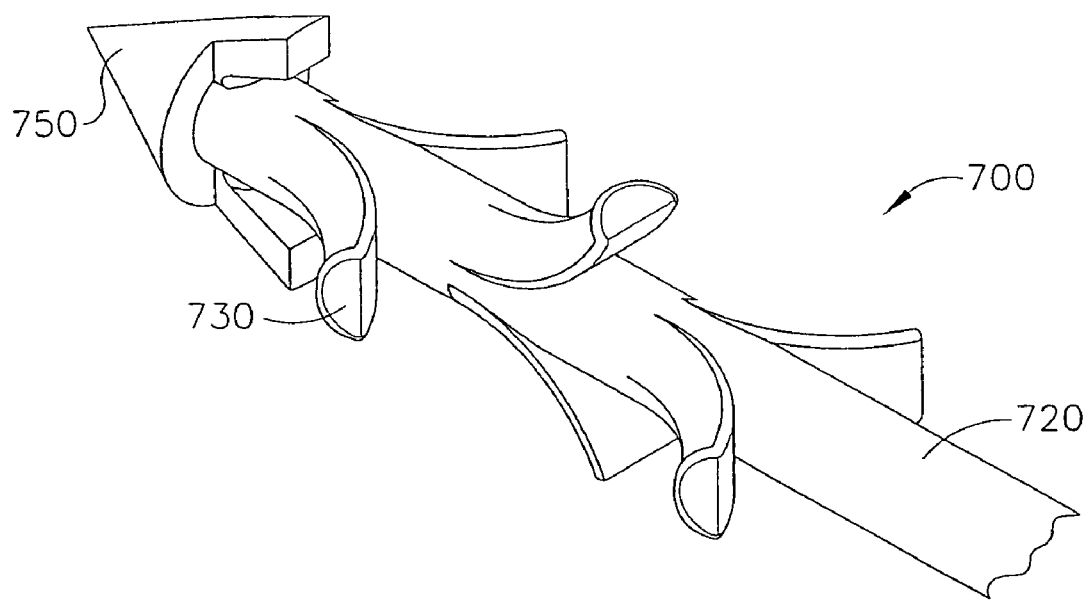
FIG. 40 is a perspective illustration of an alternate embodiment of an anchor.
Figure 41:
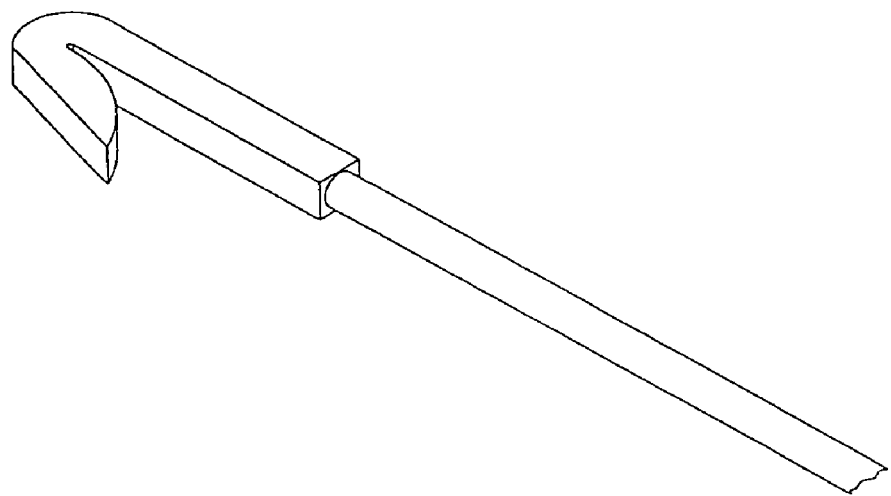
FIG. 41 is a perspective illustration of an alternate embodiment of an anchor shaft and tip.
Figure 42:
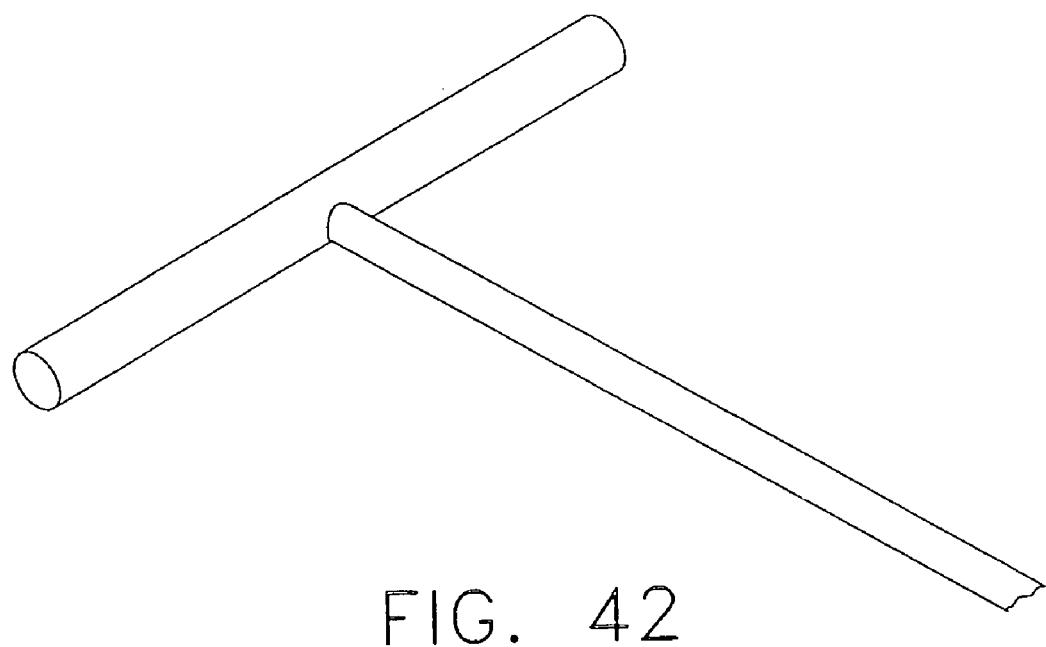
FIG. 42 is a perspective illustration of an alternate embodiment of an anchor shaft and tip.
Figure 43:
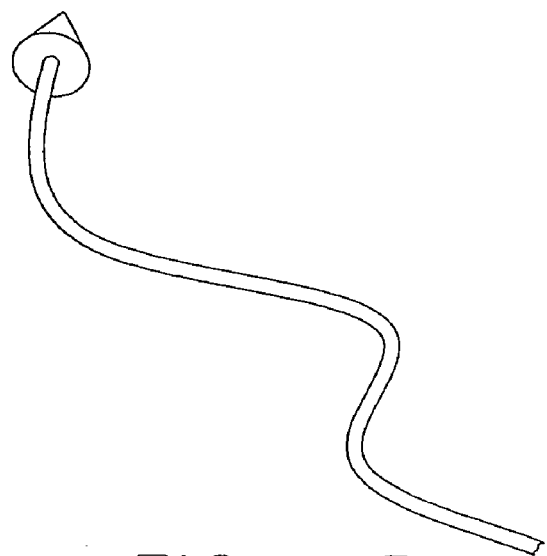
FIG. 43 is a perspective illustration of an alternate embodiment of an anchor shaft and tip.
Figure 44:
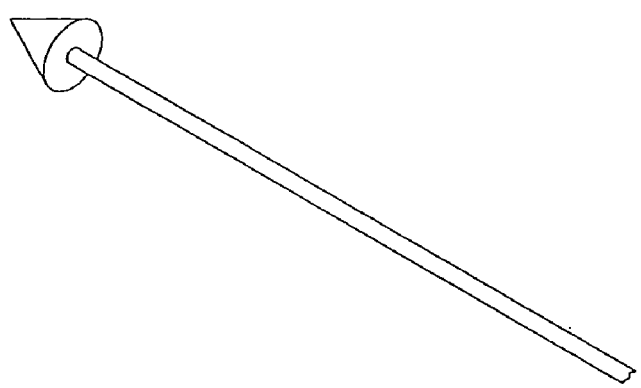
FIG. 44 is a perspective illustration of an alternate embodiment of an anchor shaft and tip.
Figure 45:
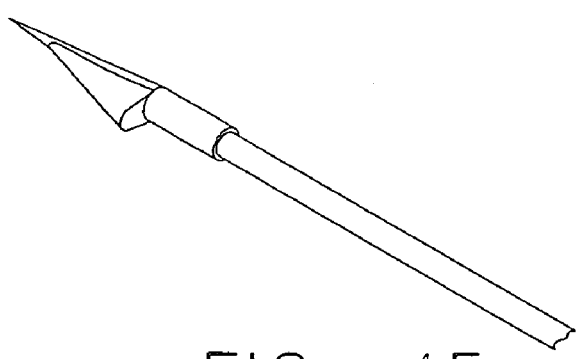
FIG. 45 is a perspective illustration of an alternate embodiment of an anchor shaft and tip.
Figure 46:
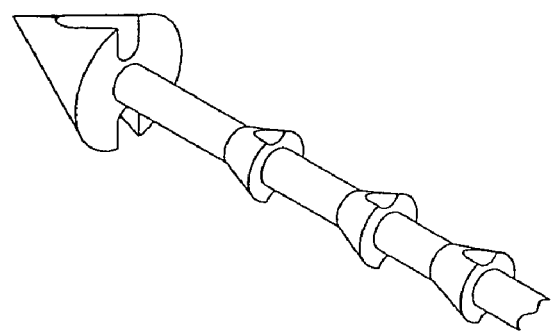
FIG. 46 is a perspective illustration of an alternate embodiment of an anchor shaft and tip.
Figure 47:
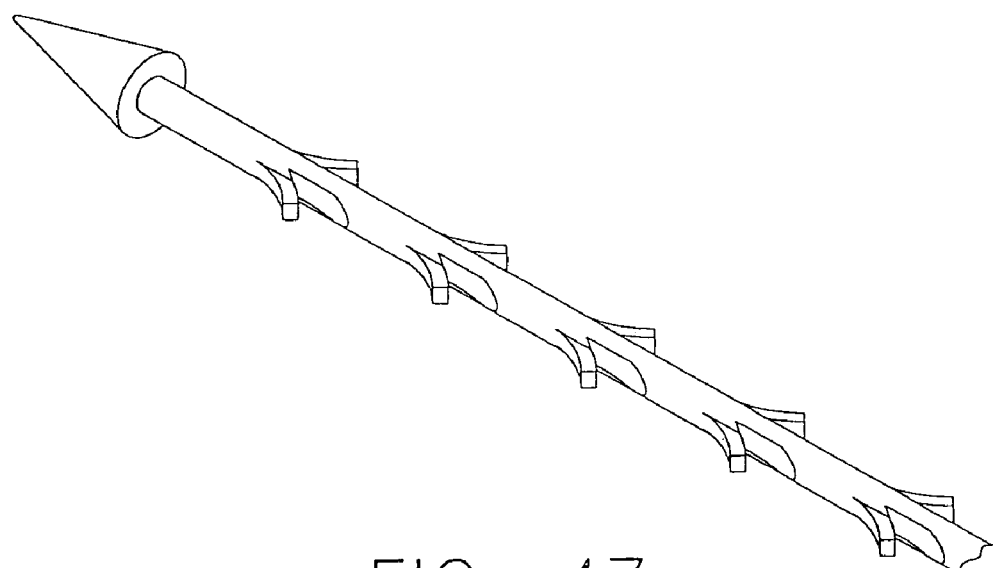
FIG. 47 is a perspective illustration of an alternate embodiment of an anchor shaft and tip.
Figure 48:
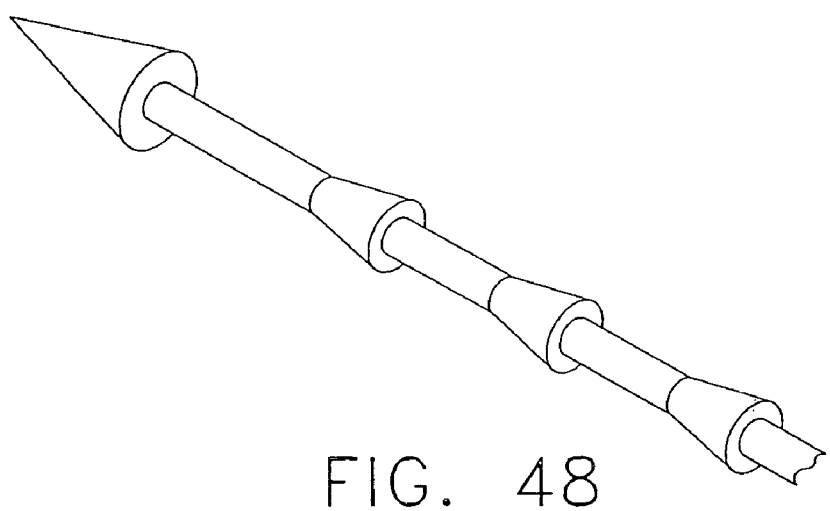
FIG. 48 is a perspective illustration of an alternate embodiment of an anchor shaft and tip.
Figure 49:
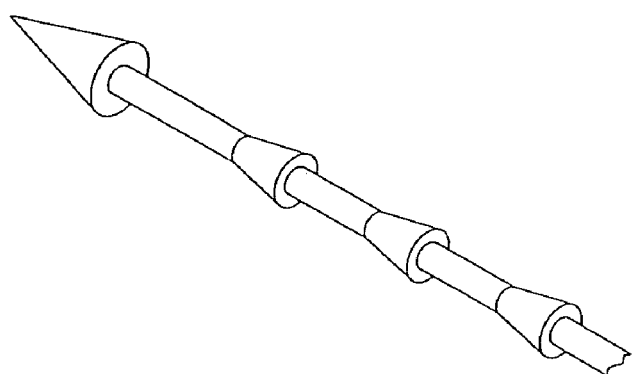
FIG. 49 is a perspective illustration of an alternate embodiment of an anchor shaft and tip.
Figure 50:
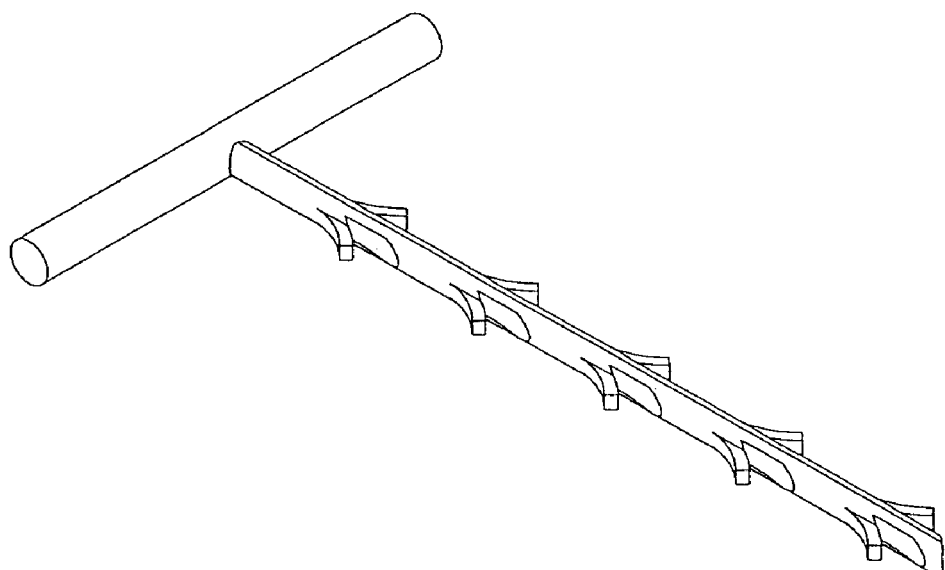
FIG. 50 is a perspective illustration of an alternate embodiment of an anchor shaft and tip.
Figure 51:
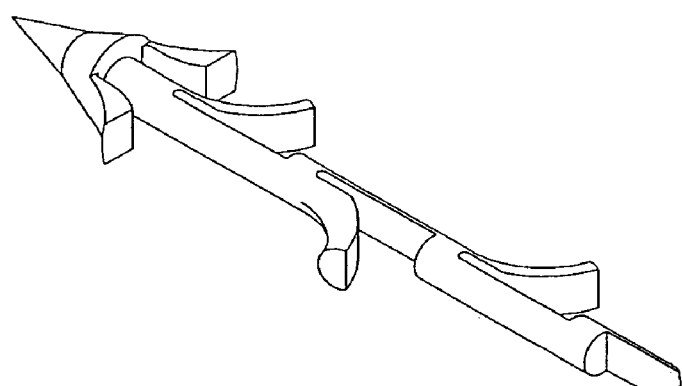
FIG. 51 is a perspective illustration of an alternate embodiment of an anchor shaft and tip.

Referring to FIG. 38, guide wire 80 may then be used to guide a balloon catheter system 90 into the bladder lumen 8. As shown in FIG. 38, one embodiment provides for a balloon catheter system 90 wherein a balloon 94 is expanded to hold the catheter in place. Drainage holes 92 allow urine to drain from the bladder 1 through a catheter tube 96 into a urine collection bag 98.

In another embodiment of the present invention, referring to FIGS. 3 and 4, the actuator knob 110 is depressed first to cock the actuator. Then the actuator knob is rotated causing a concurrent rotation of the distal rotation tube, which thereby opens the positioner and driver arms, and the anchors, to a distance of approximately 2-8 mm out and parallel with the longitudinal axis of the driver assembly.

It can be appreciated by one skilled in the art that the positioner and driver assemblies may have alternate configurations providing an instrument adapted to for use in a retrograde manner as described above, or in an antegrade manner.

It can be appreciated by one skilled in the art that the positioner assembly may have a variety of alternative configurations including but not limited to embodiments described herein (and thus including, without limitation, shuttlecock assembly 800 with positioner petals 830 (FIGS. 17-21), umbrella assembly 900 with reverse positioner petals 930 (FIGS. 22-27), positioner assembly 1440 with positioner arms 1441 (FIGS. 56-64; 70, 71, 77, 78), or positioner 2017 (FIGS. 122-126), 2090 (FIGS. 110-118), 2122 (FIGS. 95, 96, 103-109) and 2168 (FIGS. 83, 84, 89-94) (all of which are described below)), providing an alternately retractable and transversely extendible device useful for, referring to FIG. 2, insertion in a retracted position in a retrograde direction through the urethra 5 and into bladder opening 4, extending or expanding within bladder lumen 8, catching in bladder opening 4 and manipulating to urge bladder wall 2 surrounding bladder opening 4 into contact with pelvic floor 7 surrounding urethra opening 6 with the respective openings aligned; or alternatively, insertion in a retracted position in an antegrade direction through an incision in the abdomen and an upper surface of the bladder 1, extending or expanding within bladder lumen 8, catching in bladder opening 4 and manipulating to urge bladder wall 2 surrounding bladder opening 4 into contact with pelvic floor 7 surrounding urethra opening 6 with the respective openings aligned. Generally, the positioner assembly may comprise and make use of any number of alternately extendable and retractable projections, petals, arms, claws, or other grasping or catching members for catching and gaining control of bladder wall 2 surrounding bladder opening 4. The positioner assembly may have at least one member operably connected to a longitudinal member of the instrument and alternately transversely extendable from and retractable toward the longitudinal axis thereof in response to input by a surgeon at a proximal end of the instrument.

Alternatively, it can be appreciated by one skilled in the art that when an anchor driver assembly is included with the instrument that is functional to open and subsequently drive anchors through the bladder wall and into the pelvic floor as described herein, the positioner assembly or positioner as shown may be dispensed with in some circumstances. For example, referring to FIGS. 32 and 33, it can be appreciated that driver assembly 300, when opened and drawn downwardly until the distal ends of anchors 700 contact and possibly puncture bladder wall 2 surrounding bladder opening 4, can be sufficient for use in capturing bladder wall 2 and drawing it downward into contact with, and securing it to, pelvic floor 7, with bladder opening 4 and urethra opening 6 aligned, without the need for positioner assembly 400 as shown, in some circumstances. Thus, driver assembly 300 with anchors 700 may serve a dual function as a positioner and as an anchor driver assembly.

"Shuttlecock" Embodiment

Figure 19:
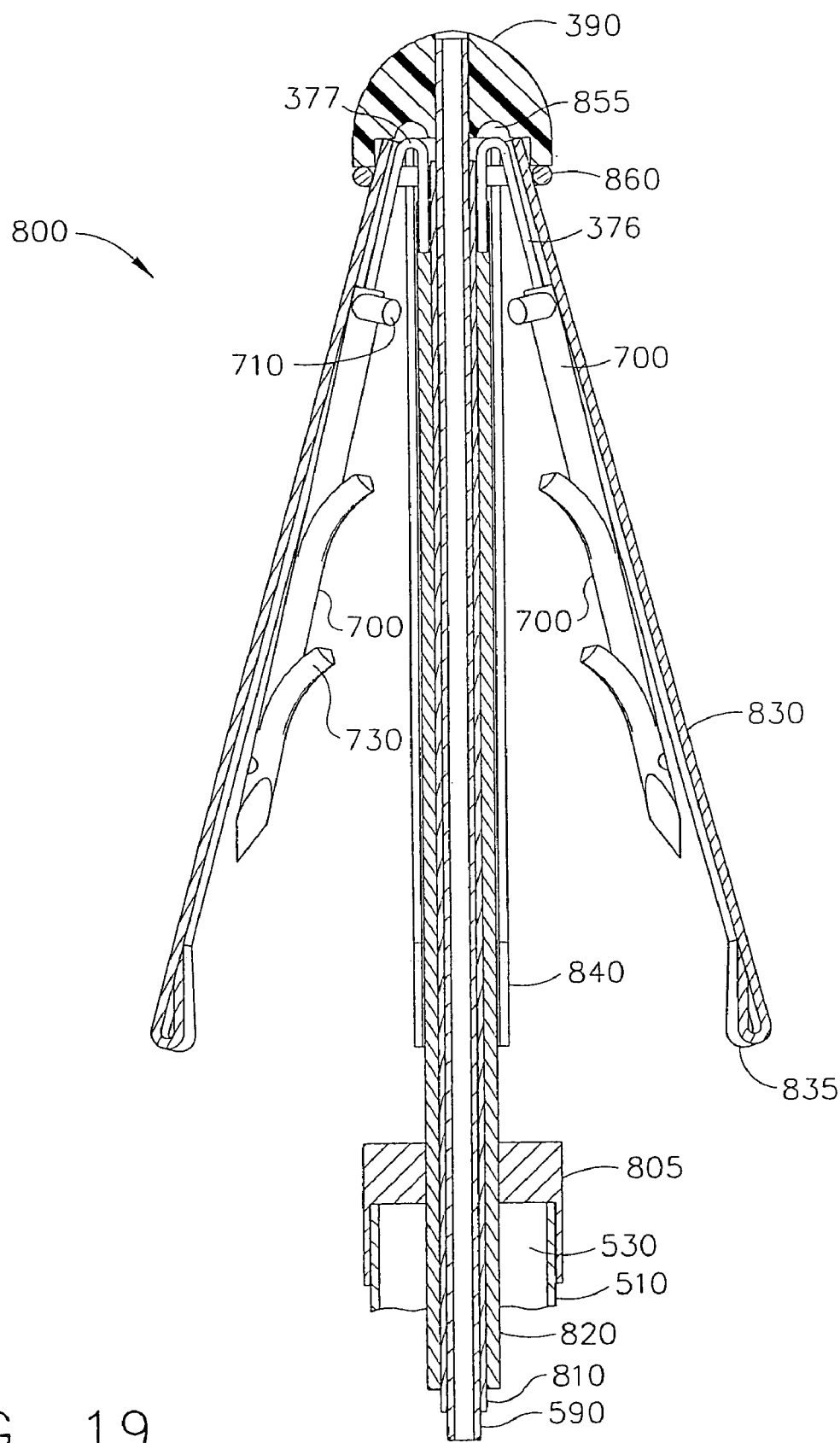
FIG. 19 is a longitudinal cross-sectional view of the anastomotic instrument shown in FIG. 17, with driver and positioner petal assemblies shown in opened positions.

FIGS. 17-21 illustrate another embodiment of a method and apparatus of the invention. As shown in FIGS. 17-19, a "shuttlecock" assembly 800 is provided. (As used herein, the term "shuttlecock" is only used for convenient reference to the present embodiment described, because as depicted in the drawings it bears some resemblances to a shuttlecock. The term is not, however, intended to connote any limitations, concerning appearance or otherwise. Those skilled in the art will appreciate that an instrument incorporating the features and functions described may or may not bear resemblances to a shuttlecock.) Affixed at the distal end of central tube 590 is distal end cap 390. Central tube 590 may be located within positioner petal retainer actuator tube 810, and positioner petal retainer actuator tube 810 may be located within driver pin actuator tube 820, and it can be appreciated from FIGS. 17 and 18 that the three tubes 590, 810 and 820 may be substantially coaxial. Tubes 590, 810 and 820 can also be longitudinally movable with respect to each other.

Driver pins 376 may be affixed at one end to the distal end of driver pin actuator tube 820. Driver pins 376 may be made of spring wire or other suitable material having shape memory, and may include shorter lengths affixed to the distal end of driver pin actuator tube 820, bends 377, and greater lengths which receive detachable hollow anchors 700. Prior to use of the instrument, anchors 700 may be loaded onto driver pins 376, and may be releasably held thereon by friction fit or any other suitable means. When assembly 800 is in the retracted position shown in FIG. 17, the greater lengths of driver pins 376 may be held in a retracted position lying substantially along tube 820 as shown. When assembly 800 is in the opened position shown in FIG. 19, the spring bias in bends 377 of driver pins 376 can cause the greater lengths and free ends of driver pins 376, and correspondingly, anchors 700 on driver pins 376, to move outwardly to the opened position shown. Anchors 700 may have hollow bores within, opening at their heads 710, and extending substantially within their lengths, and driver pins 376 may extend within such bores substantially the entire lengths thereof, so that the distal ends of driver pins 376 may apply driving force proximate to the forward ends of anchors 700, so as to prevent anchors 700 from buckling or veering off-direction as they might otherwise do if driven at their rearward ends proximate to heads 710.

Each of positioner petals 830 may be affixed at one end to distal end cap 390. Positioner petals 830 may be made of a spring metal or other suitable material having shape memory, biased so as to spring outwardly to the opened position shown in FIG. 19 when unrestrained, or may simply ride passively on top of driver pins 376 and anchors 700, being flexibly affixed or hinged to distal end cap 390. When assembly 800 is in the retracted position shown in FIG. 17, positioner petals 830 lie in a retracted position as shown, to the outside of driver pins 376 and anchors 700. When assembly 800 is in the opened position shown in FIG. 19, the tips 835 of positioner petals 830 have been moved outwardly to an opened position shown, wherein the angle formed by the lengths of positioner petals 830 and the axis of tubes 590, 810 and 820 may be approximately 15 degrees.

When assembly 800 is in the retracted position shown in FIG. 17, positioner petals 830, and driver pins 376 and anchors 700, may be retained against the urging of the spring bias in driver pins 376, by positioner petal retainer 860. As shown in FIG. 18, positioner petal retainer 860 is connected to and made integral with positioner petal retainer actuator tube 810 by positioner petal retainer braces 862. As noted above, positioner petal retainer actuator tube 810 is longitudinally movable with respect to central tube 590 and driver pin actuator tube 820.

As shown in FIG. 19, driver pins 376 and positioner petals 830 are allowed to move to their opened positions when positioner petal retainer 860 is moved upwardly toward distal end cap 390 (see also FIG. 29). Because positioner petal retainer 860 is integral with positioner petal retainer actuator tube 810 via positioner petal retainer braces 862, pushing positioner petal retainer actuator tube 810 toward distal end cap 390, while holding central tube 590 and driver pin actuator tube 820 stationary, moves positioner petal retainer 860 toward distal end cap 390, releasing and allowing positioner petals 830 and driver pins 376 and anchors 700 to open to the position shown in FIG. 19 (see also FIGS. 28, 29). It can be understood from FIG. 18 that the positioning of positioner petal retainer braces 862 between the separate positioner petals 830 permits this relative motion.

As may be seen in FIG. 17, the entire shuttlecock assembly 800, including the central tube 590, positioner petal retainer actuator tube 810 and driver pin actuator tube 820, are carried by the outer tube 510 and centered therein by the outer tube end collar 805. It will be understood by those skilled in the art that tubes 590, 810, 820 and 510 may be held stationary and/or selectively longitudinally moved with respect to each other by any suitable proximal actuating mechanism.

Use and operation of this embodiment to perform anastomosis in a retrograde manner to join a patient's bladder and urethra following radical prostatectomy will now be described. Referring to FIG. 2 for anatomical reference, shuttlecock assembly 800 (in a retracted position such as shown in FIG. 17) is inserted into the patient's urethra, and guided up through the urethra 5, through bladder opening 4, and into the bladder lumen 8, to a fully inserted position whereby shuttlecock assembly 800 may be opened within the bladder as will be hereinafter described.

Once assembly 800 is in the fully inserted position, referring back to FIGS. 17 and 19, positioner petals 830 and driver pins 376 with anchors 700 are opened by pushing positioner petal retainer actuator tube 810 toward distal end cap 390 while holding central tube 590 and driver pin actuator tube 820 stationary. Positioner petal retainer 860, being integral with positioner petal retainer actuator tube 810 via positioner petal retainer braces 862, is thus moved toward distal end cap 390, which in turn allows positioner petals 830 and driver pins 376 with anchors 700 to spring outwardly into the opened position as shown in FIG. 19.

Again referring to FIG. 2 for anatomical reference, the entire assembly 800, now in the opened position within the patient's bladder, is then pulled toward the urethra opening 6 by withdrawing tubes 590, 810, 820 and 510, together, back down through the urethra. This brings positioner petal tips 835 into contact with the inside of the bladder wall 2 at positions about bladder opening 4, and urges bladder wall 2 surrounding bladder opening 4 toward pelvic floor 7 surrounding urethra opening 6, bringing these tissues into contact with openings 4 and 6 aligned.

Figure 20:
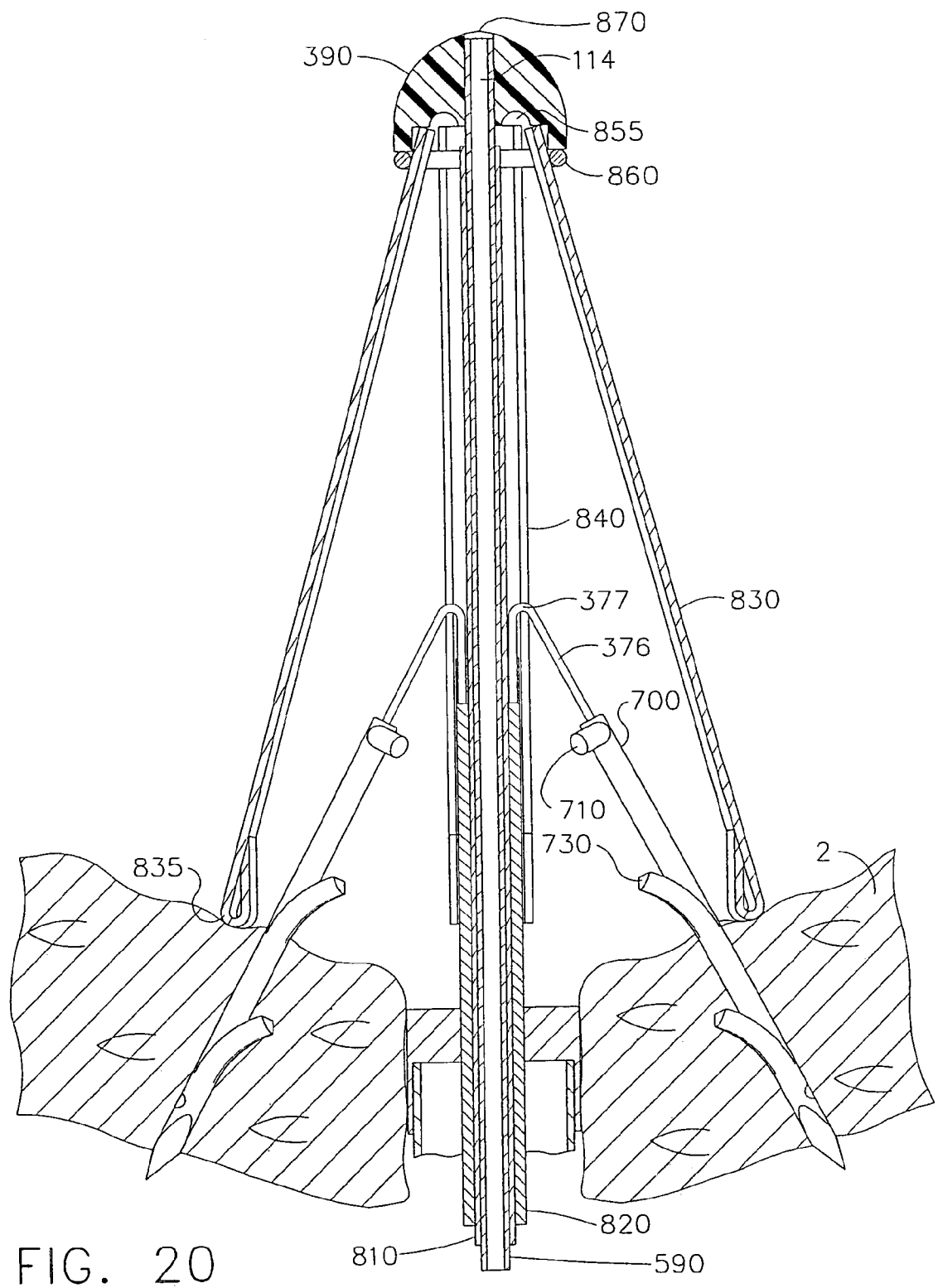
FIG. 20 is a longitudinal cross-sectional view of the anastomotic instrument shown in FIG. 17, showing positioner petals in contact with tissue and anchor driver pins and anchors partially deployed into tissues.
Figure 21:
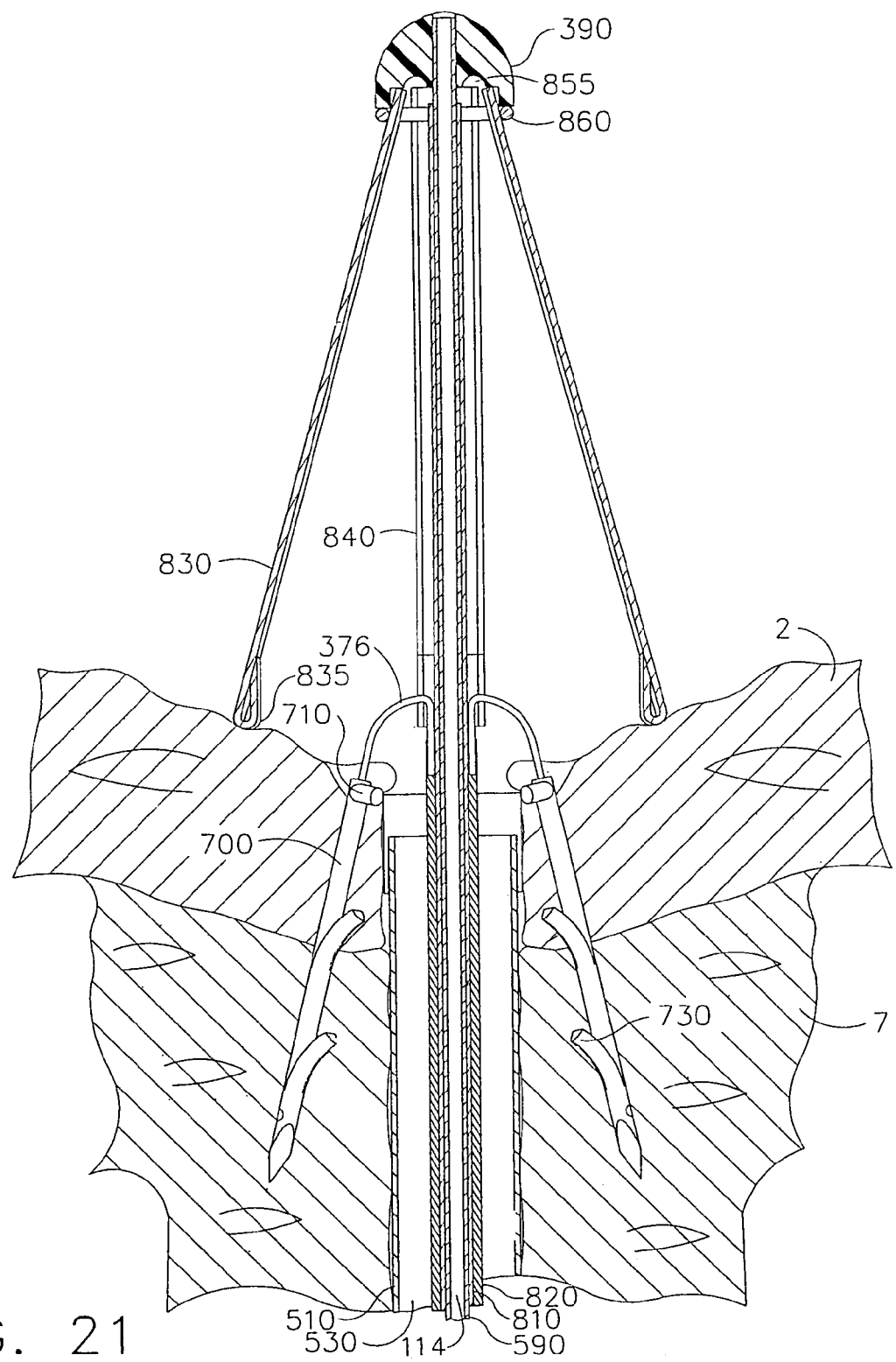
FIG. 21 is a longitudinal cross-sectional view of the anastomotic instrument shown in FIG. 17, showing positioner petals in contact with tissues and anchor driver pins and anchors driven into tissues.

Once the bladder wall 2 and pelvic floor 7 are brought into contact, the next step is to drive anchors 700, by retracting driver pin actuator tube 820 while holding the remaining tubes 590 and 810 stationary. Retracting driver pin actuator tube 820 causes affixed driver pins 376 to drive anchors 700 into and through bladder wall 2, as shown in FIG. 20, and then into pelvic floor 7, as shown in FIG. 21. It will be appreciated that barbs 730 on anchors 700 cause anchors 700 to lodge in pelvic floor 7, and that heads 710 on anchors 700 act to retain bladder wall 2 in a position in contact with pelvic floor 7, such that bladder opening 4 is held in communication with urethra opening 6.

Figure 37:
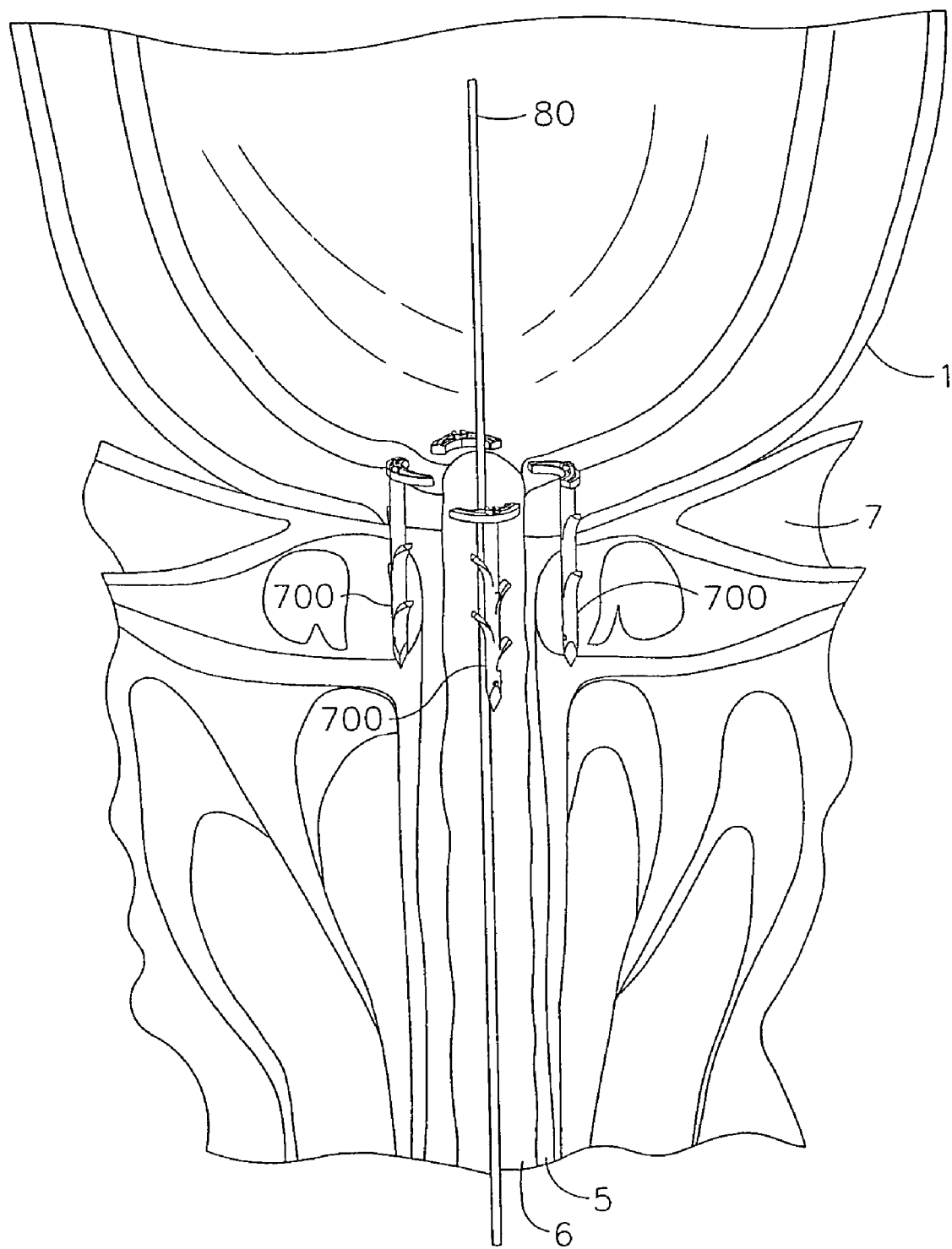
FIG. 37 is an illustration showing the bladder and urethra after installation of anchors and removal of an anastomotic instrument used to effect such installation, and showing a guide wire left in place for guiding a catheter into the bladder through the urethra.

As with the first embodiment described herein, optionally, prior to withdrawal of the instrument from the urethra, a guide wire may be inserted through the instrument (via a guide wire passage) and into the bladder lumen, and left behind for use described above after withdrawal of the instrument, see FIGS. 37 and 38.

The sequence of steps described above is then reversed to enable withdrawal of the shuttlecock instrument 800 from the patient. Driver pin actuator tube 820 is pushed while holding remaining tubes 590 and 810 stationary, causing driver pins 376 to withdraw from anchors 700, which are now lodged in pelvic floor 7 through bladder wall 2. The entire assembly 800, still in the opened position inside bladder lumen 8, is then pushed slightly further into the bladder lumen and away from the urethra by pushing tubes 590, 810, 820 and 510, together, back upwardly. The instrument 800 is then brought into a closed position by retracting positioner petal retainer actuator tube 810 while holding central tube 590 and driver pin actuator tube 820 stationary. Positioner petal retainer 860, being integral with positioner petal retainer actuator tube 810 via positioner petal retainer braces 862, is thus moved in a proximal direction to a position away from distal end cap 390, which in turn urges positioner petals 830 and driver pins 376 inwardly into the retracted position (but now without anchors 700) as shown in FIG. 17. In a retracted position, the entire assembly 800 may then be withdrawn downwardly through the urethra and out of the patient.

It can be appreciated by one skilled in the art that the shuttlecock assembly described above may be in alternate configurations providing an instrument adapted for use in a retrograde manner as described above, or an antegrade manner.

It can be appreciated by one skilled in the art that the mechanism comprising the positioner petals and performing the bladder positioning function thereof may have a variety of alternative configurations including but not limited to embodiments described herein (and thus including, without limitation, the positioner assembly 400 described above (FIGS. 11, 13-14), umbrella assembly 900 with reverse positioner petals 930 (FIGS. 22-27), positioner assembly 1440 with positioner arms 1441 (FIGS. 56-64; 70, 71, 77, 78), or positioner 2017 (FIGS. 122-126), 2090 (FIGS. 110-118), 2122 (FIGS. 95, 96, 103-109) and 2168 (FIGS. 83, 84, 89-94) (all of which are described below), providing a transversely retractable and extendible device useful for, referring to FIG. 2, insertion in a retracted position in a retrograde direction through the urethra 5 and into bladder opening 4, extending or expanding within bladder lumen 8, catching in bladder opening 4 and manipulating to urge bladder wall 2 surrounding bladder opening 4 into contact with pelvic floor 7 surrounding urethra opening 6 with the respective openings aligned; or alternatively, insertion in a retracted position in an antegrade direction through an incision in the abdomen and an upper surface of the bladder 1, extending or expanding within bladder lumen 8, catching in bladder opening 4 and manipulating to urge bladder wall 2 surrounding bladder opening 4 into contact with pelvic floor 7 surrounding urethra opening 6 with the respective openings aligned. Generally, the positioner assembly may comprise and make use of any number of alternately extendable and retractable projections, petals, arms, claws, or other grasping or catching members for catching and gaining control of bladder wall 2 surrounding bladder opening 4. The positioner assembly may have at least one member operably connected to a longitudinal member of the instrument and alternately transversely extendable from and retractable toward the longitudinal axis thereof in response to input by a surgeon at a proximal end of the instrument.

Alternatively, it can be appreciated by one skilled in the art that when an anchor driver assembly is included with the instrument, that is functional to open and subsequently drive anchors through the bladder wall and into the pelvic floor as described herein, the positioner assembly or positioner petals as shown may be dispensed with in some circumstances. For example, referring to FIGS. 20 and 21, it can be appreciated that anchor driver pins 376 and anchors 700, when opened within the bladder lumen and drawn downwardly until the distal ends of anchors 700 contact and possibly puncture bladder wall 2 surrounding bladder opening 4, can be sufficient for use in capturing bladder wall 2 and drawing it downward into contact with, and securing it to, pelvic floor 7, with bladder opening 4 and urethra opening 6 aligned, without the need for positioner petals 830 as shown, in some circumstances. Thus, driver pins 376 with anchors 700 may serve a dual function as a positioner and as an anchor driver assembly.

"Umbrella" Embodiment

FIGS. 22-27 illustrate another embodiment of the method and apparatus of the invention. As shown in FIGS. 22-25, an "umbrella" assembly 900 is provided. (As used herein, the term "umbrella" is only used for convenient reference to the present embodiment described, because as depicted in the drawings it bears some resemblances to an umbrella. The term "umbrella" is not, however, intended to connote any limitations, concerning appearance or otherwise. Those skilled in the art will appreciate that an instrument incorporating the features and functions described may or may not bear resemblances to an umbrella.) Affixed at the distal end of central tube 590 is distal end cap 390, and central tube 590 and distal end cap 390 are integral. Central tube 590 may be located within driver pin spreader tube 893, and driver pin spreader tube 893 is located within reverse positioner petal tube 935, and it can be appreciated from FIG. 22 that the three tubes 590, 893 and 935 may be substantially coaxial. Tubes 590, 893 and 935 can be also longitudinally movable with respect to each other.

Figure 24:
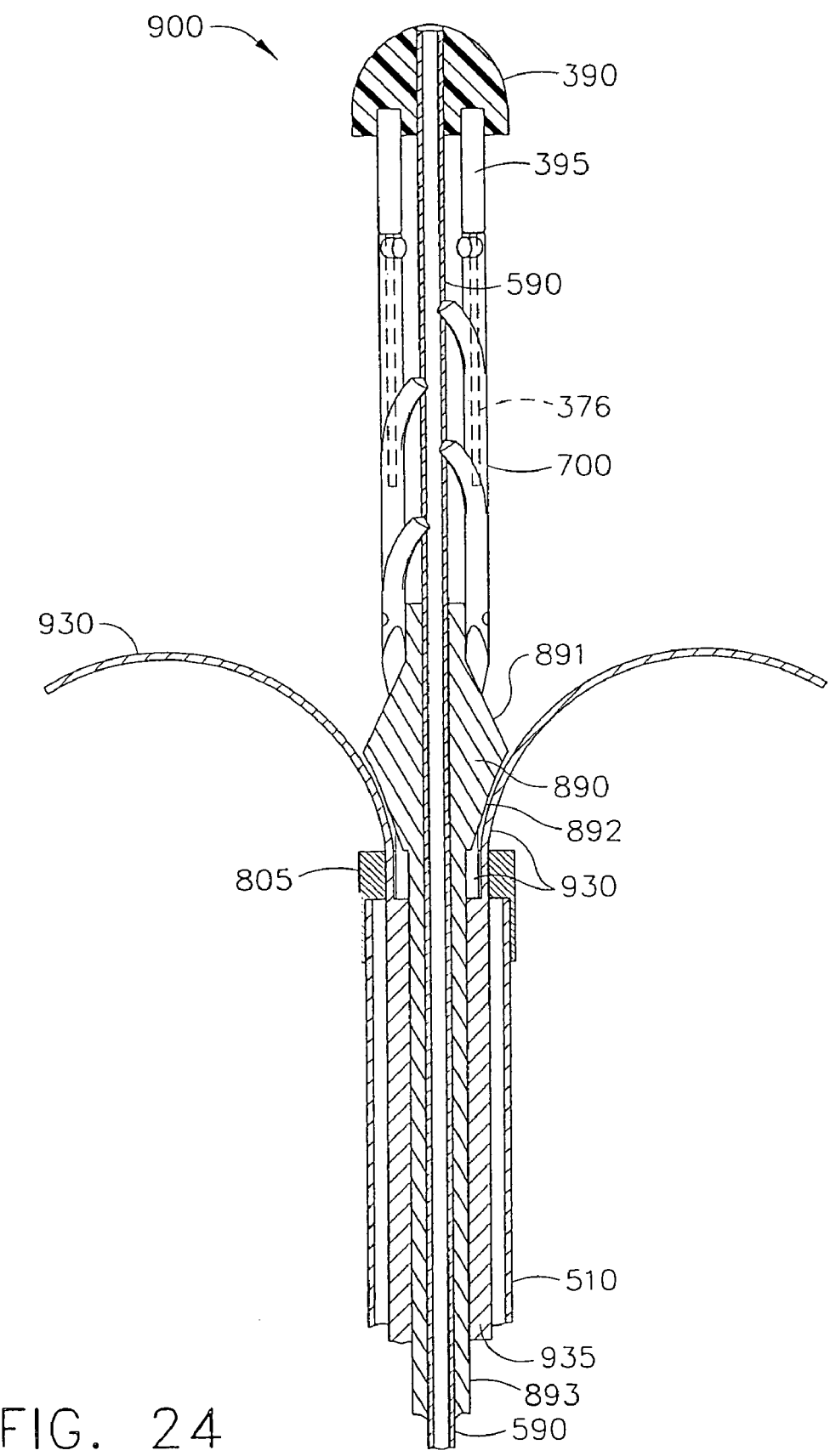
FIG. 24 is a longitudinal cross-sectional view of the anastomotic instrument shown in FIG. 22, with positioner petals shown in opened positions.
Figure 25:
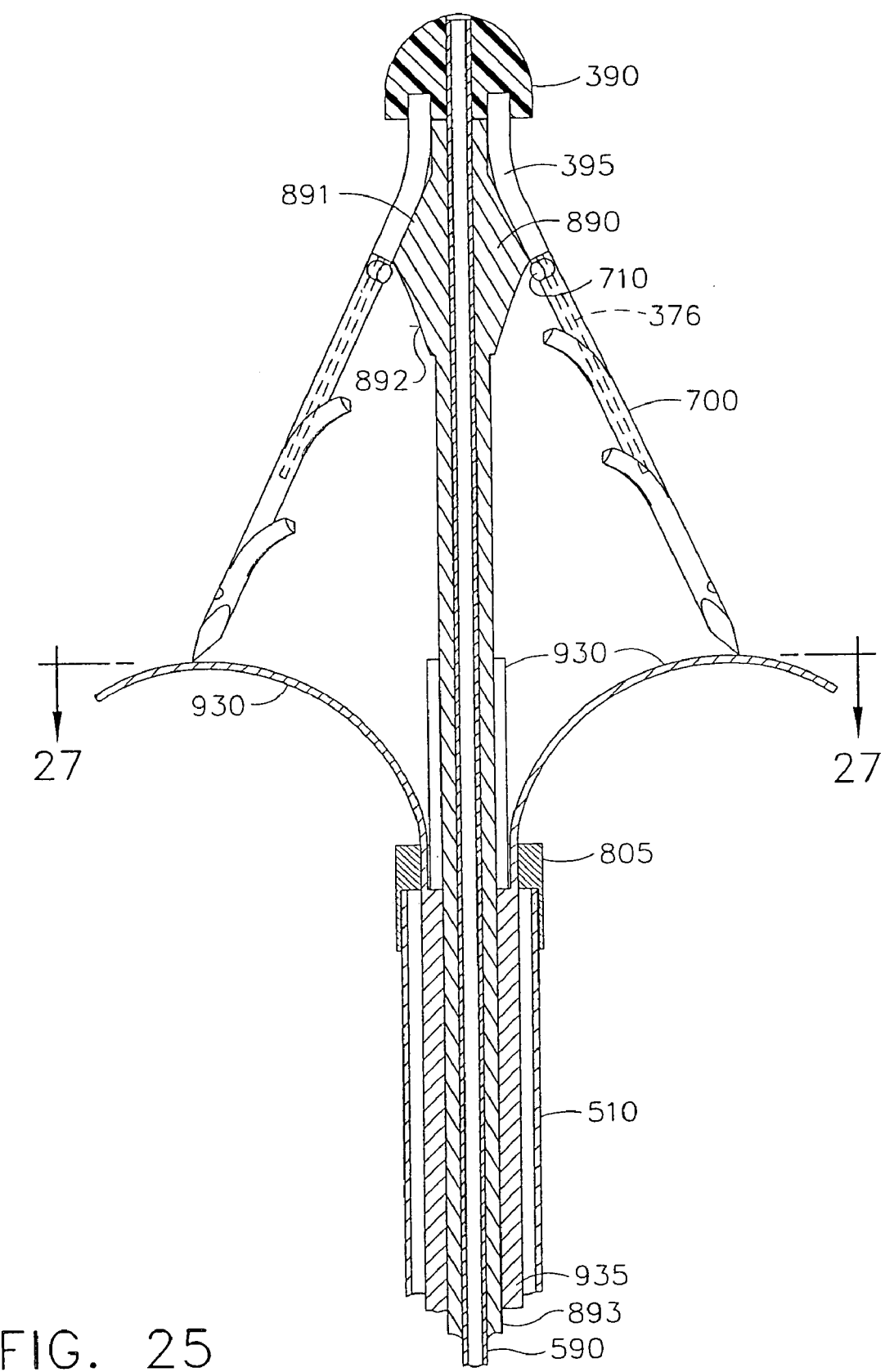
FIG. 25 is a longitudinal cross-sectional view of the anastomotic instrument shown in FIG. 22, with positioner petals and a driver assembly shown in opened positions.

Driver pins 376 having bases 395 are affixed to end cap 390. Driver pins 376 may be made of spring wire or other suitable material having shape memory, and include lengths and free ends that receive detachable hollow anchors 700. Prior to use of the instrument, hollow anchors 700 may be loaded onto driver pins 376, and releasably held thereon by friction fit or any other suitable means. When assembly 900 is in the retracted position shown in FIG. 22, the greater lengths of driver pins 376 may be held in a retracted position substantially parallel with the axis of tubes 590, 893 and 935, by spring bias or shape memory in driver pins 376. When assembly 900 is in the fully opened position shown in FIG. 25, the lengths and free ends of driver pins 376 have been urged outwardly to an opened position as shown. Anchors 700 may have hollow bores within, opening at their heads 710, and extending substantially within their lengths, and driver pins 376 may extend within such bores substantially the entire lengths thereof, so that the distal ends of driver pins 376 may apply driving force proximate to the forward ends of anchors 700, so as to prevent anchors 700 from buckling or veering off-direction direction as they might otherwise do if driven at their rearward ends proximate to heads 710.

may be appreciated by comparing FIGS. 24 and 25, driver pins 376 with anchors 700 are moved from the retracted position to the opened position by movement of driver pin spreader 890 toward distal end cap 390. Driver pin spreader is hollow and integral with driver pin spreader tube 893, and may move longitudinally with respect to central tube 590 and reverse positioner petal tube 935. Thus, as driver pin spreader tube 893 is moved toward distal end cap 390, angled upper spreader face 891 of driver pin spreader 890 urges anchors 700 and correspondingly, driver pins 376, radially outwardly to the opened position shown in FIG. 25.

As may be seen in FIGS. 23 and 24, reverse positioner petals 930 are integral with reverse positioner petal tube 935. Reverse positioner petals 930 are made of spring metal or other suitable material having shape memory, and are biased to assume the opened position shown in FIG. 24. Thus, pushing reverse positioner petal tube 935 toward distal end cap 390 while holding the other tubes 590, 893 and 510 stationary pushes positioner petals 930 out of outer tube 510 through outer tube end collar 805 and allows them to open to their biased positions shown in FIGS. 24 and 25.

As may be seen in FIG. 22, the entire umbrella assembly 900, including the central tube 590, driver pin spreader tube 893 and reverse positioner petal tube 935, are carried by the outer tube 510 and centered therein by the outer tube end collar 805. It will be understood by those skilled in the mechanical design arts that tubes 590, 893, 935 and 510 may be held stationary or selectively longitudinally moved with respect to each other by any suitable proximal actuating mechanism.

Use and operation of this embodiment to perform anastomosis to join a patient's bladder and urethra following radical retropubic prostatectomy will now be described. Referring to FIG. 2 for anatomical reference, umbrella assembly 900 (in retracted position as shown in FIG. 22) is inserted into the patient's urethra, and guided up through the urethra 5, and into bladder lumen 8 through bladder opening 4, to a fully inserted position whereby umbrella assembly 900 may be opened within the bladder lumen as will be hereinafter described.

Once assembly 900 is in the fully inserted position, referring back to FIGS. 22 and 24, reverse positioner petals 930 are extended and opened by pushing reverse positioner petal tube 935 toward distal end cap 390 while holding central tube 590 and driver pin spreader tube 893 stationary. Next, referring to FIGS. 24 and 25, driver pins 376 with anchors 700 are opened by pushing driver pin spreader tube 893 toward distal end cap 390 while holding central tube 590 and reverse positioner petal tube 935 stationary. Thus assembly 900 is brought into the fully opened position shown in FIG. 25.

Again referring to FIG. 2 for anatomical reference, the entire assembly 900, now in the fully opened position within bladder lumen 8, is then pulled toward urethra opening 6 by withdrawing all tubes 590, 893, 935 and 510, together, back down through the urethra. This brings reverse positioner petals 930 into contact with bladder wall 2 at positions about bladder opening 4, and urges bladder wall 2 toward and into contact with pelvic floor 7 about urethra opening 6, with the respective openings 4 and 6 aligned.

Figure 26:
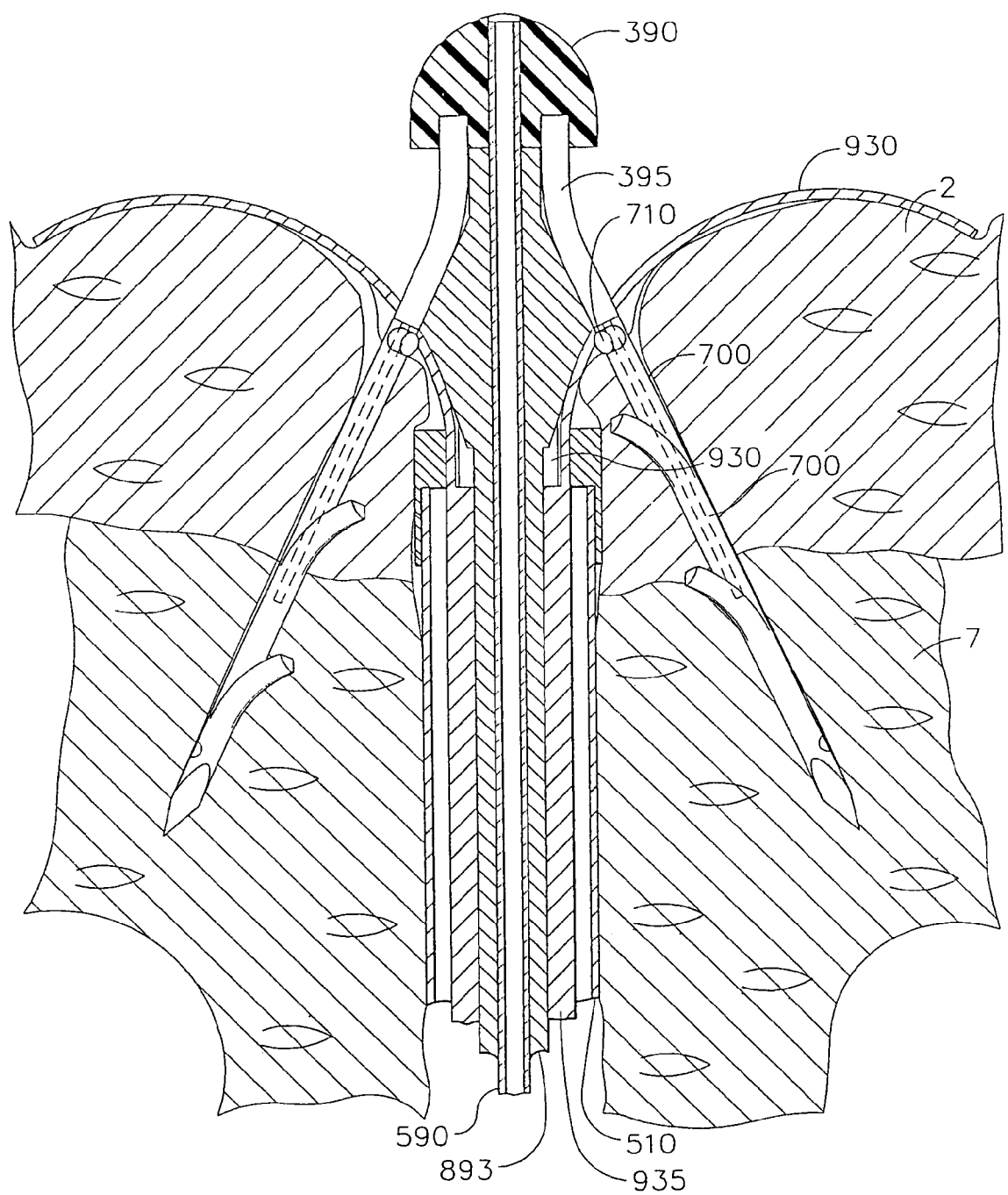
FIG. 26 is a longitudinal cross-sectional view of the anastomotic instrument shown in FIG. 22, showing positioner petals in contact with tissue and anchor driver pins and anchors driven into tissues.
Figure 27:
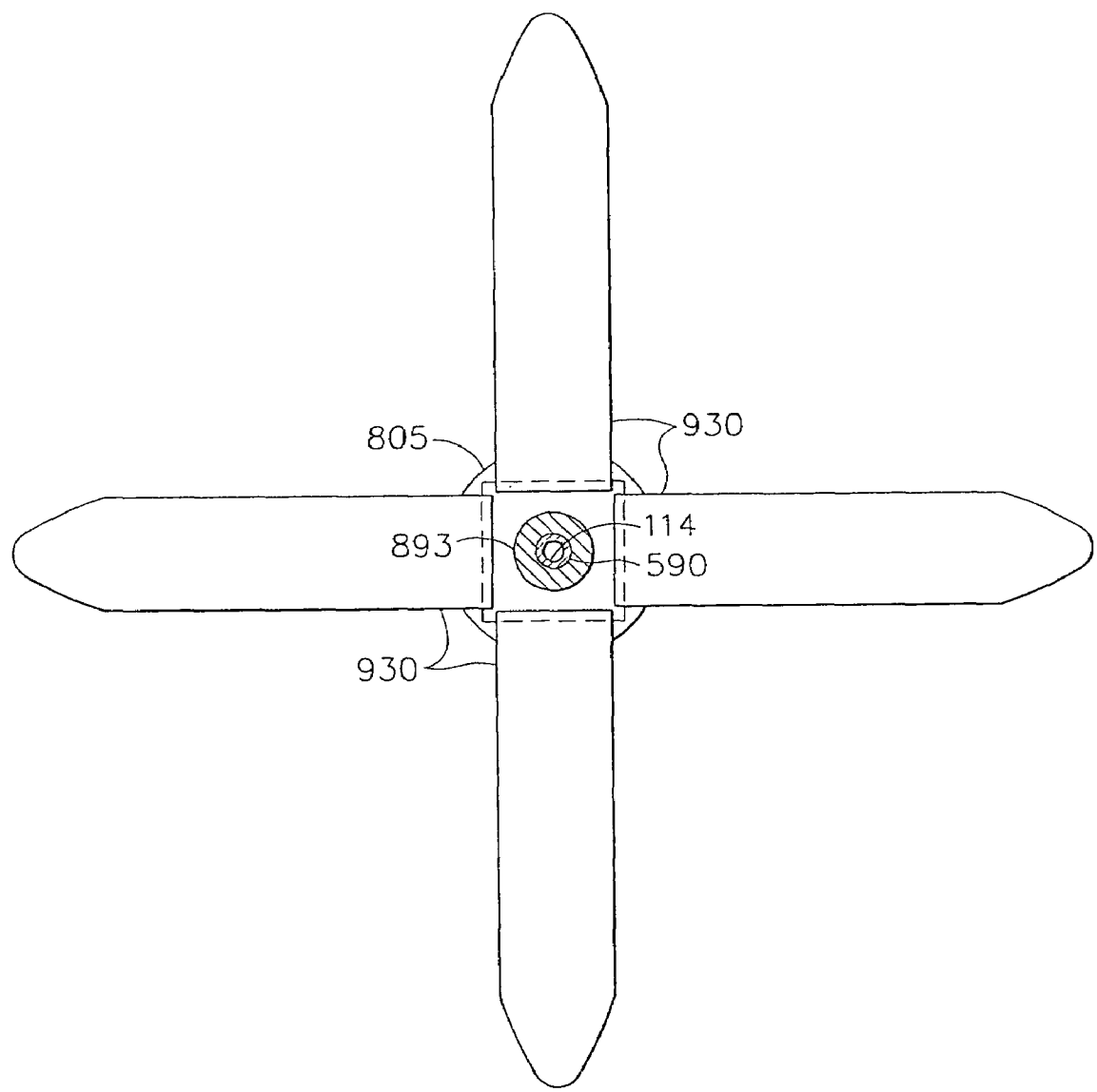
FIG. 27 is an overhead view of the positioner assembly of the anastomotic instrument shown in FIG. 24 with the driver assembly removed for purposes of illustration, showing the positioner petals in opened positions.
Figure 30:
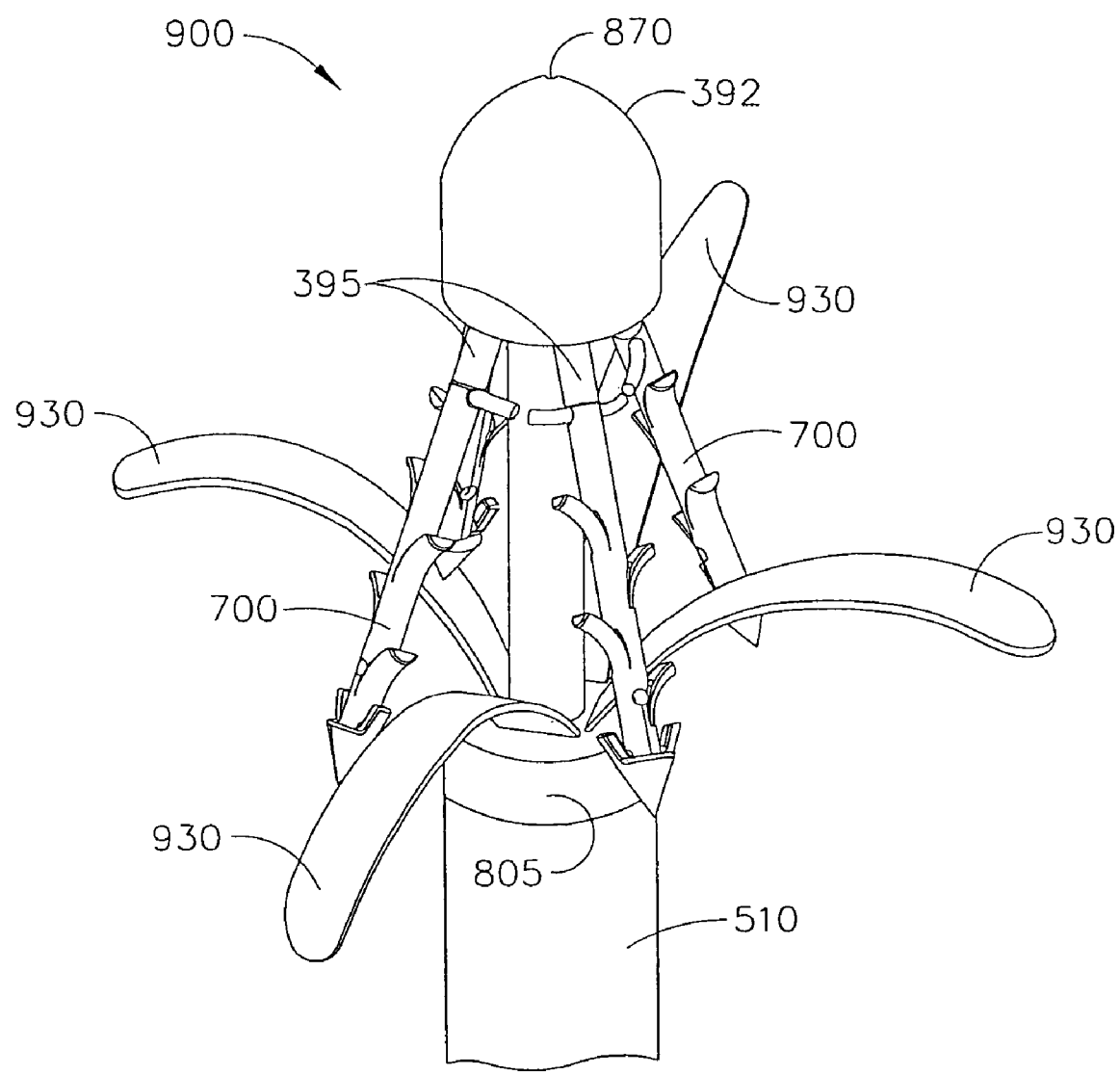
FIG. 30 is a perspective illustration of the alternate anastomotic instrument shown in FIG. 22, shown in an opened position.
Figure 31:
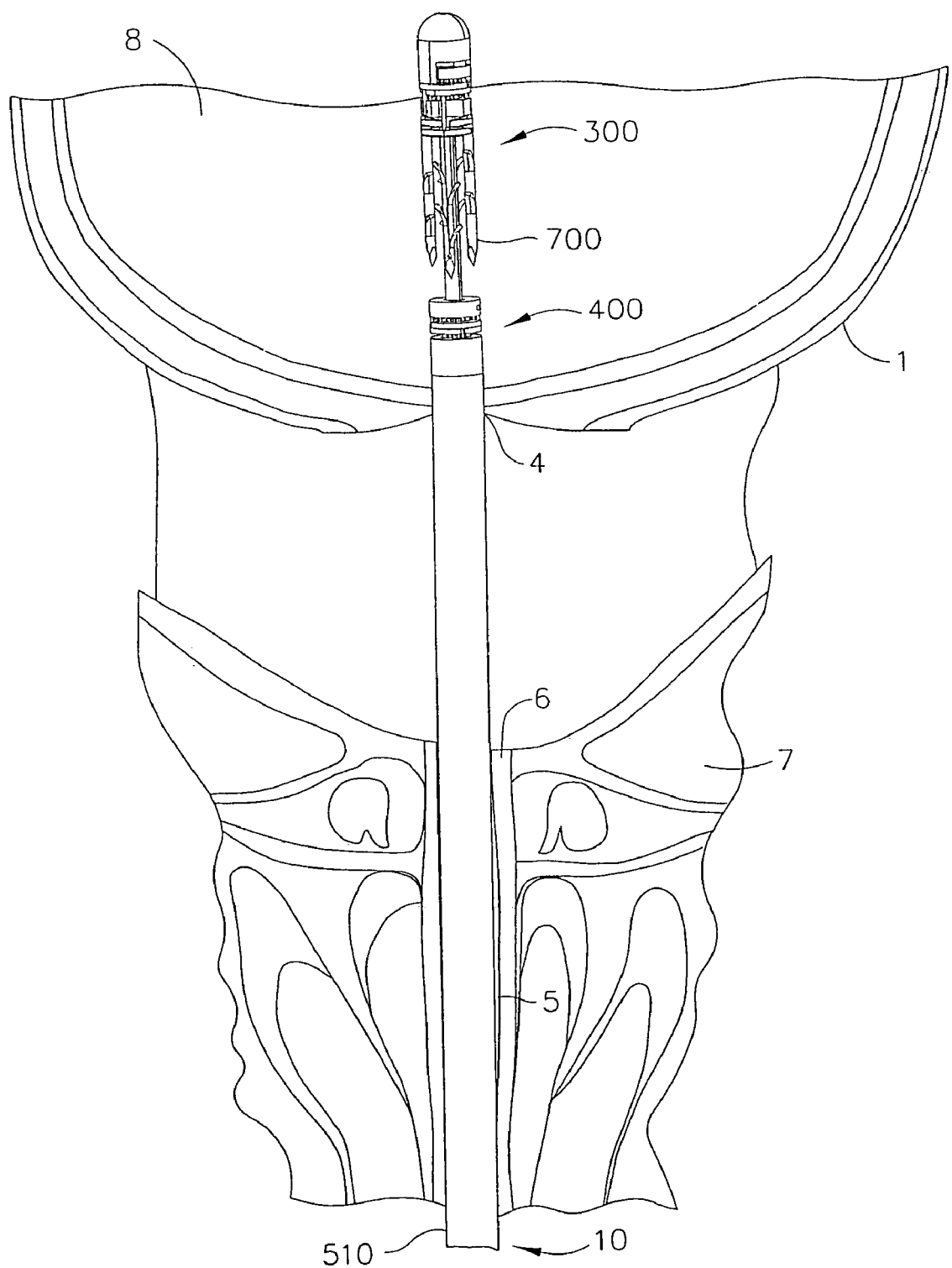
FIG. 31 is an illustration of an anastomotic instrument fully inserted through a patient's urethra and into the bladder, following a prostatectomy.

Once the bladder wall and pelvic floor are brought into contact, the next step is to drive anchors 700, by pulling central tube 590 while holding the remaining tubes 893 and 935 stationary. Pulling central tube 590 causes driver pins 376 to drive anchors 700 into and through bladder wall 20, and then into pelvic floor 7, as shown in FIG. 26. It will be appreciated that barbs 730 on anchors 700 cause anchors 700 to lodge in pelvic floor 7, and that heads 710 on anchors 700 act to retain bladder wall 20 in a position in contact with pelvic floor 7, such that bladder opening 4 is held in communication with urethra opening 6.

As with the first embodiment described herein, optionally, prior to withdrawal of the instrument from the urethra, a guide wire may be inserted through the instrument (via a guide wire passage) and into the bladder lumen, and left behind for use described above after withdrawal of the instrument, see FIGS. 37 and 38.

The sequence of steps described above is then reversed to enable withdrawal of the umbrella instrument 900 from the patient. Central tube 590 is pushed while holding the remaining tubes 893 and 935 stationary, causing driver pins 376 to withdraw from anchors 700, which are now lodged in pelvic floor 7 through bladder wall 2. The entire assembly 900, still in the opened position inside the patient's bladder, is then pushed slightly further into the bladder and away from the urethra by pushing tubes 590, 893, 935 and 510, together, back into the urethra. The instrument 900 is then brought into the retracted position as follows: Pulling driver pin spreader tube 893 while holding central tube 590 and reverse positioner petal tube 935 stationary moves driver pin spreader 890 from the position shown in FIG. 25 to the position shown in FIG. 24, allowing driver pins 376 to return to their normally biased, retracted positions shown in FIG. 24 (but now without anchors 700). Next, pulling reverse petal tube 935 while holding central tube 590 and driver pin spreader tube 893 stationary withdraws reverse positioner petals 930 from their normally biased, opened positions shown in FIG. 24, to their retracted positions inside outer tube 510, shown in FIG. 22. In the retracted position shown in FIG. 22, the assembly 900 may then be withdrawn downwardly through the urethra and out of the patient.

It can be appreciated by one skilled in the art that the positioner assembly may be in alternate configurations providing an applier adapted to for use in a retrograde manner as describe above, or an antegrade manner.

It can be appreciated by one skilled in the art that the mechanism comprising the positioner petals and performing the bladder positioning function thereof may have a variety of alternative configurations including but not limited to embodiments described herein (and thus including, without limitation, the positioner assembly 400 (FIGS. 11, 13, 14) or shuttlecock assembly 800 with positioner petals 830 (FIGS. 17-21) described above, positioner assembly 1440 with positioner arms 1441 (FIGS. 56-64; 70, 71, 77, 78), or positioner 2017 (FIGS. 122-126), 2090 (FIGS. 110-118), 2122 (FIGS. 95, 96, 103-109) and 2168 (FIGS. 83, 84, 89-94) (all of which are described below)), providing a transversely retractable and extendible device useful for, referring to FIG. 2, insertion in a retracted position in a retrograde direction through the urethra 5 and into bladder opening 4, extending or expanding within bladder lumen 8, catching in bladder opening 4 and manipulating to urge bladder wall 2 surrounding bladder opening 4 into contact with pelvic floor 7 surrounding urethra opening 6 with the respective openings aligned; or alternatively, insertion in a retracted position in an antegrade direction through an incision in the abdomen and an upper surface of the bladder 1, extending or expanding within bladder lumen 8, catching in bladder opening 4 and manipulating to urge bladder wall 2 surrounding bladder opening 4 into contact with pelvic floor 7 surrounding urethra opening 6 with the respective openings aligned. Generally, the positioner assembly may comprise and make use of any number of alternately extendable and retractable projections, petals, arms, claws, or other grasping or catching members for catching and gaining control of bladder wall 2 surrounding bladder opening 4. The positioner assembly may have at least one member operably connected to a longitudinal member of the instrument and alternately transversely extendable from and retractable toward the longitudinal axis thereof in response to input by a surgeon at a proximal end of the instrument.

Alternatively, it can be appreciated by one skilled in the art that when an anchor driver assembly is included with the instrument, that is functional to open and subsequently drive anchors through the bladder wall and into the pelvic floor as described herein, the positioner assembly or positioner petals as shown may be dispensed with in some circumstances. For example, referring to FIGS. 25 and 26, it can be appreciated that anchor driver pins 376 and anchors 700, when opened within the bladder lumen and drawn downwardly until the distal ends of anchors 700 contact and possibly puncture bladder wall 2 surrounding bladder opening 4, can be sufficient for use in capturing bladder wall 2 and drawing it downward into contact with, and securing it to, pelvic floor 7, with bladder opening 4 and urethra opening 6 aligned, without the need for reverse positioner petals 930 as shown, in some circumstances. Thus, driver pins 376 with anchors 700 may serve a dual function as a positioner and as an anchor driver assembly.

Balloon/Harness Embodiment

FIGS. 55-64 depict another embodiment of a method and instrument in accordance with the present invention (shown in an antegrade configuration), the instrument having a handle assembly 1100, a straight tube assembly 1200, a curved tube assembly 1300, and an end effector assembly 1400. In one embodiment of the present invention, instrument 1000 may be endo-scopically inserted into the abdominal cavity of a patient to effect an anastomosis between the urethra and bladder of a patient, thereby re-establishing the fluid connection between bladder 1 and the urethra 5.

Figure 56:
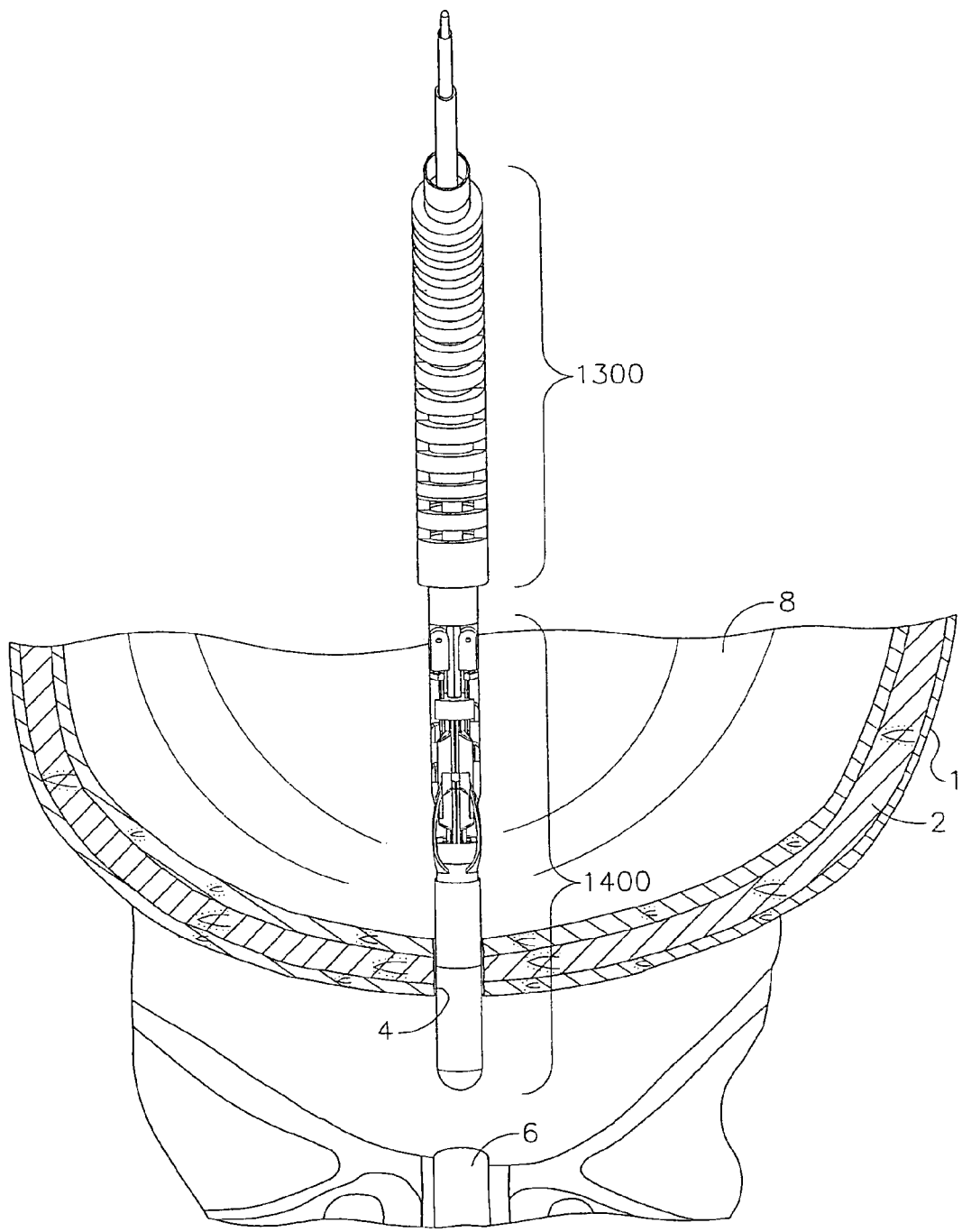
FIG. 56 is a partial view of the instrument shown in FIG. 55, including a curved tube assembly and anastomosis end effector, inserted into the bladder of a patient as used in accordance with the present invention.

FIG. 56 depicts curved tube assembly 1300 and end effector assembly 1400 after insertion into the bladder lumen 8 of a patient through an opening in the abdomen and upper surface of the bladder (not shown). The openings may be made, and abdominal insertion of the instrument may be accomplished by, for example, inserting a cannula with a trocar (not shown) into the abdomen and guiding it to and through an upper surface of the bladder in a generally antegrade direction, withdrawing the trocar, and inserting the instrument through the cannula and into the bladder lumen. Curved tube assembly 1300 may be flexible and may be provided with a bias at a bend angle (from about approximately 55 degrees to about approximately 90 degrees may be suitable) to provide curvature that may be desirable for inserting end effector assembly 1400 into the urethra 5 and actuating the instrument in an antegrade procedure. The bend angle of curved tube assembly 1300 may vary depending upon the particular needs of the procedure or surgeon utility.

Figure 57:
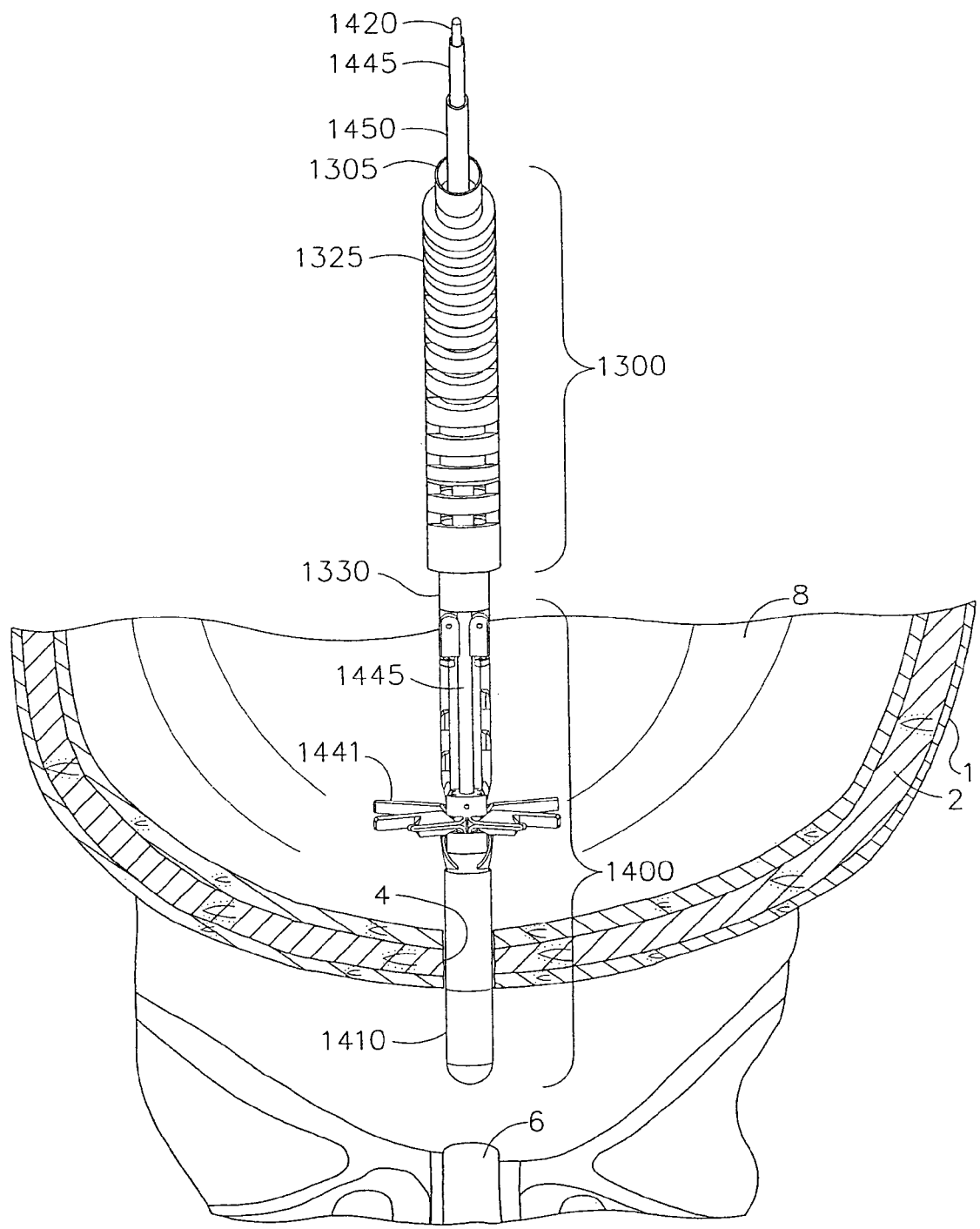
FIG. 57 is a partial view of the instrument shown in FIG. 55, including an opened positioner assembly as used in accordance with the present invention.

FIG. 57 depicts end effector assembly 1400 with opened positioner arms 1441 inside the bladder lumen 8. Following the insertion of balloon assembly 1410 into bladder opening 4, distal positioner tube 1445 has been moved downwardly and distally, causing positioner arms 1441 to open to positions transverse to the longitudinal axis of end effector assembly 1400. Positioner arms 1441 are adapted to be effective for use in catching and urging bladder wall 2 surrounding bladder opening 4 toward pelvic floor 7 surrounding urethra opening 6.

Figure 58:
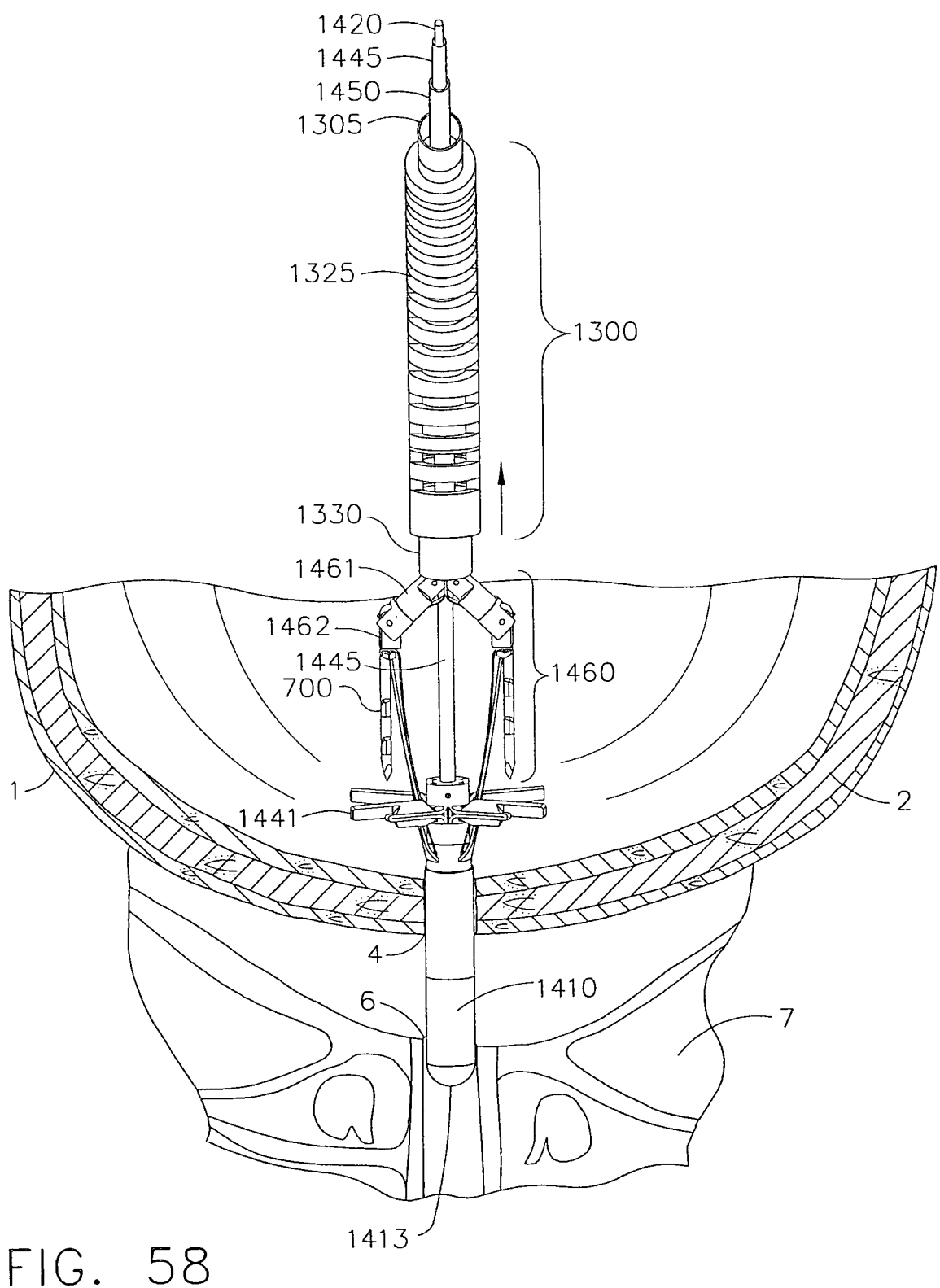
FIG. 58 is a partial view of the instrument shown in FIG. 55, including an opened anchor assembly as used in accordance with the present invention.

FIG. 58 depicts the end effector assembly with anchor driver assembly 1460 opened inside the bladder lumen. During the insertion of end effector assembly 1400 into the bladder to the position shown in FIG. 56, the anchor pivot arms 1461 of anchor driver assembly 1460 are sheathed by anchor closing collar 1330 and are restrained in a closed position lying along distal positioner tube 1445, as may be seen by comparing FIGS. 57 and 58. When anchor closing collar 1330 is moved upwardly with respect to distal anchor driver tube 1450, the anchor pivot arms 1461 are unsheathed, allowing them to swing outwardly, under spring bias, to the position shown in FIG. 58, bringing anchors 700 into a position reading for driving.

FIG. 58 further illustrates positioning of the distal balloon assembly 1410 in the urethra opening 6. Locating the urethra opening 6 with end 1413 and inserting end 1413 into the urethra opening 6 ensures that when the positioner arms 1441 contact and urge the bladder wall 2 toward the pelvic floor 7, the urethra opening 6 and the bladder opening 4 will be substantially aligned.

Figure 59:
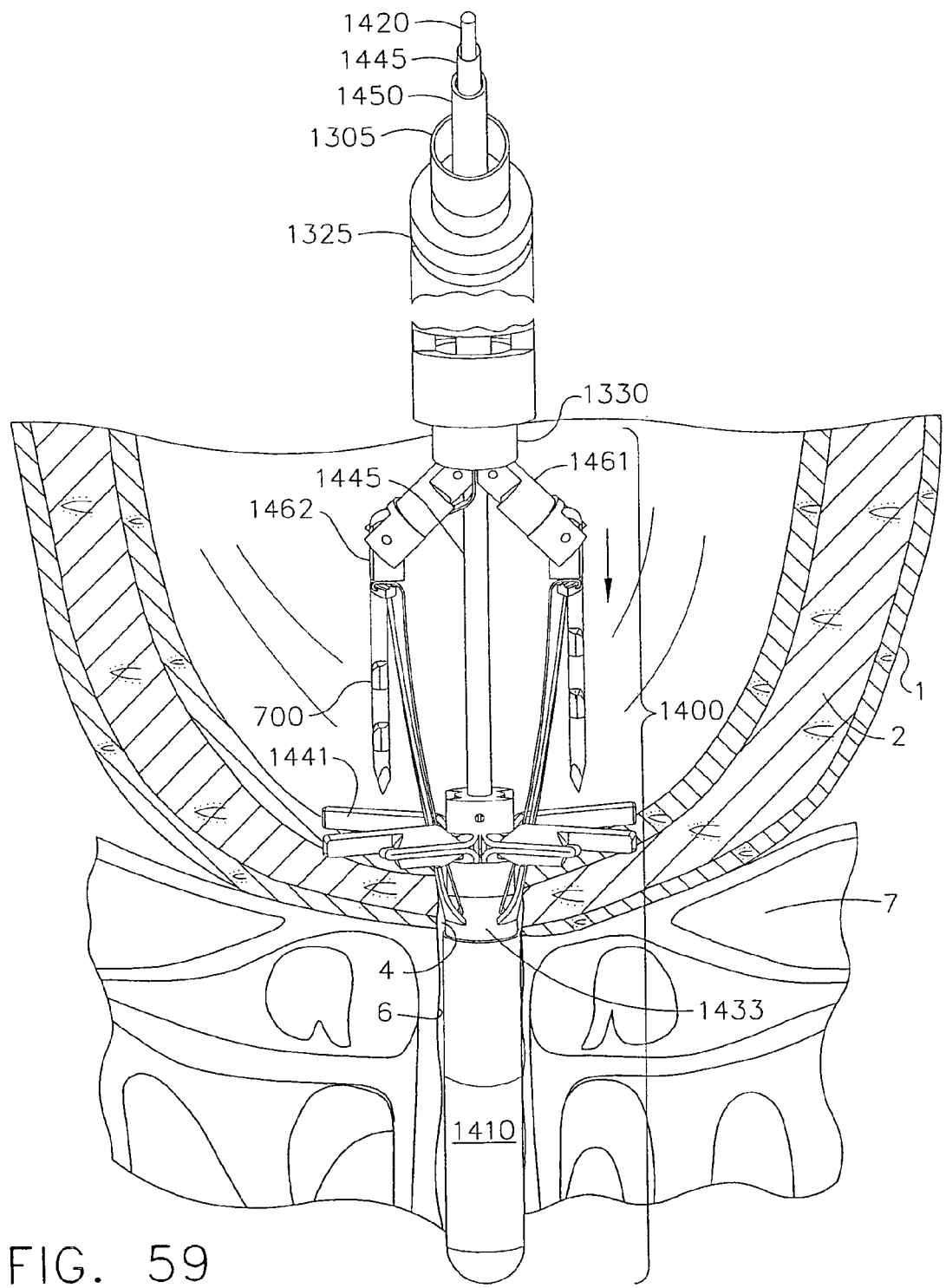
FIG. 59 is a partial view of the instrument shown in FIG. 55, showing positioner arms urging the bladder wall into contact with the pelvic floor in accordance with the present invention.

FIG. 59 illustrates the positioning of end effector assembly 1400, bladder wall 2, and pelvic floor 7 after instrument 1000 has been urged downward, thus causing positioner arms 1441 to urge bladder wall 2 downward into contact with pelvic floor 7, which may be accomplished by pushing the entire instrument toward the pelvic floor. As bladder wall 2 surrounding bladder opening 4 is urged into contact with pelvic floor 7 surrounding urethra opening 6, balloon assembly 1410 is urged into urethra opening 6

Figure 60:
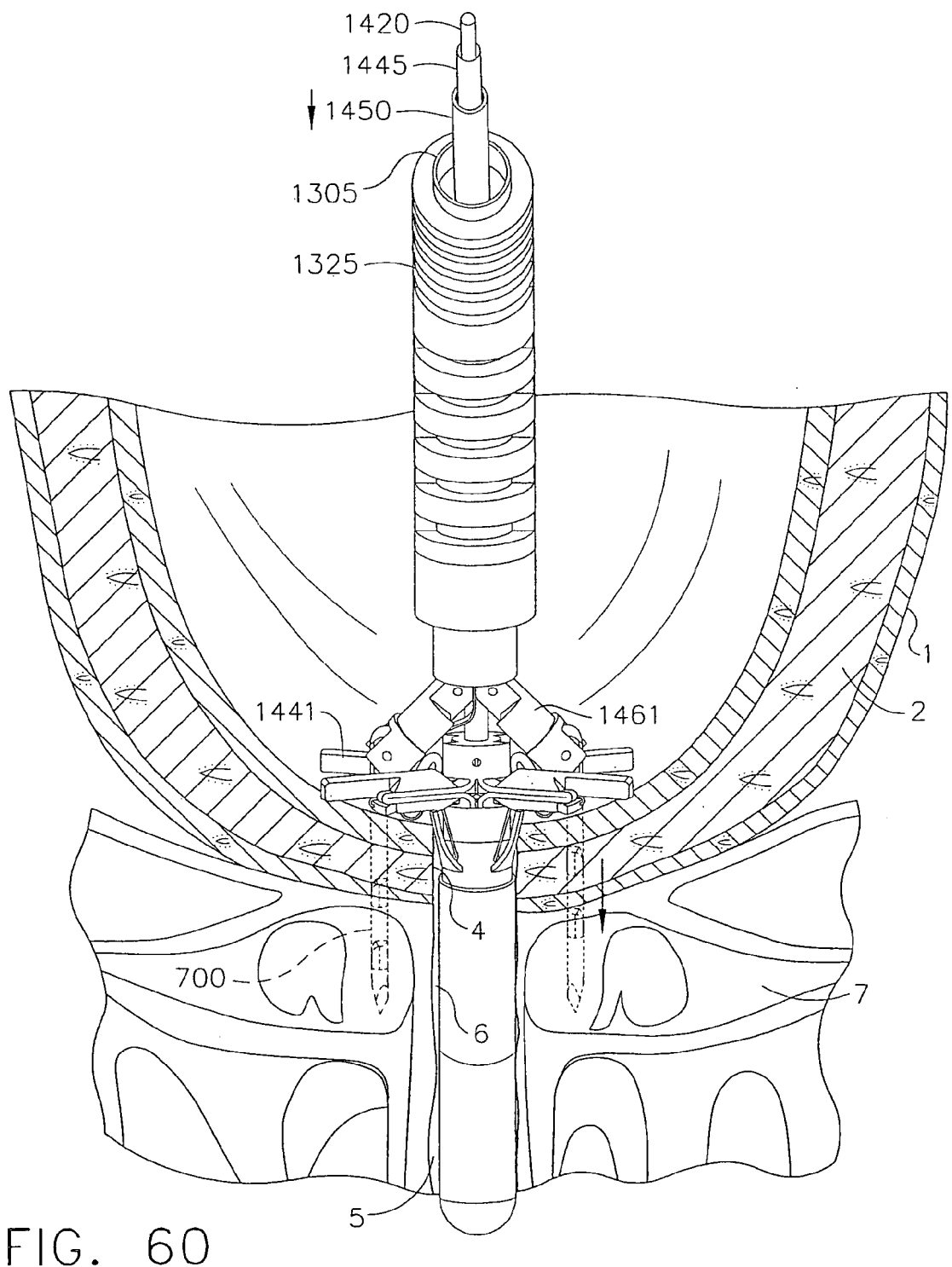
FIG. 60 is a partial view of the instrument shown in FIG. 55, after anchors have been driven through the bladder wall into the pelvic floor in accordance with the present invention.

FIG. 60 illustrates the instrument after anchors 700 of anchor driver assembly 1460 have been driven through the bladder wall 2 into the pelvic floor 7 to secure bladder wall 2 surrounding bladder opening 4 in contact with pelvic floor 7 surrounding urethra opening 6, with bladder opening 4 and urethra opening 6 substantially aligned. Once in the opened and ready position, as shown in FIG. 58, the anchors 700 may be driven through the bladder wall into the pelvic floor by moving distal anchor driver tube 1450 in a distal direction (toward the distal end of the instrument), which correspondingly moves the anchor pivot arms 1461, anchor driver pin bases 1462, anchor driver pins (concealed within anchors 700 as shown), and thus anchors 700. Driving anchors 700 through bladder wall 2 and into pelvic floor 7 positions the distal portion of balloon assembly 1410 within the urethra 5 to insure that anchors 700 are installed such that the bladder opening 4 and the urethra opening 6 remain substantially aligned.

Figure 61:
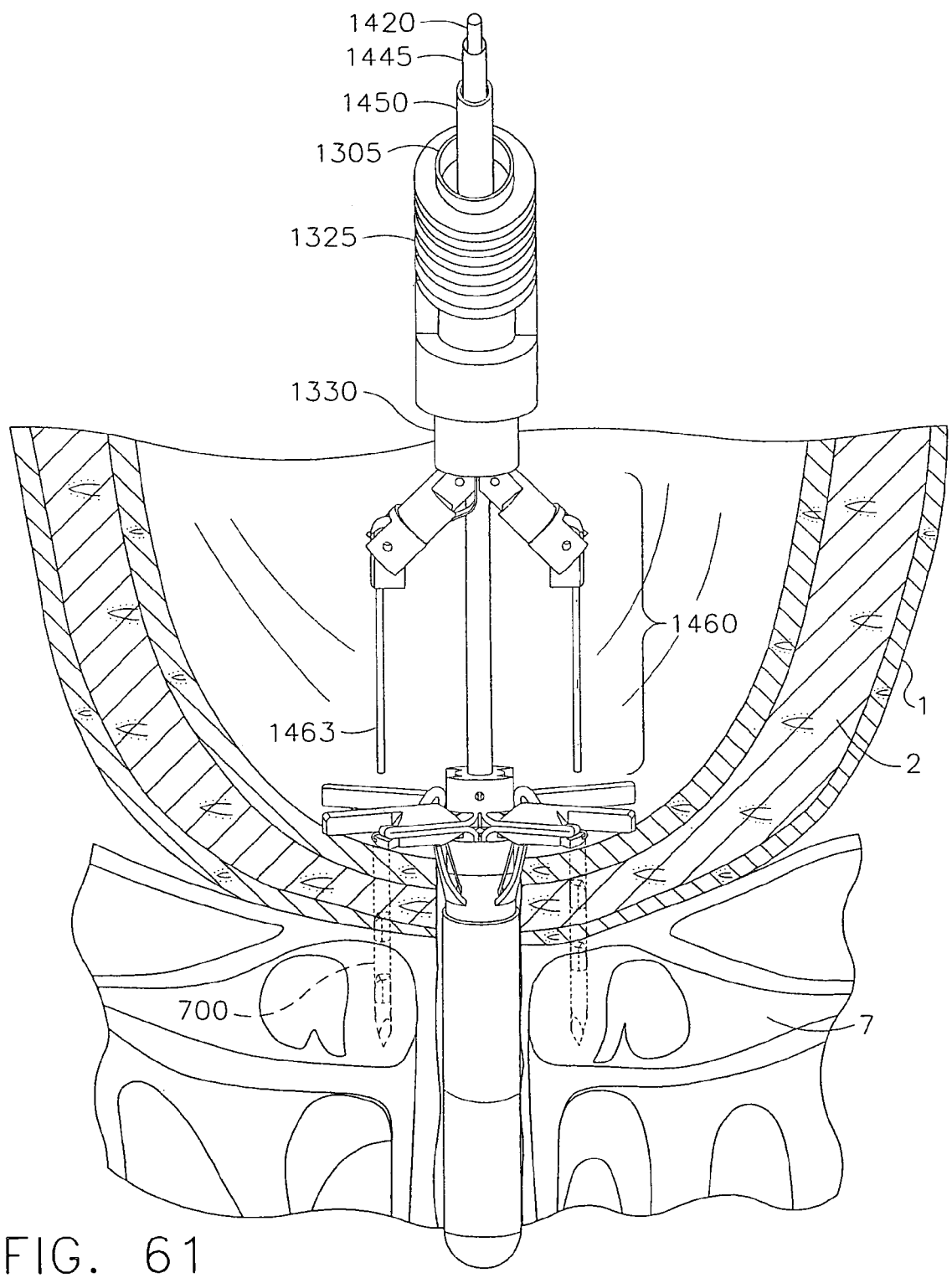
FIG. 61 is a partial view of the instrument shown in FIG. 55, following withdrawal of anchor driver pins from installed anchors in accordance with the present invention.

FIG. 61 illustrates the instrument after withdrawal of anchor driver pins 1463 from the installed anchors 700 that are now lodged in the pelvic floor 7 to secure the bladder wall 2 to the pelvic floor 7. Anchors 700 may be provided with barbs or other suitable structures adapted to lodge anchors 700 in tissues. As such, when anchor driver assembly 1460 is withdrawn by remotely pulling distal anchor driver tube 1450 while holding distal positioner tube 1445 substantially stationary, anchors 700 remain lodged in the tissue. Prior to use of the instrument, anchors 700 have been pre-loaded and may be releaseably held on the anchor driver pins 1463 by a friction fit or any other suitable means which will allow release when anchors 700 are lodged in tissues and anchor driver pins 1463 are withdrawn therefrom.

Figure 62:
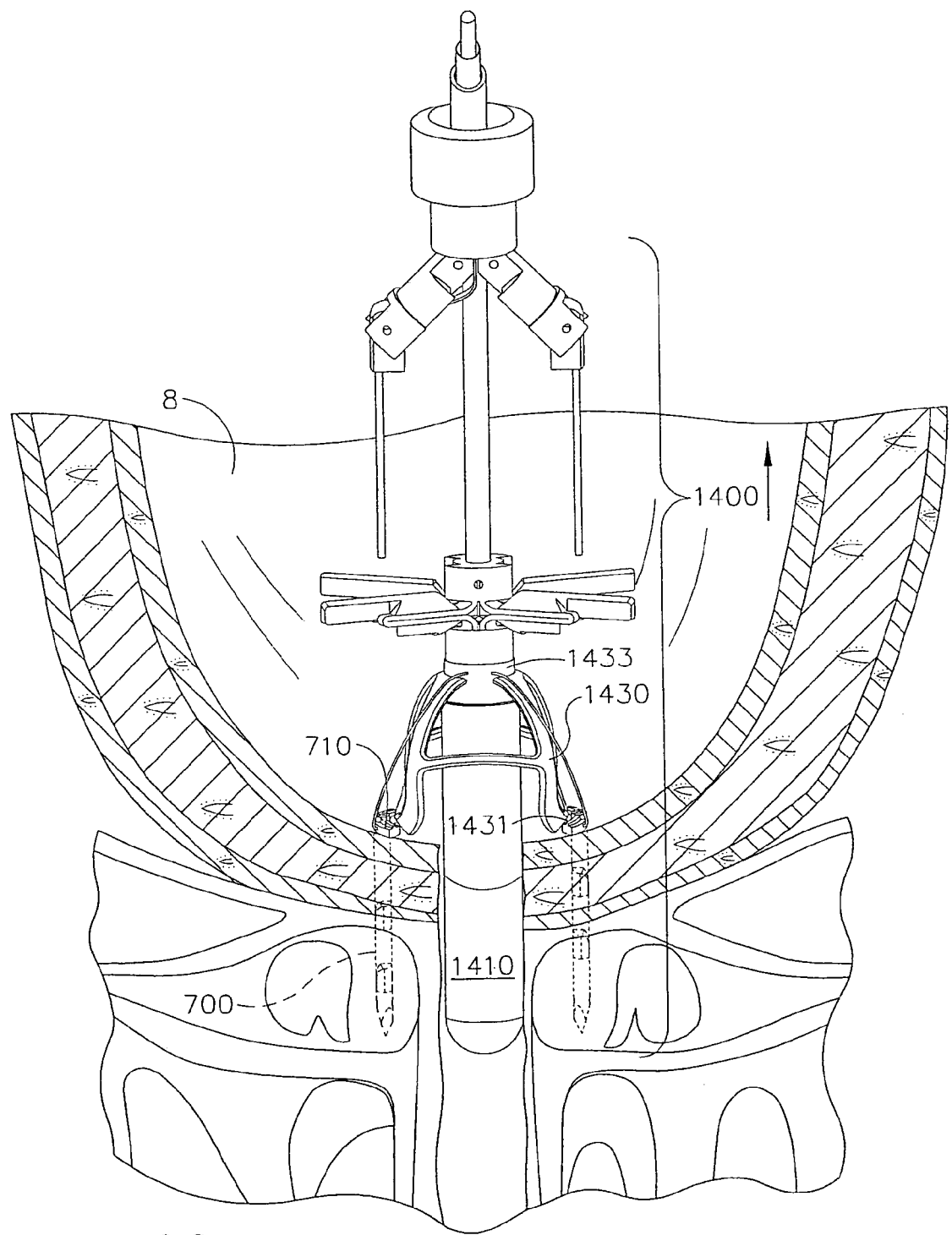
FIG. 62 is a partial view of the instrument shown in FIG. 55, after partial retraction of the instrument to unfold a harness in accordance with the present invention.

FIG. 62 illustrates the end effector assembly 1400 after it has been partially retracted so as to situate the proximal portion of the balloon assembly 1410 within the bladder lumen 8. As the end effector assembly 1400 is retracted, harness 1430 is unfolded and exposed. Harness 1430 may be integral with harness collar 1433 and may be affixed to anchors 700 at the anchor heads 710 with an anchoring loop, that may consist of suture material, running through both the anchor head 710 and the harness 1430. As the end effector assembly 1400 is retracted, harness 1430 becomes unfolded as the harness collar 1433 is moved upward. End effector assembly 1400 may be retracted until harness 1430 resists retraction as a result of the attachment of harness 1430 to the anchor heads 710.

Figure 63:
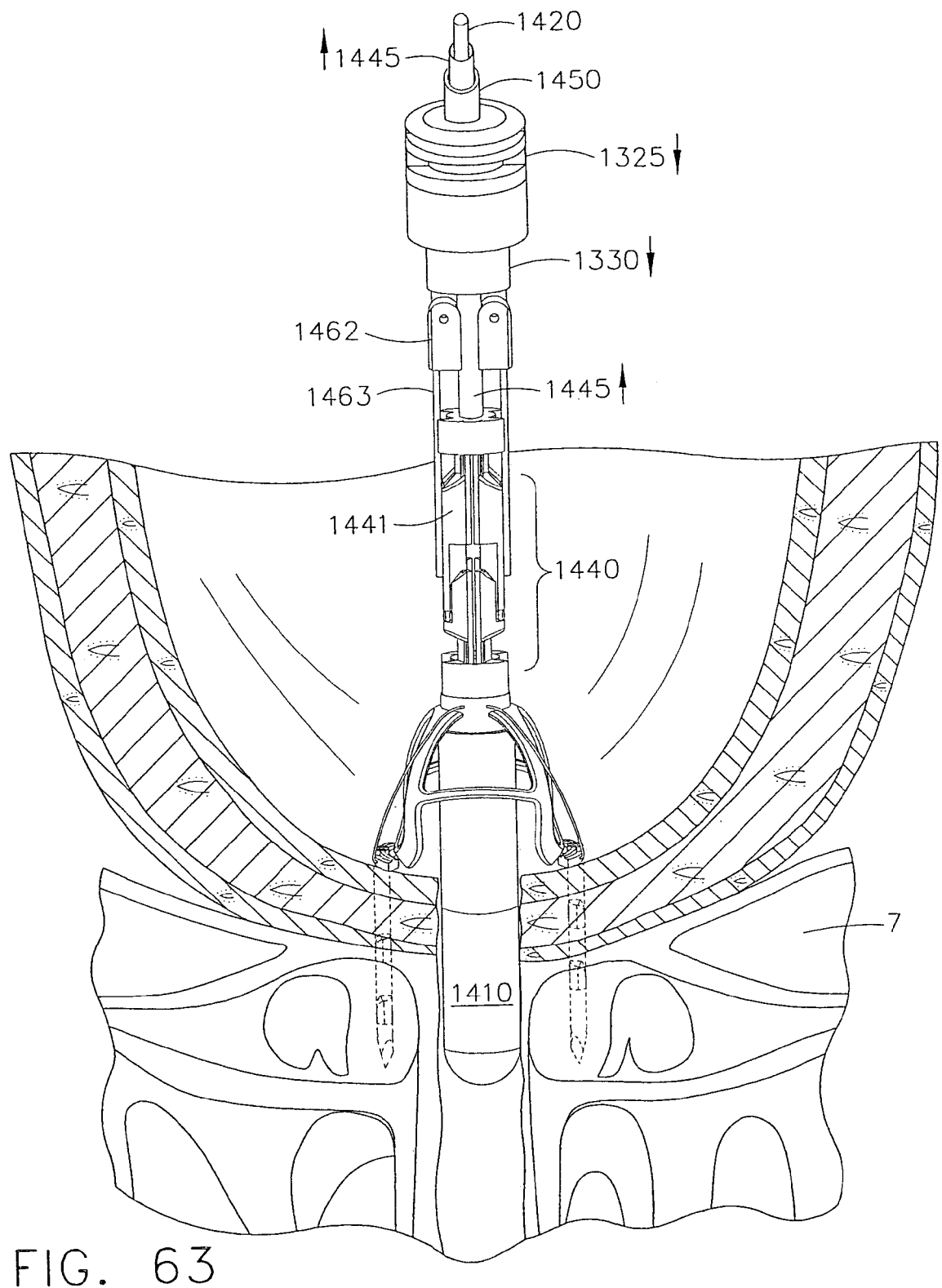
FIG. 63 is a partial view of the instrument shown in FIG. 55, following closing of an anchor assembly and positioner assembly in preparation for their withdrawal, to leave a balloon assembly and catheter behind in accordance with the present invention.

FIG. 63 illustrates the instrument after the positioner arms 1441 of the positioner assembly 1440 have been closed by retracting the positioner tube 1445 away from the pelvic floor 7, and after the anchor pivot arms 1461 have been closed by moving anchor closing collar 1330 towards the pelvic floor while holding catheter tube 1420 and distal anchor driver tube 1450 substantially stationary. As will be apparent to a person of ordinary skill in the art, the steps of closing the positioner arms 1441 and closing the anchor pivot arms 1461 may be accomplished at any suitable time or sequence during the procedure.

Figure 64:
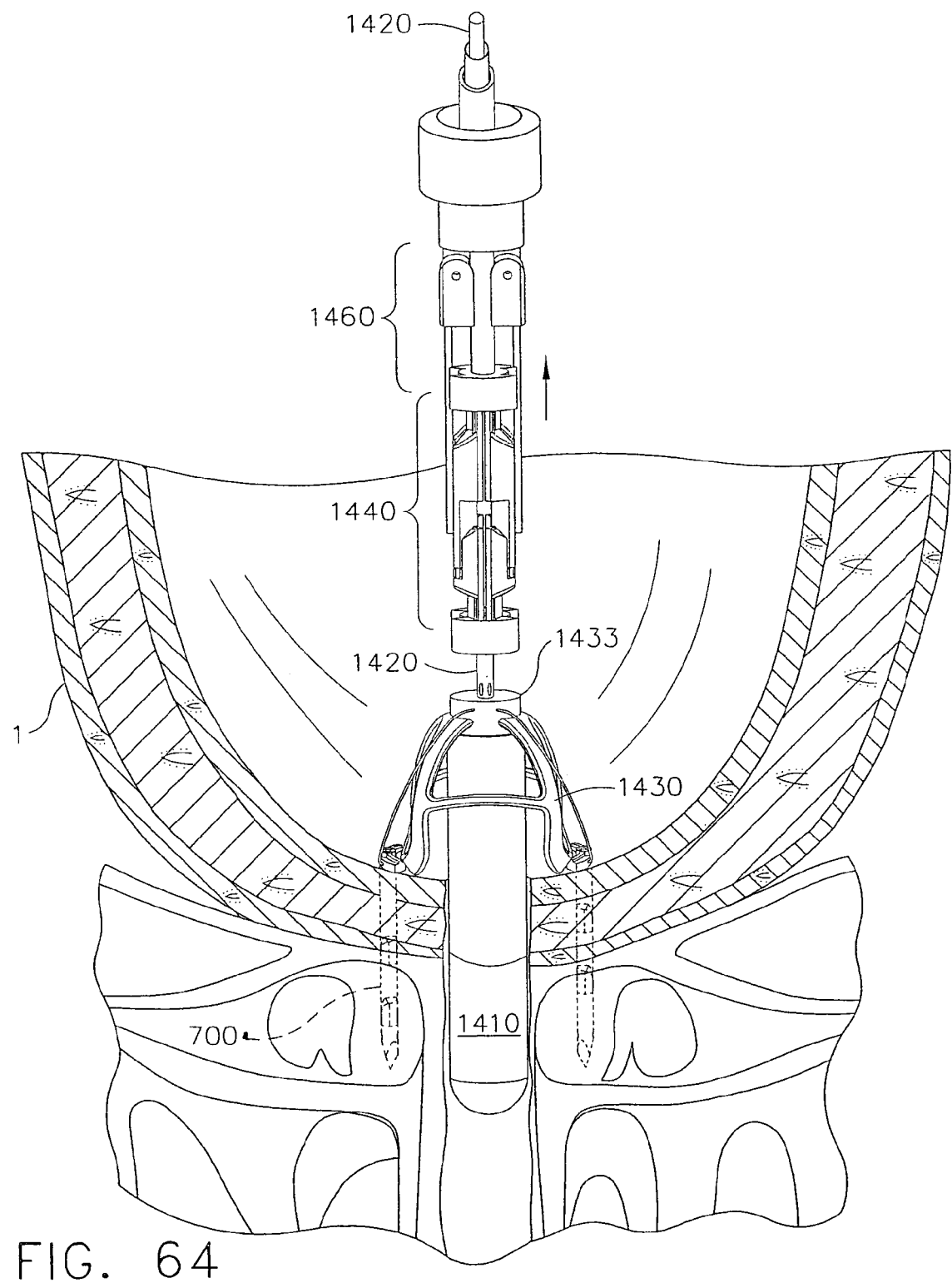
FIG. 64 is a partial view of the instrument shown in FIG. 55, after removal of a positioner assembly and anchor assembly, used in accordance with the present invention, has commenced.

FIG. 64 illustrates the anchor driver assembly 1460 and the positioner assembly 1440 after their withdrawal from the bladder 1 has been commenced. Removing anchor driver assembly 1460 and positioner assembly 1440 leaves behind catheter tube 1420, in communication with balloon assembly 1410, also left behind. Catheter tube 1420 may be a catheter that is left in place until anastomosis is complete, to enable drainage of urine during recovery and healing.

Figure 65:
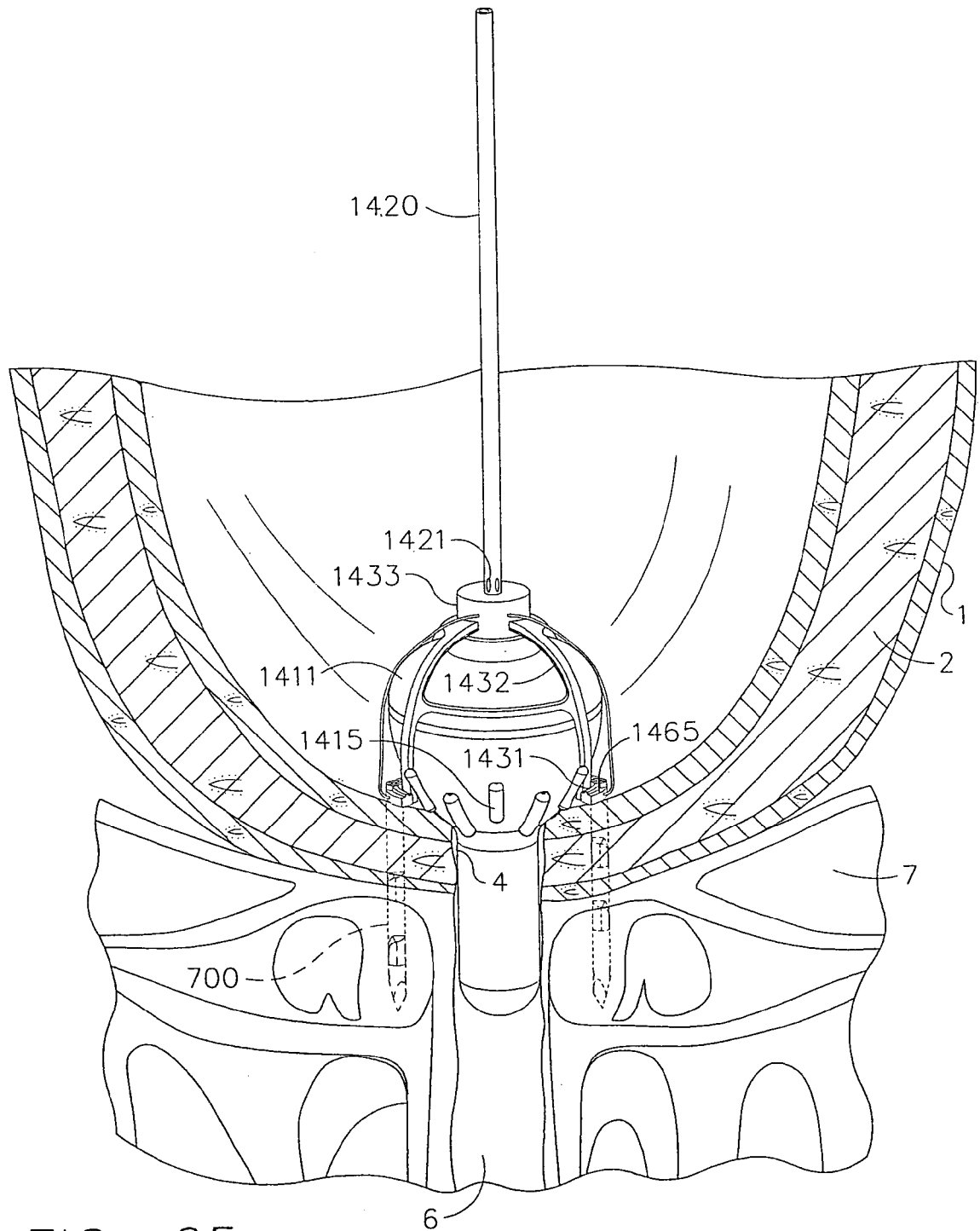
FIG. 65 is a partial view of the instrument shown in FIG. 55, after removal of a positioner assembly and anchor assembly, and after inflation of a balloon secured with an anchored harness, used in accordance with the present invention.
Figure 67:
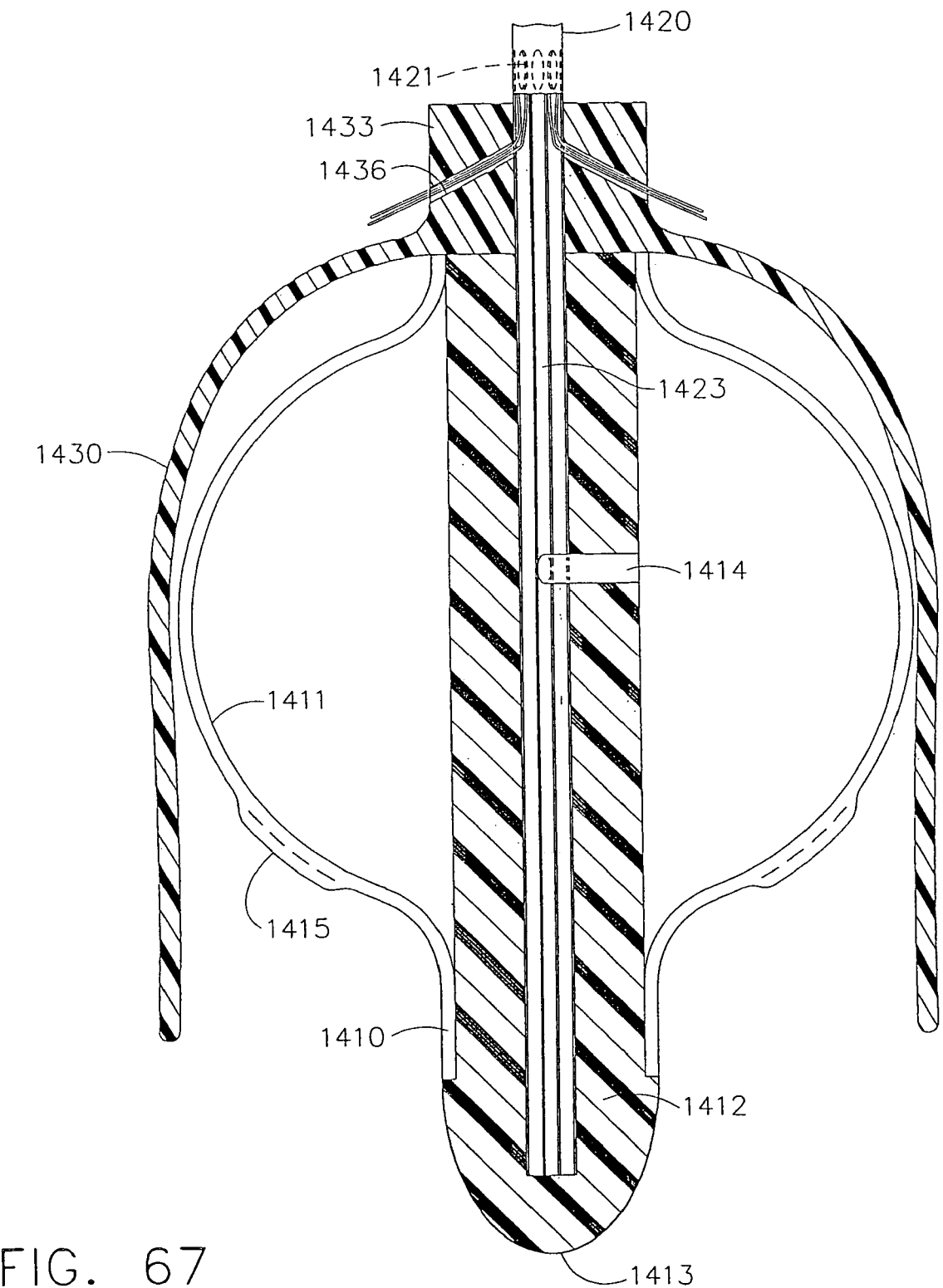
FIG. 67 is a longitudinal cross-sectional view of an embodiment of a balloon assembly that may be adapted for use in accordance with the present invention.
Figure 68:
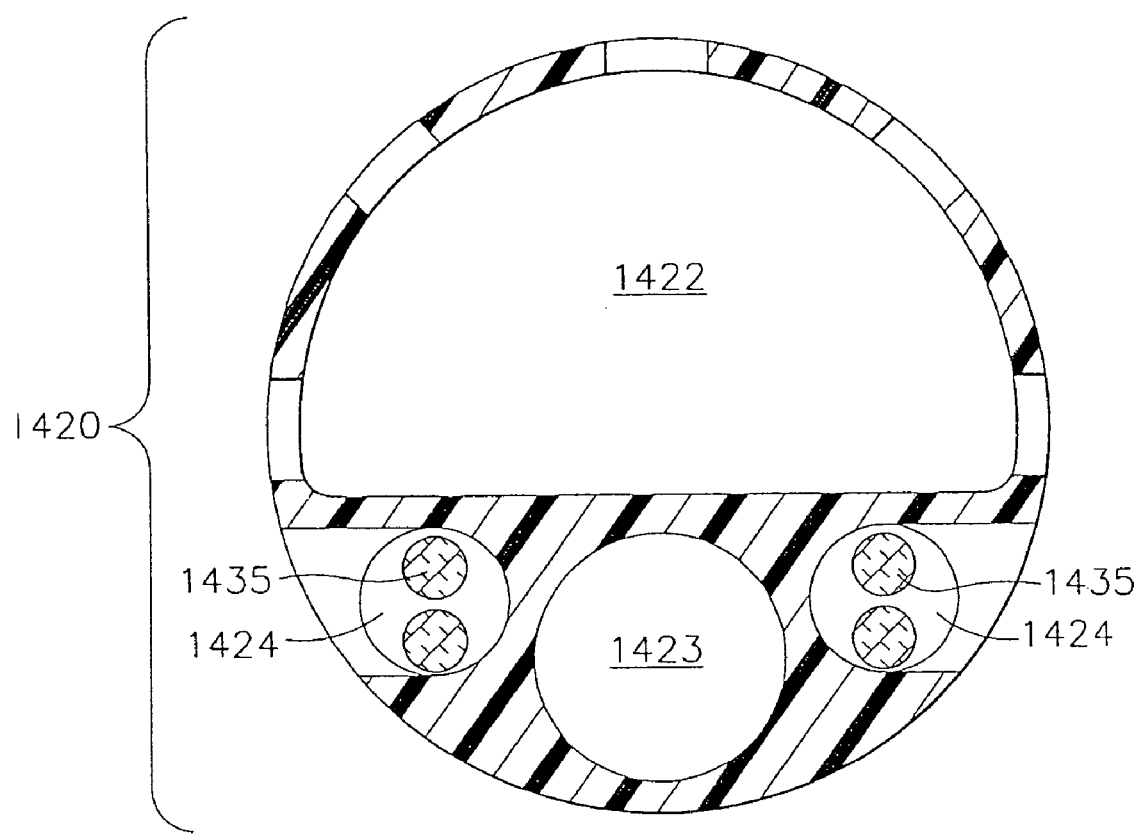
FIG. 68 is a transverse cross-sectional view of a catheter that may be used in accordance with the present invention.

FIG. 65 illustrates balloon 1411 of balloon assembly 1410 after it has been inflated by pumping gas or fluid through an inflation lumen 1423 in catheter tube 1420 (see FIGS. 67, 68). Balloon 1411 may be inflated until it is restrained by harness straps 1432, which then press balloon 1411 against the tissue surrounding bladder opening 4 so as to apply sufficient pressure to maintain contact between bladder wall 2 surrounding bladder opening 4 and pelvic floor 7 surrounding urethra opening 6, to effect knitting of the respective tissues and thus effect anastomosis.

During recovery and healing, urine from the patient's bladder may be drained through drainage holes 1421 that are in communication with a urine drainage lumen 1422 in catheter tube 1420 (see FIGS. 67, 68). Drainage holes 1421 may be positioned, for example, distally on the catheter tube 1420, or in any other suitable location. Suitable gas or fluid pressure within balloon 1411 may be maintained until the anastomosis is complete, by monitoring and adjusting the pressure within balloon 1411 through inflation lumen 1423. The possibility of pressure necrosis in the tissues beneath the balloon may be reduced by including, for example, ribs 1415, or other bumps, nodules, projections, or other features on the underside of balloon 1411, which may be effective to reduce the loss of blood flow to tissue in contact with balloon 1411. These features may be solid or of uniform wall thickness.

Additionally, balloon 1411 may be designed with features that effect the shape that it assumes upon inflation, and thus, effect the shape and area of the lower surface of balloon 1411 that contacts the bladder wall 2 upon inflation. For example, balloon 1411 may be designed and manufactured so as to have walls that are thicker on an upper portion and thinner on a lower portion, so that the lower portion of balloon 1411 is predisposed to expand downwardly and outwardly between the harness straps, and thereby present a larger surface area to contact the bladder wall 2. Alternatively, balloon 1411 may be designed with features that cause it to assume a specific advantageous shape upon inflation.

Figure 66:
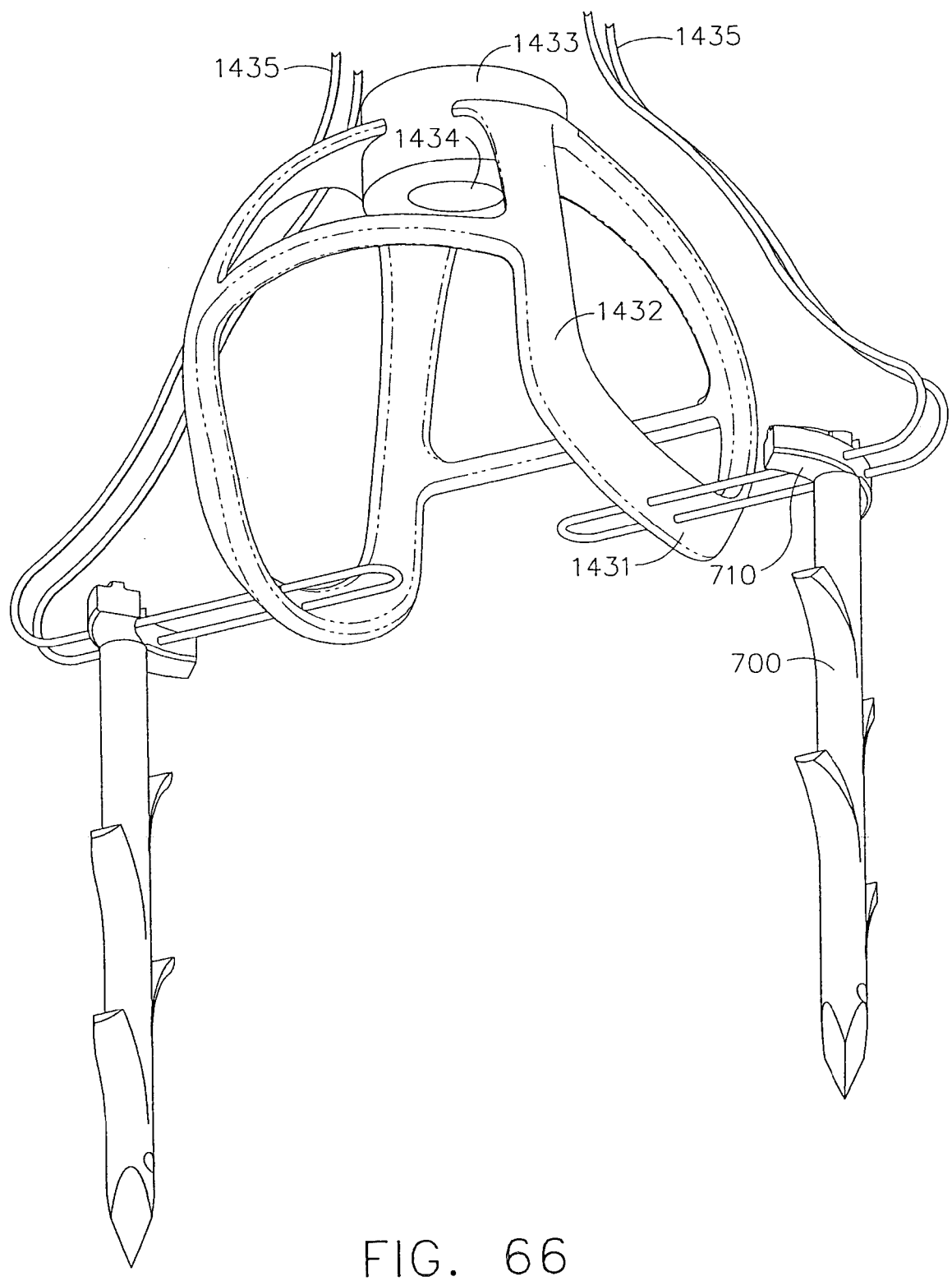
FIG. 66 is a perspective view of a harness portion of the instrument shown in FIG. 55, as it may be secured to anchors via harness anchoring loops.

Balloon assembly 1410, harness 1430, and catheter tube 1420 may removed from the patient by removing the harness anchoring loop 1435 attachment from the anchor heads 710 and harness straps 1432. As shown in FIG. 66, harness straps 1432 may be affixed to the anchor heads 710 by one or more harness anchoring loops 1435 that pass through holes located in both the harness straps 1432 and the anchor heads 710. As may be appreciated from FIGS. 66-69, free ends of harness anchoring loops 1435 may extend through catheter tube 1420 to its proximal end. Thus, the balloon assembly 1410 may be removed by pulling harness loop plug 1485 attached to one free end of each of harness anchoring loops 1435 and pulling the harness loop plug 1485 until the harness anchoring loops 1435 are completely removed from the instrument. Removing the harness anchoring loops 1435 from anchor heads 710 and harness straps 1432 disassociates the anchors 700 from the harness 1430 allowing the balloon assembly 1410 to be retracted. FIG. 67 illustrates anchoring loop passages 1436 where, in one embodiment of the present invention, harness anchoring loops 1435 may pass through the anchoring loop passage 1436 into the anchoring loop lumens 1424 of catheter tube 1420 (FIG. 68). Harness anchoring loops 1435 may comprise suture material.

FIGS. 67 and 68 illustrate an embodiment of a method and configuration of an instrument adapted to enable inflation of balloon 1411 of balloon assembly 1410 in accordance with the present invention. Catheter tube 1420 may include an inflation lumen 1423 that extends distally through the balloon assembly body 1412. An inflation port 1414 provides a passageway between inflation lumen 1423 and the balloon cavity to enable inflation, deflation and balloon pressure regulation. Gas or fluid pressure, provided and regulated through inflation lumen 1423 may pass through inflation port 1414 to adjust and regulate the pressure within the balloon 1411 as may be desired to affect the pressure the balloon exerts on the tissues. In one embodiment of the present invention, balloon 1411 may be expanded until restricted by harness straps 1432 of harness 1430. Balloon 1411 may be constructed from an elastomeric material that fully encircles the balloon assembly body 1412. The proximal and distal portions of balloon 1411 may be glued or otherwise adhered to the balloon assembly body 1512 by any suitable means.

FIG. 68 illustrates an embodiment of a catheter tube 1420 in accordance with the present invention having a urine drainage lumen 1422, at least one anchoring loop lumen 1424, and an inflation lumen 1423. It will be apparent to one of ordinary skill in the art that various types of lumens are within the scope of the present invention and that the lumens or catheter cross sections described may be maintained within a single catheter or housed separately depending on the needs of the user. Catheter tube 1420 may be any suitable diameter.

Figure 69:
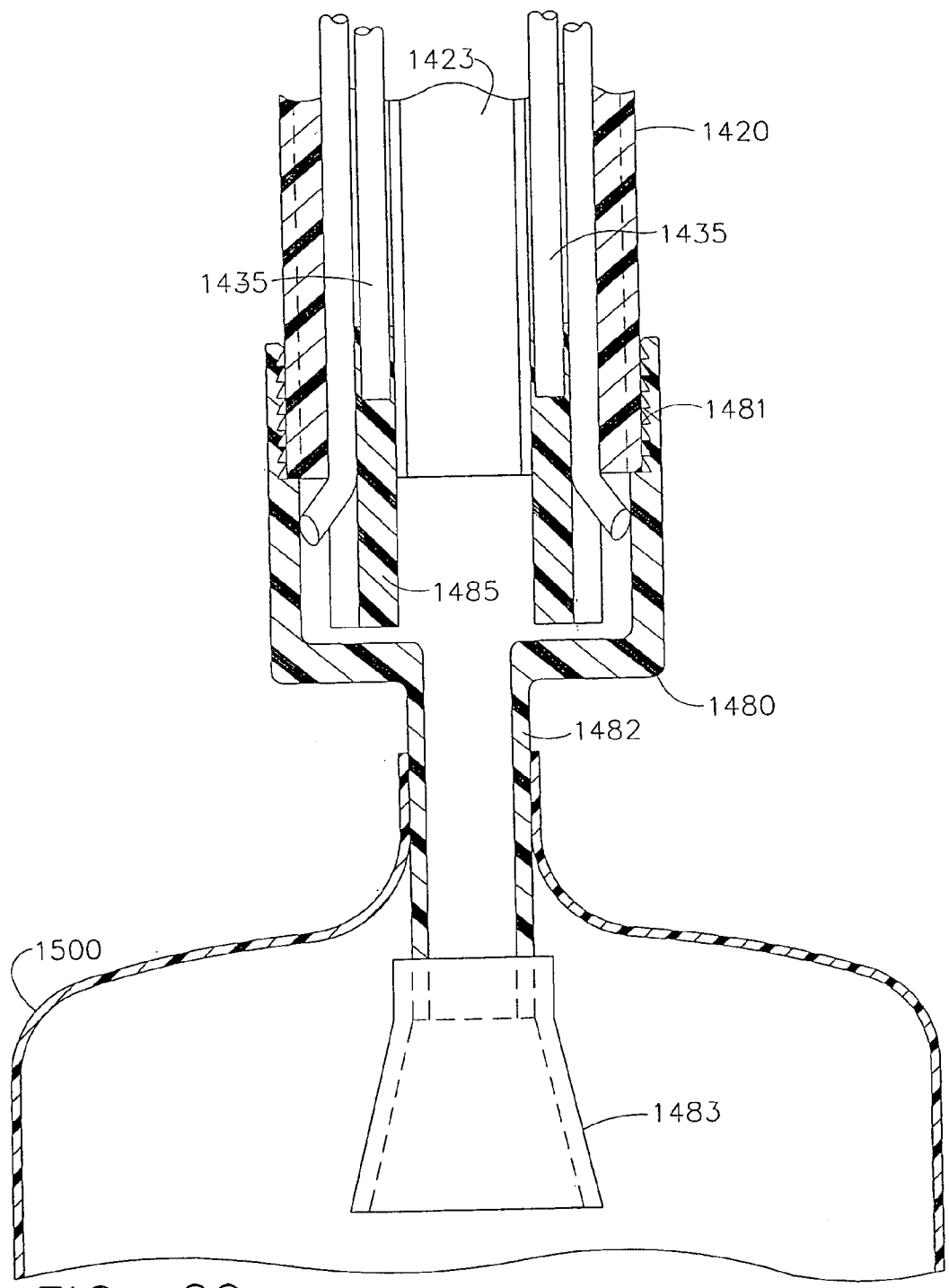
FIG. 69 is a longitudinal cross-sectional view of one embodiment of a catheter cap and a urine collection bag that may be used in accordance with the present invention.

FIG. 69 illustrates an embodiment of the proximal end of a catheter tube 1420 as may be connected to a urine collection bag 1500. Gas or fluid may be delivered through backflow stop valve 1483 located in the collection bag (as shown) and/or in the catheter. This may be accomplished by, for example, applying sufficient positive pressure to open backflow stop valve 1490, or by inserting a needle through the valve to apply pressure.

Still referring to FIGS. 68 and 69, a catheter cap 1480 is provided, connected to urine collection bag 1500 via urine tube 1482. Urine tube 1482 may be provided with a urine backflow stop valve 1483 to prevent urine backflow. Catheter cap 1480 may be removably attached to catheter tube 1420 by, for example, threads 1481.

FIGS. 66-69 illustrate a way in which one or more harness anchoring loops 1435 may be routed and contained within an instrument, and within a tube such as, for example, catheter tube 1420. Those skilled in the art will appreciate that other configurations are possible, as are other ways of attaching and detaching anchor heads 710 with a harness strap 1432. Catheter tube 1420 may be constructed from any material that is substantially biocompatible or suitable for use within the human body such as, for example, latex, other suitable polymers, nitinol, or combinations thereof.

Referring to FIGS. 58, 59, 64 and 70, catheter tube 1420 may be located within distal positioner tube 1445 and positioner assembly 1440. The distal end of positioner assembly 1440 may abut harness collar 1433 of harness 1430. Positioner arms 1441 of the positioner assembly 1440 are opened when the distal positioner tube 1445 is driven in a distal direction with respect to catheter tube 1420, compressing positioner assembly 1440 longitudinally against harness collar 1433. Distal positioner tube 1445 may be coupled with the positioner assembly 1440 by, for example, a pin or other suitable attachment mechanism.

Referring to FIGS. 58, 59, 63, 64 and 70, distal positioner tube 1445 may be located within distal anchor driver tube 1450. When the anchor pivot arms 1461 are opened (as shown in FIGS. 58 and 59), the distal anchor driver tube 1450 may be moved to drive the anchor driver assembly 1460 distally (and thus, in use, downward towards the pelvic floor), so as to drive the anchors 700 through the bladder wall 2 and into the pelvic floor 7. Distal anchor driver tube 1450 is coupled with anchor pivot arm yoke 1467 of anchor driver assembly 1460. Anchor pivot arm yoke 1467 may be coupled with the anchor pivot arms 1461 by, for example, pins, or any other suitable means, and biased to swing outwardly by anchor pivot arm springs 1466 or other suitable biasing means. The anchor pivot arms 1461 may be hingeably coupled with an anchor driver pin base 1462 with an affixed anchor driver pin 1463. Pins, or any other suitable attachment means permitting swinging movement, may be used to couple the anchor driver pin base 1462 to the anchor pivot arm 1461, and anchor pivot arm 1461 and driver pin base 1462 may have suitable cooperating shapes that limit the range of relative swinging movement between them to a suitable angle as may be appreciated from FIG. 59. Anchor pivot arm springs 1466 may be included to bias anchor pivot arms 1461 toward an open position shown in FIG. 59. Anchor driver assembly 1460 may be brought to a closed position (shown in FIG. 63), with anchor pivot arms 1461 lying substantially alongside distal positioner tube 1445, by moving anchor closing tube 1220 distally, which correspondingly pushes ribbed flex tube 1325 and anchor closing collar 1330 distally, with respect to distal anchor driver tube 1450, causing anchor closing collar 1330 to contact anchor pivot arms 1461, urge them to a closed position, and then sheath and restrain them. This motion is reversed in order to permit anchor pivot arms 1461 to open.

Distal anchor driver tube 1450 may be substantially coaxially located within curved spine tube 1305. Curved spine tube 1305 functions as a portion of a skeleton, on, in or about which the other components reside and move. It may be desirable for purposes of manipulability and use of the instrument that curved spine tube 1305 be substantially rigid, or somewhat flexible, and it may be formed of nitinol, or any other material having the desired properties.

Still referring to FIGS. 59, 63, 64 and 70, curved spine tube 1305 may be located within flex tube 1325. Flex tube 1325 may be constructed from any suitable material such as, for example, a substantially biocompatible polymer having sufficient flexibility to permit the longitudinal movement of flex tube 1325 over and with respect to curved spine tube 1305. Flex tube 1325 may be provided with ribs, as shown, or other suitable features that impart or increase flexibility. Flex tube 1325 may be affixed at its proximal end to anchor closing tube 1220 via flex tube coupling 1225, and affixed at its distal end to anchor closing collar 1330, by a pin or other suitable attachment means. Anchor closing collar 1330 may be adapted to contact, urge closing of, and sheath and restrain anchor pivot arms 1461. Thus, anchor pivot arms 1461 and thus anchor driver assembly 1460 may be placed in a closed position by moving anchor closing tube 1220 distally, and placed in an open position by moving anchor closing tube 1220 proximally, with respect to distal anchor driver tube 1450.

Figure 55:
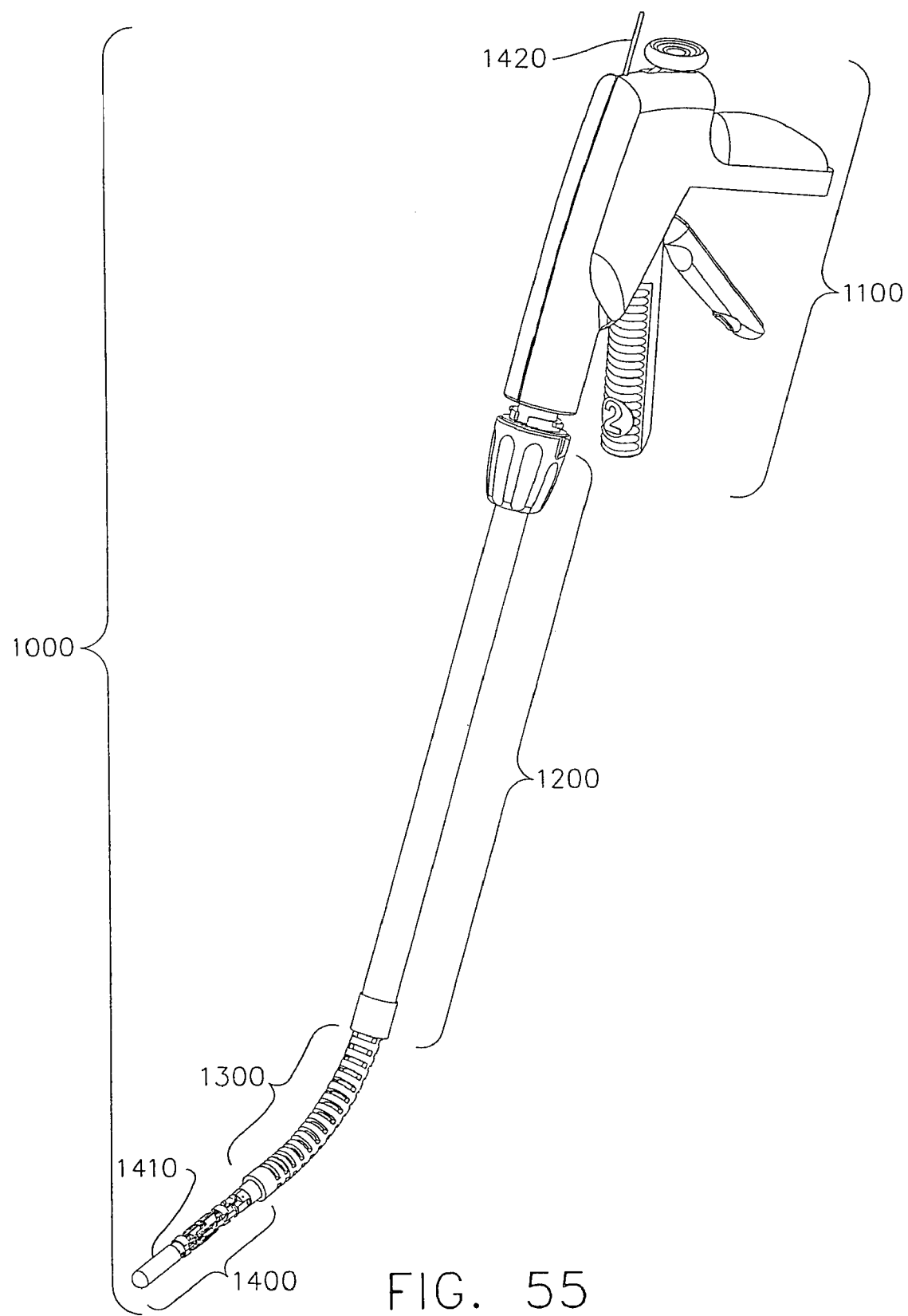
FIG. 55 is a perspective view of an embodiment of an antegrade vesico urethral anastomosis instrument in accordance with the present invention.
Figure 70:
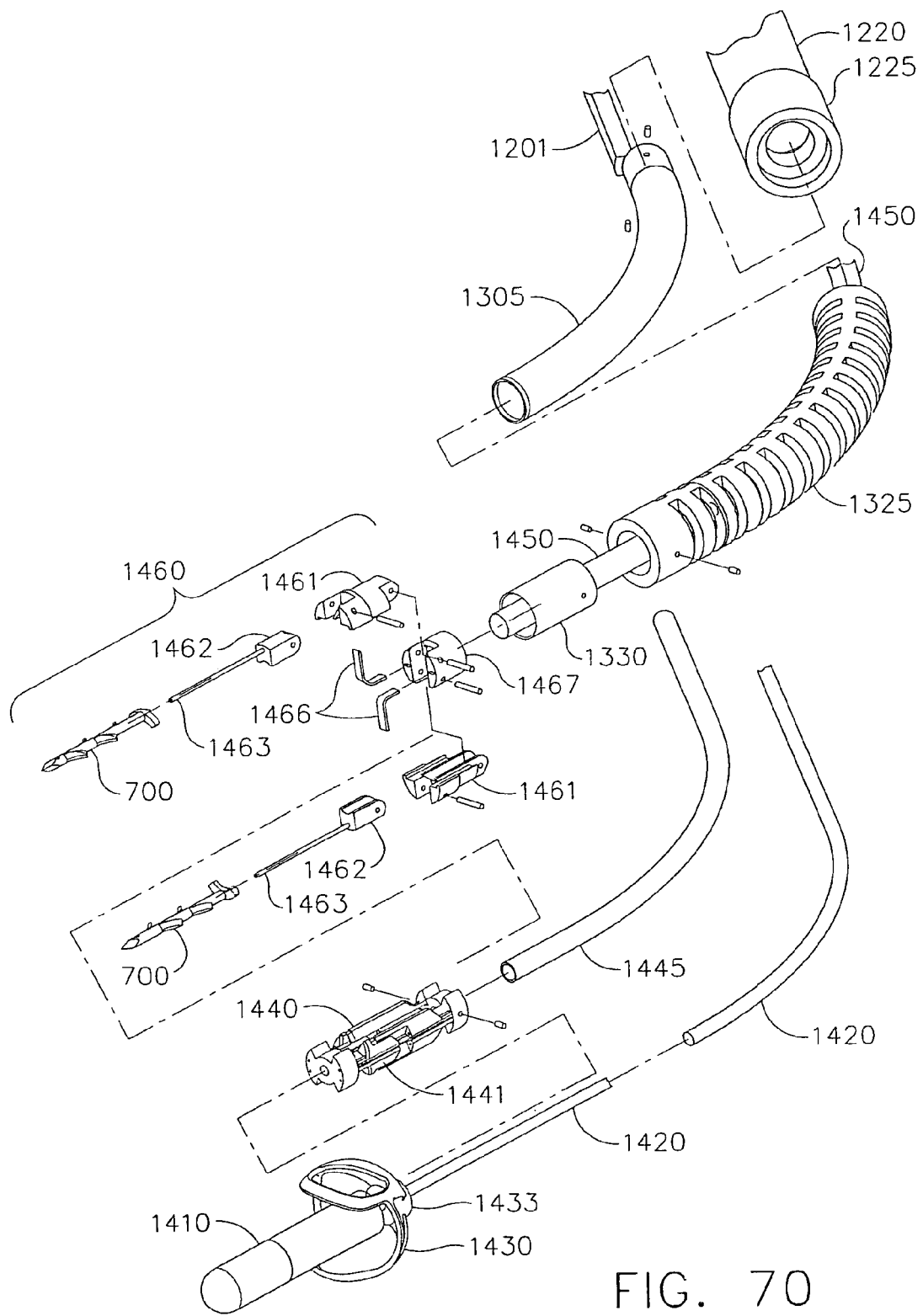
FIG. 70 is an exploded view of an embodiment of an end effector assembly of the instrument shown in FIG. 55.
Figure 71:
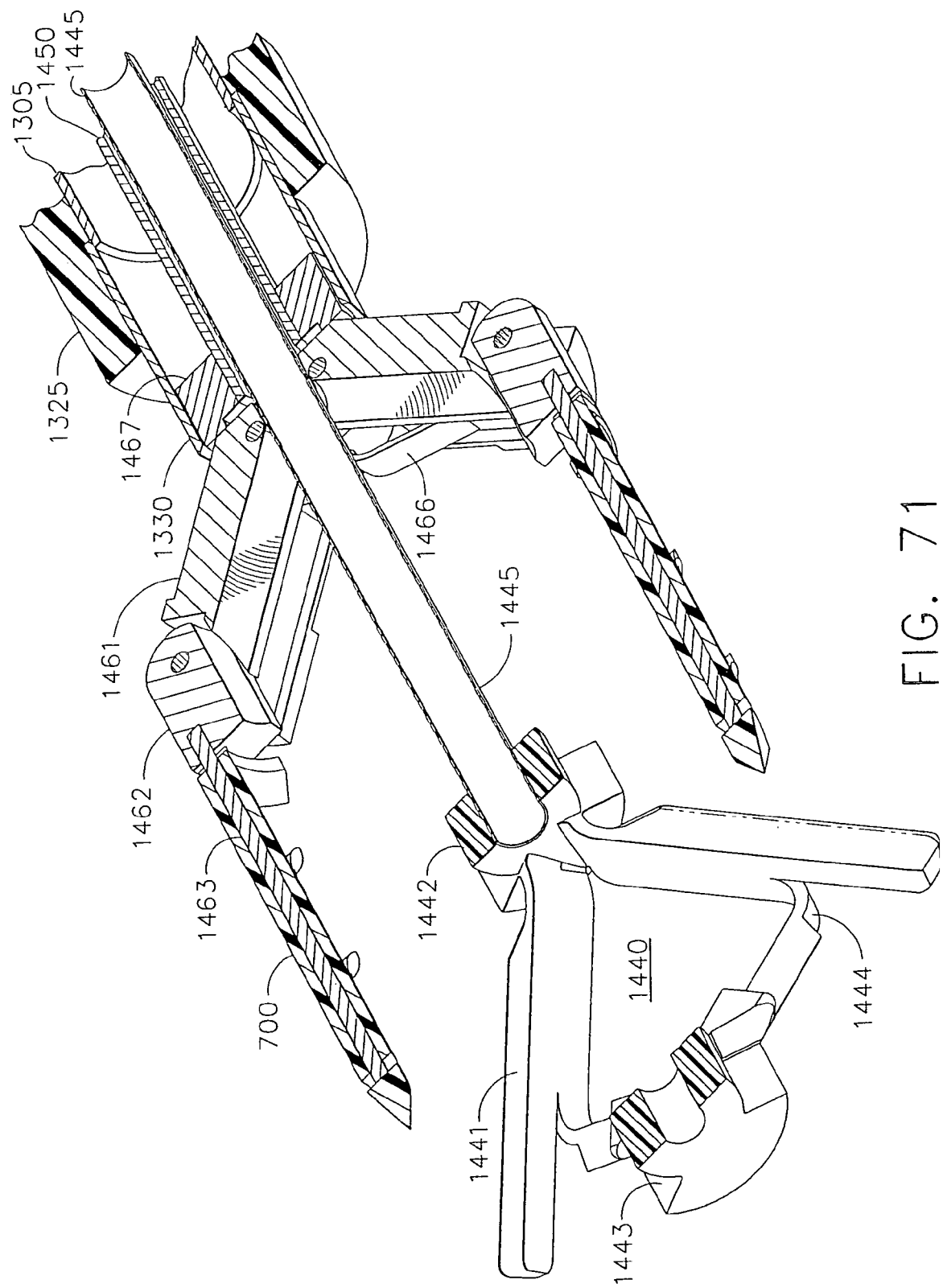
FIG. 71 is a longitudinal and perspective sectional, partial view of an embodiment of an end effector assembly of the instrument shown in FIG. 55, showing an open anchor assembly and partially open positioner assembly.

FIG. 71 is a partial cross-sectional view, taken through the central axis of the distal end of the instrument shown in FIG. 55, illustrating particular exemplary components of the anchor and positioner assemblies of the instrument and the manner in which they may be connected to actuating tubes. Distal positioner tube 1445 is the innermost tube shown in FIG. 71, and terminates at positioner proximal collar 1442, with which it may be made integral by suitable means. Positioner arms 1441 are hingeably affixed to positioner proximal collar 1442 at their proximal ends, and to positioner distal collar 1443 at their distal ends. It will be understood from examination of FIGS. 64 and 70 that catheter tube 1420, not shown in FIG. 71, may be located inside distal positioner tube 1445, positioner distal collar 1442, and positioner proximal collar 1443, when the instrument is completely assembled. It will also be understood from FIGS. 64 and 70 that harness collar 1433 is located on catheter tube 1420 adjacent to positioner distal collar 1443, when the instrument is completely assembled. Referring again to FIG. 71, it can be understood that distal longitudinal movement of distal positioner tube 1445, with respect to and toward harness collar 1433, causes longitudinal compression of positioner assembly 1440 against harness collar 1433, which in turn causes positioner arms 1441 to open outwardly from and transversely to the longitudinal axis of the assembly as shown partially in FIG.

Figure 78:
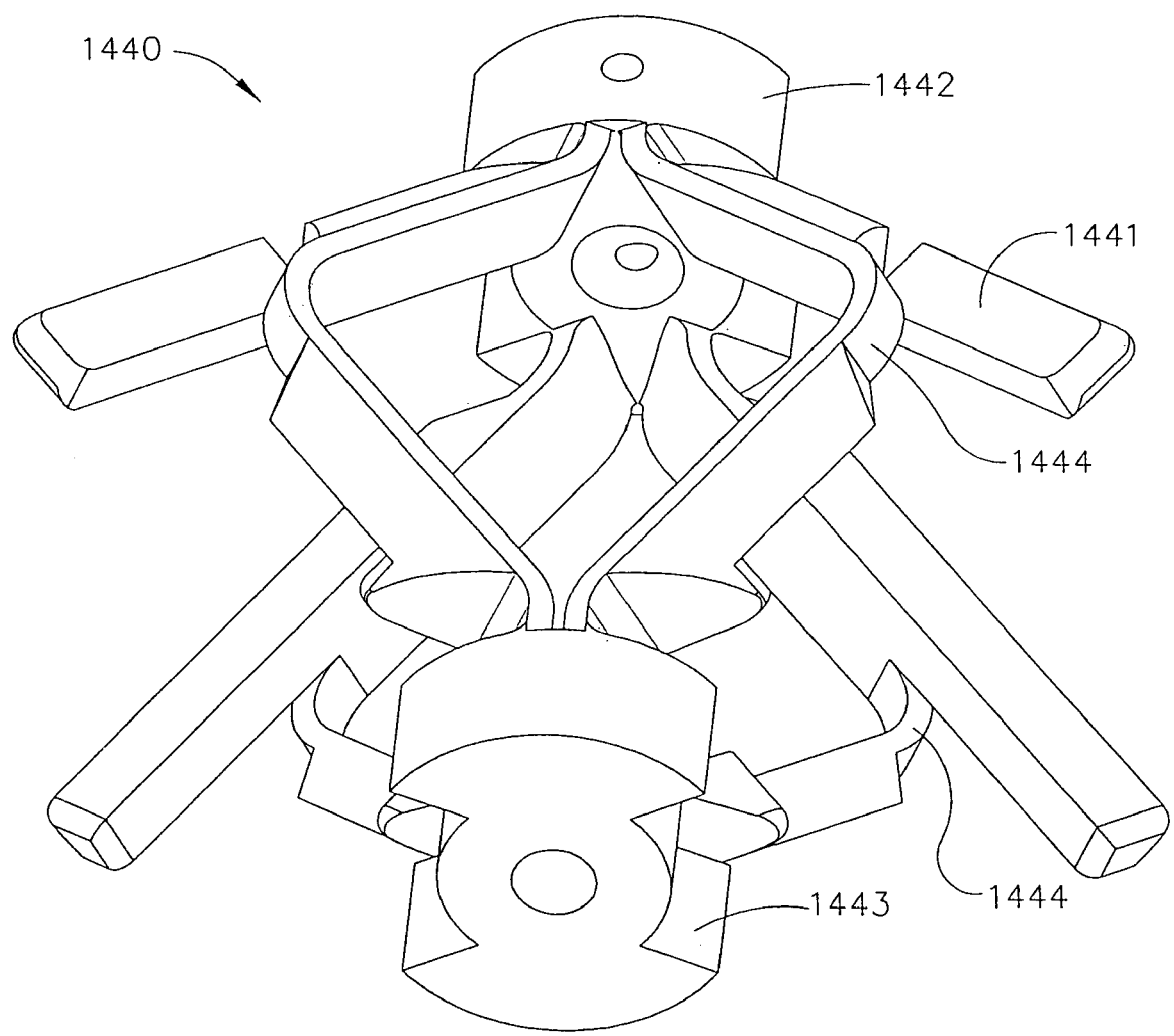
FIG. 78 is a perspective view of a positioner assembly of the instrument shown in FIG. 55, shown partially open.

71, toward fully opened positions that may be seen in FIGS. 58-62. The construction of positioner assembly 1440 in this embodiment may be seen in more detail in FIG. 78. It can be seen that longitudinal compression of positioner assembly 1440 causes positioner arms 1441 to extend outwardly as enabled by their shapes and hinges 1444 between proximal and distal segments of positioner arms 1441. As shown, positioner assembly 1440 may include positioner proximal collar 1442, positioner arms 1441, and positioner distal collar 1443, may be a single unitary part formed of a substantially biocompatible and flexible polymeric material suitable to allow integral hinges 1444 to flex as shown when opening of bladder assembly 1440 is required, and to return to an unflexed position when closing of the positioner assembly 1440 is required.

Referring to FIGS. 58 and 59, in an open position, positioner assembly 1440 is adapted to be useful for catching at bladder opening 4 and urging bladder wall 2 thereabout downwardly into contact with pelvic floor 7. Positioner assembly 1440 may comprise the embodiment shown or any other suitable mechanism that transversely extends one or more members that will catch in bladder opening 4 and be useful for urging the bladder wall downwardly into contact with the pelvic floor, in response to force and movement translated from input from the surgeon at the proximal portion of the instrument, and then retracts or closes such members in response to force and movement translated from input from the surgeon, when it is desired that the mechanism be withdrawn.

Referring again to FIG. 71, distal anchor driver tube 1450 may be affixed to, and integral with, anchor pivot arm yoke 1467. Anchor pivot arms 1461 may be attached to pivot arm yoke 1467 by pins as shown or other suitable means, and biased to swing outwardly by springs 1466. The angle through which anchor pivot arms 1461 may swing outwardly may be restricted by suitably cooperating shapes of pivot arm yoke 1467 and anchor pivot arms 1461. Anchor driver pin bases 1462 may be pivotably attached to anchor pivot arms 1461 by pins as shown or other suitable means. The angle through which anchor driver pin bases 1462 may move with respect to anchor pivot arms 1461 may be restricted by suitably cooperating shapes of anchor pivot arms 1461 and pin bases 1462. Anchor driver pins 1463 are affixed to pin bases 1462 and may be integral therewith.

Anchors 700 may be hollow so as to fit onto anchor driver pins 1463 and be releasably held thereon by friction fit or any other suitable releasable means. Anchors 700 may have hollow bores within, opening at their heads, and extending substantially within their lengths, and driver pins 1463 may extend within such bores substantially the entire lengths thereof, so that the distal ends of driver pins 1463 may apply driving force proximate to the forward ends of anchors 700, so as to prevent anchors 700 from buckling or veering off-direction as they might otherwise do if driven at their rearward ends. When anchors 700 are inserted into tissues, barbs thereon, or any other suitable lodging structures, cause anchors 700 to lodge in the tissues. Following insertion of anchors 700 in tissues, anchor driver pins 1463 may then be retracted from anchors 700 by retracting distal anchor driver tube 1450. It will be appreciated that it may be desirable that distal anchor driver tube 1450 be flexible. Distal anchor driver tube 1450 may be formed from any suitable material such as, for example, nitinol. The anchor pivot arm springs may be for example, leaf springs, or any other suitable biasing device for biasing anchor driver assembly 1460 in an open position when unsheathed by anchor closing collar 1330.

Still referring to FIG. 71, anchor closing collar 1330 may be integrally affixed to the distal end of flex tube 1325. Referring to FIG. 70, the proximal end of flex tube 1325 may be integrally affixed to anchor closing tube 1220 via flex tube coupling 1225. Referring again to FIG. 71, flex tube 1325 and integral anchor closing collar 1330 are not affixed to, and longitudinally movable with respect to, anchor pivot arm yoke 1467 and curved spine tube 1305. Thus, it can be appreciated that distal longitudinal movement of anchor closing tube 1220, with distal anchor driver tube 1450 held stationary, can cause corresponding distal longitudinal movement of anchor closing collar 1330, causing it to contact anchor pivot arms 1461, urge them to a closed position lying substantially alongside distal positioner tube 1445, and sheath and restrain them, in positions that may be seen, for example, in FIGS. 57 and 63. Conversely, moving anchor closing tube 1220 in a proximal direction, with distal anchor driver tube 1450 held stationary, pulls anchor closing collar 1330 up and off anchor pivot arms 1461, allowing them to spring to an opened position shown, for example, in FIGS. 58 and 71.

Distal positioner tube 1445 and distal anchor driver tube 1450 are not affixed to one another, and therefore, may be longitudinally moved with respect to each other. This enables, for example, distal anchor driver tube 1450 to be moved distally while distal positioner tube is stationary, as would occur when anchors 700 are being driven through a bladder wall held stationary and in contact with a pelvic floor, by positioner assembly 1440.

Figure 72:
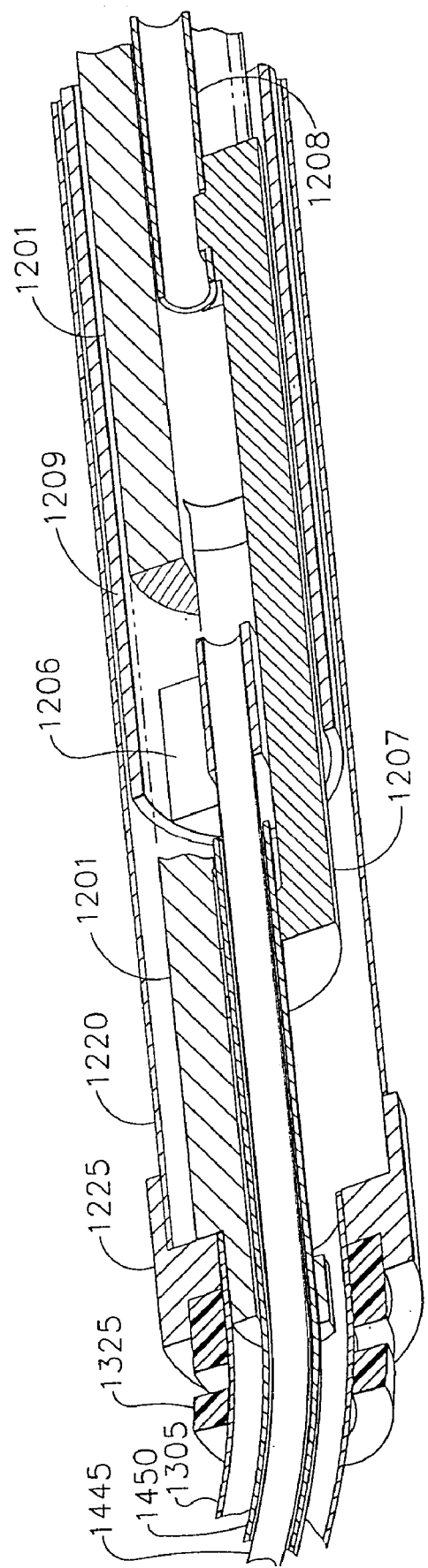
FIG. 72 is a longitudinal and perspective sectional view of a transitional tube portion of an anastomosis instrument such as shown in FIG. 55, showing exemplary linkages for actuator tubes.
Figure 73:
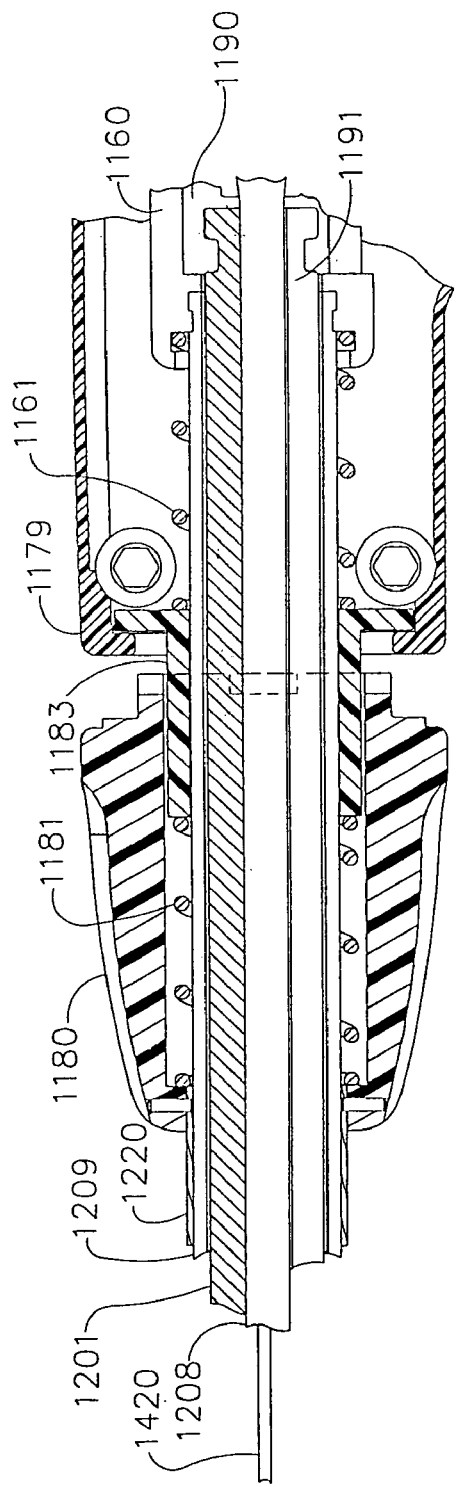
FIG. 73 is a longitudinal cross-sectional view of a closing tube latching collar portion of the instrument shown in FIG. 55, in a closed position.
Figure 74:
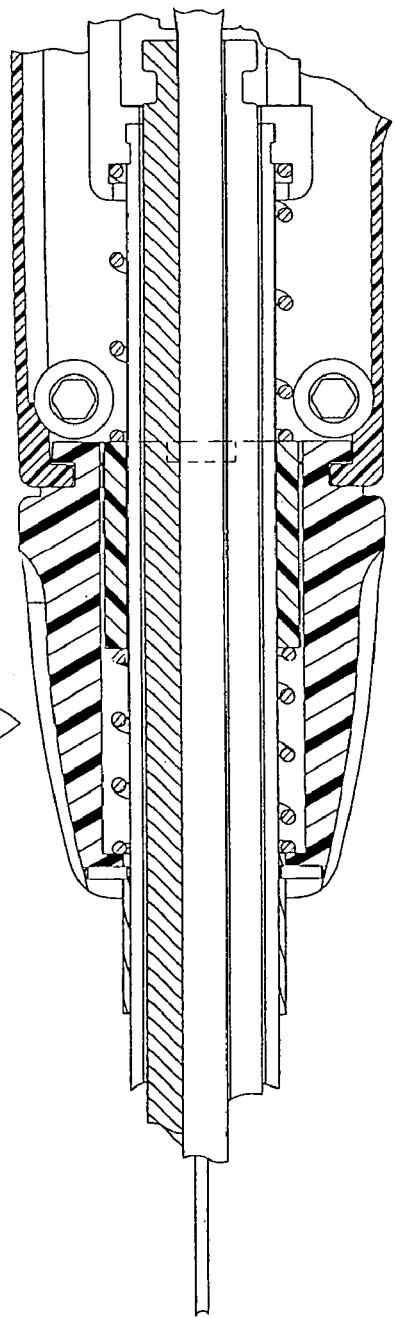
FIG. 74 is a longitudinal cross-sectional view of a closing tube latching collar portion of the instrument shown in FIG. 55, in an open position.
Figure 79:
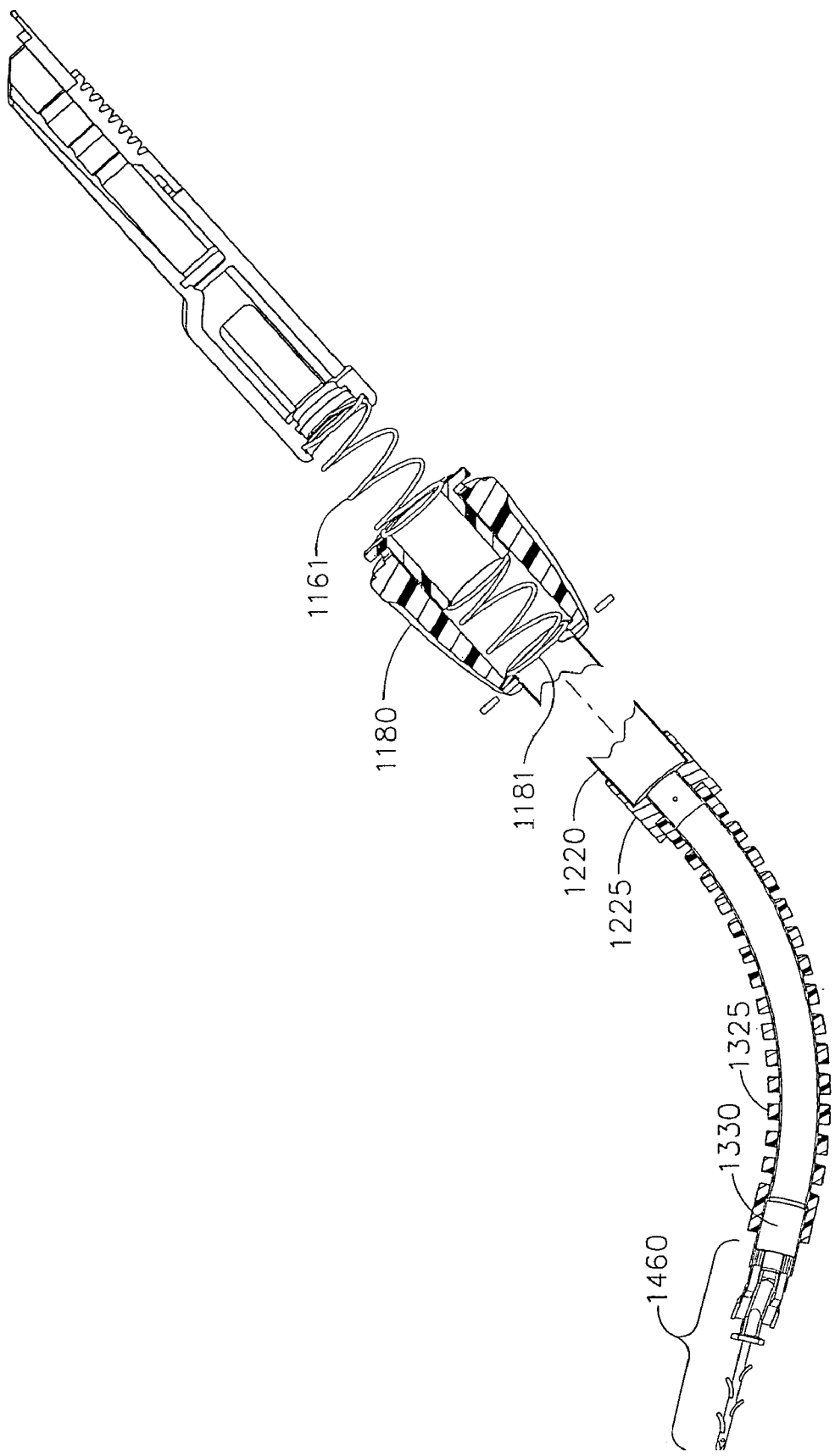
FIG. 79 is a sectional view of an anchor assembly and connected portions of the handle assembly shown in FIG. 55, showing the components involved in opening and closing the anchor assembly.

FIG. 72 illustrates an exemplary configuration of a transition assembly that can be effective for translating relative force and movement of/between actuating members of a handle assembly 1100 to actuating members of an end effector assembly 1400, such as shown in FIG. 55. Distal positioner tube 1445 is integral with positioner tube coupling 1206, which is in turn integral with straight positioner tube 1209, which is operatively connected with handle assembly 1100 as may be seen in FIGS. 55, 72 and 77. Thus, longitudinal force and movement in straight positioner tube 1209 effected by the handle assembly is directly translated to distal positioner tube 1445 via positioner tube coupling 1206. Referring again to FIG. 72, distal anchor driver tube 1450 is integral with anchor driver tube coupling 1207, which is in turn integral with straight anchor driver tube 1208, which is operatively connected to handle assembly 1100 as may be seen in FIGS. 55, 72 and 81. Thus longitudinal force and movement in straight anchor driver tube coupling 1207 effected by the handle assembly is directly translated to distal anchor driver tube 1450 via anchor driver tube coupling 1207. Referring to FIGS. 72 and 82, curved spine tube 1305 is integral with spine 1201, which is in turn integral with handle housing 1101, and thus curved spine tube 1305, spine 1201 and handle housing 1101 form the instrument's relative stationary skeleton about which the actuating components move. As may be seen in FIGS. 73 and 74, spine tube 1201 may be integrally fitted and affixed to the handle housing by a spine retainer structure 1190 or other suitable structure integral with the handle housing. Finally, still referring to FIG. 72, and also FIGS. 55 and 79, flex tube 1325 is integral with flex tube coupling 1225 and anchor closing tube 1220, which is operatively connected to handle assembly 1100. Thus, longitudinal force and movement in anchor closing tube 1220 effected by the handle assembly is directly translated to flex tube 1325 and thus anchor closing collar 1330. It will be apparent to a person of ordinary skill in the art that the configuration of components illustrated in FIG. 72 is only an example by which force and movement in components effected by a handle assembly may be translated to components in an end effector, and that this translation may be accomplished in a variety of ways in accordance with the present invention.

FIG. 82 depicts an exemplary structure that may be incorporated into the instrument to provide a skeletal ("ground") structure about which other components move and are actuated, and which can provide a structure to support manipulation of the entire instrument as a unit. As previously noted, curved spine tube 1305 is integral with spine 1201. Spine 1201 is integral with handle housing 1101. These three components are, thus, substantially integral. Housing 1101 may be molded or formed of a suitable rigid polymeric material. It may be desirable that spine 1201 and curved spine tube 1305 be substantially rigid, and have suitable stiffness and strength to support exertion of manipulative forces by the surgeon upon the instrument necessary to insert the instrument into a patient's abdomen, locate the bladder opening, urge the bladder into contact with the pelvic floor, and hold the bladder in contact with the pelvic floor during actuation of the instrument to drive anchors. Spine 1201 and curved spine tube 1305 may be formed of stainless steel, nitinol or any other suitable material. Curved spine tube 1305 may be affixed or joined to spine 1201 by any suitable means including but not limited to pins, welding, press fitting, cooperating threads, adhesives, etc. Spine 1201 may be affixed or joined to housing 1101 by any suitable means.

Figure 80:
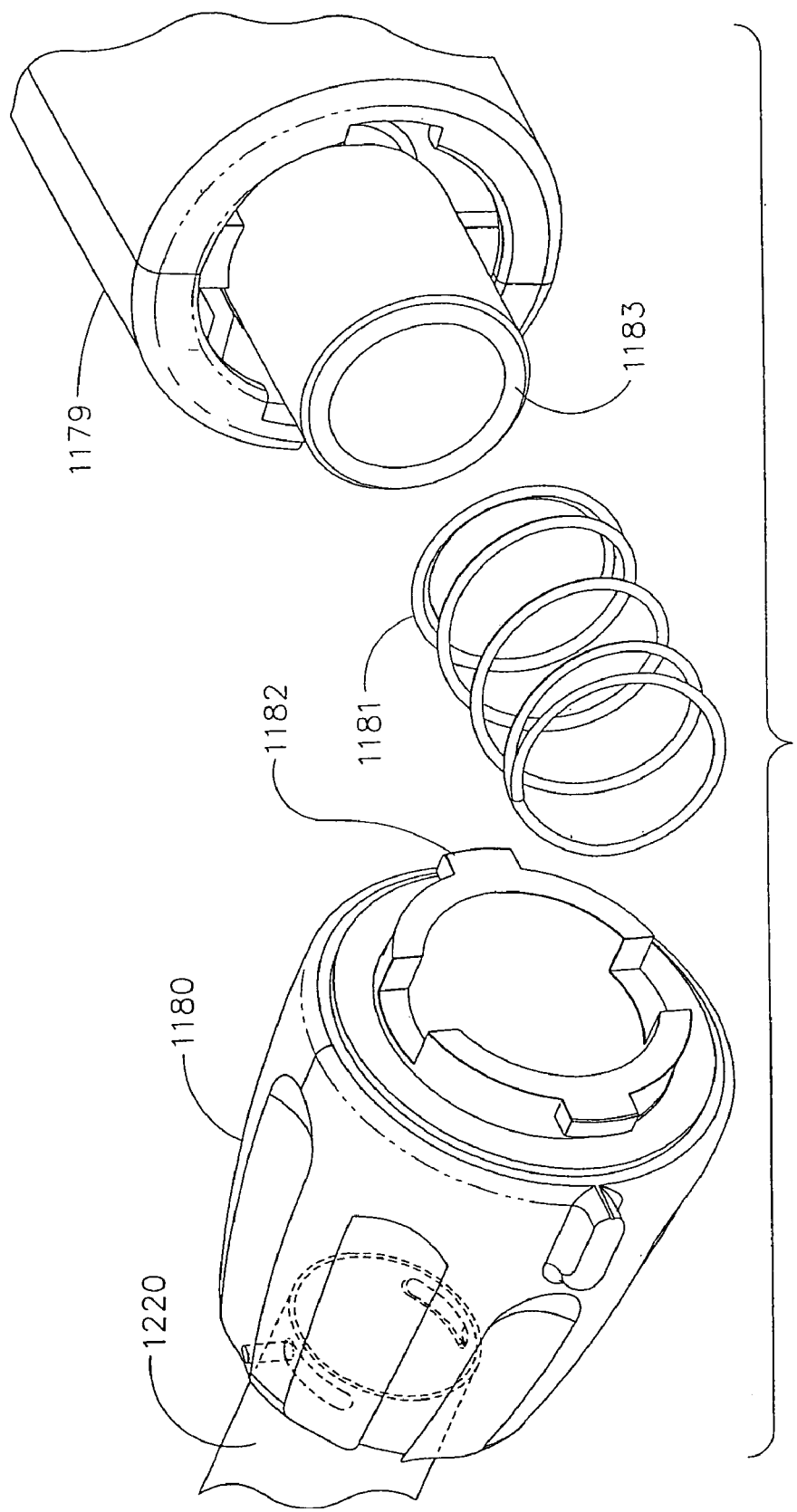
FIG. 80 is an exploded perspective view of a closing tube latching collar, and associated components, of the instrument shown in FIG. 55.

FIGS. 73, 74, 79 and 80 illustrate an exemplary mechanism that may be incorporated into a handle assembly, by which an anchor closing tube 1220 may be alternately, selectively, longitudinally moved in proximal or distal directions and held so as to alternatively, selectively, open or close an anchor assembly to alternate positions shown, for example, in FIGS. 57 and 58. Anchor closing tube 1220 may be coupled with closing tube latching collar 1180 by pins as shown in FIG. 80 or any other suitable means so that the two components move together longitudinally as a unit. Closing tube latch base 1179 may be integral with handle housing 1101, and thus may be part of the instrument's skeleton. Closing tube latching collar 1180 freely rides upon closing tube spindle 1183, which assures suitable alignment of closing tube latching collar with latch base 1179, and supports a proximal end of closing tube spring 1181. Closing tube latching collar 1180 includes latch members 1182 adapted to interact with cooperating features of closing tube latch base 1179 so as to alternately, selectively, be pushable proximally and rotatable to latch and be longitudinally restrained within latch base 1179 in the position shown in FIG. 74, or rotatable to unlatch and be released from latch base 1179 to assume the position shown in FIG. 75. When in a position released from latch base 1179, closing tube latching collar 1180 is biased toward a distal position by closing tube spring 1181. Closing tube latching collar 1180 may be restrained from disassociating distally from closing tube spindle 1183 may be cooperating rims or lips or any other suitable means (not shown). Thus, it can be appreciated that by the exemplary configuration of components shown, anchor closing tube 1220 is biased in a distal position (thus, biasing anchor closing collar 1330 in a distal position holding anchor driver assembly 1460 in a closed position through exemplary mechanisms described above) by closing tube spring 1181. When the surgeon wishes to open the anchor assembly, he or she may push closing tube latching collar 1180 proximally with respect to the handle housing until closing tube latching members 1182 engage with cooperating features of closing tube latch base 1179, and then turn closing tube latching collar 1180 to latch into closing tube latch base 1179. This pulls anchor closing tube 1220 proximally, pulling anchor closing collar 1330 proximally to release the anchor pivot arms into an opened position.

Figure 75:
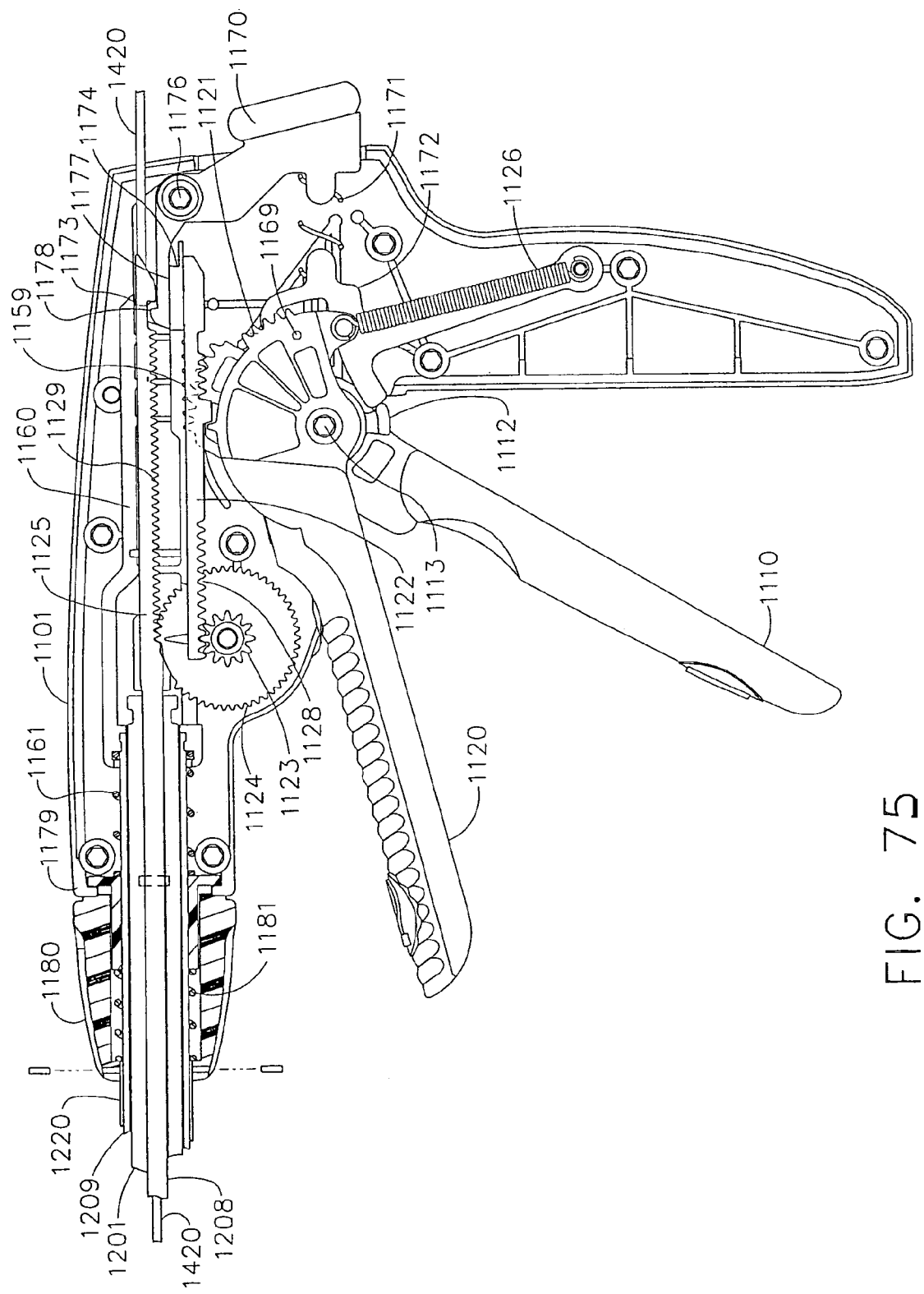
FIG. 75 is a side cross-sectional view of an embodiment of a handle assembly of the instrument shown in FIG. 55.
Figure 76:
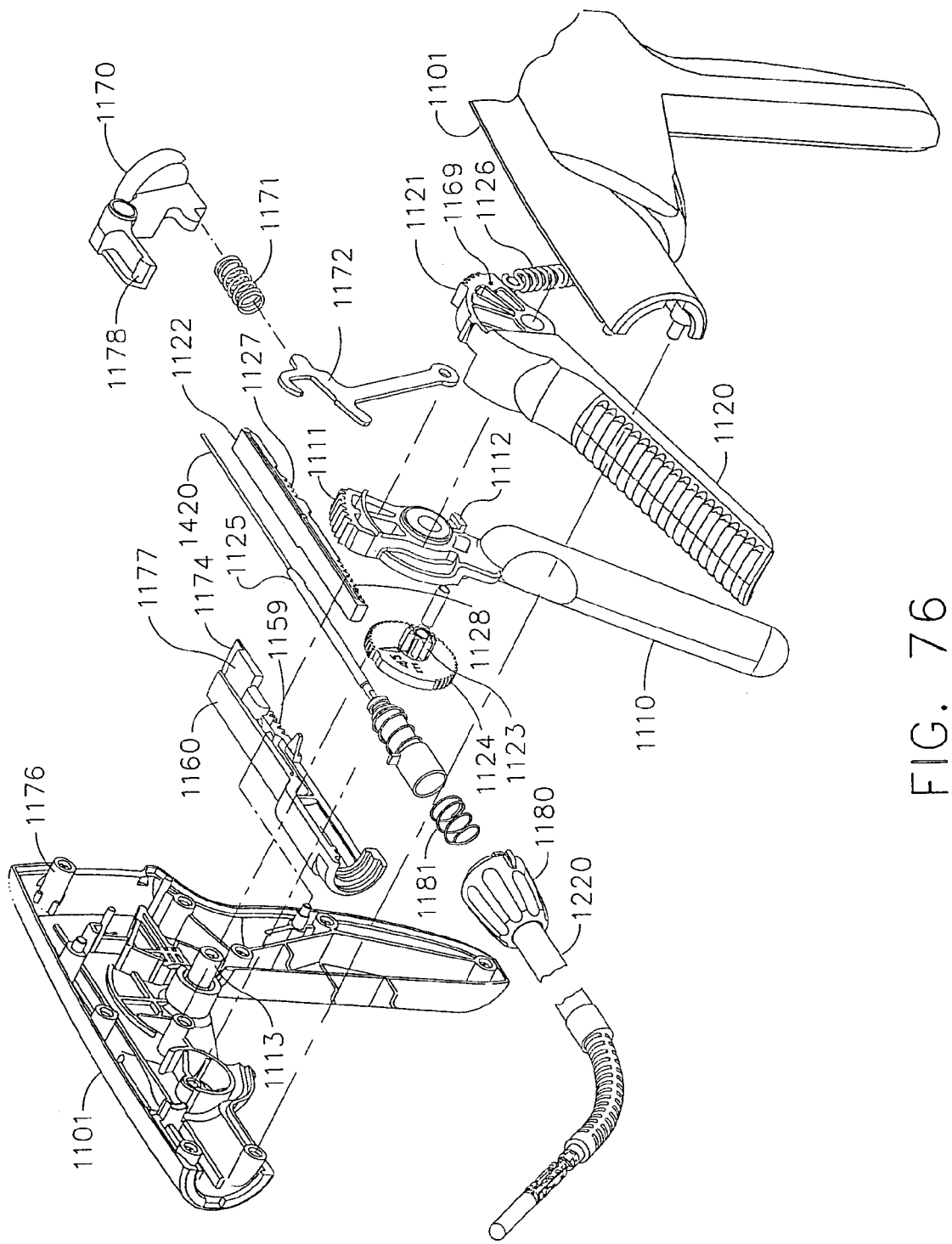
FIG. 76 is an exploded perspective view of the handle assembly shown in FIG. 75.
Figure 77:
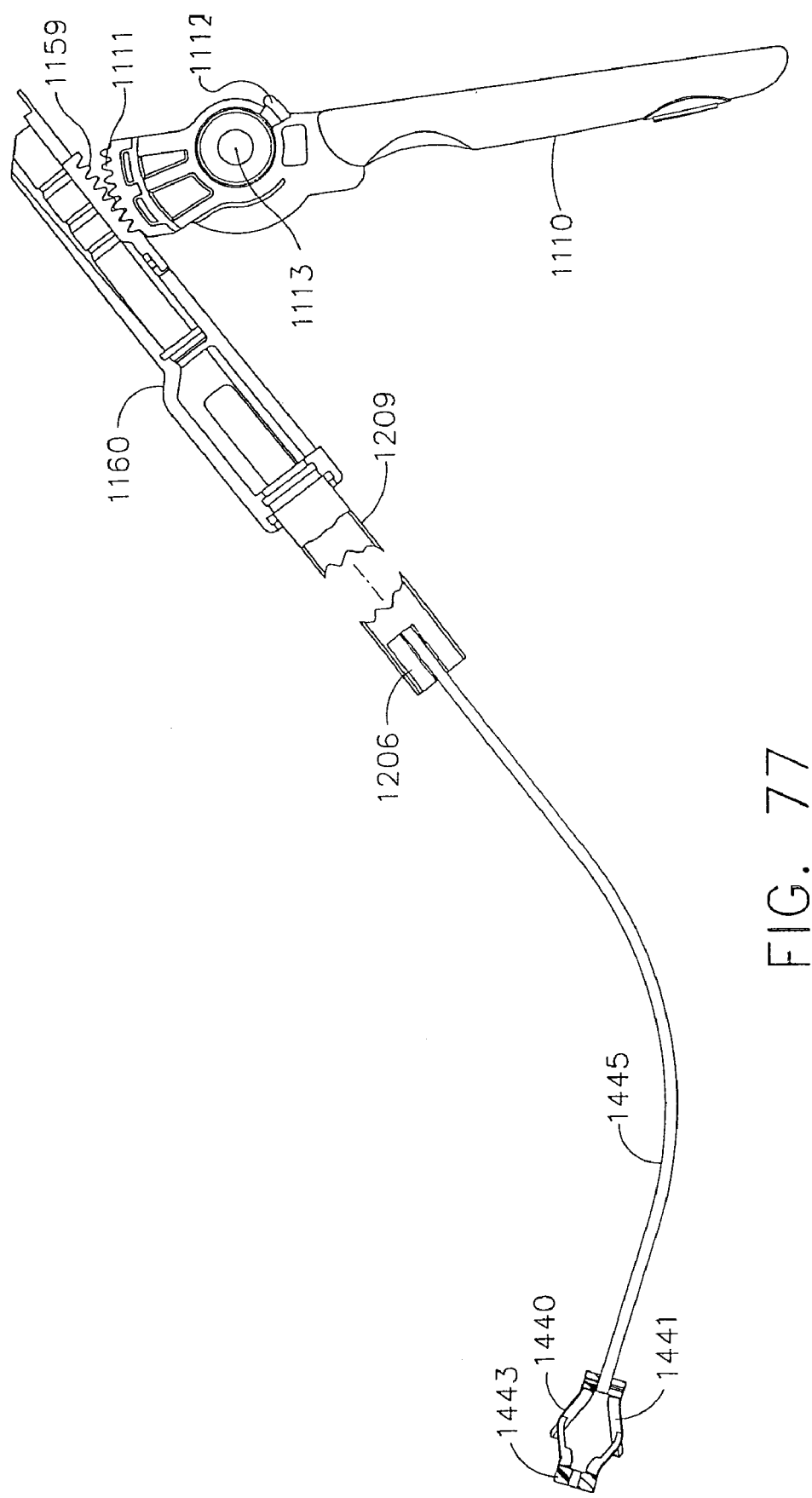
FIG. 77 is a sectional view of a positioner assembly and connected portions of the handle assembly shown in FIG. 55, showing the components involved in the operation of the positioner assembly.

FIGS. 75-77 illustrate an exemplary mechanism that may be incorporated into the instrument to effect and translate force and movement to open and hold open a positioner assembly in accordance with the present invention. Positioner lever 1110 is pivotably mounted on, and may pivot about, axle 1113 which is integral with housing 1101. Positioner lever 1110 has a longer portion and a shorter portion; the shorter portion has thereon positioner lever teeth 1111. Positioner tube actuator rack 1160 rides longitudinally between guides or a track integral with housing 1101, and is longitudinally movable proximally and distally. positioner tube actuator rack 1160 has teeth 1159 thereon. Positioner lever 1110 and positioner tube actuator rack 1160 are situated such that positioner tube actuator rack teeth 1159 and positioner lever teeth 1111 are enmeshed. Thus, with respect to FIGS. 75-77, it can be appreciated that counterclockwise angular movement of positioner lever 1110 about axle 1113 is translated to distal linear movement of positioner tube actuator rack 1160, and vice versa. The distal end of positioner tube actuator rack 1160 may be coupled with straight positioner tube 1209 by cooperating rims or lips forming an annular collar or other suitable means, such that the two parts move longitudinally together as a unit, and straight positioner tube 1209 may be made integral with distal positioner tube 1445 via positioner tube coupling 1206 as previously described. Thus, it can be appreciated that when a surgeon holding handle assembly 1100 pulls or squeezes positioner lever 1110, distal positioner tube 1445 is urged distally. Referring to FIG. 77, it can be appreciated that when the entire instrument is assembled and positioner distal collar 1443 is restrained distally by a balloon assembly (see, e.g., FIGS. 56, 57), distal longitudinal movement of distal positioner tube 1445 causes longitudinal compression of positioner assembly 1440, which causes positioner arms 1441 to open outwardly of the longitudinal axis, and vice versa. Positioner tube spring 1161, in compression, biases positioner tube actuator rack 1160 toward a proximal position. Thus, it can be appreciated from FIG. 77 that as a result, distal positioner tube 1445 is biased in a proximal position, allowing positioner arms 1441 and positioner assembly 1440 to assume a closed position. Driver/positioner locking lever 1170 is pivotably mounted on and pivots about pin 1176, which may be integral with housing 1101, and is biased by spring 1171, in compression, in a counterclockwise direction (with respect to FIG. 75). Driver/positioner locking lever 1170 comprises a driver/positioner locking latch 1178. When the handle assembly is assembled and ready for use, a lower surface of driver/positioner locking latch 1178 rests upon and is urged against an upper surface of the proximal end 1177 of positioner tube actuator rack 1160. As positioner lever 1110 is pulled or squeezed in counterclockwise direction (with respect to FIG. 75), moving positioner tube actuator rack 1160 distally as previously described, a notch 1174 at the proximal end 1177 of positioner tube actuator rack 1160 moves beneath locking latch 1178 of driver/positioner locking lever 1170, and locking latch 1178 moves into notch 1174 by urging of spring 1171. This locks actuator rack 1160 into a distal position. As a result, as may be appreciated from FIG. 77, positioner arms 1441 and positioner assembly 1440 may be locked into an opened position. In order to then close positioner assembly 1440, the surgeon may depress driver/positioner locking lever 1170, which lifts locking latch 1178 out of notch 1174, permitting positioner tube actuator rack 1160 to return to a proximal position under urging of spring 116 1.

Figure 81:
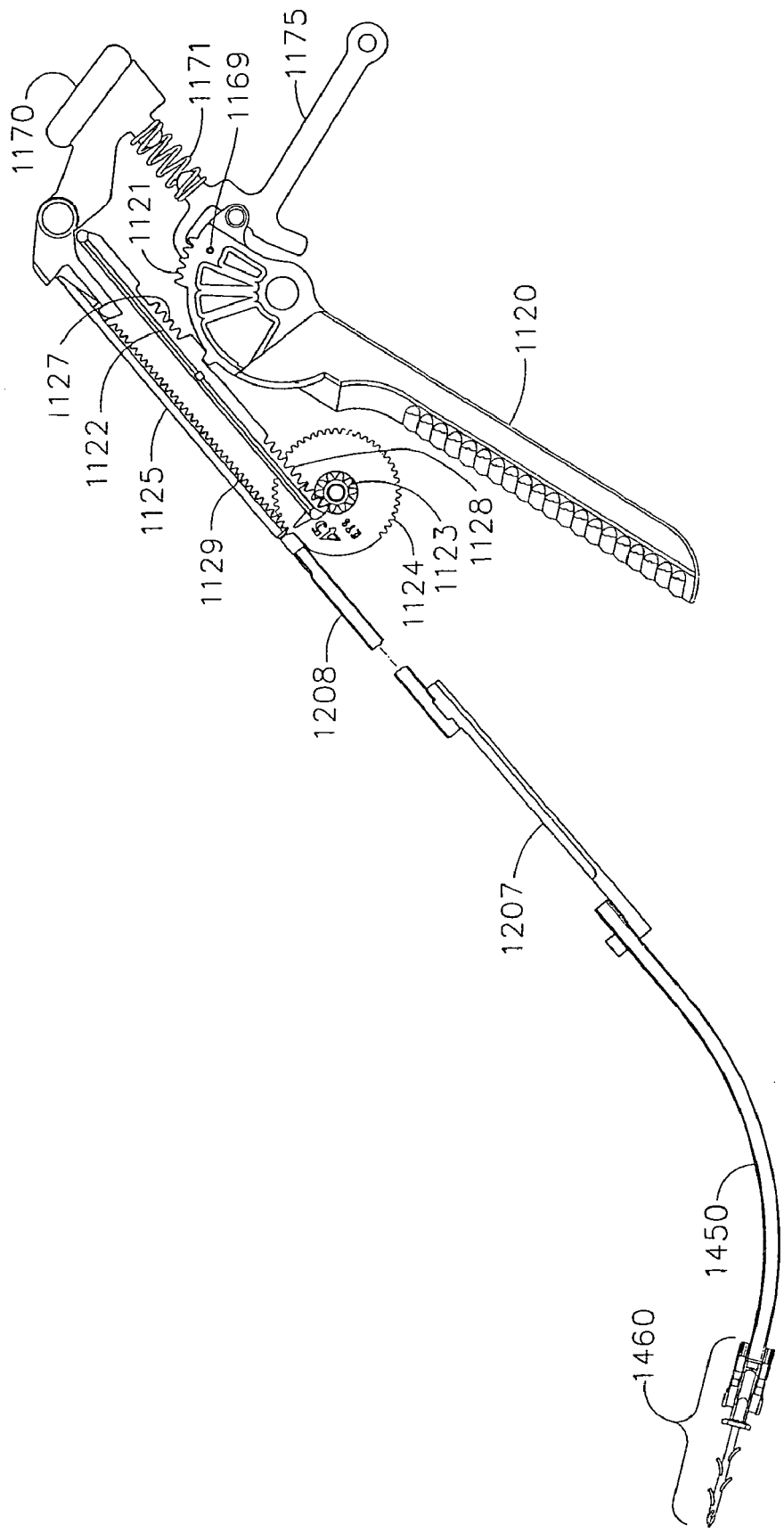
FIG. 81 is a sectional view of an anchor assembly and connected portions of the handle assembly shown in FIG. 55, showing the components involved in driving anchors.
Figure 82:
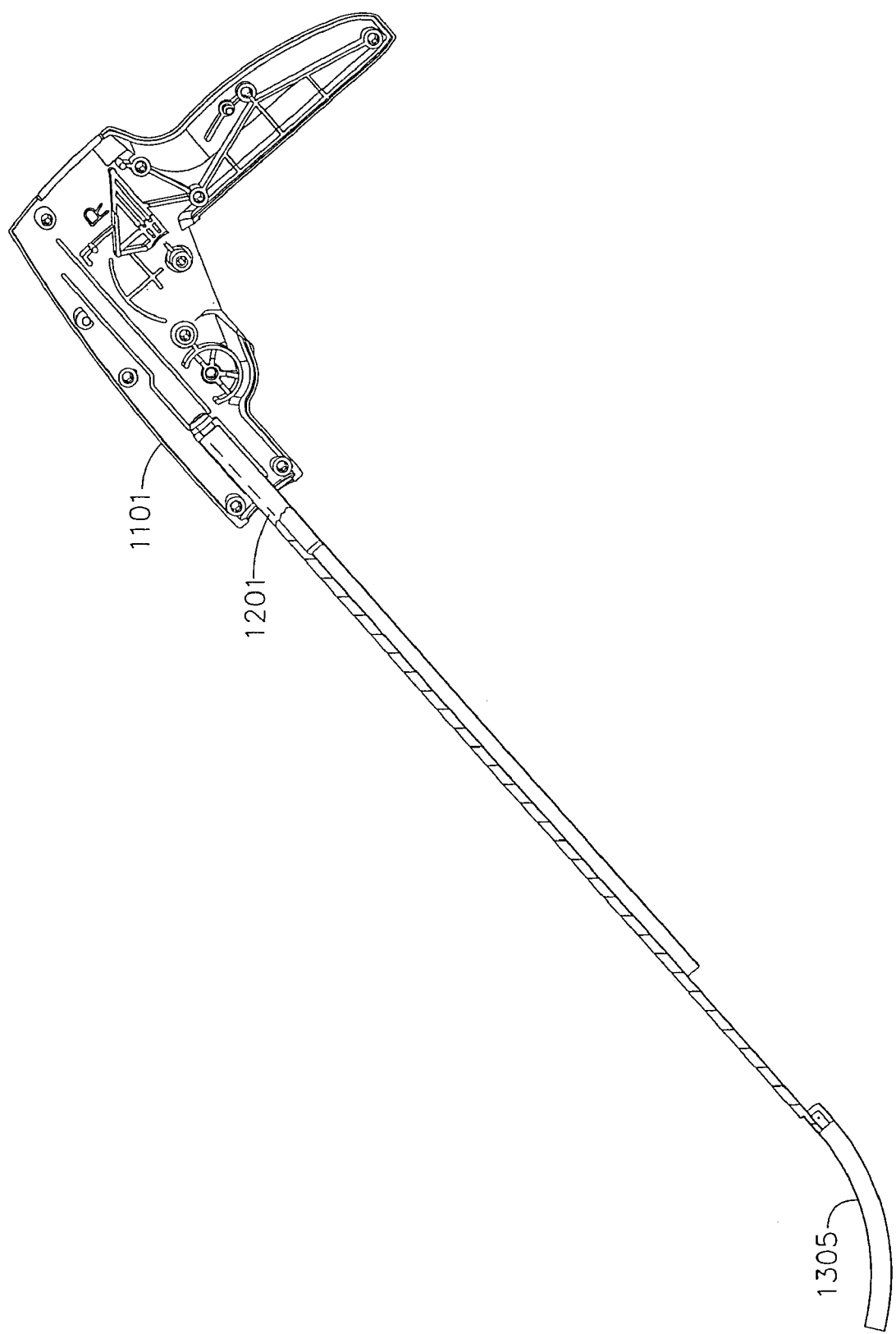
FIG. 82 is a sectional view of a curved spine tube and connected portions of the handle assembly shown in FIG. 55, showing a fixed, skeletal structure of the instrument.

FIGS. 75, 76 and 81 illustrate an exemplary mechanism that may be incorporated into the instrument to effect and translate force and movement to drive an anchor assembly in accordance with the present invention. Anchor driver lever 1120 is pivotably mounted on, and may pivot about, axle 1113 which is integral with housing 1101. Anchor driver lever 1120 has a longer portion and a shorter portion; the shorter portion has thereon anchor driver lever teeth 1121. Anchor driver intermediate rack 1122 rides longitudinally between guides or a track integral with housing 1101, and is longitudinally movable proximally and distally. Anchor driver intermediate rack 1122 has proximal teeth 1127 and distal teeth 1128 thereon. Anchor driver lever 1120 and anchor driver intermediate rack 1122 are situated such that anchor driver intermediate rack proximal teeth 1127 will engage anchor driver lever teeth 1121 when anchor driver lever 1120 is moved counterclockwise through a suitable angle (with respect to FIG. 75). Small anchor driver pinion 1123 and large anchor driver pinion 1124 are integral, and rotate about a pin supported by bosses in housing 1101. Small anchor driver pinion 1123 and anchor driver intermediate rack are situated such that small anchor driver pinion 1123 is enmeshed with anchor driver intermediate rack distal teeth 1128. Anchor driver rack 1125 rides longitudinally between guides or a track integral with positioner tube actuator rack 1160, and a length and a distal end of anchor driver rack 1125 may extend into and be supported within spine 1201 as may be seen in FIG. 75. Anchor driver rack 1125 has anchor driver teeth 1129 thereon. Anchor driver rack 1125 and anchor driver lever 1120 are situated such that anchor driver teeth 1129 are enmeshed with large anchor driver pinion 1124. The distal end of anchor driver rack 1125 is affixed by any suitable means to straight anchor driver tube 1208. Thus, it may be appreciated from the foregoing, and examination of FIGS. 75, 76 and 81, that moving anchor driver lever 1120 so as to cause it to rotate counterclockwise (with respect to FIGS. 75 and 81) to the point where driver lever teeth 1121 mesh with proximal teeth 1127 on intermediate driver rack 1122, will drive intermediate driver rack 1122 distally, which in turn, will cause small anchor driver pinion and large anchor driver pinion 1123 and 1124 to rotate counterclockwise, which, in turn, will drive anchor driver rack 1125, straight anchor driver tube 1208, anchor driver tube coupling 1207, distal anchor driver tube 1450, and thus, anchor driver assembly 1460, distally. As may be appreciated from, for example, FIGS. 59 and 60, when the instrument is fully assembled and being used, this distal movement of anchor driver assembly 1460 drives anchors 700 into the tissues.

Positioner lever 1110 and anchor driver lever 1120 abut one another in side-by-side relationship, and both are mounted upon and pivot about axle 1113. Positioner lever 1110 and anchor driver lever 1120 are formed so as to have cooperating features where they abut, such that counterclockwise movement of positioner lever 1110 effects corresponding counterclockwise movement of anchor driver lever 1120 (with respect to FIG. 75). Driver lever spring 1126, in tension, is connected between a hook or other suitable attachment point in housing 1101 and an attachment point on the shorter portion of anchor driver lever 1120 as shown. Thus, anchor driver lever 1120 is biased in a clockwise direction (with respect to FIG. 75).

Additionally, anchor driver lever 1120 is prevented from being depressed prior to activation of anchor positioner lever 1110. Driver lever locking hook 1172 is pivotably mounted on and may rotate about a pin supported in housing 1101 as shown, and is biased in a counterclockwise direction by spring 1171 in compression, such that it hooks over a pin 1169 transversely protruding from the shorter portion of anchor driver lever 1120 at the position shown, preventing driver lever 1120 from moving counterclockwise (the pin is not directly shown; it protrudes from the back side of the component with respect to FIG. 75). However, when positioner lever 1110 is depressed, locking hook release member 1112 thereon engages locking hook 1172 and urges it in a clockwise direction (with respect to FIG. 75), which causes it to disengage from pin 1169, thereby releasing anchor driver lever 1120 so that it may move in a counterclockwise direction.

Additionally, when the instrument is ready for use, but prior to deployment, anchor driver rack 1125 (and thus, anchor driver assembly 1460) is locked in a proximal position, by engagement of locking latch 1178 of driver/positioner locking lever 1170, with driver rack notch 1173. When actuation of the instrument is begun by pulling and thereby rotating positioner lever 1110 counterclockwise, moving positioner tube actuator rack 1160 distally as previously described, a notch 1174 at the proximal end 1177 of positioner tube actuator rack 1160 moves beneath locking latch 1178 of driver/positioner locking lever 1170, and locking latch 1178 moves into notch 1174 by urging of spring 1171. As locking latch 1178 moves into notch 1174, it moves out of driver rack notch 1173, releasing driver rack 1125 so that it may be driven by pulling anchor driver lever 1120 as previously described.

Thus, it may be appreciated from the above description and from FIGS. 73-82, that when the instrument is assembled and made ready for use, positioner assembly 1440 is in a closed position, and anchor driver assembly 1460 is held closed by anchor closing collar 1330 and locked in a proximal position with respect to positioner assembly 1440, placing the instrument in position to facilitate insertion into the patient. After insertion of the instrument into proper position within the patient with the end effector assembly within a lumen, actuation may be commenced by pulling positioner lever 1110 to the position in which it opens positioner assembly 1440 and is locked in such position by driver/positioner locking lever 1170 under urging of spring 1171. When driver/positioner locking lever 1170 locks positioner lever 1110, it simultaneously unlocks anchor driver rack 1125 by disengaging driver positioner locking latch 1178 from driver rack notch 1173, freeing anchor driver rack 1125 to be driven in a distal direction. Anchor driver assembly 1460 may then be opened by pulling closing tube latching collar 1180 distally until it engages latch base 1179, and rotating latching collar 1180 to latch into latch base 1179. Anchor driver rack may then be driven in a distal direction (to drive anchors) by pulling anchor driver lever 1120. After anchors are driven, spring 1126 in tension urges anchor driver lever 1120 to return, thus causing anchor driver rack 1125 and correspondingly anchor driver assembly 1460 to return to their original proximal positions (and pulling anchor driver pins out of anchors installed into tissues). Anchor driver assembly 1460 may then be returned a closed position by rotating and disengaging closing tube latching collar 1180 from latch base 1179, which allows latching collar 1180 to return to its distal position urged by spring 1181, moving closing collar 1330 distally and causing it to close anchor driver assembly 1460. Finally, positioner assembly 1440 may be closed by depressing driver/positioner locking lever 1170, which lifts driver/positioner locking latch 1178 from notch 1174 in the proximal end 1177 of positioner tube actuator rack 1160, allowing positioner tube actuator rack 1160 to return to a proximal position under urging of positioner tube spring 1161, closing positioner assembly 1440. Thus, the instrument is returned to a closed position ready for withdrawal from the patient.

Referring to FIGS. 55, 64, 65 and 75, it may be appreciated that catheter tube 1420 may be routed through handle assembly 1100, and through the entire instrument, to balloon assembly 1410, where it may be affixed to harness collar 1433. In one embodiment the catheter tube 1420 may extend proximally through the handle housing 1101 and out of the rear of the instrument 1000 as shown in FIG. 75. Anchor driver rack 1125 may be hollow, or may have a channel and "U"-shaped cross-section, and driver/positioner locking lever 1170 and handle housing 1101 may have suitable holes or other features, to accommodate passage of catheter tube 1420 therethrough. When the instrument is readied for use to install anchors, catheter tube 1420 may be releasably gripped at or within handle assembly 1110 by any suitable means so as to be held stationary with respect to handle housing 1101, placing it in tension with respect to positioner assembly 1440 when positioner assembly 1440 is longitudinally compressed against harness collar 1433 to cause positioner assembly 1440 to open. After the instrument has been actuated to drive anchors and returned a closed position, catheter tube 1420 may then be released to permit withdrawal of all components except for catheter tube 1420 and balloon assembly 1410, for use in completing the anastomosis procedure as described above.

Levers 1110, 1120 and 1170 and positioner tube actuator rack 1160 may be formed of any material having suitable properties of strength, stiffness and formability or moldability, including polymeric materials.

Small anchor driver pinion 1123, large anchor driver pinion 1124, anchor driver intermediate rack 1122, anchor driver rack 1125, positioner tube actuator rack 1160 and driver lever locking hook 1172 may be made of any material having suitable strength for small mechanical components, including steel or high-strength polymers.

The above-described embodiment is only one example describing portions of an instrument that may be used for one or more of the bringing and holding of the bladder in contact with the pelvic floor with the openings in the bladder and urethra aligned, driving anchors through the bladder wall and into the pelvic floor and securing a harness within the bladder lumen, inflating a balloon within the harness and thereby applying pressure to the bladder wall to effect knitting of the bladder wall with the pelvic floor, and draining urine from the bladder during the time required for recovery and healing, to effect an anastomosis between the bladder and the urethra following a prostatectomy.

It will be appreciated by one skilled in the art that the components described above may have alternative configurations and embodiments useful for effecting the same steps. It will be appreciated by one skilled in the art that the components described above may, alternatively, be designed and configured so as to be useful for effecting the above-described steps in a retrograde direction rather than an antegrade direction as described above.

It can be appreciated by one skilled in the art that the mechanism comprising the positioner assembly 1440 and performing the bladder positioning function thereof may have a variety of alternative configurations including but not limited to embodiments described herein (and thus including, without limitation, the positioner assembly 400, shuttlecock assembly 800 with positioner petals 830 (FIGS. 17-21), umbrella assembly 900 with reverse positioner petals 930 (FIGS. 22-27), described above, or positioner 2017 (FIGS. 122-126), 2090 (FIGS. 110-118), 2122 (FIGS. 95, 96, 103-109) and 2168 (FIGS. 83, 84, 89-94) (all of which are described below)), providing a transversely retractable and extendible device useful for, referring to FIG. 2, insertion in a retracted position in a retrograde direction through the urethra 5 and into bladder opening 4, extending or expanding within bladder lumen 8, catching in bladder opening 4 and manipulating to urge bladder wall 2 surrounding bladder opening 4 into contact with pelvic floor 7 surrounding urethra opening 6 with the respective openings aligned; or alternatively, insertion in a retracted position in an antegrade direction through an incision in the abdomen and an upper surface of the bladder 1, extending or expanding within bladder lumen 8, catching in bladder opening 4 and manipulating to urge bladder wall 2 surrounding bladder opening 4 into contact with pelvic floor 7 surrounding urethra opening 6 with the respective openings aligned. Generally, the positioner assembly may comprise and make use of any number of alternately extendable and retractable projections, petals, arms, claws, or other grasping or catching members for catching and gaining control of bladder wall 2 surrounding bladder opening 4. The positioner assembly may have at least one member operably connected to a longitudinal member of the instrument and alternately extendable transversely from and retractable toward the longitudinal axis thereof in response to input by a surgeon at a proximal end of the instrument.

Alternatively, it can be appreciated by one skilled in the art that when an anchor driver assembly is included with the instrument, that is functional to open and subsequently drive anchors through the bladder wall and into the pelvic floor as described herein, the positioner assembly or positioner arms as shown may be dispensed with in some circumstances. For example, referring to FIGS. 58-61, it can be appreciated that anchor driver pins 1463 and anchors 700, when opened within the bladder lumen and pushed downwardly until the distal ends of anchors 700 contact and possibly puncture bladder wall 2 surrounding bladder opening 4, can be sufficient for use in capturing bladder wall 2 and pushing it downward into contact with, and securing it to, pelvic floor 7, with bladder opening 4 and urethra opening 6 aligned, without the need for positioner assembly 1400 as shown, in some circumstances. Thus, anchor driver assembly 1460 with anchors 700 may serve a dual function as a positioner and as an anchor driver assembly.

Alternative Balloon/Harness Embodiment

FIG. 136 depicts another exemplary embodiment of an instrument 3000 of the present invention, adapted for use in effecting the anastomosis of the bladder and urethra tissues following a radical prostatectomy in accordance with a method of the present invention. The instrument may comprise a handle assembly 3100, a tube assembly 3200 and an end effector assembly 3400. End effector assembly 3400 is adapted to facilitate retrograde insertion into and through a patient's urethra 5 and into the bladder lumen 8 through bladder opening 4. It will be understood by those skilled in the art that instrument 3000 can, alternatively, be designed and configured in an embodiment to be effective to perform steps substantially similar to those herein described via insertion from an antegrade direction, i.e., through incisions through the abdomen and an upper surface of the bladder (not shown), and downwardly through the bladder opening 4 and into urethra opening 6. An example of such an embodiment is depicted and described in co-pending U.S. applications Ser. Nos. 60/639,836 and 60/582,302.

FIG. 135 is a longitudinal cross-sectional view of end effector assembly 3400 after insertion into and through the patient's urethra 5 and into the bladder opening 4. It can be seen that end effector assembly 3400 may comprise distal end cap assembly 3410, balloon harness 3430, anchor driver assembly 3460, and positioner assembly 3440. End effector assembly 3400 and the assemblies it comprises, just identified, may be operably connected to, and controlled by, handle assembly 3100 (shown in FIG. 136), via tube assembly 3200, which may comprise spine tube 3210, central rod or guide wire 3230, inner positioner tube 3240, outer positioner tube 3241, anchor driver closing tube 3260 and anchor driver tube 3261. These tubes and rod may be assembled so as to be substantially coaxial. Central rod or guide wire 3230 may pass through the length of the instrument within anchor driver closing tube 3260, and may be affixed and made integral with end cap 3411 by any suitable means. Anchor driver closing tube 3260 may be longitudinally movable with respect to central rod or guide wire 3230, and may be affixed and made integral with anchor closing collar 3464 by any suitable means. Anchor driver closing tube 3260 may be located within anchor driver tube 3261, and may be longitudinally movable with respect thereto. Anchor driver tube 3261 may be affixed and made integral with anchor pivot arm yoke 3467 by any suitable means. Anchor driver tube 3261 may be located within inner positioner tube 3240, and may be longitudinally movable with respect thereto. Inner positioner tube 3240 may be affixed and made integral with positioner distal collar 3443 by any suitable means. Inner positioner tube 3240 may be located within outer positioner tube 3241, and may be longitudinally movable with respect thereto. Outer positioner tube 3241 may be affixed and made integral with positioner proximal collar 3442 and spine tube 3210 by any suitable means. Tubes 3210, 3241, 3240, 3261 and 3260, and rod 3230, may be made of nitinol or any other material having suitable combined properties of strength, stiffness and biocompatibility as may be desirable for purposes of the present embodiment. The instrument also includes balloon harness 3430, which is attached at a distal end to end cap assembly 3410, and releasably attached at proximal ends to anchors 700. Anchors 700 are releasably held by the instrument as will be described below. Use of the present embodiment of an instrument and method, in accordance with the present invention, and remaining components and operation thereof, for effecting anastomosis of a patient's bladder and urethra following a radical prostatectomy, will now be described.

As previously noted, and as shown in FIG. 135, end effector assembly 3400 may be inserted into and through the patient's urethra in a retrograde direction and into the bladder opening 4, and then into the bladder lumen as may be appreciated from FIG. 136. FIG. 136 depicts the end effector assembly after insertion completely into the bladder lumen 8, after anchor driver assembly 3460 and positioner assembly 3440 have been opened for use, and after positioner assembly 3440 has been brought into contact with bladder wall 2 and used to urge the bladder wall 2 surrounding the bladder opening into contact with the pelvic floor 7. To open the positioner assembly 3440, the surgeon holds spine tube 3210 and outer positioner tube 3241 stationary, and withdraws inner positioner tube 3240 proximally, using handle assembly 3100 (shown in FIG. 136). This draws positioner distal collar 3443 toward positioner proximal collar 3442. Positioner arms 3441 have upper segments hinged by any suitable means to positioner distal collar 3443 and lower segments hinged by any suitable means to positioner proximal collar 3442, and also hinged together by any suitable means. Thus, drawing positioner distal collar 3443 toward positioner proximal collar 3442 in the manner described above causes positioner arms 3441 to fold outwardly and transversely with respect to the longitudinal axis of the instrument, as may be appreciated from a comparison of FIGS. 135 and 136.

Once positioner arms 3441 of positioner assembly 3440 are opened, the surgeon may manipulate the instrument to cause positioner arms 3441 to urge bladder wall 2 downward into contact with pelvic floor 7, as may be appreciated from FIG. 136. It will also be appreciated from FIG. 136 that the respective openings in the bladder and the urethra are aligned.

The surgeon may open the anchor driver assembly 3460 by holding anchor driver closing tube 3260 stationary while withdrawing anchor driver tube 3261 proximally, or, alternatively, by holding anchor driver tube 3261 stationary while advancing anchor driver closing tube 3260 distally, again, via use of handle assembly 3100 (shown in FIG. 136). As noted above, anchor pivot arm yoke 3467 is integral with anchor driver tube 3261, and anchor closing collar 3464 is integral with anchor driver closing tube 3260. Anchor pivot arms 3461 are pivotably connected to anchor pivot arm yoke 3467, and are biased to swing outwardly by anchor pivot arm springs 3466. As shown in FIG. 135, when anchor driver assembly 3460 is in a closed position, anchor closing collar 3464 sheaths and restrains anchor pivot arms 3461 in a retracted position. When anchor pivot arm yoke 3467 is urged proximally down and away from stationary anchor closing collar 3464, or alternatively, when anchor closing collar 3464 is urged distally up and away from stationary anchor pivot arm yoke 3467, anchor pivot arms 3461 are released from anchor closing collar 3464 and allowed to swing outwardly under urging of springs 3466, as may be appreciated from a comparison of FIGS. 135 and 136. The angle at which anchor pivot arms 3461 swing outwardly as described above may be limited by, for example, suitable cooperating shapes of pivot arms 3461 and anchor pivot arm yoke 3467, or, alternatively for example, by cooperating shapes and limiting the relative longitudinal travel between anchor closing collar 3464 and anchor pivot arms 3461.

Referring to FIG. 136, it can be seen that anchor driver pin bases 3462 are pivotably connected to anchor pivot arms 3461, and may be biased to swing inwardly with respect thereto by any suitable means, to assume a substantially downward orientation as shown in FIG. 136. Anchor driver pins 3463 may be affixed and made integral with anchor driver pin bases 3462. Anchors 700 may be loaded onto anchor driver pins 3463 and held thereon by friction fit or any other suitable releasable means. Anchors 700 may include harness hooks 760 (as may be seen in greater detail in FIG. 141). As may be appreciated from a comparison of FIGS. 135 and 136, anchors 700 may be moved outwardly and into a position ready for driving by opening anchor driver assembly 3460 as described above.

Referring now to FIGS. 136 and 137, using handle assembly 3100 (see FIG. 136) the surgeon may drive anchors 700 downwardly through the bladder wall 2 and into tissues of the pelvic floor 7 by withdrawing anchor driver tube 3261, which pulls anchor pivot arm yoke 3467, and correspondingly, anchor pivot arms 3461, anchor driver pin bases 3462, anchor driver pins 3463, and anchors 700, downward. Anchor pivot arms 3461 and anchor driver pin bases 3462 may be situated on the instrument so that when driven downward, anchors 700 do not interfere with, and are driven down between, positioner arms 3441. Anchors 700 may comprise barbs or other suitable lodging structures (not shown) on their shafts, so as to cause them to be lodged in and resist withdrawal from the tissues of the pelvic floor.

Referring now to FIGS. 137 and 138, the surgeon may retract the driver pins 3463 from the now-installed anchors 700, by advancing anchor driver tube 3261 distally, which will move anchor pivot arm yoke 3467, and correspondingly, anchor pivot arms 3461, anchor driver pin bases 3462, and anchor driver pins 3463, distally upward. If anchors 700 are lodged or otherwise remain in the tissues of the pelvic floor 7, anchor driver pins 3463 onto which anchors 700 are held by releasable means, will release from anchors 700, leaving anchors 700 installed and lodged in the tissues as shown in FIG. 138.

Referring to FIGS. 138 and 139, again, using handle assembly 3100 (shown in FIG. 136), the surgeon may close the anchor driver assembly, and return it to its original position to facilitate withdrawal from the patient, by distally advancing anchor driver tube 3261 while holding anchor driver closing tube 3260 stationary. Alternatively, the surgeon may proximally retract anchor driver closing tube 3260 while holding anchor driver tube 3261 stationary. Either sequence will bring anchor pivot arm yoke 3467, and correspondingly, anchor pivot arms 3461, within anchor closing collar 3464, causing anchor pivot arms 3461 to be moved upwardly and inwardly relative to anchor closing collar 3464 and be sheathed and restrained thereby, as depicted in FIG. 139.

final preparation for withdrawal of anchor driver and positioner assemblies, referring to FIGS. 139 and 140, the surgeon may retract positioner arms 3441 by distally advancing inner positioner tube 3240 while holding outer positioner tube 3241 and spine tube 3210 stationary. This moves positioner distal collar 3443 distally and away from positioner proximal collar 3442, drawing positioner arms 3441 inwardly to the position shown in FIG. 140.

With the anchor driver and positioner assemblies retracted to the positions shown in FIG. 140, the surgeon may withdraw these assemblies from the patient by withdrawing, together as a group, spine tube 3210, outer positioner tube 3241, inner positioner tube 3240, anchor driver tube 3261 and anchor driver closing tube 3260, leaving behind end cap assembly 3410, harness 3430 and anchors 700, as may be seen by comparing FIGS. 140 and 141. Referring to FIG. 141, it can be seen that balloon harness 3430 has been attached to bladder walls 2 surrounding bladder opening 4, which, in turn, may be held in contact with the tissues of pelvic floor 7 surrounding urethra opening 6, by installed anchors 700. Tails 3433 of harness 3430 may be held by anchors 700 by way of hooks 760 as shown or by any other suitable means. Central rod 3230 can now serve as a guide wire as will be described below, and may also be used to withdraw the remaining portions of the instrument following completion of the procedure.

It will be apparent to persons skilled in the art that a variety of mechanisms might be comprised by handle assembly 3100 and configured and adapted to transmit longitudinal (advancement and retraction) forces and movement to an end effector assembly 3400, in order to effect and translate the forces and movement therein necessary to actuate the exemplary embodiments as described above.

FIG. 146 shows end cap assembly 3410 and balloon harness 3430 in more detail. End cap assembly 3410 may comprise drainage extension 3413 having thereon harness attachment neck 3415 and one or more drainage holes 3414. End cap assembly 3410 may also include snap-in collar 3412 and end cap 3411, which may be integrally formed or assembled. End cap 3411 may be connected or affixed to and made integral with central rod or guide wire 3230 by any suitable means. Balloon harness 3430 may include attachment collar 3431, to fit around harness attachment neck 3415 and be held thereon by their respective cooperating shapes and dimensions. Balloon harness 3430 may also includes tails 3433 having therein anchor hook holes 3432, through which anchor hooks 760 may pass, thus attaching balloon harness 3430 to anchors 700 (see, again, FIG. 141). Balloon harness 3430 may be made of any suitable biocompatible polymer having properties of flexibility but effectively limited elasticity so as to render it suitable for remaining held in position and serving the balloon restraining function that will be described below.

Returning to FIG. 141, and also referring to FIG. 142, the next step in the exemplary method described herein is for the surgeon to insert balloon catheter assembly 3500 into the patient and into the balloon harness 3430 via central rod 3230, serving as a guide wire.

Central rod 3230, serving as a guide wire, may be provided with one or more markings along its length (not shown) that enable the surgeon to determine the distance that a balloon catheter assembly is inserted into the patient. By noting the length of the balloon catheter assembly and its position with respect to the one or more markings on central rod or guide wire 3230 after insertion, the surgeon can determine whether the catheter assembly has been inserted to the correct depth within the patient with respect to the harness and distal end cap assembly.

Referring to FIGS. 142, 143 and 146, balloon catheter assembly 3500 may comprise catheter tube 3510, balloon 3520 attached thereto, and catheter end plug 3530. Catheter tube 3510 may include inflation lumen 3511 and inflation port 3512. Balloon 3520 may have proximal and distal portions attached in any substantially gas and/or fluid-tight manner at proximal and distal points on catheter tube 3510, and may be ring-shaped upon inflation or otherwise have a central passage through which catheter tube 3510 passes, as may be appreciated from FIG. 143. Catheter end plug 3530 may comprise snap-in button 3531, one or more drainage holes 3414, and catheter tube insert 3534, with stop collar 3535.

Referring again to FIG. 142, upon insertion of balloon catheter assembly 3500, snap-in button 3531 of catheter end plug 3530 cooperates with and snaps into snap-in collar 3412 of distal end cap assembly 3410, and is held thereby. Referring to FIGS. 142 and 143, balloon 3520 may then be inflated, and have its internal pressure regulated, via inflation lumen 3511 and inflation port 3512 in catheter tube 3510. Referring to FIG. 143, it may be seen that balloon 3520, upon inflation, may expand outwardly between the straps of harness 3430, and be used to exert pressure on the bladder walls 2 surrounding the bladder opening in order to, both, press bladder walls 2 into contact with the tissues of pelvic floor 7, and seal off the bladder opening, pelvic floor and urethra from urine and other materials collecting in the bladder during recovery and healing. During recovery and healing, urine and other materials collecting in the bladder may be drained into catheter tube 3510 via drainage holes 3414 and 3533, in distal end cap assembly 3410 and catheter end plug 3530, respectively. During recovery and healing, catheter tube 3510 may be connected at a proximal end to a urine collection bag (not shown).

It may be appreciated that the combination of a harness structure anchored to the pelvic floor as depicted and described herein, constraining and holding the inflated balloon of a balloon catheter, has the desirable effect of constraining the catheter from substantial axial or longitudinal movement within the urethra during the period required for anastomosis.

Suitable gas or fluid pressure within balloon 3520 may be maintained until anastomosis is complete, by monitoring and adjusting the pressure within balloon 3520 through inflation lumen 3511. About 1 to 6 p.s.i. pressure within the balloon may be suitable, and about 1.5 to 2.5 p.s.i. is preferred. The possibility of pressure necrosis in the tissues beneath the balloon may be reduced by including, for example, ribs or other bumps, nodules, projections, or other features (not shown) on the underside of balloon 3520, which may be effective to reduce the loss of blood flow to tissue in contact with balloon 3520. These features may be solid or of uniform wall thickness. Additionally, balloon 3520 may be designed with features that effect the shape that it assumes upon inflation, and thus, effect the shape and area of the lower surface of balloon 3520 that contacts the bladder wall 2 upon inflation. For example, balloon 3520 may be designed and manufactured so as to have walls that are thicker on an upper portion and thinner on a lower portion, so that the lower portion of balloon 3520 is predisposed to expand downwardly and outwardly between the harness straps, and thereby present a larger surface area to contact the bladder wall 2. Alternatively, balloon 3520 may be designed and manufactured so as to have walls that are thicker on a lower portion and thinner on an upper portion, so that the upper portion of balloon 3520 is predisposed to inflate first, within the bladder lumen, and thereby draw the remaining portion of the balloon up into the bladder lumen, and substantially out of the pelvic floor region, before the lower portion fully inflates. Alternatively, balloon 3520 may be designed with features that cause it to assume other specific advantageous shapes upon inflation to, for example, fill a large portion of the space defined by the harness straps.

In order to facilitate inflation and assist in maintaining suitable gas or fluid pressure within balloon 3520, a two-way check valve may be installed along the inflation gas or fluid passage including inflation lumen 3511. For example, a two-way check valve may comprise a "duckbill" type valve or other valve that functions to permit gas or fluid to pass into inflation lumen 3511 but prevents gas or fluid from passing back out, in conjunction with a pressure release valve that functions to permit gas or fluid to pass out of the system if pressure within balloon 3520 and/or the fluid passage exceeds a desired maximum amount.

FIG. 144 depicts an alternative manner of attachment of balloon 3520 to the distal end of catheter tube 3510. In comparison with balloon 3520 as depicted in FIG. 143, it can be seen in FIG. 144 that the sheet-like material forming the upper wall of balloon 3520 has been attached to the distal end of catheter tube 3510 in inverted orientation, which may serve to enhance sealing at the attachment point and improve the balloon's ability to sustain gas or fluid pressure when inflated.

Following substantial completion of the anastomosis procedure, i.e., following substantial knitting of the tissues of the bladder walls and the pelvic floor surrounding the respective openings of the bladder and the urethra, the balloon may be deflated and the balloon catheter assembly 3500 withdrawn from the patient. This leaves behind the end cap assembly 3410, harness 3430 and anchors 700, may be seen by comparing FIGS. 144 and 145. Following withdrawal of the balloon catheter assembly, end cap assembly 3410 and harness 3430 may be withdrawn from the patient by proximally withdrawing central rod or guide wire 3230 (shown in progress in FIG. 145). It can be seen in FIG. 145 that the tails 3433 of harness 3430 may be removed from and released by harness hooks 760 of anchors 700 by inversion of the position of harness 3430, and subsequent proximal tension exerted thereon, effected by withdrawing distal end cap assembly 3230, causing harness tails 3433 to slide off attachment hooks 760. Anchors 700 may be left behind in the patient.

As noted, central rod or guide wire 3230 may be attached to and made integral with end cap 3411 by any suitable means. When central rod or guide wire 3230 is made integral with end cap 3411, it is substantially integral with the other components of end cap assembly 3410 as described herein, and thus also with attachment collar 3431 of balloon harness 3430. As such, central rod or guide wire 3230 may be used for withdrawal of balloon harness 3430 following substantial completion of the anastomosis procedure.

The above-described embodiment is only one example describing portions of an instrument that may be used for one or more of the bringing and holding of the bladder in contact with the pelvic floor with the openings in the bladder and urethra aligned, driving anchors through the bladder wall and into the pelvic floor and securing a harness within the bladder lumen, inflating a balloon within the harness and thereby applying pressure to the bladder wall to effect knitting of the bladder wall with the pelvic floor, and draining urine from the bladder during the time required for recovery and healing, to effect an anastomosis between the bladder and the urethra following a prostatectomy.

It will be appreciated by one skilled in the art that the components described above may have alternative configurations and embodiments useful for effecting the same steps. It will be appreciated by one skilled in the art that the components described above may, alternatively, be designed and configured so as to be useful for effecting the above-described steps in an antegrade direction rather than a retrograde direction as described above.

It can be appreciated by one skilled in the art that the mechanism comprising the positioner assembly 3440 and performing the bladder positioning function thereof may have a variety of alternative configurations including but not limited to embodiments described herein (and thus including, without limitation, the positioner assembly 400, shuttlecock assembly 800 with positioner petals 830 (FIGS. 17-21), umbrella assembly 900 with reverse positioner petals 930 (FIGS. 22-27), described above, or positioner 2017 (FIGS. 122-126), 2090 (FIGS. 110-118), 2122 (FIGS. 95, 96, 103-109) and 2168 (FIGS. 83, 84, 89-94) (all of which are described below)), providing a transversely retractable and extendible device useful for, referring to FIG. 2, insertion in a retracted position in a retrograde direction through the urethra 5 and into bladder opening 4, extending or expanding within bladder lumen 8, catching in bladder opening 4 and manipulating to urge bladder wall 2 surrounding bladder opening 4 into contact with pelvic floor 7 surrounding urethra opening 6 with the respective openings aligned; or alternatively, insertion in a retracted position in an antegrade direction through an incision in the abdomen and an upper surface of the bladder 1, extending or expanding within bladder lumen 8, catching in bladder opening 4 and manipulating to urge bladder wall 2 surrounding bladder opening 4 into contact with pelvic floor 7 surrounding urethra opening 6 with the respective openings aligned. Generally, the positioner assembly may comprise and make use of any number of alternately extendable and retractable projections, petals, arms, claws, or other grasping or catching members for catching and gaining control of bladder wall 2 surrounding bladder opening 4. The positioner assembly may have at least one member operably connected to a longitudinal member of the instrument and alternately extendable transversely from and retractable toward the longitudinal axis thereof in response to input by a surgeon at a proximal end of the instrument.

Alternatively, it can be appreciated by one skilled in the art that when an anchor driver assembly is included with the instrument, that is functional to open and subsequently drive anchors through the bladder wall and into the pelvic floor as described herein, the positioner assembly or positioner arms as shown may be dispensed with in some circumstances. For example, referring to FIGS. 135 and 136, it can be appreciated that anchor driver pins 3463 and anchors 700, when opened within the bladder lumen and pushed downwardly until the distal ends of anchors 700 contact and possibly puncture bladder wall 2 surrounding bladder opening 4, can be sufficient for use in capturing bladder wall 2 and pushing it downward into contact with, and securing it to, pelvic floor 7, with bladder opening 4 and urethra opening 6 aligned, without the need for positioner assembly 3440 as shown, in some circumstances. Thus, anchor driver assembly 3460 with anchors 700 may serve a dual function as a positioner and as an anchor driver assembly.

"H" Anchor Embodiment

Figure 83:
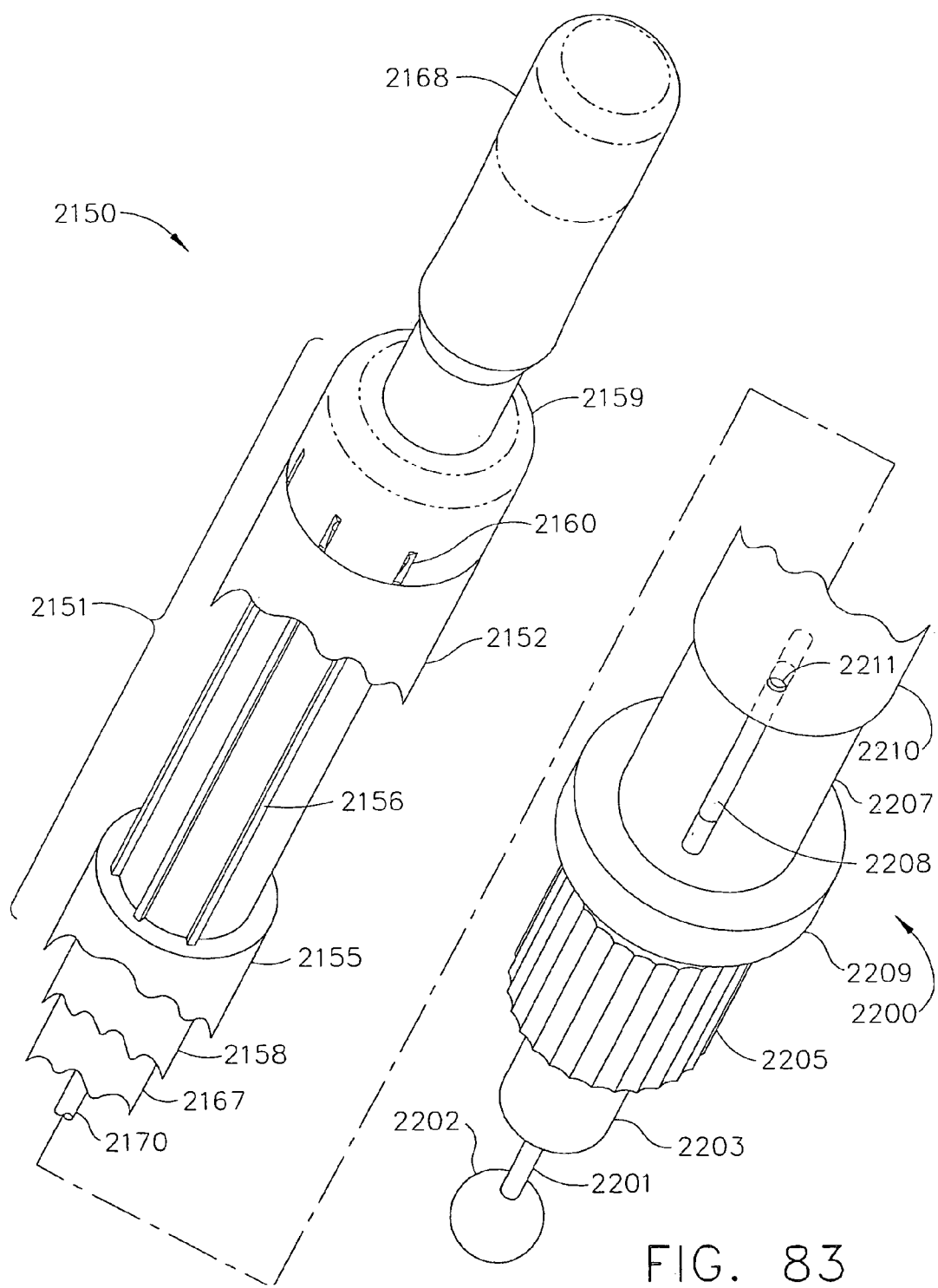
FIG. 83 is a perspective view of the distal and proximal ends of another embodiment of an anastomotic instrument of the present invention, shown in a retracted, pre-deployment position, with the intermediate section removed for ease of depiction in the drawing.

FIG. 83 is a perspective view of another embodiment of an anastomotic instrument 2150 of the present invention, in its pre-deployment position, and FIG. 84 is a longitudinal cross-sectional view of the distal end of the instrument, also shown in its pre-deployment position. The instrument may comprise anchor driver assembly 2151, which may include outer driver assembly tube 2152, having distal end 2154, anchor driver tube 2155 which distally terminates with anchor driver pins 2156, and inner driver assembly tube 2158 which distally terminates with anchor track collar 2159. The described embodiment of the instrument may further comprise positioner tube 2167, positioner 2168 affixed to the distal end of positioner tube 2167, rod 2170 and rod cap 2171. When the instrument is assembled and prepared for use, anchor driver assembly 2151 may be loaded with one or more anchors 700, each of which may comprise a forward member 750, shaft 720 and rearward member 710.

Figure 86:
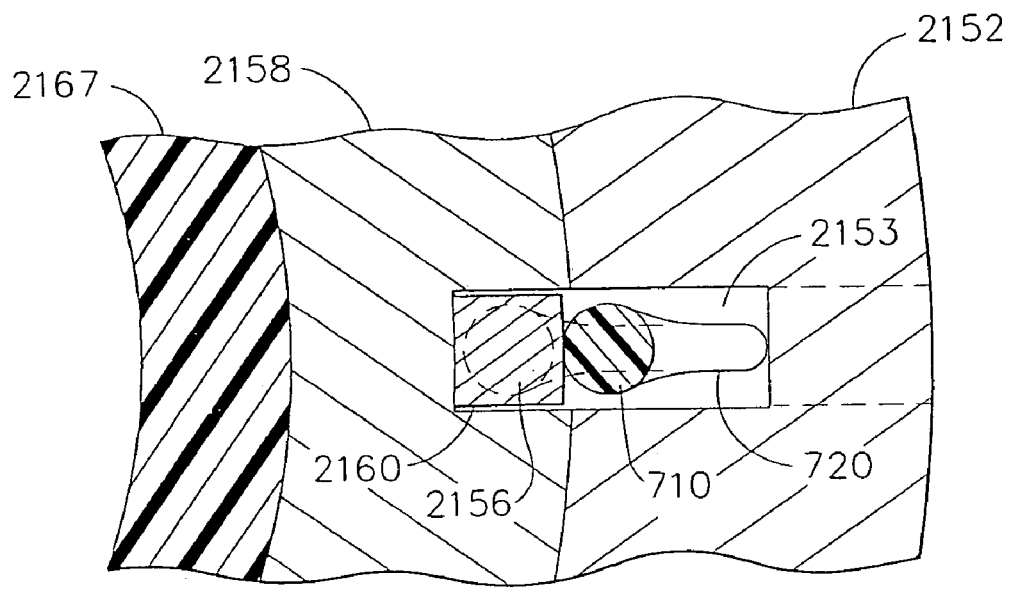
FIG. 86 is a partial transverse cross section of the instrument shown in FIG. 84, indicated at 86-86 of FIG. 84, showing sectional views of an outer driver assembly tube, anchor driver pin, inner driver assembly tube, positioner tube, and anchor, loaded into the instrument in a pre-deployment position.

Referring to FIG. 84 and as may be seen in more detail in FIG. 86, positioner tube 2167, inner driver assembly tube 2158 distally terminating in anchor track collar 2159, and outer driver assembly tube 2152, may be assembled such that they are substantially coaxial. Anchor track collar 2159 and inner driver assembly tube 2158 may have in their outer surfaces one or more longitudinally-oriented anchor tracks 2160 which direct upwardly and radially outwardly, moving longitudinally, proximally to distally. Outer driver assembly tube 2152 may have one or more anchor storage grooves 2153 on its inside surface, situated opposite anchor tracks 2160. When the instrument is assembled and ready for use, inner driver assembly tube 2158, with anchor track collar 2159, and outer driver assembly tube 2152, are made integral with respect to each other by any suitable means.

Figure 87:
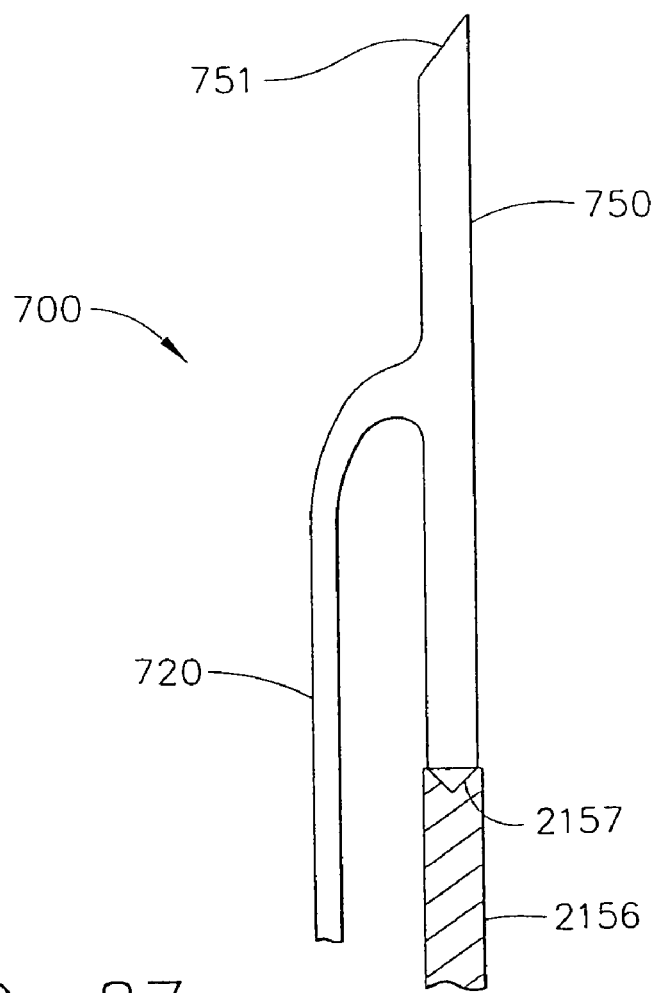
FIG. 87 is a side view of a forward member of an anchor that may be used with the instrument shown in FIG. 83, shown in a pre-deployment position as in contact with an anchor driver pin.

FIG. 87 is an enlarged view of the forward end of an anchor that may be used in the present embodiment. Anchor 700 has forward member 750 which may have a sharp forward end 751, and has shaft 720 which connects with a rearward member 710 (not shown in FIG. 87). Anchor 700 may be manufactured so as to be biased with shape memory to assume an "H" shape, with the forward and rearward members forming the vertical legs and the connecting member forming the horizontal connection of the "H", and may be made of a material having suitable properties of strength, flexibility, shape memory, non-reactivity with body tissues and fluids, and biocompatibility. Anchor 700 may also be made of one or more dissolving bioabsorbable materials. Anchor 700 may, alternatively, be manufactured in a variety of suitable shapes as depicted in FIGS. 40-51, and one of the embodiments of the instrument described herein suitably adapted for use with such anchors substantially as hereinafter described.

FIGS. 84 and 86 depict anchors 700 loaded into the instrument of the present embodiment, ready for deployment. As can be seen from the drawings, as loaded, anchors 700 reside in the spaces defined by anchor tracks 2160 and anchor storage grooves 2153. As can be appreciated from the drawings, the spaces defined by the anchor tracks 2160 and anchor storage grooves 2153 restrain the anchors 700 while the anchors are loaded in the instrument, holding them such that forward lodging members 750 and penetration limiting members 710 are positioned lying longitudinally alongside connecting members 720.

As can be seen in FIGS. 84 and 86, when the instrument is ready for use, anchor driver pins 2156 also reside in anchor tracks 2160 with their distal ends behind the forward lodging members 750 in a position ready for driving anchors 700 as will be hereinafter described. Anchor driver pins 2156 are integral with a distal end of anchor driver tube 2155 (shown in FIG. 83). Anchor driver tube 2155 is longitudinally movable with respect to outer driver assembly tube 2152 and inner driver assembly tube 2158. Anchor driver pins 2156 are formed from a suitable flexible, shape memory material such as nitinol, and are biased so as to be substantially straight in their natural positions.

As may be seen in FIG. 87, the end of anchor driver pin 2156 may have a recess 2157 or any other suitable feature for receiving and holding forward member 750 during the anchor driving step as will be hereinafter described.

The instrument may comprise one or more anchors, and the associated tracks, grooves and anchor driver pins described above, situated about the instrument in positions such that upon correct rotational orientation of the instrument, the anchors may be driven upwardly and radially outwardly into tissues in directions selected to avoid nerve and/or circulatory system bundles or other sensitive areas.

Figure 89:
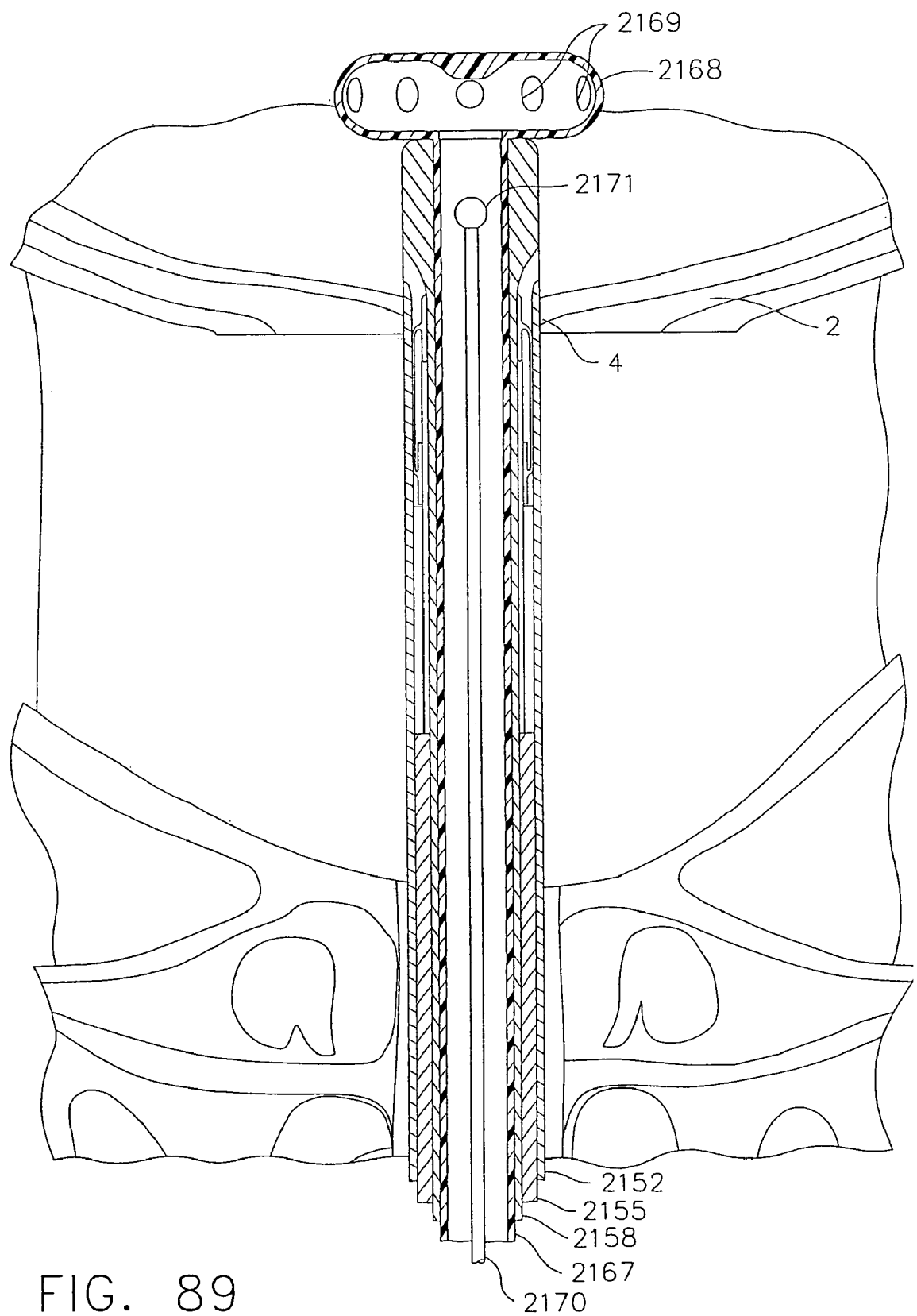
FIG. 89 is a longitudinal cross section of the instrument shown in FIG. 83, shown after insertion into and through a patient's urethra and into the bladder, and after a positioner has been moved to a deployed position.

Referring again to FIG. 84, the instrument of the present embodiment also includes positioner tube 2167. Affixed at the distal end of positioner tube 2167 is positioner 2168, shown in its pre-deployment shape in FIGS. 83 and 84. The pre-deployment shape of positioner 2168, shown in FIGS. 83 and 84, facilitates insertion of the instrument into the patient. Positioner 2168 may be made of a suitable elastic and flexible polymeric material having shape memory, manufactured so as to be biased to assume a normally transversely-oriented shape such as, for example, that shown in FIG. 89, upon retraction of rod 2170. As shown in FIG. 89, positioner 2168 may have, about its perimeter, one or more drainage holes 2169 which can permit urine, fluids or clotted material to drain into positioner tube 2167 after the instrument has been deployed. Positioner 2168 is alternately moved to its pre-deployment position shown in FIGS. 83 and 84, or allowed to return via shape memory to its normal (deployed) position shown in FIG. 89, by longitudinal movement of rod 2170, and correspondingly, end cap 2171, which is integrally affixed to rod 2170. Positioner tube 2167 is longitudinally movable with respect to inner driver assembly tube 2158, and vice versa.

Outer driver assembly tube 2152, anchor driver tube 2155, inner driver assembly tube 2158, positioner tube 2167 and rod 2170 may be made of one or more materials having suitable combined properties of shape memory, flexibility, strength and stiffness that both enable the tubes and rod to flex during insertion into the patient's body and through the urethra as will be hereinafter described, but also will prevent them from collapsing, kinking, binding, or breaking during use. The selected materials may also be substantially non-reactive with body fluids and tissues, and be substantially biocompatible. The inventors have determined that nitinol, known in the art as suitable for a variety of surgical devices and tubes, is one example of a suitable material.

It will be appreciated that a hollow tube may be used in the instrument for positioner tube 2167 when a coaxial arrangement with rod 2170 is desirable, or when positioner tube 2167 is to serve as a catheter, such as will be further described below, but that a rod may be substituted for positioner tube 2167 and be used to provide substantially the same mechanical function, i.e., transmission of forces to actuate the positioner, and thus may be used when a catheter function, or a coaxial arrangement, and thus a tube, is not required. Conversely, a tube can serve the purpose of rod 2170. Thus, for purposes of claims set forth, unless otherwise specified in a claim, the term "tube" where such element is operably affixed or connected with, or contacts, the positioner, is intended to include and cover a rod, and vice versa.

A method for performing anastomosis in a retrograde manner using the above-described instrument, following a prostatectomy, will now be described. Following a prostatectomy, the patient's bladder 1 and urethra opening 6 are separated by a void formerly occupied by the prostate, as shown in FIG. 2. It is necessary to connect the bladder 1 with the urethra 5, with bladder opening 4 and urethra opening 6 aligned, to restore urinary functions after recovery and healing.

Figure 88:
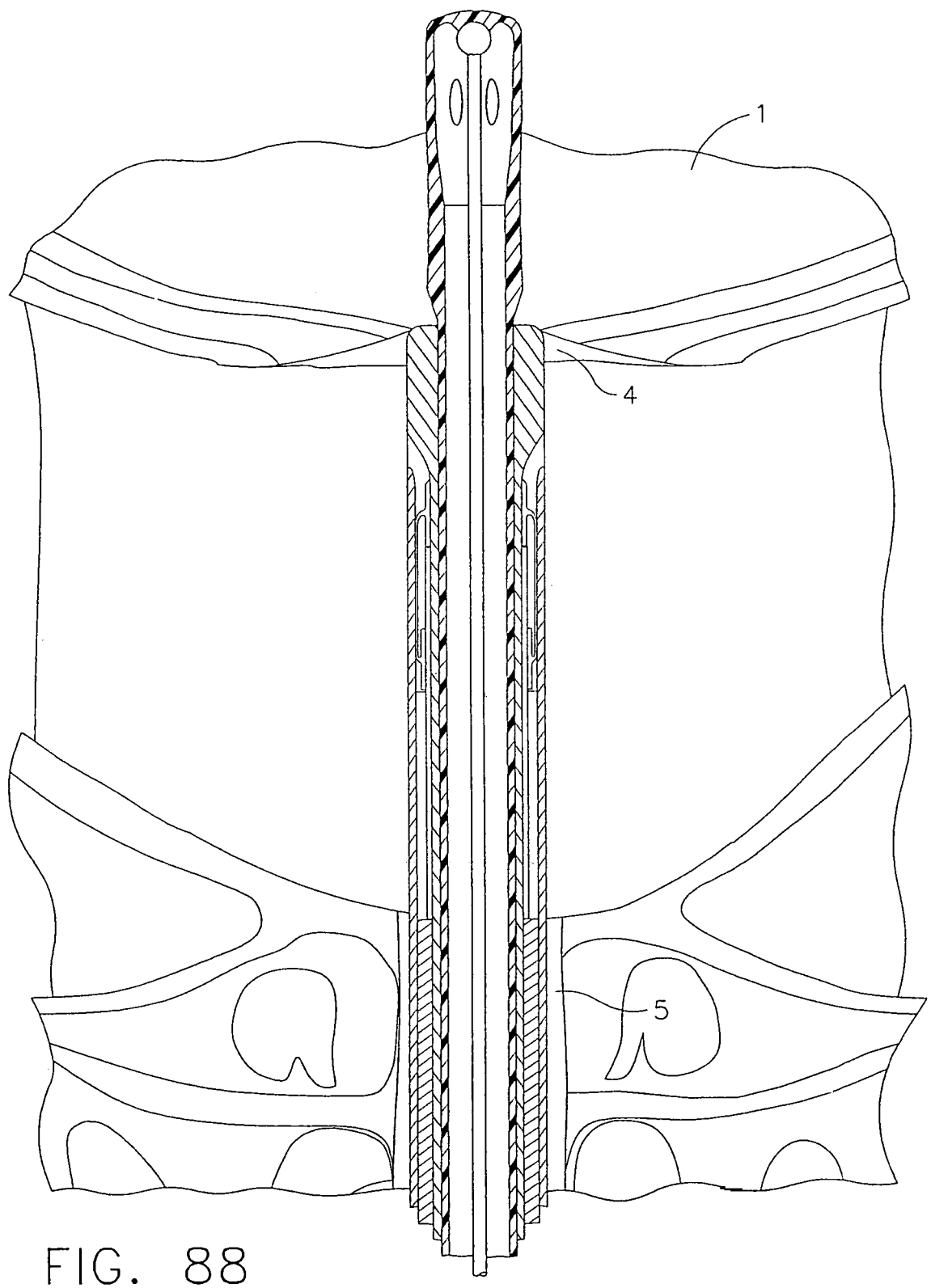
FIG. 88 is a longitudinal cross section of the instrument shown in FIG. 83, shown in a retracted, pre-deployment position after insertion into and through a patient's urethra and into the bladder, following a prostatectomy.

As shown in FIG. 88, the anastomotic instrument is inserted upwardly into and through the patient's urethra 5, through the bladder opening 4, and into the bladder 1. The surgeon then retracts rod 2170 and correspondingly, end cap 2171, which allows positioner 2168 to assume its normal transversely-oriented shape via shape memory, as shown in FIG. 89. The now-transverse orientation of positioner 2168 prevents it from being retracted without pulling bladder wall 2 surrounding bladder opening 4 with it.

Figure 90:
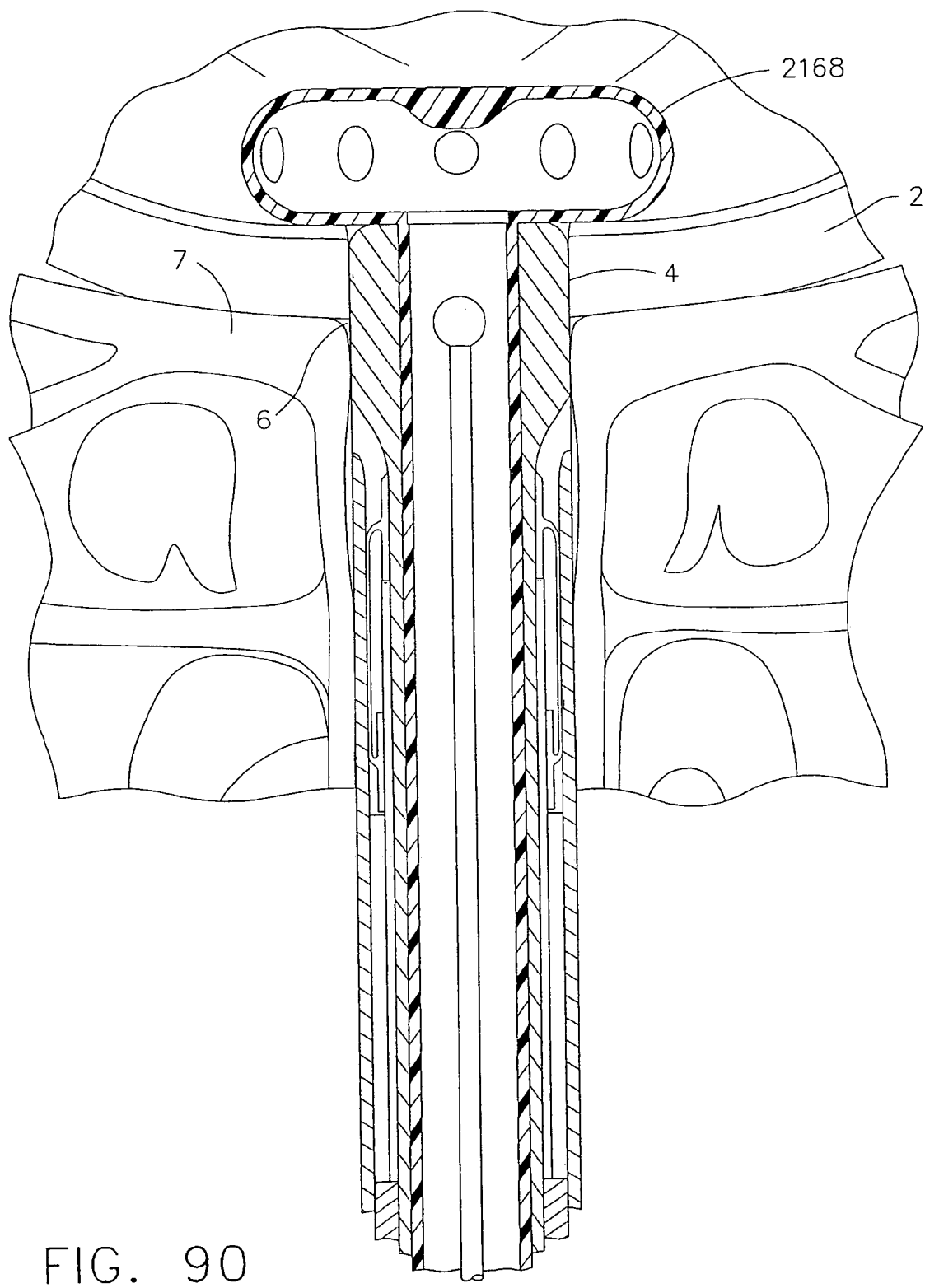
FIG. 90 is a longitudinal cross section of an embodiment of the instrument shown in FIG. 83, shown after insertion into and through a patient's urethra and into the bladder, after a positioner has been moved to a deployed position, and after the bladder wall has been urged into contact with the pelvic floor with the openings in the bladder and urethra aligned.

Next, the surgeon retracts the entire instrument downwardly through the urethra, which causes positioner 2168 to pull bladder walls 2 surrounding bladder opening 4 into contact with pelvic floor 7, with bladder opening 4 and urethra opening 6 aligned, to the position shown in FIG. 90.

Figure 91:
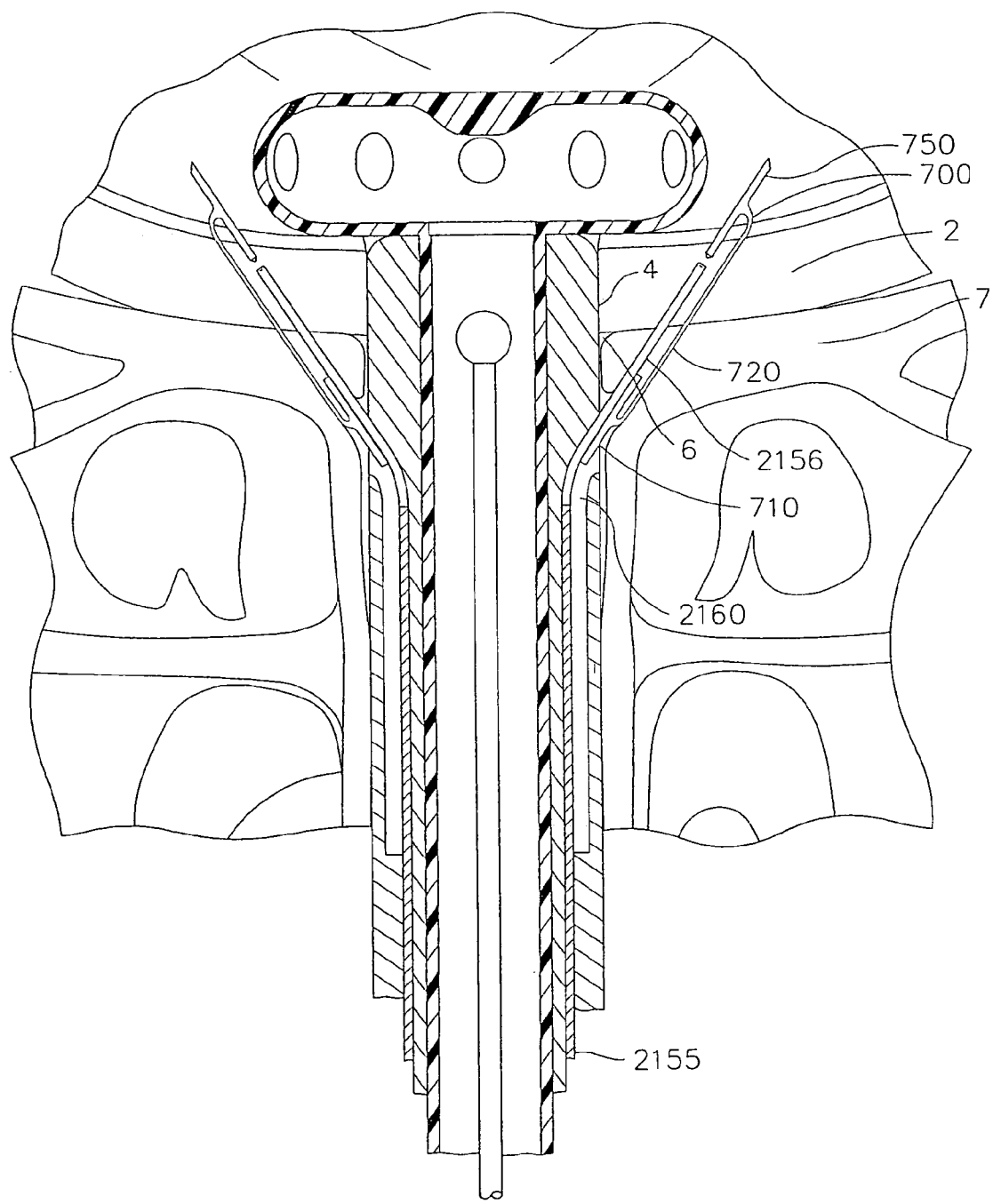
FIG. 91 is a longitudinal cross section of the instrument shown in FIG. 83, shown after insertion into and through a patient's urethra and into the bladder, after a positioner has been moved to a deployed position, after the bladder wall has been urged into contact with the pelvic floor with the openings in the bladder and urethra aligned, and after actuation of an anchor driver assembly to drive anchors into the tissues of the pelvic floor and bladder wall, surrounding the aligned urethra opening and bladder opening.
Figure 92:
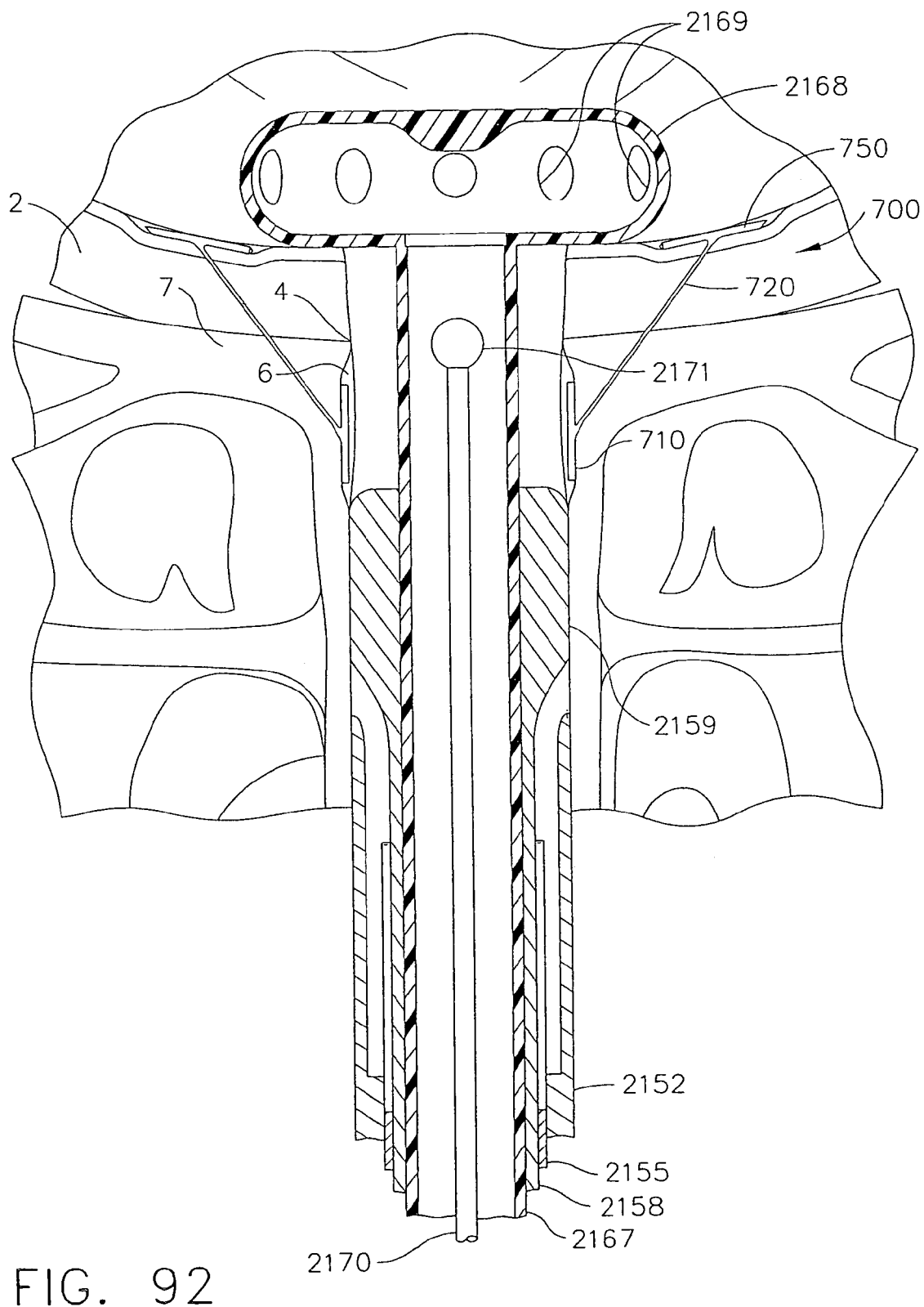
FIG. 92 is a longitudinal cross section of the instrument shown in FIG. 83, shown after insertion into and through the urethra and into the bladder, after a positioner has been moved to a deployed position, after the bladder wall has been urged into contact with the pelvic floor with the openings in the bladder and urethra aligned, after anchors have been installed, and after retraction of an anchor driver assembly has commenced, to leave a positioner and positioner tube behind to enable draining of urine from the bladder during recovery and healing.

Next referring to FIG. 91, anchor driver tube 2155 is moved longitudinally upwardly and distally, which correspondingly causes anchor driver pins 2156 to move upwardly and distally, inside anchor tracks 2160, and then upwardly and radially outwardly, driving forward lodging members 750 of anchors 700 upwardly and radially outwardly, first into and through the tissues of the pelvic floor 7 surrounding the urethra opening 6, and then into and through the tissues of the bladder wall 2 surrounding the bladder opening 4, and into the bladder, as shown in FIG. 91. As may be seen in FIG. 91, as forward lodging members 750 are driven into the tissues, connecting members 720 trail behind forward lodging members 750, into place in the tissues. Anchor driver tube 2155 and correspondingly anchor driver pins 2156 are then retracted back into the instrument, releasing lodging members 750 of anchors 700. When lodging members 750 of anchors 700 are released by retraction of anchor driver pins 2156, they are no longer restrained from their normal biased positions, and lodging members 750 move under bias and contact with the bladder wall to a position substantially transverse to the axes of connecting members 720 as may be seen in FIG. 92, such that lodging members 750 prevent anchors 700 from retracting back through the holes in the tissues made by lodging members 750 during the driving step, and thus, serve to lodge the anchors in the tissues. Similarly, when penetration limiting members 710 are pulled out of the instrument, they are no longer restrained from their normal biased positions, and penetration limiting members 710 move under bias and contact with the urethra wall to a position substantially transverse to the axes of connecting members 720 as may be seen in FIG. 92, such that penetration limiting members 710 may not be pulled through the holes in the tissues made by lodging members 750 during the driving step, and thus serve to limit further penetration of anchors 700 into the tissues. Upon completion of installation of anchors 700, as can be seen in FIG. 92, anchors 700 hold the tissues of bladder wall 2 surrounding bladder opening 4 in contact with the tissues of pelvic floor 7 surrounding urethra opening 6, with the bladder opening 4 and urethra opening 6 aligned. Thus held in contact, the tissues of the bladder wall 2 and pelvic floor 7 may knit and heal together with the bladder opening and urethra opening aligned.

Next, the entire anchor driver assembly, comprising inner driver assembly tube 2158 and anchor track collar 2159, anchor driver tube 2155, and outer driver assembly tube 2152, may be retracted as a unit (as shown in progress in FIG. 92), down the urethra and out of the patient's body, leaving behind positioner tube 2167, positioner 2168 and rod 2170. Remaining positioner 2168 and positioner tube 2167 may now be used to exert supplemental downward pressure on bladder walls 2 surrounding the bladder opening 4 so as to enhance contact and knitting between the tissues of bladder walls 2 surrounding the bladder opening 4, and the tissues of pelvic floor 7 surrounding the urethra opening 6. Additionally, or alternatively, positioner 2168, including drainage holes 2169, and positioner tube 2167, may now be used to seal off the junction between the bladder and urethra and drain urine and other fluids from the bladder during recovery and healing. Used for this purpose, positioner tube 2167 would be connected to a urine collection bag (not shown) via intermediate tubing. Following recovery and healing, rod 2170 and correspondingly end cap 2171 are moved longitudinally upwardly and distally with respect to positioner tube 2167, thus urging positioner 2168 into its pre-deployment position as shown in FIGS. 83 and 84, and enabling retraction of these remaining parts of the instrument out of the bladder, down through the urethra, and out of the patient's body.

Figure 93:
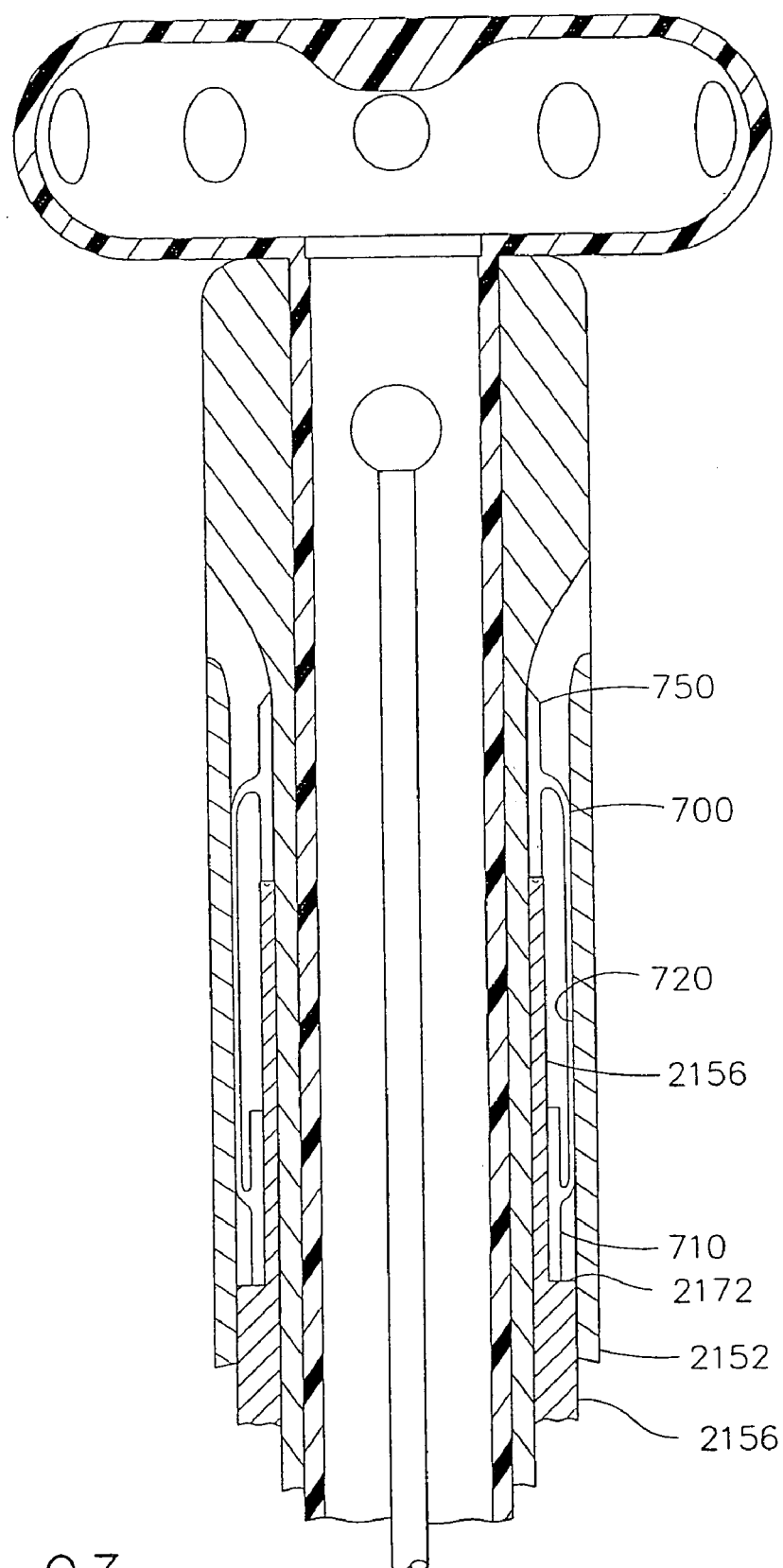
FIG. 93 is a longitudinal cross section of another alternative embodiment of an anastomotic instrument of the present invention, shown after a positioner has been moved to a deployed position, comprising an alternative configuration of driver pins and an outer driver assembly tube.
Figure 94:
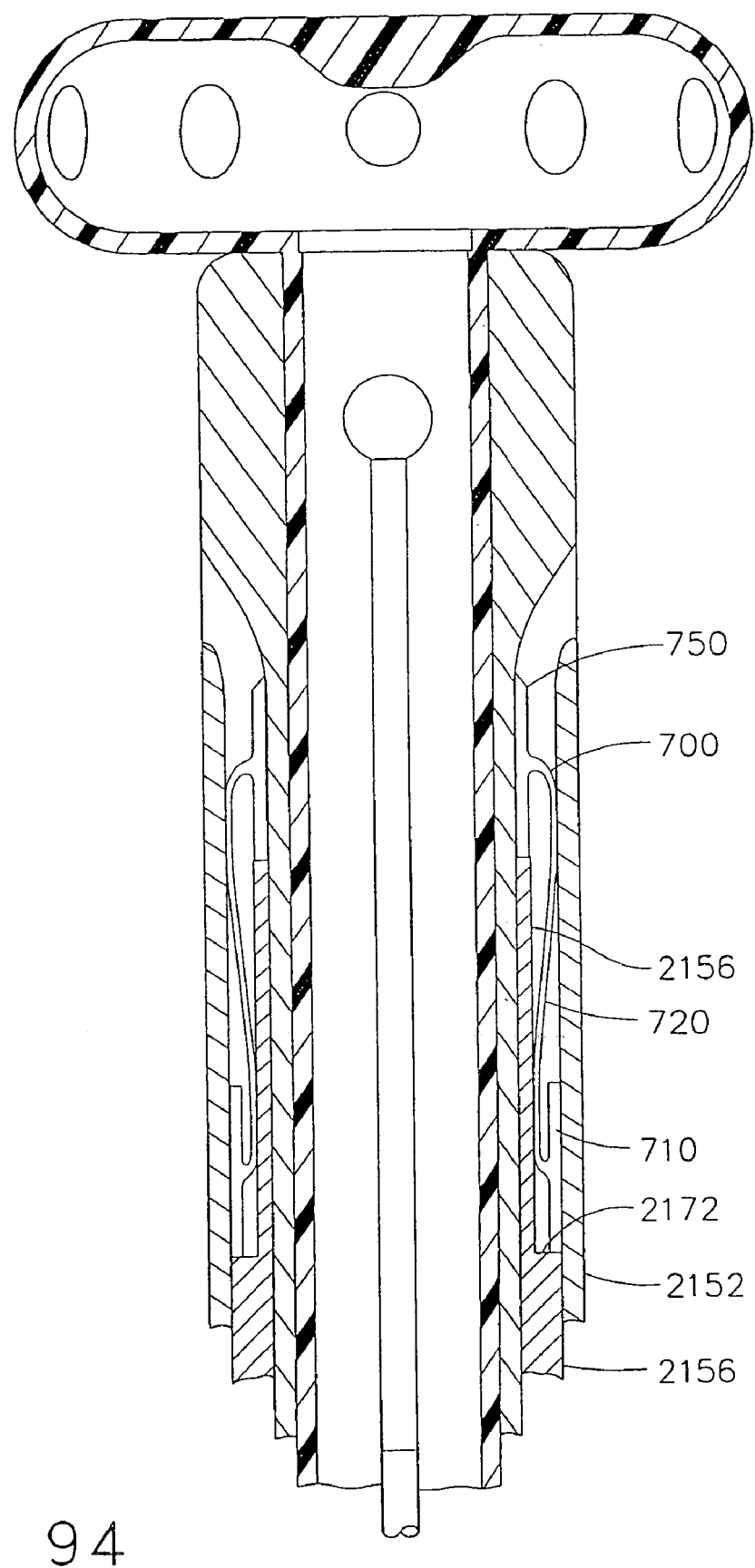
FIG. 94 is a longitudinal cross section of another alternative embodiment of an anastomotic instrument of the present invention, shown after a positioner has been moved to a deployed position, comprising an alternative configuration of driver pins and an outer driver assembly tube, and showing an alternative pre-deployment orientation of rearward members and connecting members of anchors.

FIGS. 93 and 94 depict an alternative embodiment and alternative loaded anchor positions for the instrument of the present invention. As can be seen, in this embodiment anchor driver pins 2156 include rear driver steps 2172, which function to drive penetration limiting members 710 of anchors 700 at the same time the distal ends of anchor driver pins drive forward lodging members 750 of anchors 700. The geometry of outer driver assembly tube 2152, anchor storage groove 2153 and/or anchor track 2160 are suitably modified accordingly. With this alternative embodiment, tension in shaft 720 during the driving step may be avoided and driving and ejection of the anchor from the instrument may be eased. Additionally, as depicted in FIG. 94, in this alternative embodiment anchors 700 may be loaded with forward lodging members 750 and penetration limiting members 710 oriented in opposite directions as shown, which may serve to improve the positioning of rearward member 710 in the urethra after actuation of the anchor driver assembly and driving of the anchors.

Those skilled in the art will appreciate that a variety of simple mechanical devices may be configured or adapted to operate and manipulate and outer driver assembly tube 2152 and inner driver assembly tube 2158, anchor driver tube 2155, positioner tube 2167 and rod 2170, at the proximal end of the instrument as required by the above steps, and so as to move and hold the instrument in respective pre-deployment and/or retracted, and deployed and first and second actuated, positions, including but not limited to the handle assembly now to be described.

The right-hand side of FIG. 83, and FIG. 85, depict an example of a simple proximal end handle assembly 2200 which may be designed and configured to enable the surgeon to control and manipulate various embodiments of the instrument. Handle assembly 2200 comprises rod 2201 having affixed knob 2202, fourth tube 2203, third tube 2204 with integral stop collar 2205, second tube 2207 with integral actuation collar 2209, and first tube 2210. Tubes 2210, 2207, 2204 and 2203, and rod 2201, may be substantially coaxial. Rod 2201 is longitudinally slidable with respect to fourth tube 2203. Fourth tube 2203 is longitudinally slidable with respect to third tube 2204 and stop collar 2205, and vice versa. First tube 2210 may be connected to third tube 2204 via connecting pins 2211, thus making first tube 2210 and third tube 2204 integral. Second tube 2207 is coaxially located between first tube 2210 and third tube 2204, and is longitudinally slidable therewithin, to the limits defined by longitudinal slots 2208 in second tube 2207 about pins 2211.

Thus, it can be appreciated from FIGS. 84 and 85 that handle assembly 2200 may be connected and made usable by the surgeon to manipulate and operate anastomotic instrument 2150 by connecting, or making integral, rod 2201 and rod 2170, fourth tube 2203 and positioner tube 2167, third tube 2204 and inner driver assembly tube 2158, second tube 2207 and anchor driver tube 2155, and first tube 2210 and outer driver assembly tube 2152. As so configured, second tube 2207 may be longitudinally slid with respect to the remaining parts of the assembly by the surgeon gripping tube actuation collar 2209, thus advancing or retracting anchor driver tube 2155 and correspondingly anchor driver pins 2156, thereby actuating anchor driver assembly 2151. Following installation of the anchors, the entire anchor driver assembly 2151 may be retracted from the patient's body by the surgeon gripping and pulling first tube 2210, thus also retracting third tube 2204 via connecting pins 2211 and second tube 2207, and correspondingly, retracting outer anchor driver assembly tube 2152, inner driver assembly tube 2158, and anchor driver tube 2155. This can be accomplished while leaving behind fourth tube 2203 and rod 2201, and thus positioner tube 2167 and rod 2170, as described above.

It will be appreciated by those skilled in the art of design of mechanical surgical devices that the positioner need not be limited to the exemplary embodiment made of flexible and elastic polymeric shape memory material as described above, but that alternative designs for such positioner are possible, which cause the positioner to alternately assume a retracted position and a deployed position, the deployed position suitable for catching in the bladder opening and urging the bladder into contact with the pelvic floor, in response to forces exerted or transmitted by tubes or other members. The positioner may comprise, for example, any of the positioner assemblies depicted in FIGS. 14, 19, 24 and 57, and described hereinabove. Similarly, it will be appreciated by those skilled in the art of design of mechanical surgical devices that the anchor driver assembly need not be limited to the exemplary three-tube assembly described herein, but that alternative designs for such an assembly are possible, which are effective to install one or more anchors into the tissues of the bladder and the urethra about the respective openings when they are brought together, in response to forces exerted or transmitted by tubes or other members.

As previously noted, the combination of tubes, positioner and driver assembly may be configured in an instrument adapted for a retrograde anastomosis procedure, as described above, or configured in an instrument adapted for an antegrade procedure. In an antegrade procedure, instead of being inserted upwardly through the urethra and into the bladder opening proximate the site of excision of the prostate, the instrument is inserted downwardly through a small incision in the patient's abdomen, through a small incision on an upper surface of the patient's bladder, into the bladder, through the bladder opening, and into the urethra opening. The small incisions in the abdomen and upper surface of the bladder may be made and held open for insertion of the instrument therethrough with a cannula and trocar assembly.

Connecting Anchor Embodiment

Figure 95:
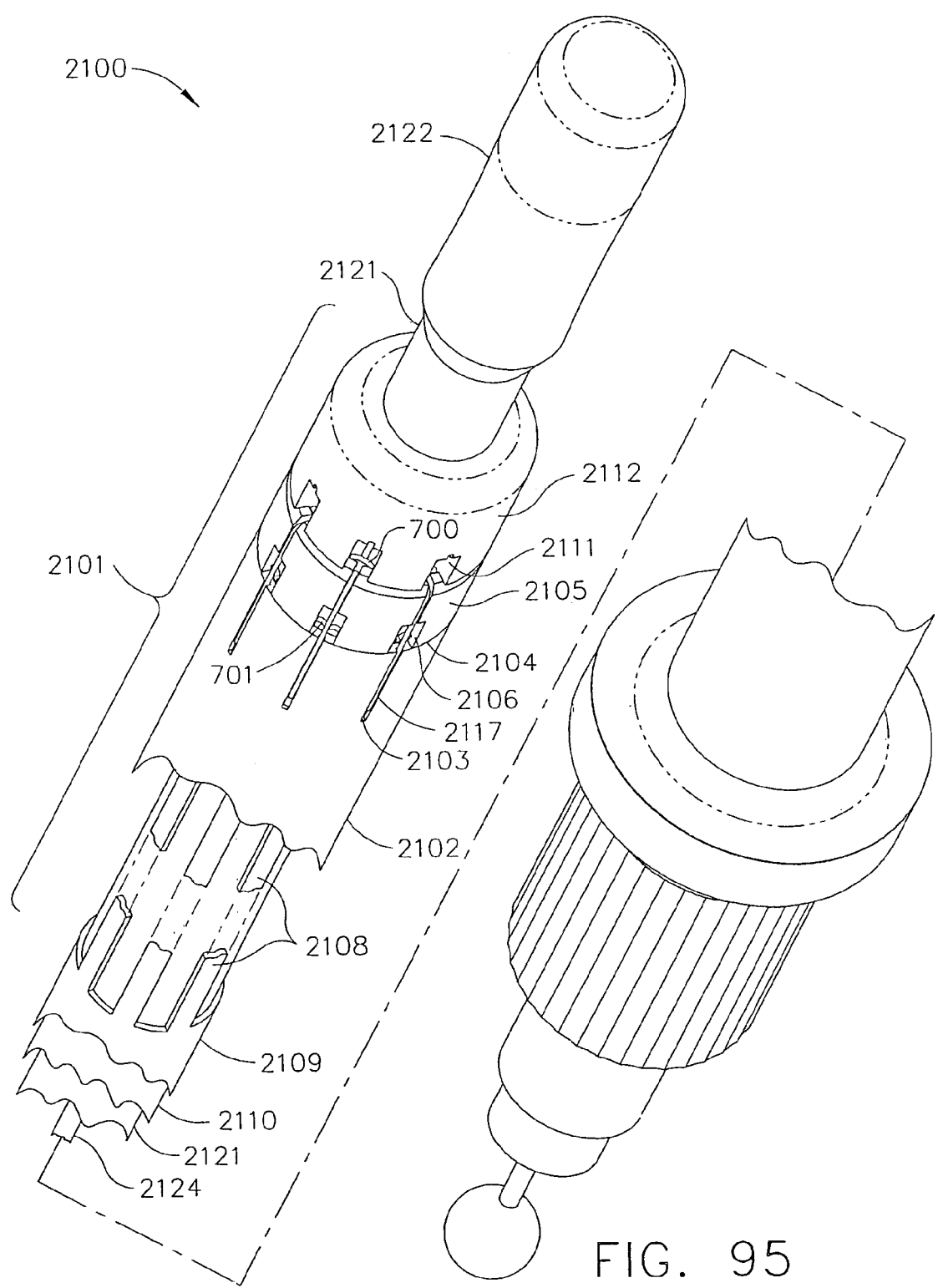
FIG. 95 is a perspective view of the distal and proximal ends of another embodiment of an anastomotic instrument in accordance with the present invention, shown in a retracted, pre-deployment position, with the intermediate section removed for ease of depiction in the drawing.
Figure 96:
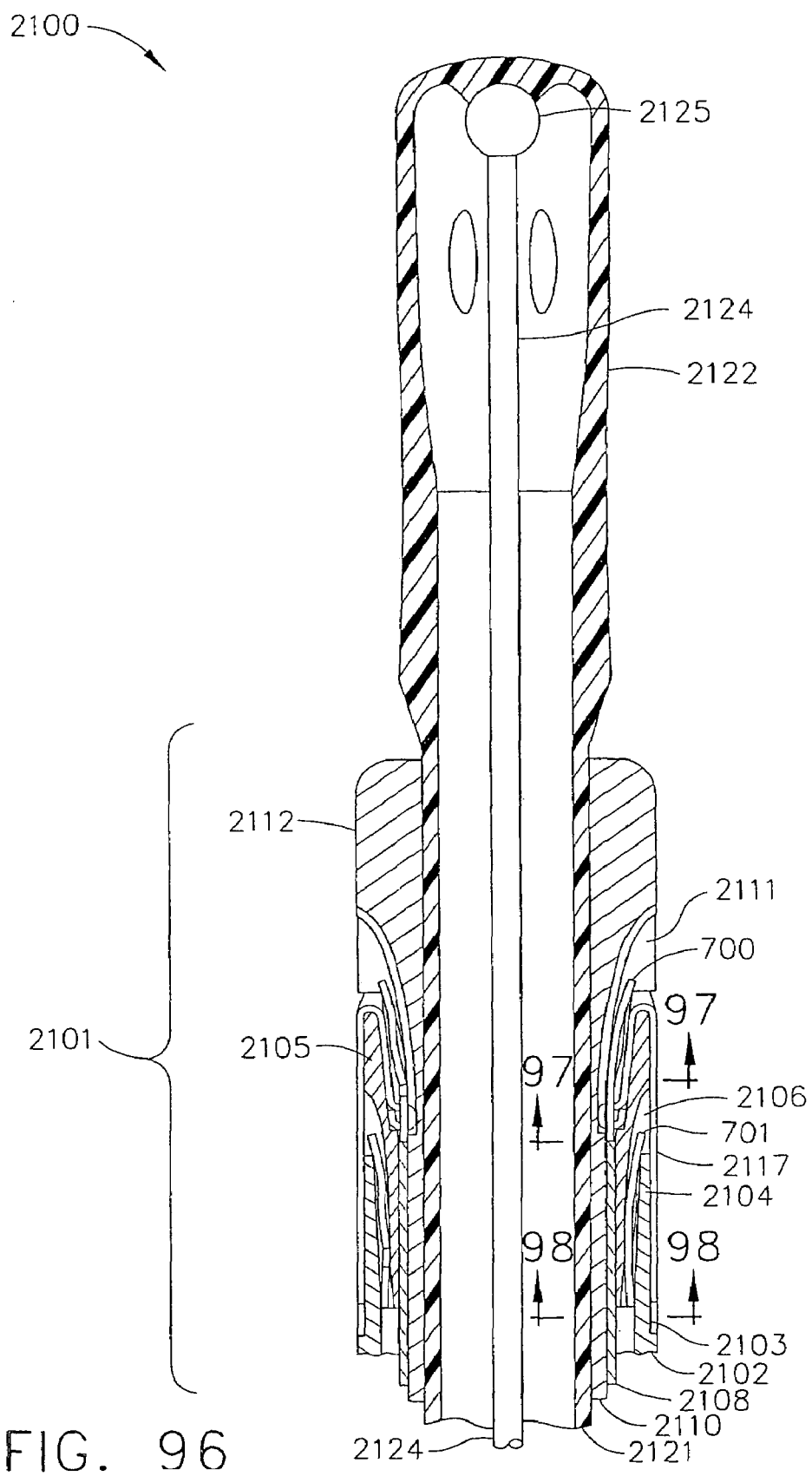
FIG. 96 is a longitudinal cross section of the distal end of the instrument shown in FIG. 95, shown in a retracted, pre-deployment position.

FIG. 95 is a perspective view of another embodiment of an anastomotic instrument 2100 of the present invention, in its pre-deployment position, and FIG. 96 is a longitudinal cross-sectional view of the distal end of the instrument, also shown in its pre-deployment position. The instrument may comprise anchor driver assembly 2101, which may include outer driver assembly tube 2102, having distal end 2104, second anchor track collar 2105, anchor driver tube 2109 which distally terminates with anchor driver pins 2108, and inner driver assembly tube 2110 which distally terminates with first anchor track collar 2112. The present embodiment may further comprise positioner tube 2121, positioner 2122 affixed to the distal end of positioner tube 2121, rod 2124 and rod cap 2125. When the instrument is assembled and prepared for use, anchor driver assembly 2101 may loaded with one or more anchor pairs, each pair comprising first anchor 700 with an attached length of suture 2117, and second anchor 701.

Figure 97:
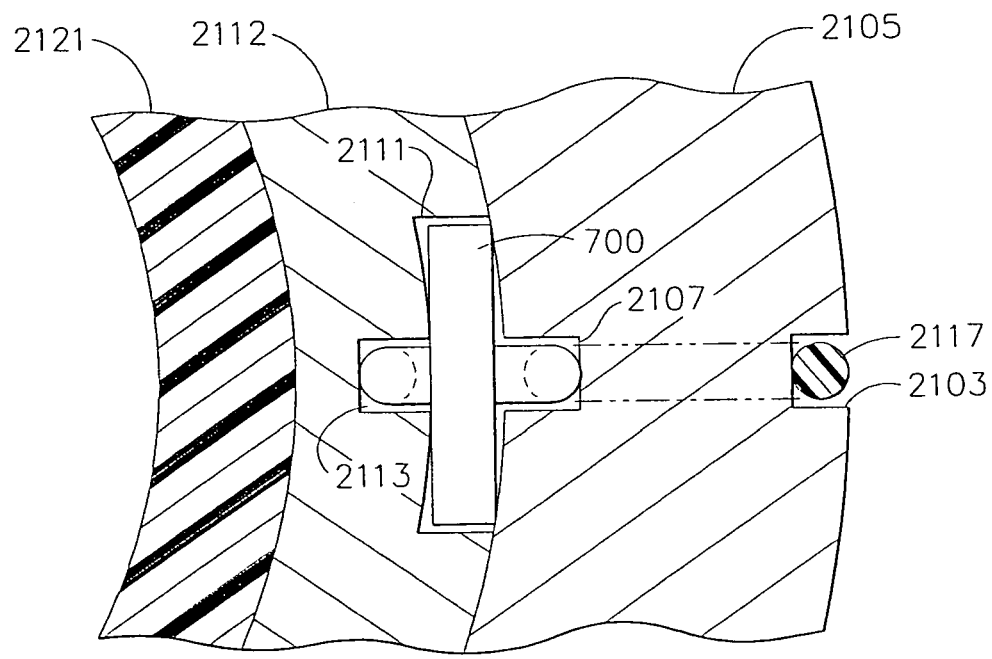
FIG. 97 is a partial transverse cross section of the instrument shown in FIG. 96, indicated at 97-97 of FIG. 96, showing sectional views of a second anchor guide collar, first anchor guide collar, positioner tube, and a first anchor and trailing suture, loaded into the instrument in pre-deployment positions.
Figure 98:
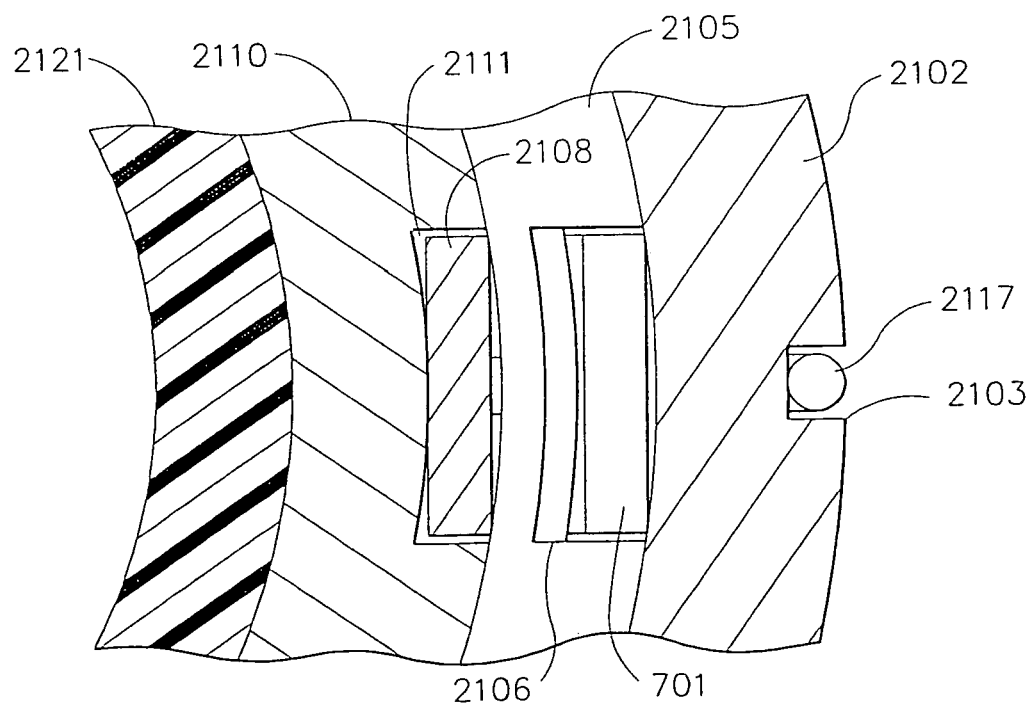
FIG. 98 is a partial transverse cross section of the instrument shown in FIG. 96, indicated at 98-98 of FIG. 96, showing sectional views of an outer driver assembly tube, anchor guide collar, anchor driver pin, inner driver assembly tube, positioner tube, and second anchor and an end of a trailing suture, loaded into the instrument in pre-deployment positions.

Referring to FIG. 96 and as may be seen in more detail in FIGS. 97 and 98, positioner tube 2121, inner driver assembly tube 2110 distally terminating in first anchor track collar 2112, second anchor track collar 2105, and outer driver assembly tube 2102, may be assembled such that they are substantially coaxial, with first anchor tracks 2111, second anchor tracks 2106 and anchor driver pins 2108 longitudinally aligned. First anchor track collar 2112 may have in its outer surface one or more longitudinally-oriented first anchor tracks 2111 including suture clearance tracks 2113, which direct upwardly and radially outwardly, moving longitudinally, proximally to distally. Second anchor track collar 2105 may have in its outer surface one or more longitudinally-oriented second anchor tracks 2106, which also direct upwardly and radially outwardly, moving longitudinally, proximally to distally. Second anchor track collar 2105 also has suture clearance tracks 2107 on its inside surface, situated opposite suture clearance tracks 2113 in first anchor track collar 2112, and one or more longitudinally-oriented suture storage grooves 2103 on its outer surface. Distal end 2104 of outer driver assembly tube 2102 may have on its outer surface one or more longitudinally-oriented suture storage grooves 2103, that align with and thereby form extensions of suture storage grooves 2103 on second anchor track collar 2105. When the instrument is assembled and ready for use, inner driver assembly tube 2110, with first anchor track collar 2112, second anchor track collar 2105, and outer driver assembly tube 2102, may be made integral with respect to each other by any suitable means.

Figure 99:
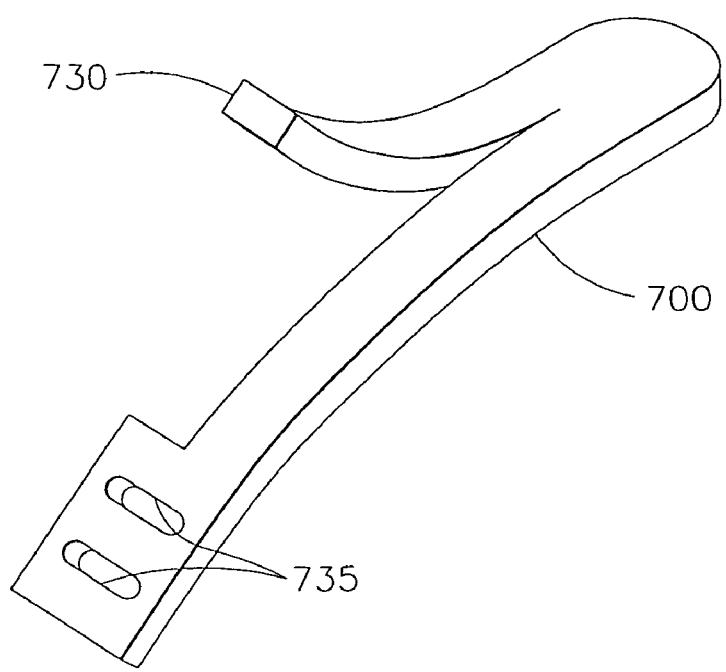
FIG. 99 is an enlarged perspective view of an embodiment of a first anchor that may be used in the instrument shown in FIG. 95, shown in a deployed shape.
Figures 100, 101:
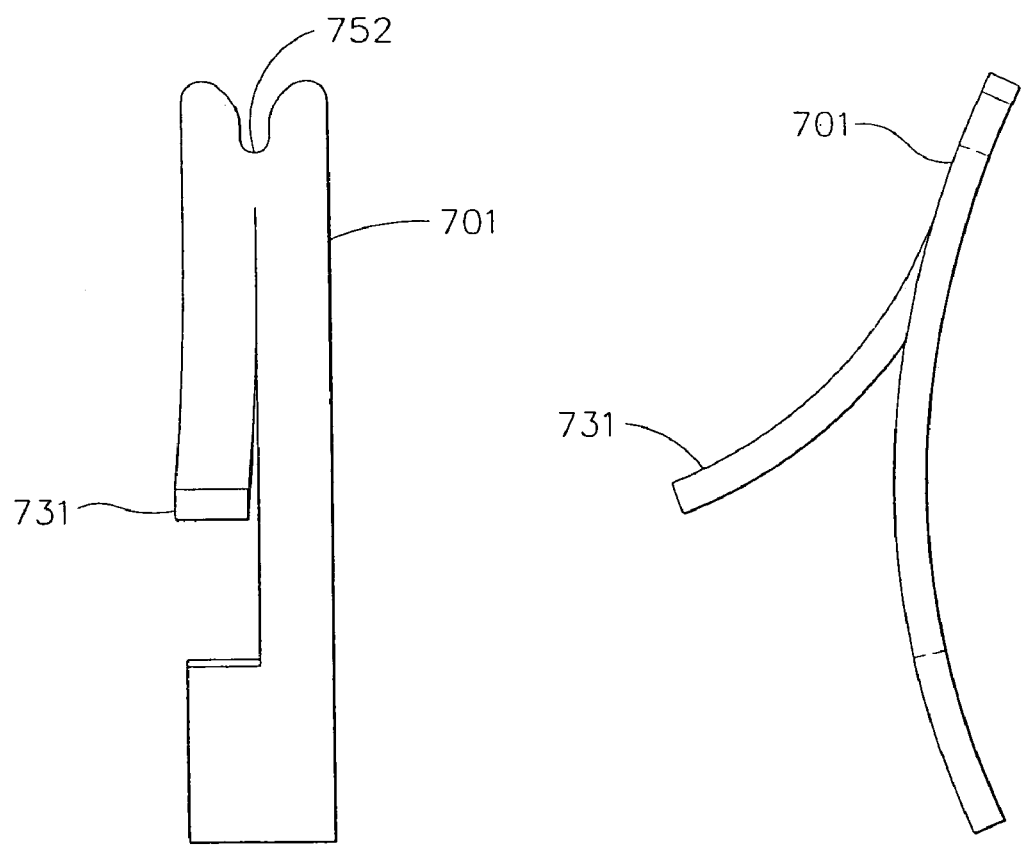
FIG. 100 is an enlarged frontal view of an embodiment of a second anchor that may be used in the instrument shown in FIG. 95, shown in a deployed shape.
FIG. 101 is an enlarged side view of the second anchor shown in FIG. 100.

FIGS. 99-101 are enlarged views of exemplary anchors that may be used in the present embodiment. First anchor 700 may have barb 730 and suture holes 735. Suture holes 735 may be used to attach a length of trailing suture or other suitable connecting member to first anchor 700 in preparation for use. Second anchor 701 may have barb 731 and suture notch 752. Suture notch 752 is shaped and sized so as to be effective to capture and bindingly hold a free end of suture or other suitable connecting member as will be hereinafter described. Anchors 700 and 701 may be manufactured so as to be biased to assume the shapes shown in FIGS. 99-101, and may be made of a material having suitable properties of strength, flexibility, shape memory, non-reactivity with body tissues and fluids, and biocompatibility. Anchors 700 and 701 may also be made of dissolving bioabsorbable materials, or may be made of suitably treated nitinol or surgical stainless steel.

FIGS. 96-98 depict first anchors 700 and second anchors 701 loaded into the present embodiment of an anastomotic instrument, ready for deployment. As can be seen from the drawings, as loaded, first anchors 700 may reside in the spaces defined by first anchor tracks 2111 and the interior surface of second anchor track collar 2105. Similarly, second anchors 701 may reside in the spaces defined by second anchor tracks 2106 and the interior surface of outer driver assembly tube 2102. As can be appreciated from the drawings, the spaces defined by the anchor tracks 2111 and 2106 restrain the barbs 730 and 731 of anchors 700 and 701 while the anchors are loaded in the instrument. Sutures 2117 or other suitable connecting members may be attached to the rear ends of first anchors 700 via suture holes 735 (shown in FIG. 99) and trail from the rear ends of first anchors 700, upwardly through suture clearance tracks 2107, radially out and over second anchor track collar 2105, and downwardly in suture storage grooves 2103, terminating with free ends.

As can be seen in FIGS. 96-98, when the instrument is ready for use anchor driver pins 2108 reside in first anchor tracks 2111 with their distal ends behind anchors 700 in preparation for driving first anchors 700 as will be hereinafter described. Anchor driver pins 2108 are integral with a distal end of anchor driver tube 2109 (shown in FIG. 95). Anchor driver tube 2109 is longitudinally movable with respect to outer driver assembly tube 2102 and inner driver assembly tube 2110. Anchor driver pins 2108 are made of a suitable flexible, shape memory material such as nitinol, and are biased so as to have their distal ends spring radially outwardly upon repositioning in preparation for driving second anchors 701, as will be described below.

The instrument may comprise one or more pairs of anchors, each pair comprising a first anchor and a second anchor, and the associated tracks, grooves and anchor driver pins described above, situated radially about the instrument in positions such upon correct rotational orientation of the instrument, the anchors may be driven into tissues in directions selected to avoid nerve and/or circulatory system bundles or other sensitive areas.

Figure 103:
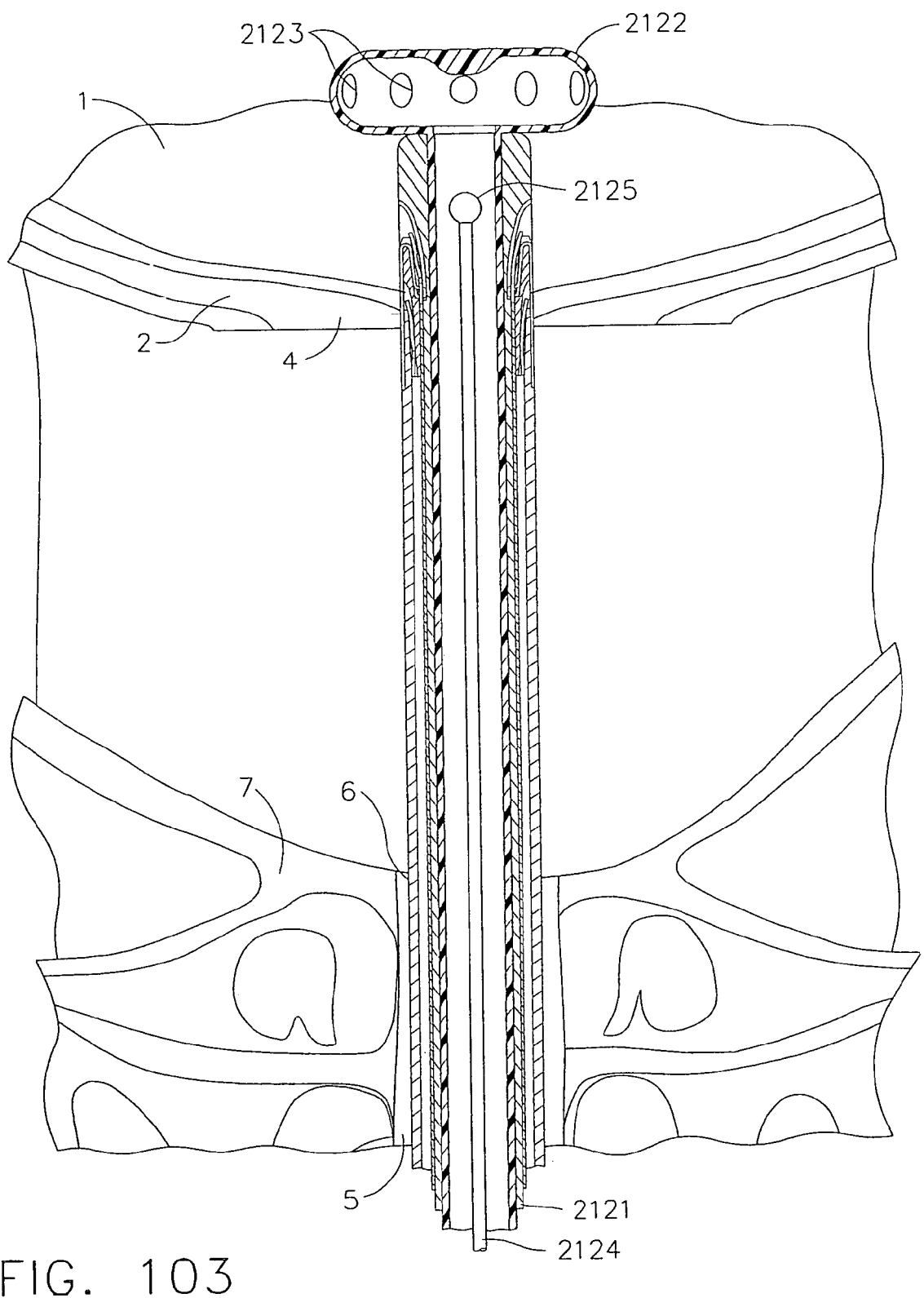
FIG. 103 is a longitudinal cross section of the instrument shown in FIG. 95, shown after insertion into and through a patient's urethra and into the bladder, and after a positioner has been moved to a deployed position.

Referring again to FIG. 96, the instrument of the present embodiment also may include positioner tube 2121. Affixed at the distal end of positioner tube 2121 is positioner 2122, shown in its pre-deployment shape in FIGS. 95 and 96. The pre-deployment shape of positioner 2122, shown in FIGS. 95 and 96, can facilitate insertion of the instrument into the patient. Positioner 2122 may be made of a suitable elastic and flexible polymeric material having shape memory, manufactured so as to be biased to assume a normally transversely-oriented shape as shown in FIG. 103, upon retraction of rod 2124. As shown in FIG. 103, positioner 2122 may have, about its perimeter, one or more drainage holes 2123 that can permit urine, fluids or clotted material to drain into positioner tube 2121 after the instrument has been deployed. Positioner 2122 may be, alternately, moved to a pre-deployment position shown in FIGS. 95 and 96, or allowed to return via shape memory to a normal (deployed) position shown in FIG. 103, by longitudinal movement of rod 2124, and correspondingly, end cap 2125, which may be integrally affixed to rod 2124. Positioner tube 2121 is longitudinally movable with respect to inner driver assembly tube 2110, and vice versa.

Outer driver assembly tube 2102, anchor driver tube 2109, inner driver assembly tube 2110, positioner tube 2121 and rod 2124 may be made of a material having suitable combined properties of shape memory, flexibility, strength and stiffness that both enable the tubes and rod to flex during insertion into the patient's body and through the urethra as will be described below, but also will prevent them from collapsing, kinking, binding, or breaking during use. The selected material may also be substantially non-reactive with body fluids and tissues, and be substantially biocompatible, or be non-biocompatible with a biocompatible coating. The inventors have determined that nitinol, known in the art as suitable for a variety of surgical devices and tubes, is one example of a suitable material.

It will be appreciated that hollow tubes may be used in the instrument for positioner tube 2121 when a coaxial arrangement with rod 2124 is desirable, or when positioner tube 2121 is to serve as a catheter, such as will be further described below, but that a rod may be substituted for positioner tube 2121 and be used to provide substantially the same mechanical function, i.e., transmission of forces to actuate the positioner, and thus may be used when a catheter function, or a coaxial arrangement, and thus a tube, is not required. Conversely, a tube can serve the purpose of rod 2124. Thus, for purposes of the claims set forth herein, unless otherwise specified in a claim, the term "tube" where such element is operably affixed or connected with, or contacts, the positioner, is intended to include and cover a rod, and vice versa.

A method for performing anastomosis of a patient's bladder and urethra using the above-described anastomotic instrument, following a prostatectomy, will now be described. Following a prostatectomy, the patient's bladder 1 and urethra opening 6 are separated by a void formerly occupied by the prostate, as shown in FIG. 2. It is necessary to connect the bladder 1 with the urethra 5, with bladder opening 4 and urethra opening 6 aligned, to restore urinary functions after recovery and healing.

Figure 102:
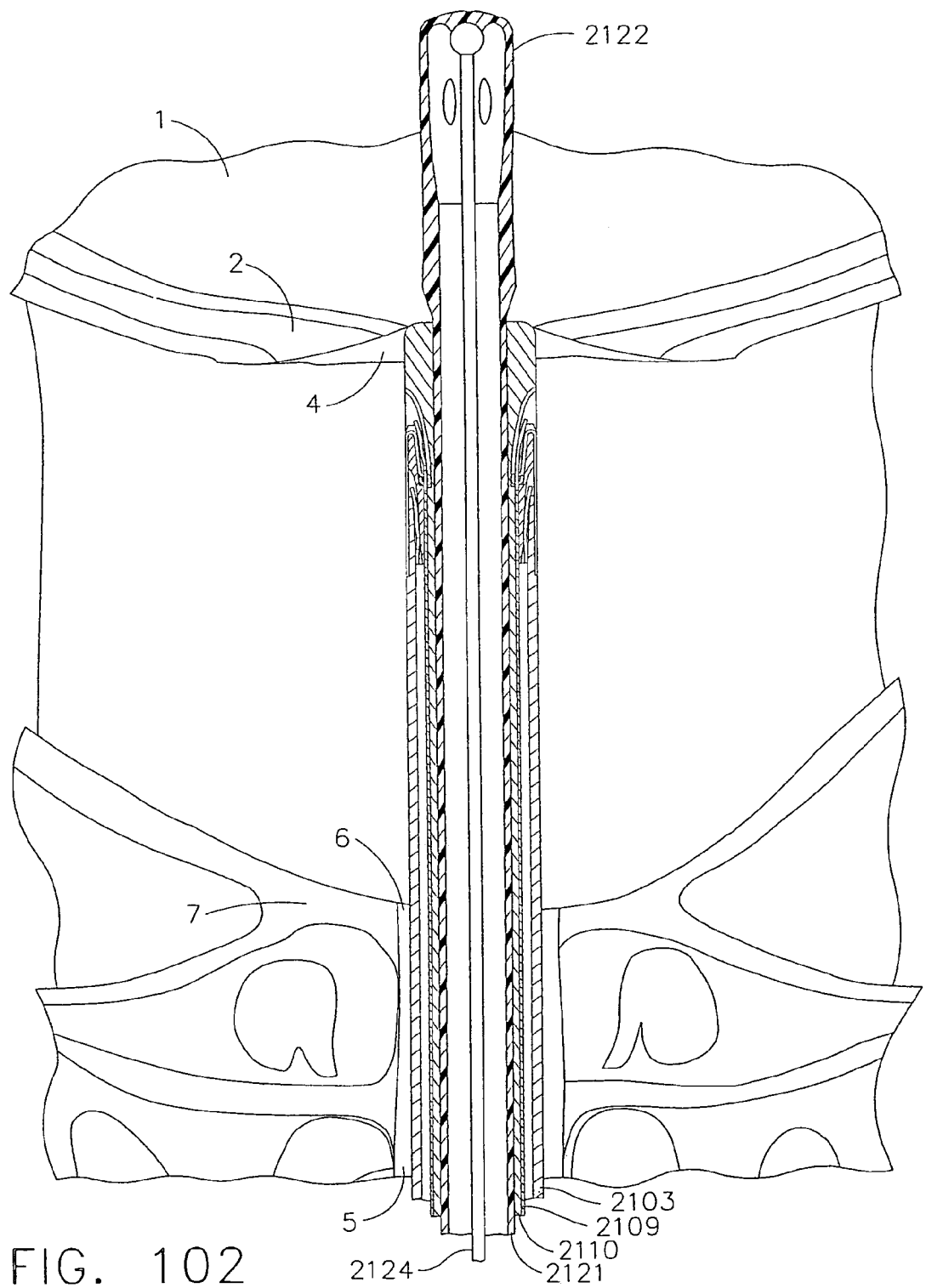
FIG. 102 is a longitudinal cross section of the instrument shown in FIG. 95, shown in a retracted, pre-deployment position after insertion into and through a patient's urethra and into the bladder, following a prostatectomy.

As shown in FIG. 102, the anastomotic instrument may be inserted upwardly into and through the patient's urethra 5, through the bladder opening 4, and into the bladder 1. The surgeon then may retract rod 2124 and correspondingly, end cap 2125, which will permit positioner 2122 to assume its normal shape via shape memory, as shown in FIG. 103. The now-transverse orientation of positioner 2122 will prevent it from being retracted without pulling bladder wall 2 surrounding bladder opening 4 with it.

Figure 104:
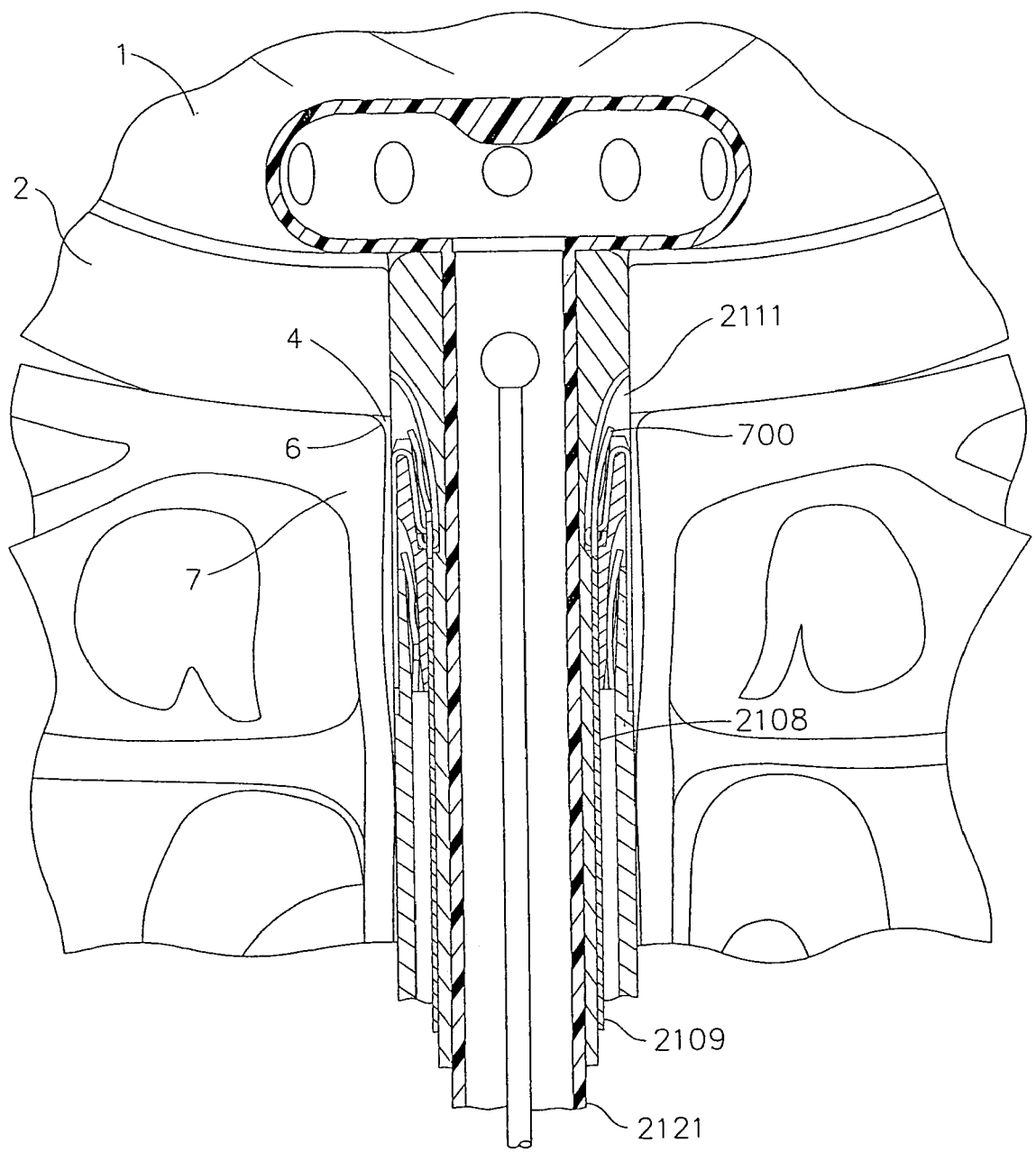
FIG. 104 is a longitudinal cross section of the instrument shown in FIG. 95, shown after insertion into and through a patient's urethra and into the bladder, after a positioner has been moved to a deployed position, and after the bladder wall has been urged into contact with the pelvic floor with the openings in the bladder and urethra aligned.

Next, the surgeon may retract the entire instrument downwardly through the urethra, which will cause positioner 2122 to pull bladder walls 2 surrounding bladder opening 4 into contact with pelvic floor 7, with bladder opening 4 and urethra opening 6 aligned, to the position shown in FIG. 104.

Figure 105:
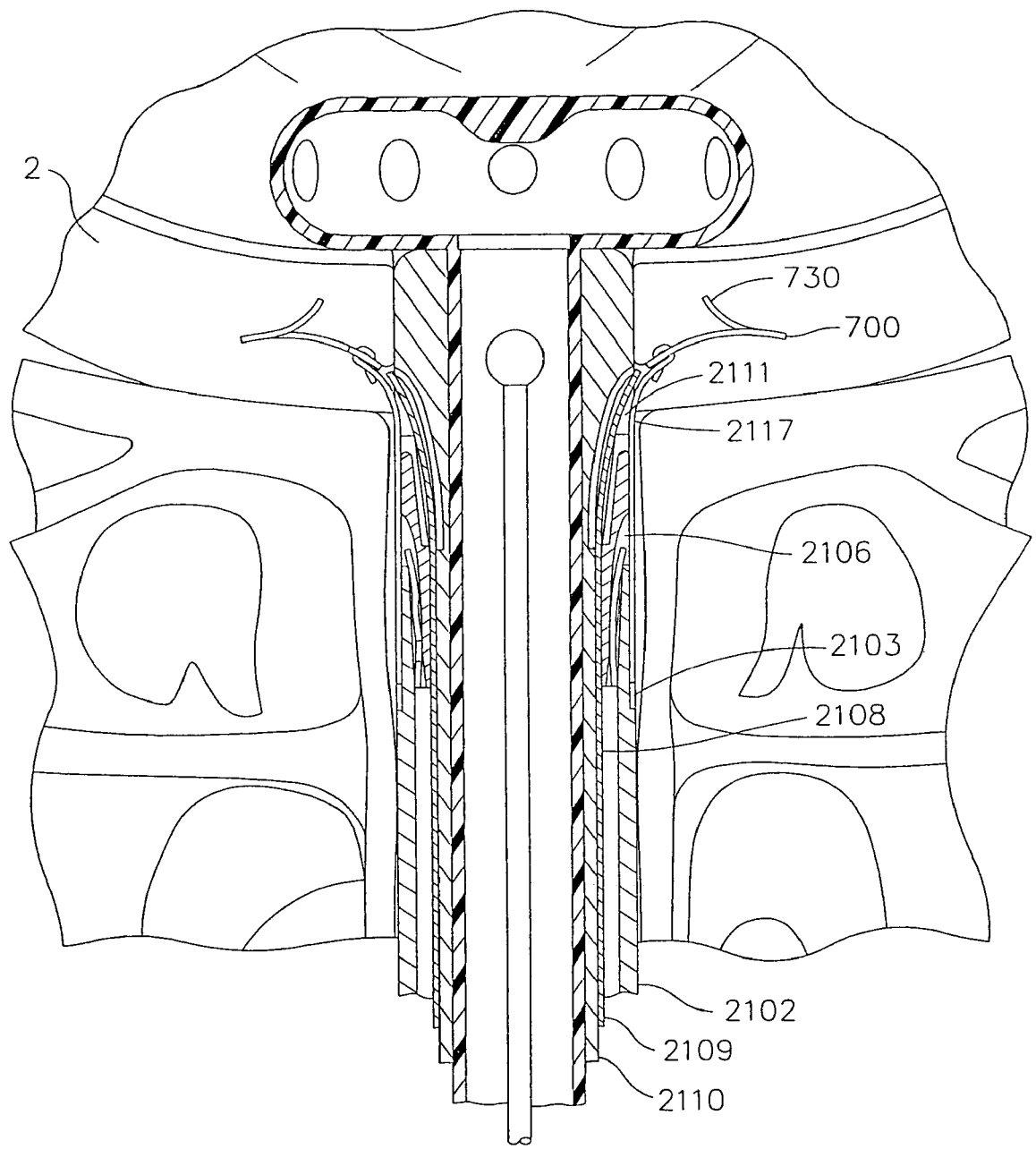
FIG. 105 is a longitudinal cross section of the instrument shown in FIG. 95, shown after insertion into and through a patient's urethra and into the bladder, after a positioner has been moved to a deployed position, after the bladder wall has been urged into contact with the pelvic floor with the openings in the bladder and urethra aligned, and after a first actuation of an anchor driver assembly to drive first anchors into the tissues of the bladder wall surrounding the bladder opening.

Next referring to FIG. 105, anchor driver tube 2109 may be moved longitudinally distally, which correspondingly will cause anchor driver pins 2108 to move upwardly and distally inside first anchor tracks 2111, driving first anchors 700 radially outwardly into the surrounding tissues of bladder wall 2, as shown in FIG. 105. When anchors 700 are driven out of the instrument, they are no longer restrained from their normal biased shapes, and thus barbs 730 can spring away from anchors 700 as shown, enabling anchors 700 to lodge in the tissues. After anchors 700 are driven into the bladder wall tissues, the attached sutures 2117 will trail from the rear ends of anchors 700, back out of the tissues, with their free ends continuing to reside in suture storage grooves 2103, passing over the exits of second anchor tracks 2106.

Figure 106:
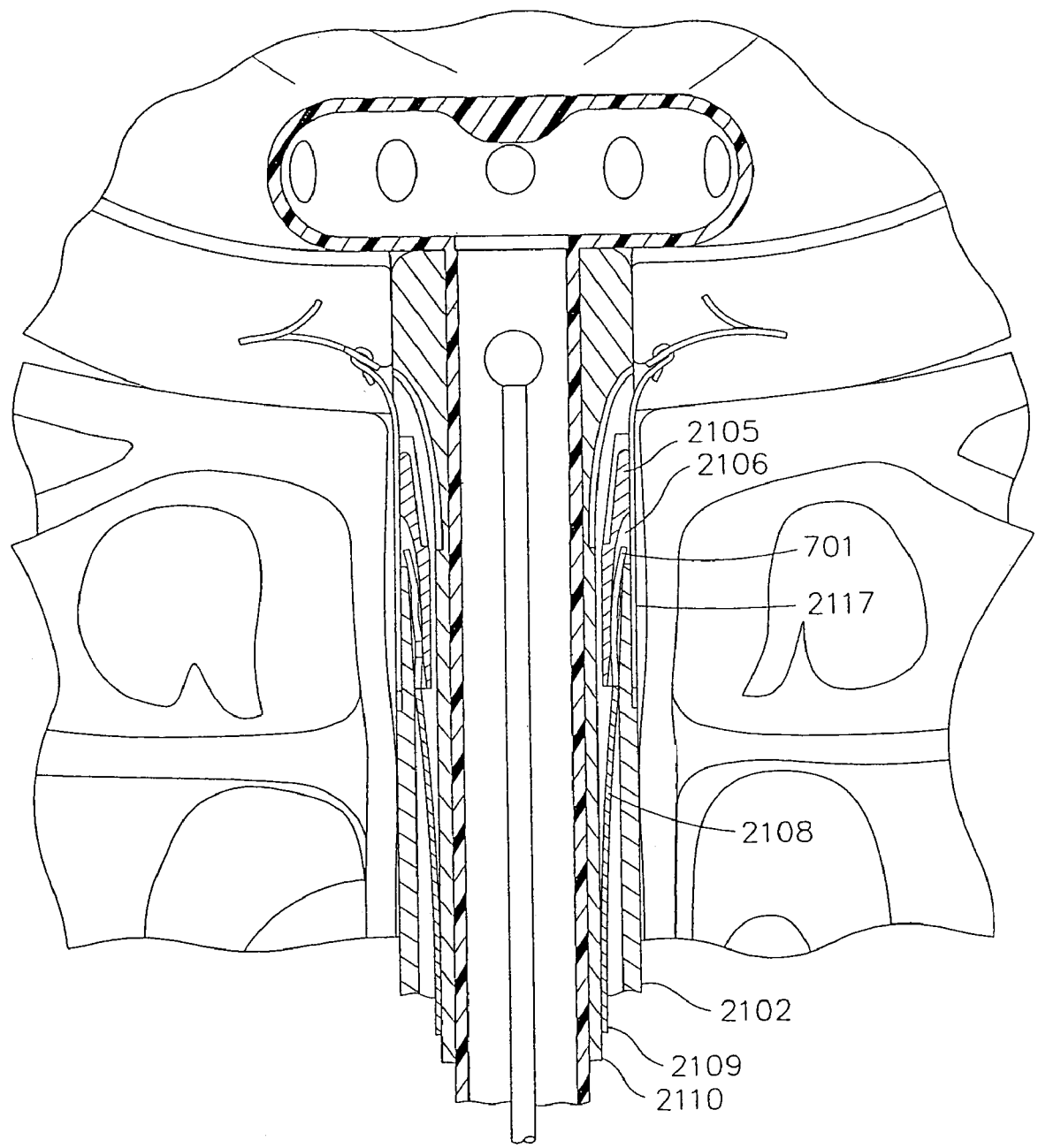
FIG. 106 is a longitudinal cross section of the instrument shown in FIG. 95, shown after insertion into and through a patient's urethra and into the bladder, after a positioner has been moved to a deployed position, after the bladder wall has been urged into contact with the pelvic floor with the openings in the bladder and urethra aligned, after a first actuation of an anchor driver assembly to drive first anchors into the tissues of the bladder wall surrounding the bladder opening, and after repositioning of anchor driver pins in preparation to drive second anchors.

Next, referring to FIG. 106, anchor driver tube 2109 and correspondingly, anchor driver pins 2108, may be longitudinally retracted proximally. When the distal ends of anchor driver pins 2108 are retracted past the proximal end of second anchor track collar 2105, the shape-memory bias of anchor driver pins 2108 will cause their distal ends to move radially outwardly into position behind second anchors 701, into the position shown in FIG. 106, ready to drive second anchors 701 upwardly and outwardly through second anchor tracks 2106.

Figure 107:
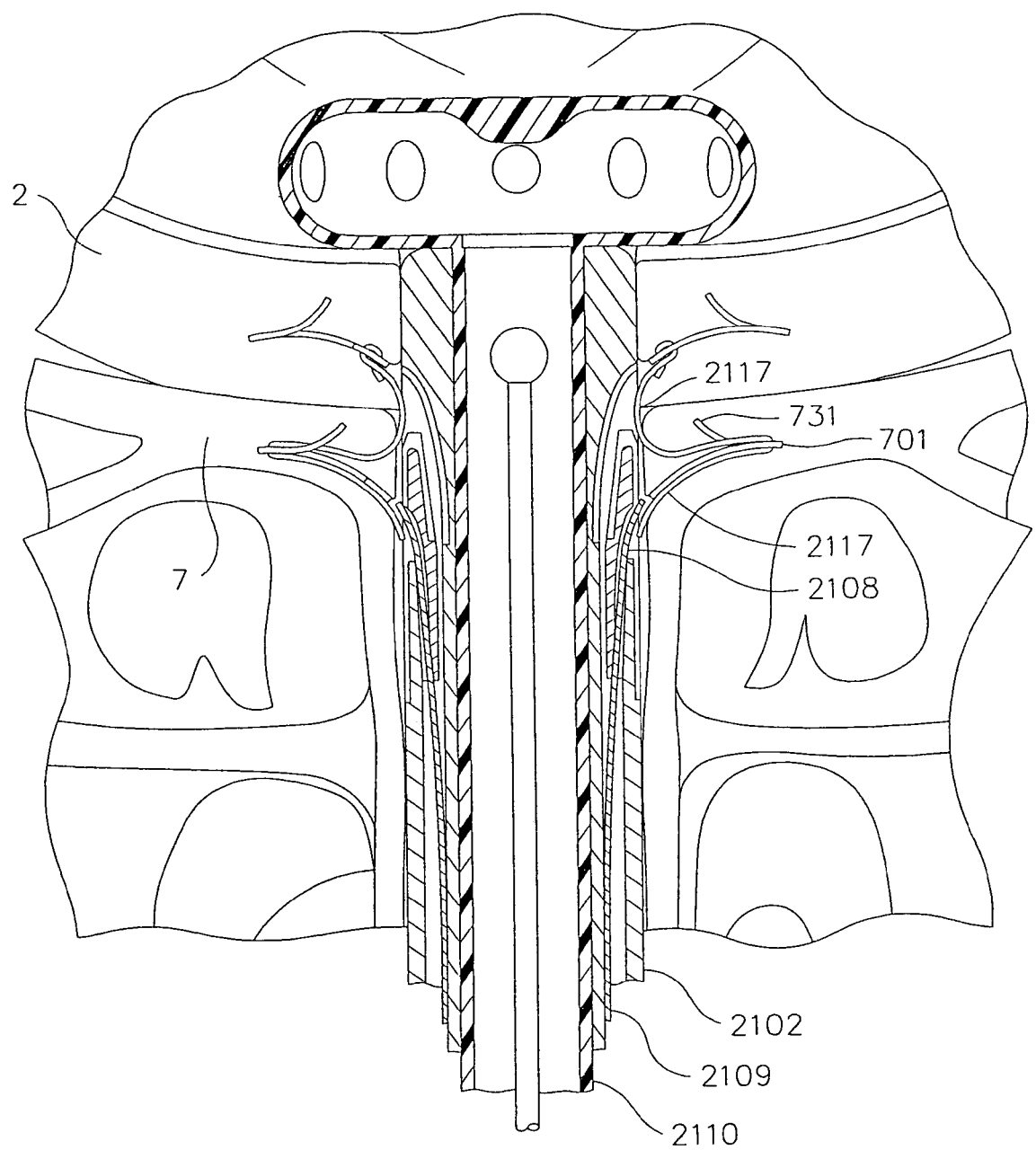
FIG. 107 is a longitudinal cross section of the instrument shown in FIG. 95, shown after insertion into and through a patient's urethra and into the bladder, after the positioner has been moved to a deployed position, after the bladder wall has been urged into contact with the pelvic floor with the openings in the bladder and urethra aligned, after a first actuation of an anchor driver assembly to drive first anchors into the tissues of the bladder wall surrounding the bladder opening, and after a second actuation of an anchor assembly to drive second anchors into the tissues surrounding the urethra opening.
Figure 108:
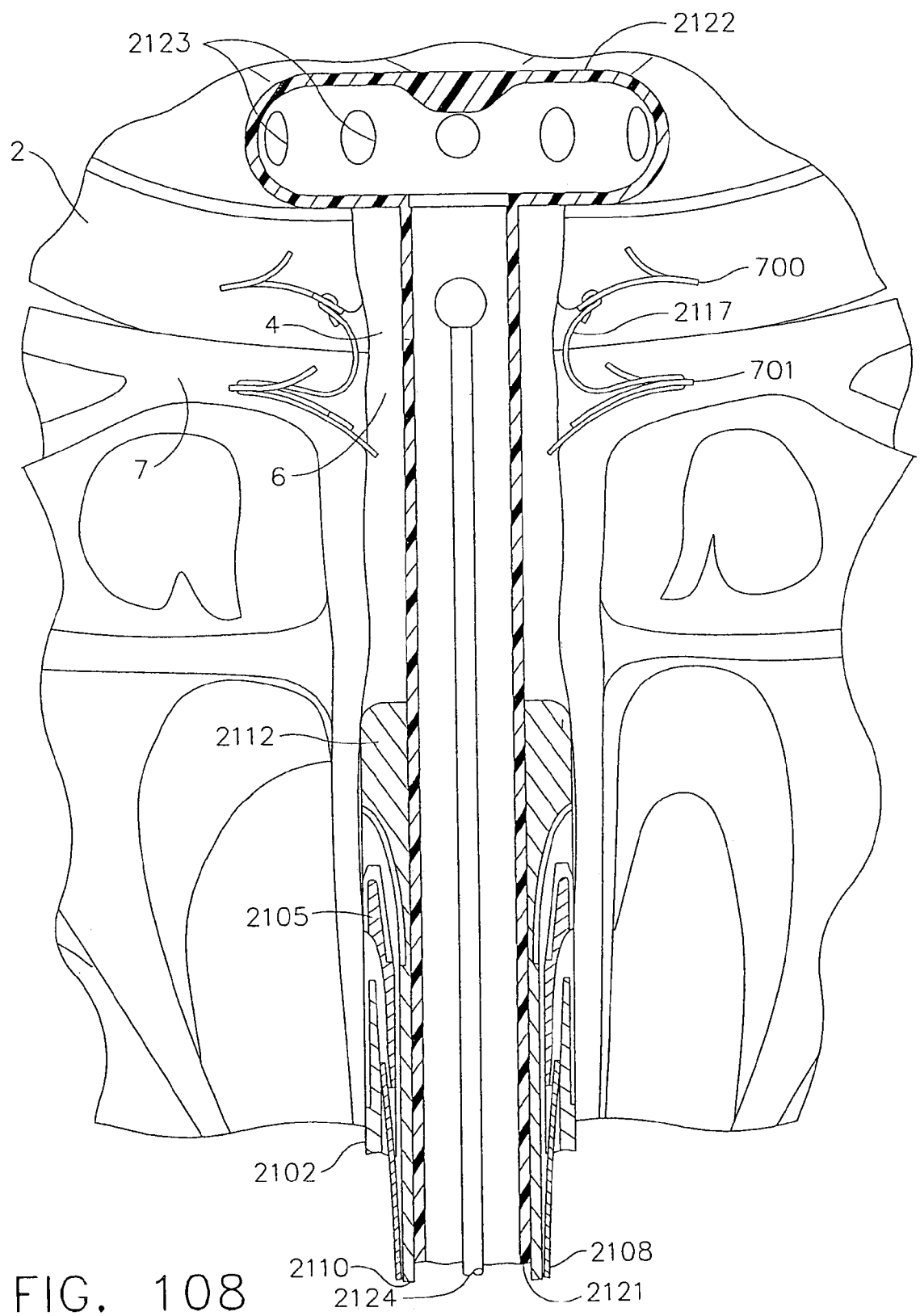
FIG. 108 is a longitudinal cross section of the instrument shown in FIG. 95, shown after insertion into and through a patient's urethra and into the bladder, after a positioner has been moved to a deployed position, after the bladder wall has been urged into contact with the pelvic floor with the openings in the bladder and urethra aligned, after anchor pairs and connecting sutures have been installed, and after retraction of an anchor driver assembly has commenced, to leave the positioner and a positioner tube behind to enable draining of urine and other fluids from the bladder during recovery and healing.

Next, referring to FIG. 107, anchor driver tube 2109 and correspondingly anchor driver pins 2108 may again be pushed longitudinally distally, while will cause the distal ends of anchor driver pins 2108 move distally into and through second anchor tracks 2106, and drive second anchors 701 radially outwardly into the surrounding tissues of pelvic floor 7, as shown in FIG. 107. As the fore ends of second anchors 701 are driven out of the instrument, suture notches 752 (see FIG. 100) will contact the trailing lengths of sutures 2117 passing over the exits of second anchor tracks 2106 (see FIG. 106), and capture and bindingly hold these trailing lengths as second anchors 701 are driven into the tissues, as shown in FIG. 107. Thus, for each installed pair of anchors comprising first and second anchors 700 and 701, a suture 2117 (or other suitable connecting member) may be anchored into a position holding the tissues of bladder wall 2 surrounding bladder opening 4 in contact with the tissues of pelvic floor 7 surrounding urethra opening 6, with the bladder opening 4 and urethra opening 6 aligned. Thus held in contact, the tissues of the bladder wall 2 and pelvic floor 7 may knit and heal together and the bladder opening and urethra opening aligned.

Figure 109:
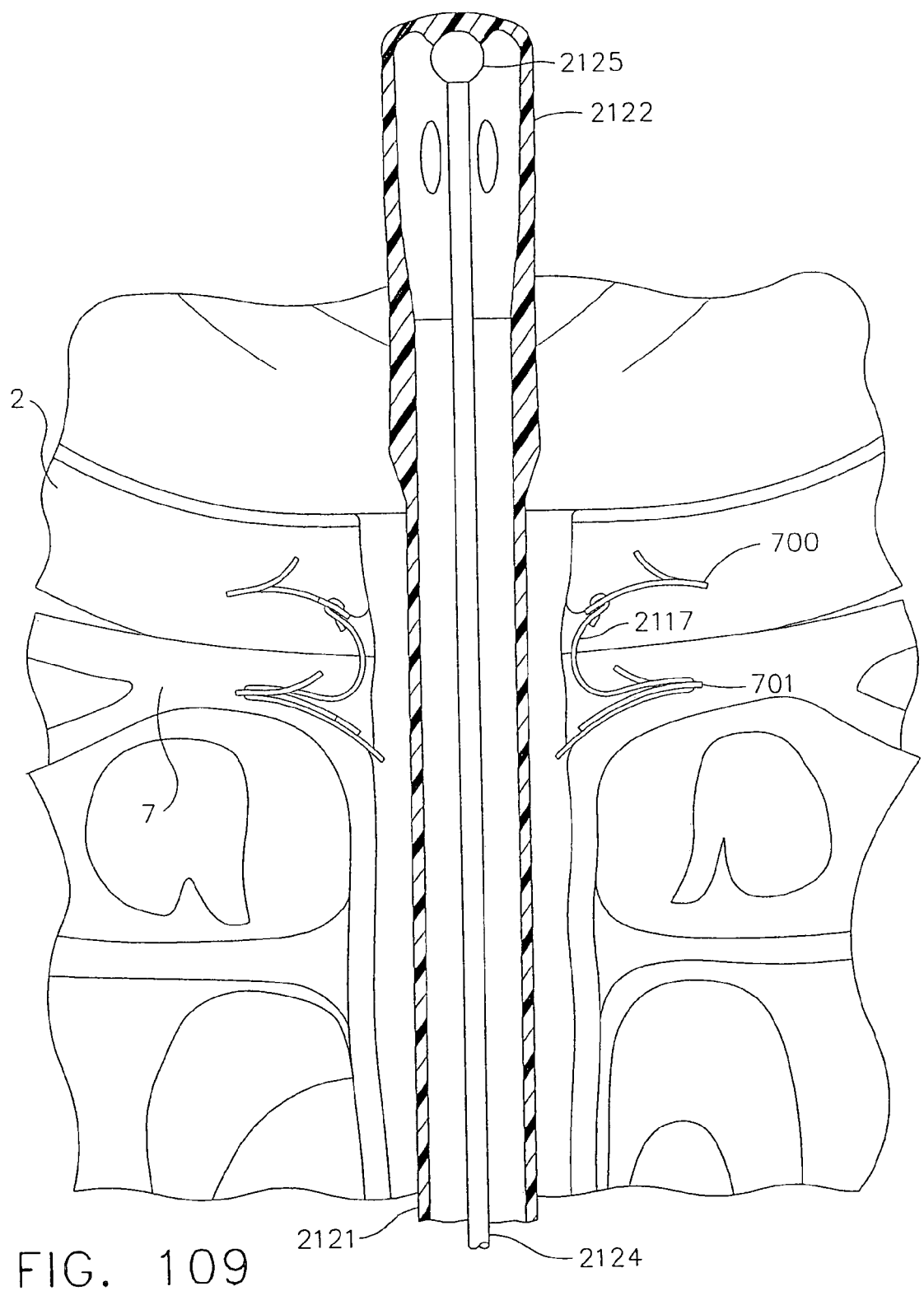
FIG. 109 is a longitudinal cross section of the instrument shown in FIG. 95, shown after retraction of an anchor driver assembly and after the anastomosis procedure has been completed, with a positioner in a retracted position ready for withdrawal of the remaining parts of the instrument from the bladder, down through the urethra and out of the patient's body.

Next, the entire anchor driver assembly, comprising inner driver assembly tube 2110 and first anchor track collar 2112, anchor driver tube 2109, second anchor track collar 2105, and outer driver assembly tube 2102, may be retracted as a unit (as shown in progress in FIG. 108), down the urethra and out of the patient's body, leaving behind positioner tube 2121, positioner 2122 and rod 2124. Remaining positioner 2122 and positioner tube 2121 may now be used to exert supplemental downward pressure on bladder walls 2 surrounding the bladder opening 4 so as to enhance contact and knitting between the tissues of bladder walls 2 surrounding the bladder opening 4, and the tissues of pelvic floor 7 surrounding the urethra opening 6. Additionally, or alternatively, positioner 2122, including drainage holes 2123, and positioner tube 2121, may now be used to seal off the junction between the bladder and urethra and drain urine, fluids and/or clotted material from the bladder during recovery and healing. Used for this purpose, positioner tube 2121 would be connected to a urine collection bag (not shown) via intermediate tubing. Following recovery and healing, rod 2124 and correspondingly end cap 2125 may be moved longitudinally upwardly or distally with respect to positioner tube 2121, thus urging positioner 2122 into its pre-deployment position as shown in FIG. 109, and enabling retraction of these remaining parts of the instrument out of the bladder, down through the urethra, and out of the patient's body.

Those skilled in the art of the design of mechanical surgical devices will appreciate that a variety of simple mechanical devices may be configured or adapted to actuate and manipulate outer driver assembly tube 2102 and inner driver assembly tube 2110, anchor driver tube 2109, positioner tube 2121 and rod 2124, at the proximal end of the instrument as required by the above steps, and so as to move and hold the instrument in respective pre-deployment and/or retracted, and deployed and first and second actuated, positions, including the handle assembly depicted in FIGS. 83 and 85 and described above, or a variation thereof.

It will be appreciated by those skilled in the art of design of mechanical surgical devices that the positioner need not be limited to the embodiment made of flexible and elastic polymeric shape memory material as described herein, but that alternative designs for such positioner are possible, which can cause the positioner to alternately assume a retracted position and a deployed position, the deployed position suitable for catching in the bladder opening and urging the bladder into contact with the pelvic floor, in response to forces exerted or transmitted by tubes or other members. The positioner may comprise, for example, any of the positioner assemblies depicted in FIGS. 14, 19, 24 and 57, and described hereinabove. Similarly, it will be appreciated by those skilled in the art of design of mechanical surgical devices that the anchor driver assembly need not be limited to the three-tube assembly described herein, but that alternative designs for such an assembly are possible, which cause the anchor driver assembly to install one or more connected pairs of anchors into the tissues of the bladder and the urethra radially about the respective openings of these lumens when they are brought together, in response to forces exerted or transmitted by tubes or other members.

As previously noted, the combination of tubes, positioner and driver assembly may be designed and configured in an instrument adapted for a retrograde anastomosis procedure, as described above, or configured in an instrument adapted for an antegrade procedure. In an antegrade procedure, instead of being inserted upwardly through the urethra and into the bladder opening proximate the site of excision of the prostate, the instrument is inserted downwardly through a small incision in the patient's abdomen, through a small incision on an upper surface of the patient's bladder, into the bladder, through the bladder opening, and into the urethra opening. The small incisions in the abdomen and upper surface of the bladder may be made with a cannula and trocar assembly and held open by the cannula for insertion of the instrument therethrough.

Deformable Fastener Embodiment

Figure 110:
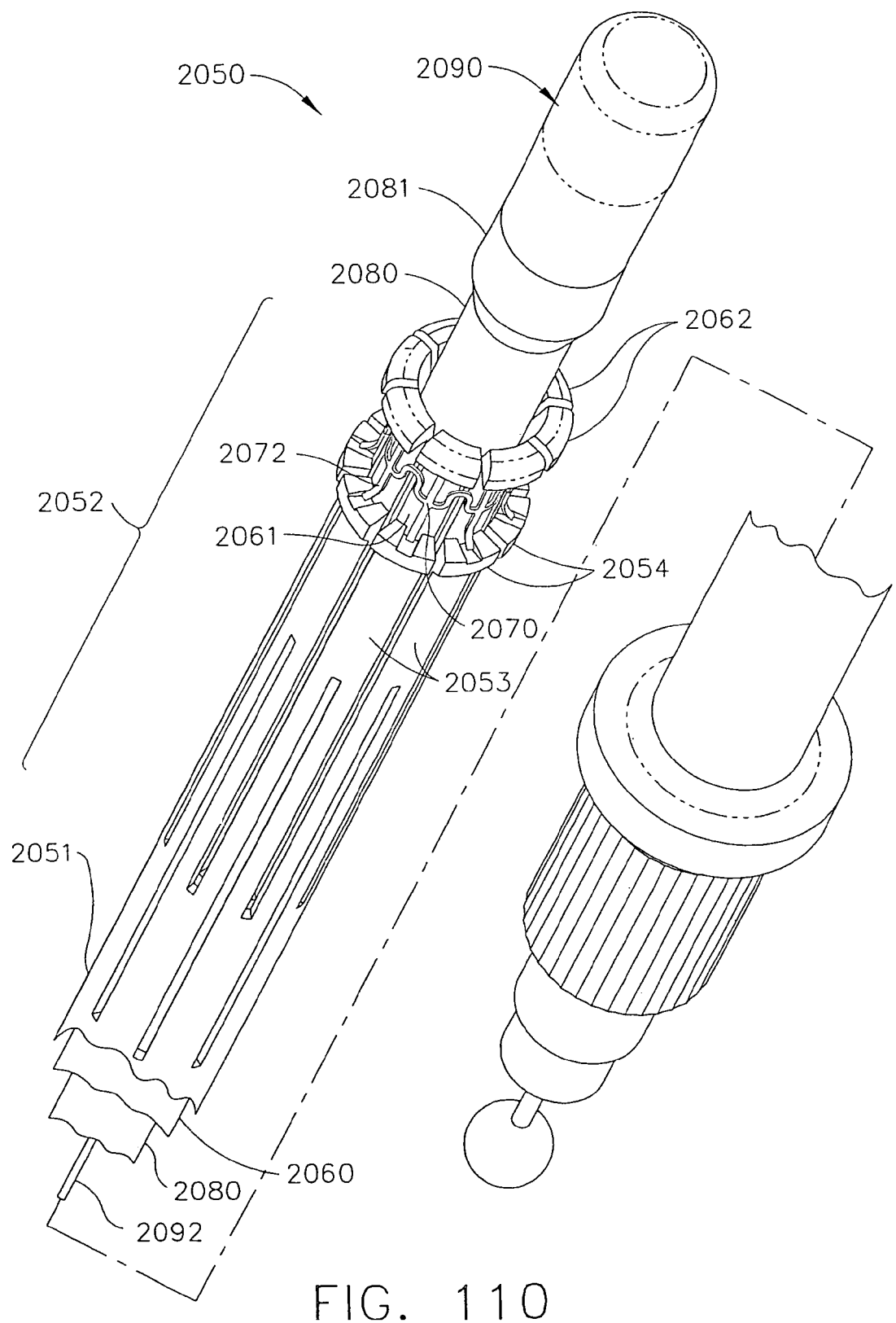
FIG. 110 is a perspective view of another embodiment of the distal and proximal ends of an anastomotic instrument of the present invention, with the intermediate section removed for ease of depiction in the drawing.
Figure 111:
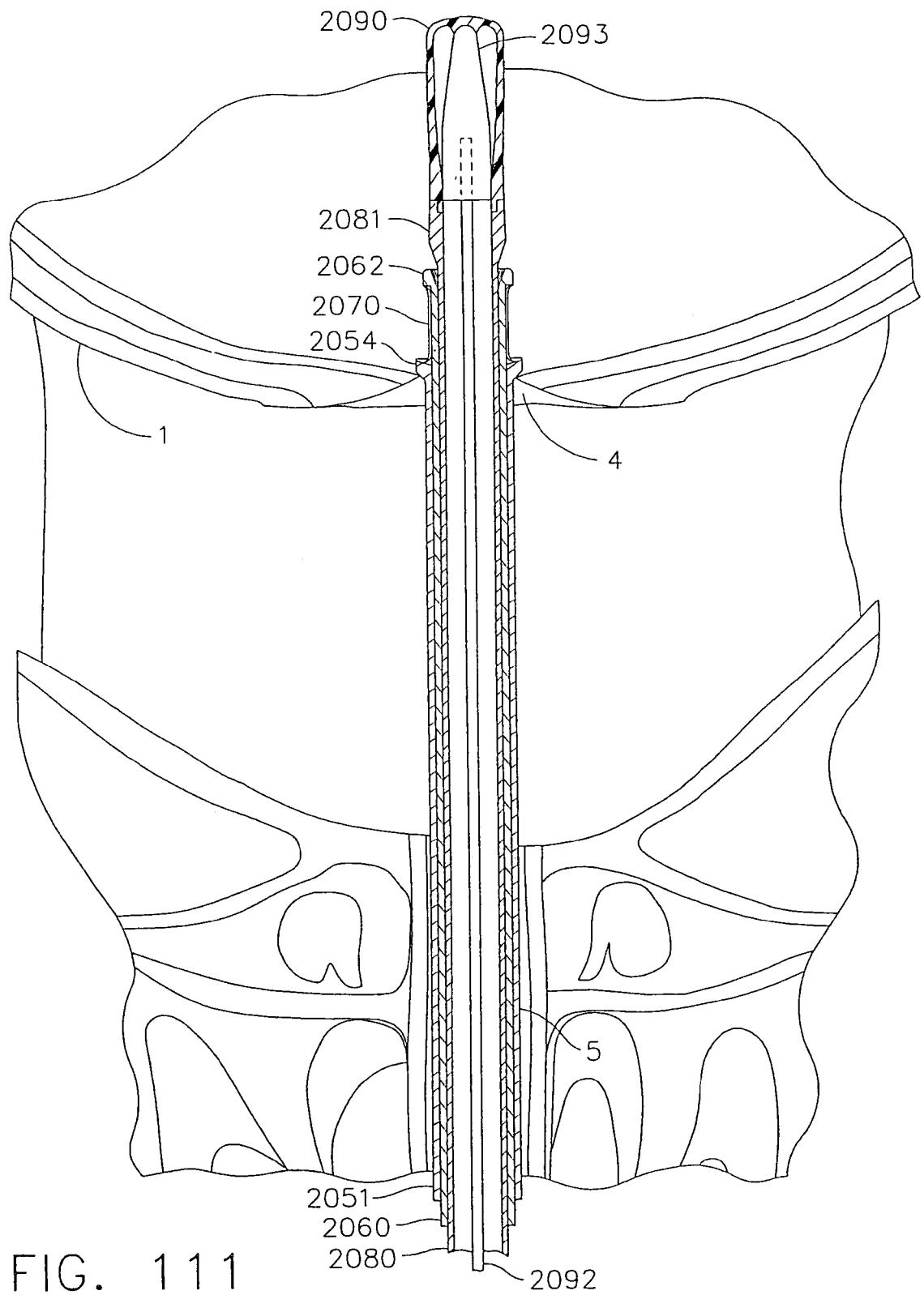
FIG. 111 is a longitudinal cross section of the instrument shown in FIG. 110, shown in a retracted and pre-deployment position after insertion into and through a patient's urethra and into the bladder, following a prostatectomy.

FIG. 110 is a perspective view of another embodiment of an anastomotic instrument 2050 of the present invention, in its pre-deployment position, and FIG. 111 is a longitudinal cross-sectional view of the instrument, also shown in its pre-deployment position, after insertion into and through the patient's urethra and into the bladder 1. The instrument may comprise fastener driver assembly 2052 including outer tube 2051 and second tube 2060. Outer tube 2051 may terminate with flexible fingers 2053, which in turn terminate with proximal fastener anvils 2054. Second tube 2060 may be immediately inside and substantially coaxial with outer tube 2051. Second tube 2060 may terminate with flexible fingers 2061, which in turn terminate with distal fastener anvils 2062, which may be longitudinally aligned with and may longitudinally oppose proximal fastener anvils 2054.

When the fastener driver assembly 2052 is being assembled in preparation for its use, fastener set 2070 in its pre-deployment shape (shown in enlarged perspective view in FIG. 119) is placed onto second tube 2060 and moved over flexible fingers 2061 to a position in which the upper prongs of fasteners 2072 of fastener set 2070 are proximate to upper anvils 2062. Next, outer tube 2051 may be slid over and up second tube 2060, until lower anvils 2054 are in a position proximate to the lower prongs of fasteners 2072 of fastener set 2070, thus holding fastener set 2070 in a position on the fastener driver assembly ready for deployment (as shown in FIG. 110) via actuation of the fastener driver assembly as will be described below.

Thus, it can be seen in FIGS. 110 and 111 that fastener driver assembly 2052 may comprise outer tube 2051 with its flexible fingers 2053 and lower anvils 2054, second tube

2060, with its flexible fingers 2061 and upper anvils 2062. When fastener assembly 2052 is assembled and made ready for use, it may include fastener set 2070 in a pre-deployment shape, placed as shown.

Figure 119:
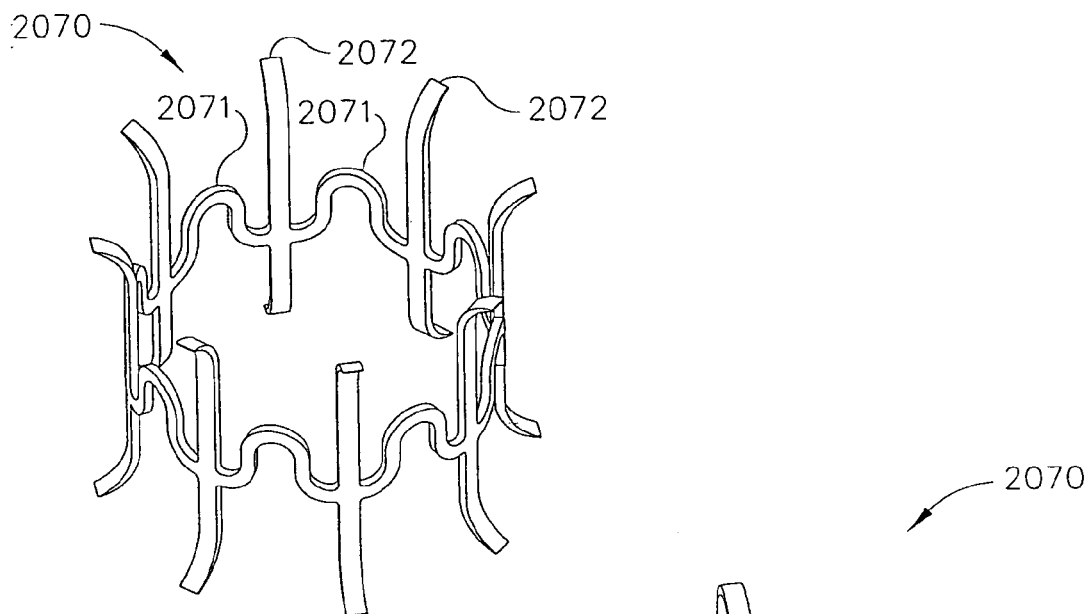
Figure 120:
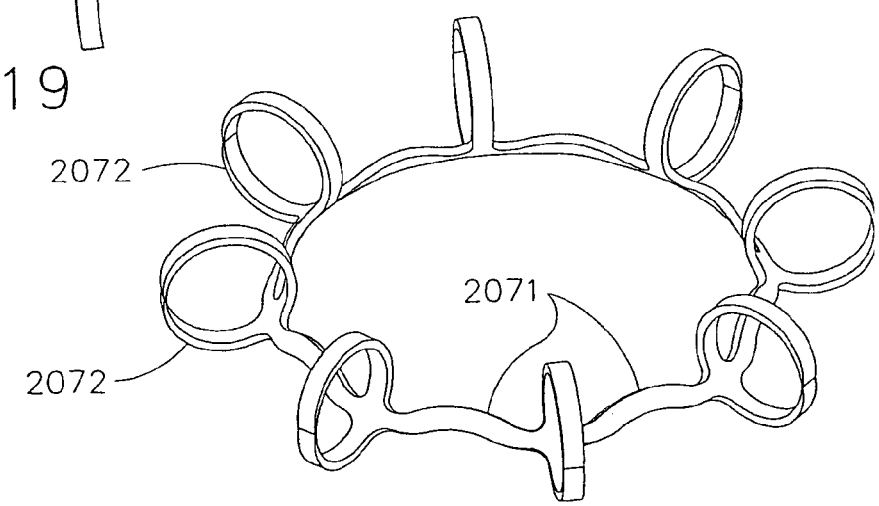

FIG. 119 shows an exemplary fastener set 2070 in a pre-deployment shape. One or more individual fasteners 2072 may have upper and lower prongs with ends turned slightly outwardly, and may be linked together via serpentine links 2071. FIG. 120 shows fastener set 2070 as it would appear following installation. In its installed shape, fastener set 2070 has been expanded in circumference and diameter via deformation of serpentine links 2071, and fasteners 2072 have been pushed and deformed so as to hook into tissues. Fastener set 2070 may be made of a suitable substantially permanently deformable material that is non-reactive with body fluids and tissues, and substantially biocompatible. The inventors have determined that suitably treated surgical stainless steel is one example of a suitable material. Alternatively, if it is desired that the fastener set be bioabsorbable, a suitably deformable substantially biocompatible and bioabsorbable material may be selected. The inventors have determined that flexible absorbable polymers (e.g., polydioxanone polymers, or polymers containing lactides, glycolides, polyglactin, etc., such as the polymers marketed by Johnson & Johnson and/or Ethicon, Inc. under the trademarks "Vicryl" and "PDS II") such that the fastener set can be absorbed (i.e., dissolved) in the patient's body after anastomosis is complete. If the selected material is one that might not sufficiently retain its position after deformation during installation, the design of the fastener set may be modified so as to include barbs on the prongs or other suitable lodging structures, or include features that cause the prongs to meet and interlock upon installation, to form substantially closed rings.

Referring back to FIGS. 110 and 111, the instrument of the present embodiment may also include third tube 2080, which may terminate with expander collar 2081. Affixed at the distal end of expander collar 2081 is positioner 2090, shown in a pre-deployment shape in FIGS. 110 and 111.

Figure 112:
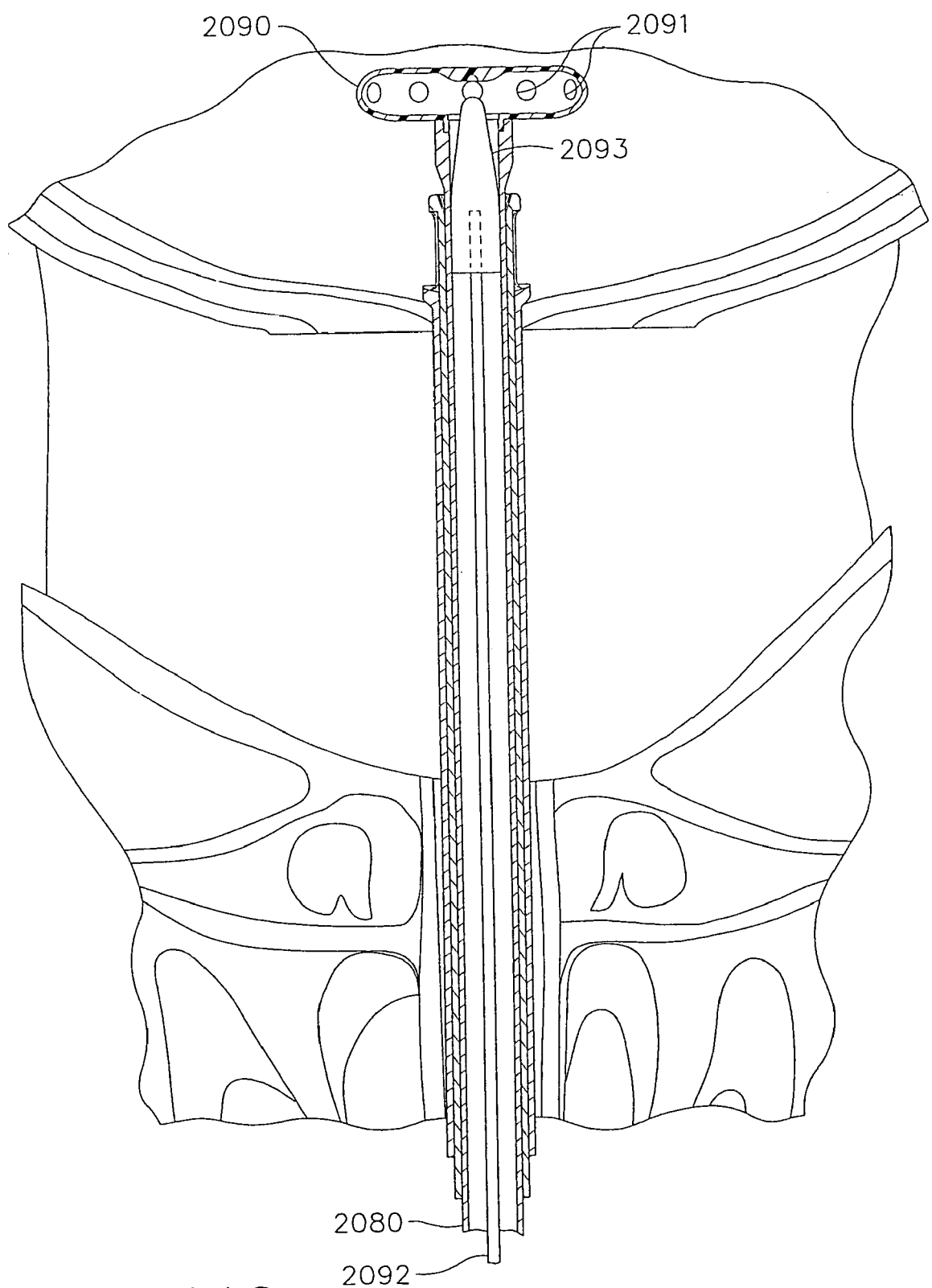
FIG. 112 is a longitudinal cross section of the instrument shown in FIG. 110, shown after insertion into and through a patient's urethra and into the bladder, and after a positioner has been moved to a deployed position.

The pre-deployment shape of positioner 2090, shown in FIGS. 110 and 111, can facilitate insertion of the instrument into the patient. Positioner 2090 may be made of a suitable elastic and flexible polymeric material having shape memory, manufactured so as to be biased to assume a normally transversely oriented shape as shown in FIG. 112, upon retraction of actuator rod 2092. As shown in FIG. 112, positioner 2090 may have situated thereabout one or more drainage holes 2091 which can permit urine, fluids or clotted material to drain into third tube 2080 after the instrument has been deployed. Positioner 2090 may be, alternately, moved to a pre-deployment position shown in FIGS. 110 and 111, or allowed to return via shape memory to a normal position shown in FIG. 112, by longitudinal movement of rod 2092, and correspondingly, end cap 2093, which may be integrally affixed to rod 2092.

Figure 121:
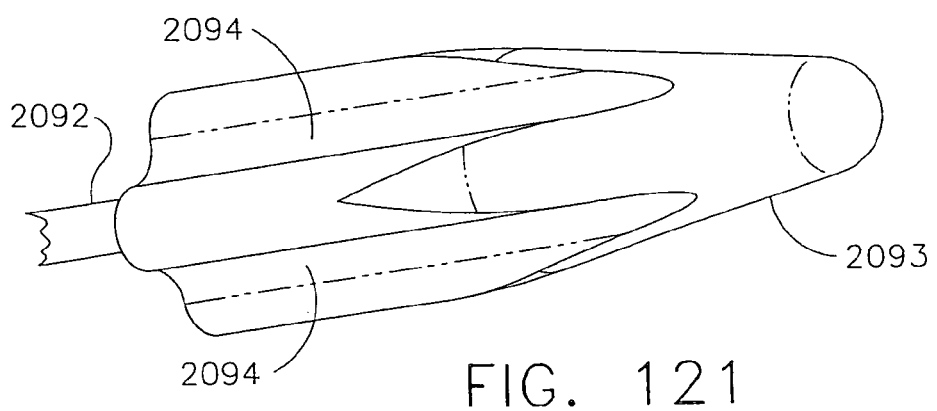

As shown in FIG. 121, end cap 2093 may have thereabout one or more flutes 2094 which can serve to allow urine or other fluids draining out of the bladder, through drainage holes 2091 in positioner 2090, past end cap 2093 and down into third tube 2080, by which they can be drained out of the patient.

Outer tube 2051, second tube 2060, third tube 2080 and rod 2092 may be made of a material having suitable combined properties of shape memory, flexibility, strength and stiffness that both enable the tubes and rod to flex during insertion into the patient's body and through the urethra as will be hereinafter described, but also will prevent them from collapsing, kinking, binding, or breaking during use. The selected material may also be substantially non-reactive with body fluids and tissues, and be substantially biocompatible. The inventors have determined that nitinol, known in the art as suitable for a variety of surgical devices and tubes, is one example of a suitable material.

It will be appreciated that hollow tubes may be used in the instrument for third tube 2080 when a coaxial arrangement with rod 2092 is desirable, or when third tube 2080 is to serve as a catheter, such as will be further described below, but that a rod may be substituted for third tube 2080 and be used to provide substantially the same mechanical function, i.e., transmission of forces to actuate the positioner, and thus may be used when a catheter function, or a coaxial arrangement, and thus a tube, is not required. Conversely, a tube can serve the purpose of rod 2092. Thus, for purposes of the claims that may be set forth, unless otherwise specified in a claim, the term "tube" where such element is operably affixed or connected with, or contacts, the positioner, is intended to include and cover a rod, and vice versa.

Referring to FIG. 110, the instrument 2050 may also comprise a movable, removable, or releasable, collar or sleeve (not shown) sheathing fastener driver assembly 2052 and/or the space between expander collar 2081 and fastener driver assembly 2052, so as to give the instrument a smoother longitudinal cross-sectional profile, to ease insertion and/or retraction of the instrument from a patient.

A method for performing anastomosis of a patient's bladder and urethra using the above-described anastomotic instrument, following a prostatectomy, will now be described. Following a prostatectomy, the patient's bladder 1 and urethra opening 6 are separated by a void formerly occupied by the prostate, as shown in FIG. 2. It is necessary to connect the bladder I with the urethra 5, with bladder opening 4 and urethra opening 6 aligned, to restore urinary functions after recovery and healing.

As shown in FIG. 111, the anastomotic instrument may be inserted upwardly into and through the patient's urethra 5, through the bladder opening 4, and into the bladder 1. The surgeon then may proximally retract rod 2092 and correspondingly, end cap 2093, which allows positioner 2090 to assume its normal shape via shape memory, as shown in FIG. 112. The now-transverse orientation of positioner 2090 will prevent it from being retracted without pulling bladder wall 2 surrounding bladder opening 4 with it.

Figure 113:
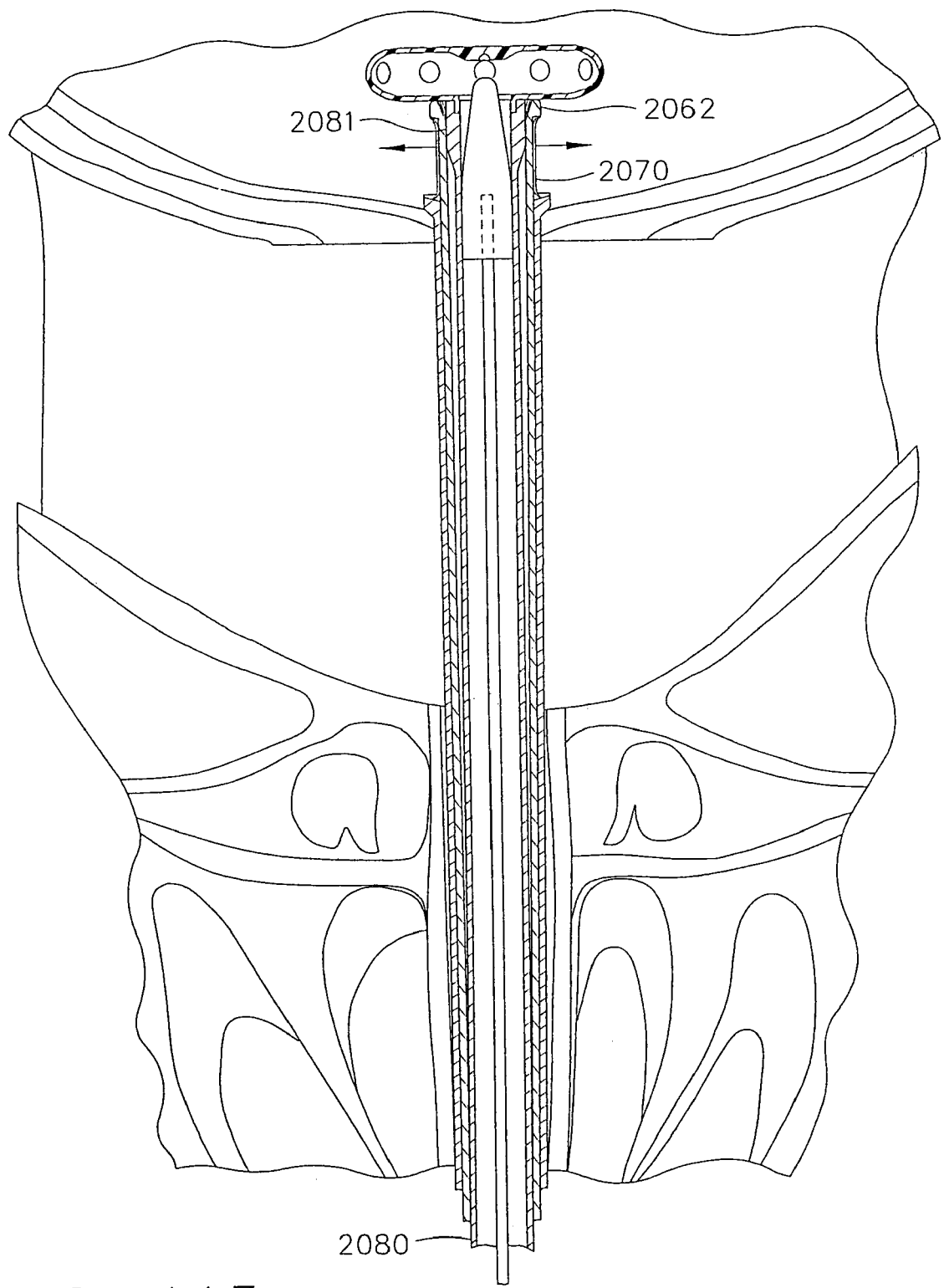
FIG. 113 is a longitudinal cross section of the instrument shown in FIG. 110, shown after insertion into and through the urethra and into the bladder, after a positioner has been moved to a deployed position, and after an expander collar has been drawn into a fastener driver assembly to expand a fastener set.

Next, the surgeon may proximally retract third tube 2080, and correspondingly, expander collar 2081, drawing expander collar 2081 inside and between distal fastener anvils 2062, to the position shown in FIG. 113. Drawing expander collar 2081 inside and between distal fastener anvils 2062 will urge distal fastener anvils 2062, and correspondingly, flexible fingers 2061 (shown in FIG. 110) radially outwardly as indicated in FIG. 113. This movement of flexible fingers 2061 radially outwardly forces fastener set 2070, residing on and around flexible fingers 2061 below distal fastener anvils 2062, to expand in diameter and circumference, via deformation of serpentine links 2071 (shown in detail in FIG. 119).

Figure 114:
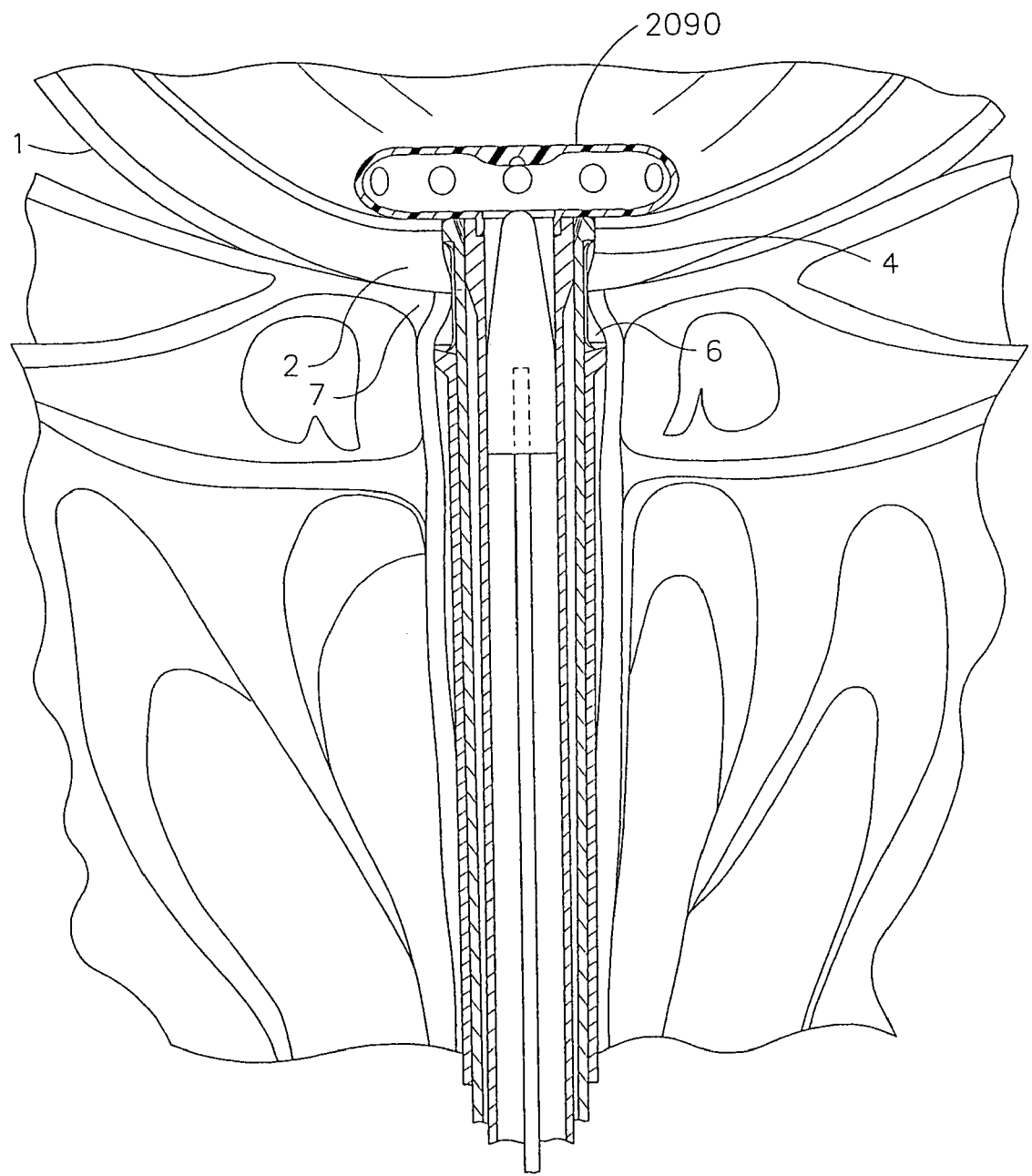
FIG. 114 is a longitudinal cross section of the instrument shown in FIG. 110, shown after insertion into and through a patient's urethra and into the bladder, after a positioner has been moved to a deployed position, after an expander collar has been drawn into a fastener driver assembly to expand a fastener set, and after the bladder wall has been urged into contact with the pelvic floor with the openings in the bladder and urethra aligned.
Figure 115:
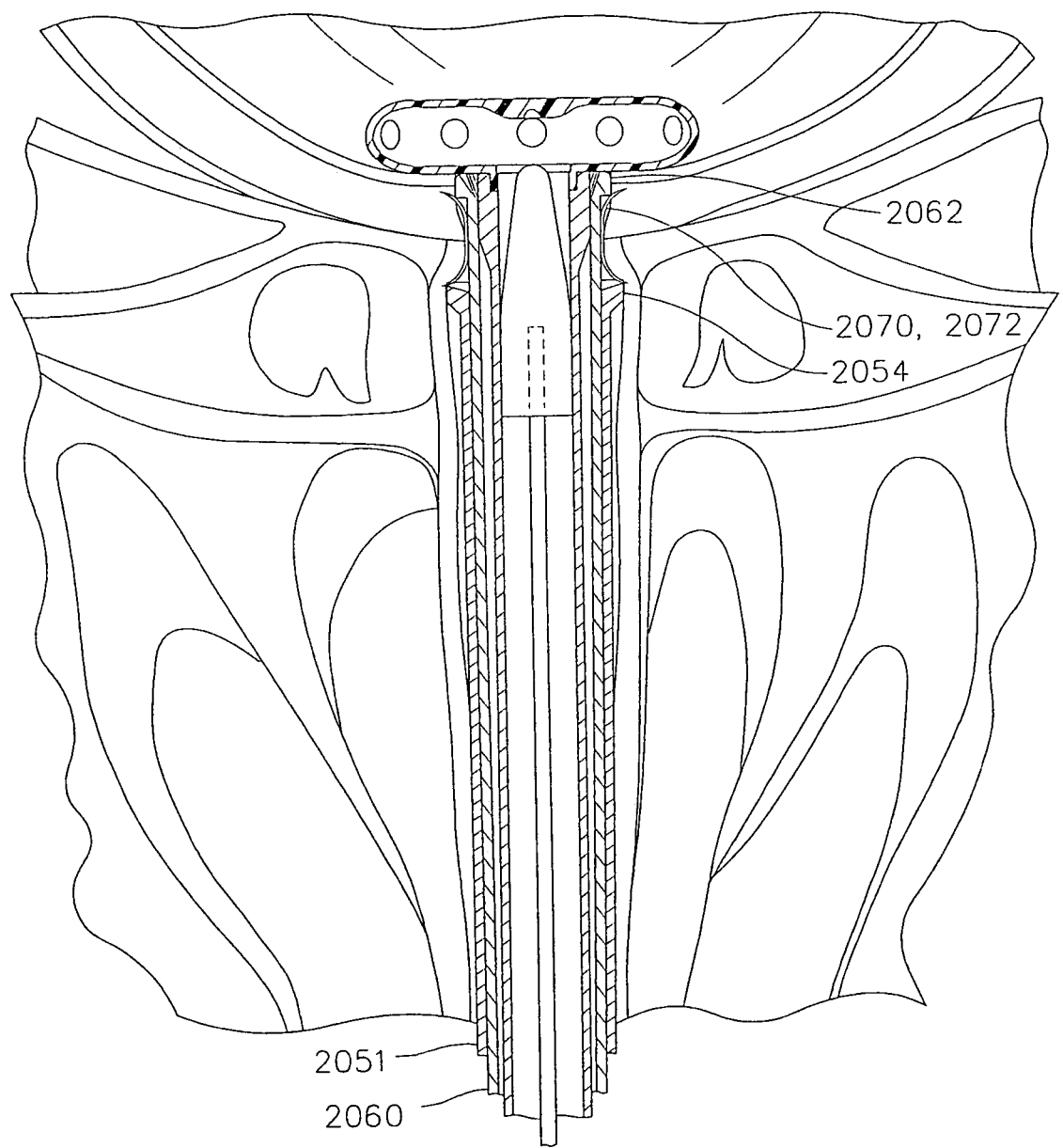
FIG. 115 is a longitudinal cross section of the instrument shown in FIG. 110, shown after insertion into and through a patient's urethra and into the bladder, after a positioner has been moved to a deployed position, after the bladder wall has been urged into contact with the pelvic floor with the openings in the bladder and urethra aligned, and after actuation of a fastener driver assembly has begun.
Figure 116:
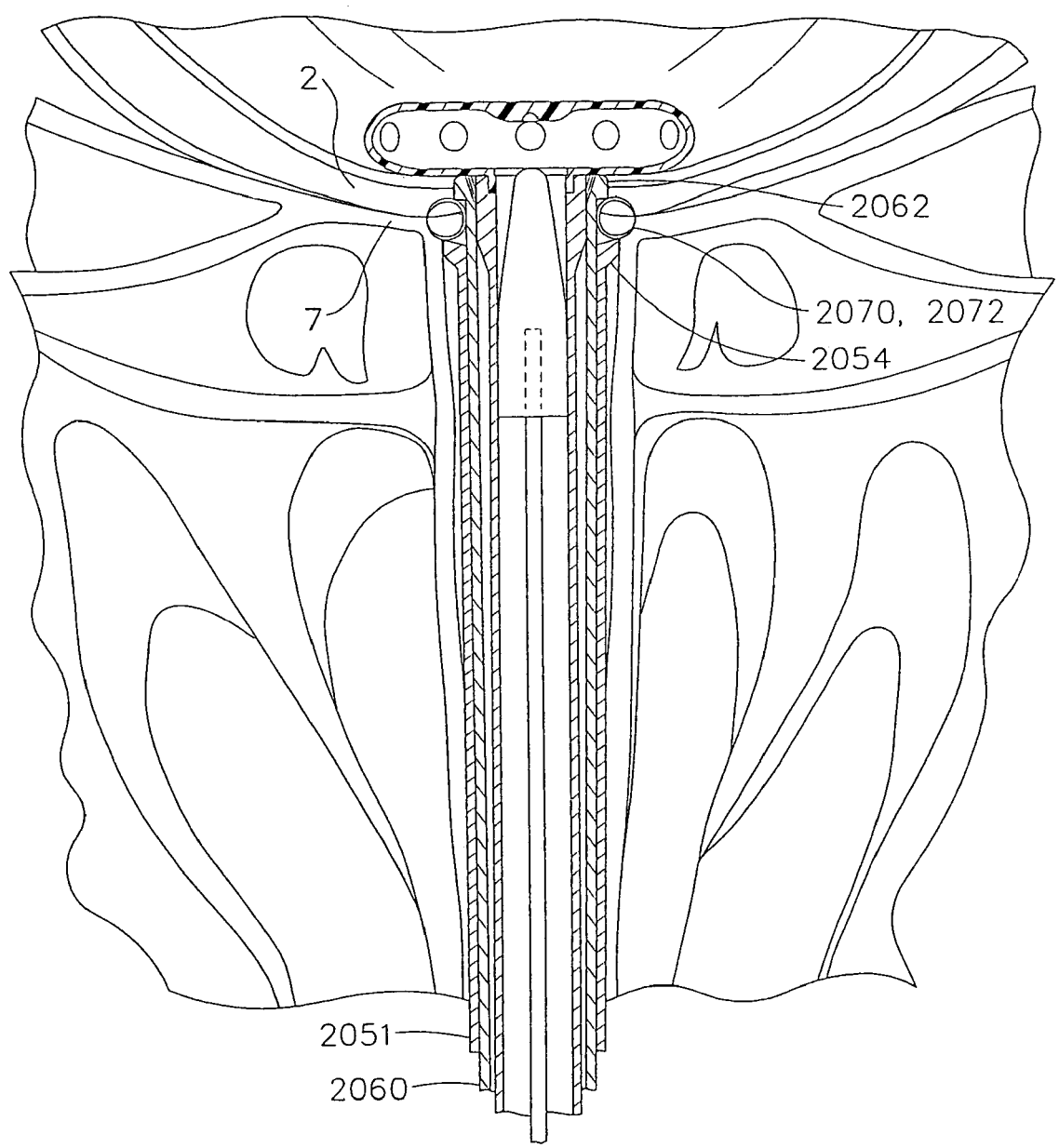
FIG. 116 is a longitudinal cross section of the instrument shown in FIG. 110, shown after insertion into and through a patient's urethra and into the bladder, after a positioner has been moved to a deployed position, after the bladder wall has been urged into contact with the pelvic floor with the openings in the bladder and urethra aligned, and after a fastener driver assembly has been fully actuated to install a fastener set.

Next, the surgeon may retract the entire instrument downwardly through the urethra, which will cause positioner 2090 to pull bladder walls 2 surrounding bladder opening 4 into contact with pelvic floor 7, with bladder opening 4 and urethra opening 6 aligned, to the position shown in FIG. 114.

Next, outer tube 2051 may be moved distally, while second tube 2060 and the remaining portions of the instrument are held immobile. As can be appreciated from FIGS. 115 and 116, this movement correspondingly moves proximal fastener anvils 2054 toward distal fastener anvils 2062, such that they opposingly contact, urge and deform upper and lower prongs of fasteners 2072 of fastener set 2070 such that they are pushed into the surrounding tissues of the bladder wall and pelvic floor, such that they form substantially opposing, joined hooks in the respective tissues, or even, possibly, ring shapes (see also FIG. 120). The fasteners, thus installed, can serve to secure the tissues of the bladder wall 2 to the tissues of the pelvic floor 7, proximate the openings of the bladder and urethra, with these openings aligned.

Figure 117:
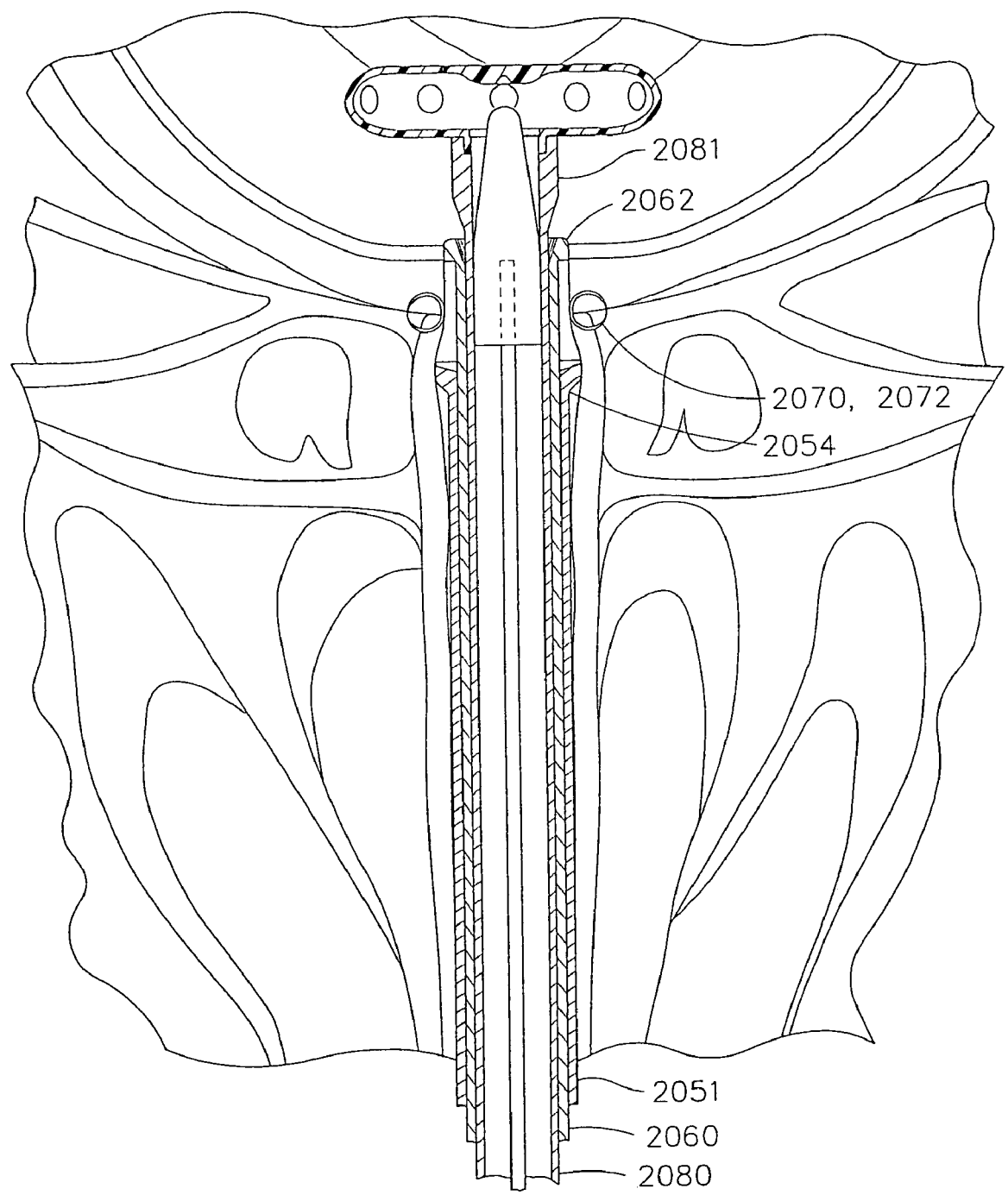
FIG. 117 is a longitudinal cross section of the instrument shown in FIG. 110, shown after insertion into and through a patient's urethra and into the bladder, after a positioner has been moved to a deployed position, after the bladder wall has been urged into contact with the pelvic floor with the openings in the bladder and urethra aligned, after a fastener driver assembly has been fully actuated to install a fastener set, and after an expander collar has been moved out of the fastener driver assembly to allow the fastener driver assembly to assume a smaller diameter which will allow it to be retracted through the installed fastener set.

Next, the surgeon may move outer tube 2051 proximally while holding second tube 2060 immobile, causing proximal fastener anvils 2054 and distal fastener anvils 2062 to release their grip on fasteners 2072 and move apart, to the position shown in FIG. 117. The surgeon then may move third tube 2080 and correspondingly, expander collar 2081, distally while holding second tube 2060 immobile, pushing expander collar 2081 distally out from between upper anvils 2062 and flexible fingers 2061, permitting flexible fingers 2061 and upper anvils 2062 to return to their pre-deployment positions, circumscribing a circle of a diameter smaller than that of the now-enlarged, deployed fastener set, so as to permit retraction of the fastener driver assembly therethrough.

Figure 118:
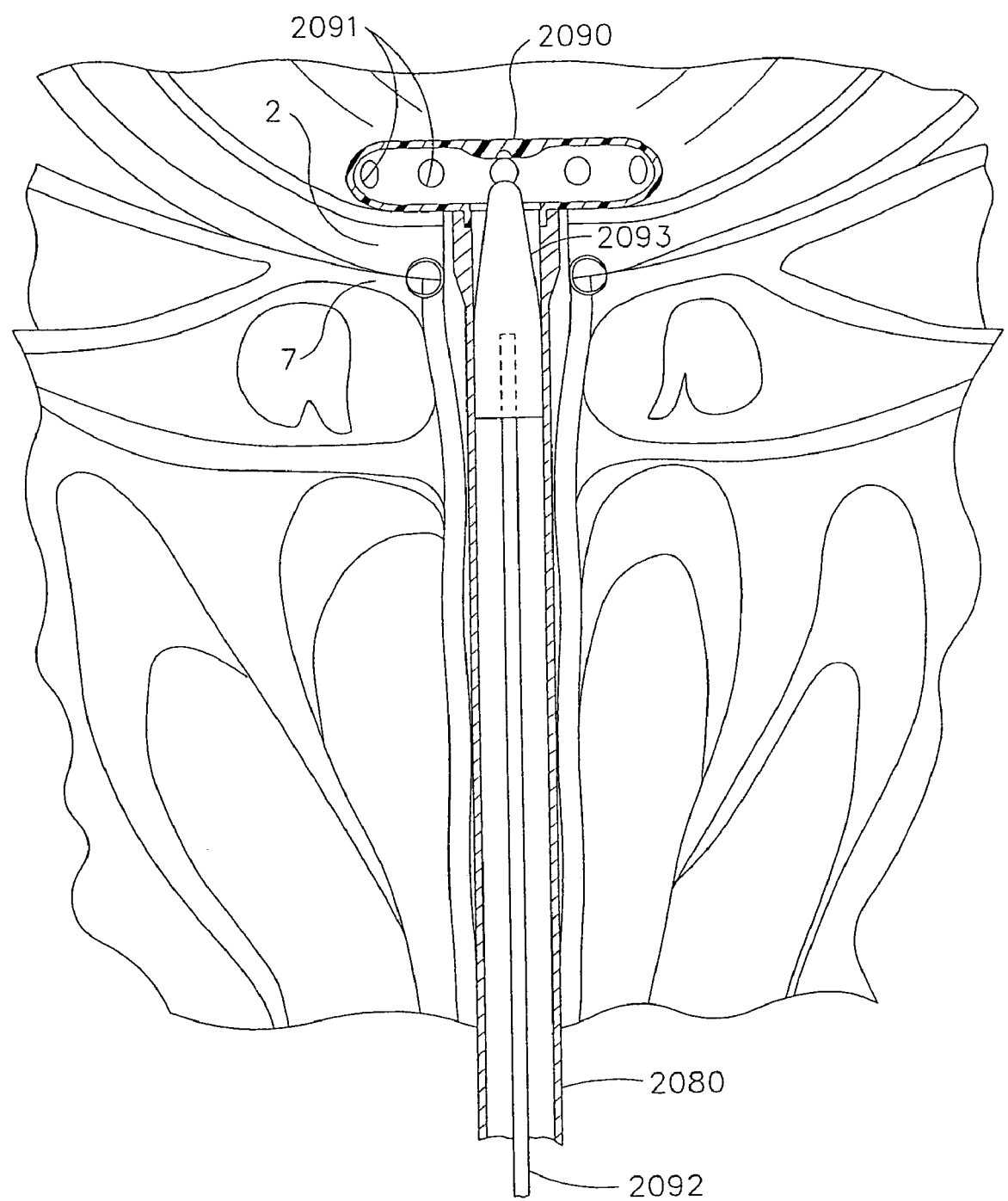
FIG. 118 is a longitudinal cross section of the instrument shown in FIG. 110, shown after insertion into and through a patient's urethra and into the bladder, after a positioner has been moved to a deployed position, after the bladder wall has been urged into contact with the pelvic floor with the openings in the bladder and urethra aligned, after a fastener set has been installed, and after a fastener driver assembly has been withdrawn from the patient to leave the positioner and a positioner tube behind to enable draining of urine and other fluids from the bladder during recovery and healing.

Next, entire fastener driver assembly 2052, comprising outer tube 2051, flexible fingers 2053, proximal fastener anvils 2054, second tube 2060, flexible fingers 2061 and distal fastener anvils 2062, may be retracted from the patient, leaving behind third tube 2080, expander collar 2081, positioner 2090, rod 2092 and end cap 2093 as shown in FIG. 118. Remaining positioner 2090 and third tube 2080 may now be used to exert supplemental downward pressure on bladder walls 2 surrounding the bladder opening so as to enhance contact and knitting between the tissues of bladder walls 2 surrounding the bladder opening, and the tissues of pelvic floor 7 surrounding the urethra opening. Additionally, or alternatively, positioner 2090, including drainage holes 2091, and third tube 2080 may now be used to seal off the junction between the bladder and urethra and drain urine, fluids and/or clotted material from the bladder during recovery and healing. Fluids are permitted to flow past end cap 2093 via flutes 2094 in end cap 2093, shown in FIG. 121. Used for this purpose, third tube 2080 would be connected to a urine collection bag (not shown) via intermediate tubing. Following recovery and healing, rod 2092 and correspondingly end cap 2093 are moved distally with respect to third tube 2080, thus urging positioner 2090 into its pre-deployment position shown in FIGS. 110 and 111, and enabling retraction of these remaining parts of the instrument out of the bladder, down through the urethra, and out of the patient's body.

Those skilled in the art of the design of mechanical surgical devices will appreciate that a variety of simple mechanical devices may be configured or adapted to operate and hold outer tube 2051, second tube 2060, third tube 2080 and rod 2092, at the proximal end of the instrument as required by the above steps, and so as to move and hold the instrument in respective pre-deployment and/or retracted, and deployed and actuated, positions, including the handle assembly depicted in FIGS. 83 and 85 and described above, or a variation thereof.

will be appreciated by those skilled in the art of design of mechanical surgical devices that the positioner need not be limited to the embodiment made of flexible and elastic polymeric shape memory material as described immediately above, but that alternative designs for such positioner are possible, which cause the positioner to assume, alternately, a retracted position and a deployed position, the deployed position suitable for catching in the bladder opening and urging the bladder into contact with the pelvic floor, in response to forces exerted or transmitted by tubes or other members. The positioner may comprise, for example, any of the positioner assemblies depicted in FIGS. 14, 19, 24 and 57, and described above. Similarly, it will be appreciated by those skilled in the art of design of mechanical surgical devices that the fastener driver assembly need not be limited to the two-tube assembly described herein, but that alternative designs for such an assembly are possible, which can cause the fastener driver assembly to install one or more fasteners in the tissues of the bladder and the urethra about the respective openings of these lumens when they are brought together, in response to forces exerted or transmitted by tubes or other members.

As previously noted, the combination of tubes, positioner and driver assembly may be configured in an instrument adapted for a retrograde anastomosis procedure, as described above, or configured in an instrument adapted for an antegrade procedure. In an antegrade procedure, instead of being inserted upwardly through the urethra, and into the bladder opening proximate the site of excision of the prostate, the instrument is inserted downwardly through a small incision in the patient's abdomen, through a small incision on an upper surface of the patient's bladder, into the bladder, through the bladder opening, and into the urethra opening. The small incisions in the abdomen and upper surface of the bladder may be made with a cannula and trocar assembly and held open by the cannula for insertion of the instrument therethrough.

Lodging Member Embodiment

FIG. 122 illustrates in longitudinal cross-section another embodiment of an anastomotic instrument 2010 of the present invention, in its pre-deployment position. The instrument may comprise inner tube 2011, outer tube 2012 and rod 2019, which may be of sizes such that inner tube 2011 can be placed and be movable within outer tube 2012, and rod 2019 can be placed and be movable within inner tube 2011, in an approximately coaxial arrangement. Inner tube 2011, outer tube 2012 and rod 2019 may be made of a material having suitable combined properties of shape memory, flexibility, strength and stiffness that both enable the tubes to flex during insertion into the patient's body and through the urethra as will be hereinafter described, but also will prevent them from collapsing, kinking, binding, or breaking during use. The selected material may also be substantially non-reactive with body fluids and tissues, and be substantially biocompatible. The inventors have determined that nitinol, known in the art as suitable for a variety of surgical devices and tubes, is an example of suitable material.

Figure 124:
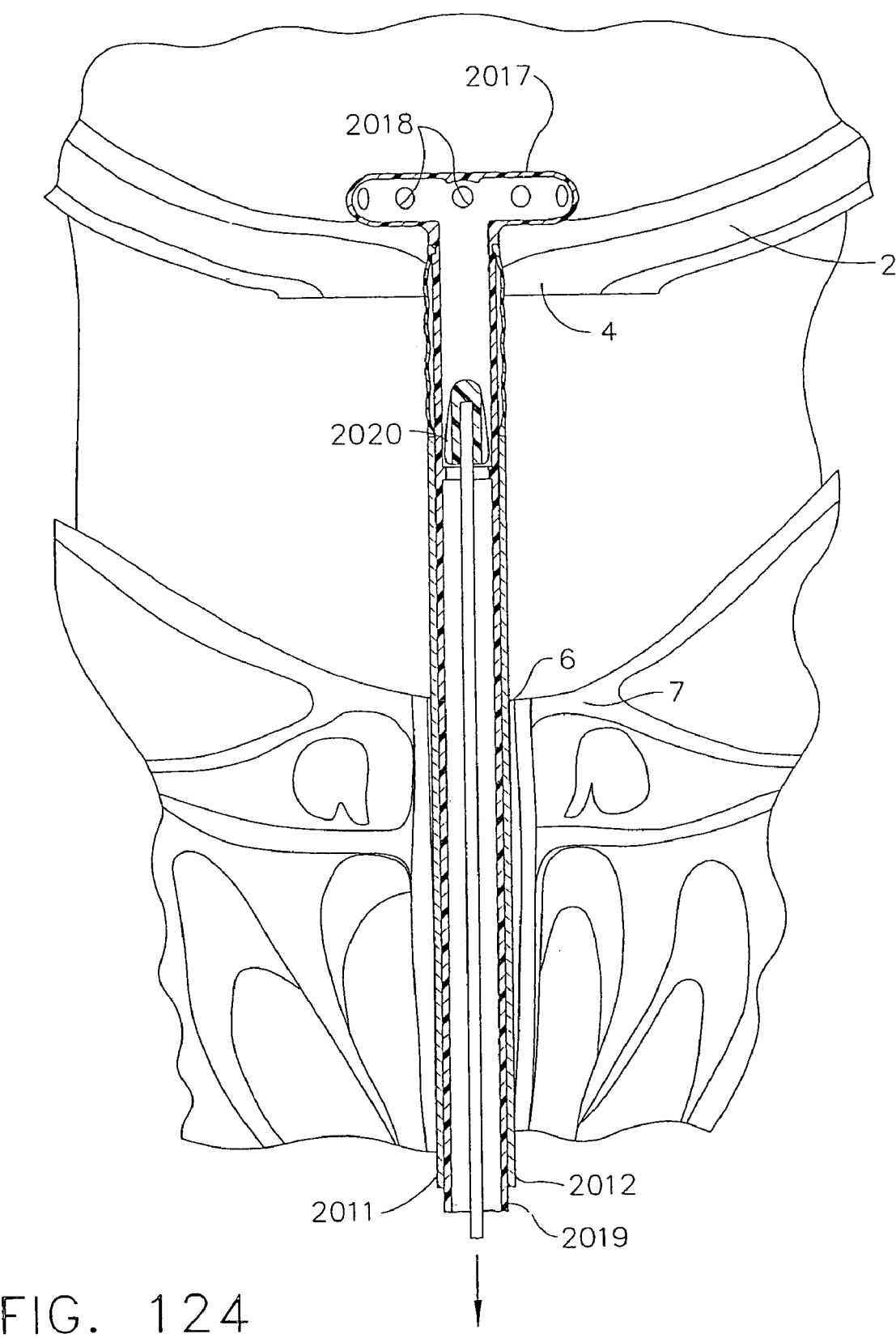

As shown in FIG. 122, instrument 2010 comprises positioner 2017. In its pre-deployment position positioner 2017 may be substantially cylindrical, having a radius smaller or approximately equal to the radius of first tube 2012, and may have a rounded distal end. The pre-deployment shape of positioner 2017 will facilitate insertion of the instrument into the patient. Positioner 2017 may be made of a suitable elastic and flexible polymeric material having shape memory, manufactured so as to be biased to assume a normally transversely-oriented shape as shown in FIG. 124, upon retraction of rod 2019. As shown in FIG. 124, positioner 2017 may have, about its perimeter, one or more drainage holes 2018 which can permit urine, fluids or clotted material to drain into inner tube 2011 when the instrument is deployed.

Instrument 2010 may also comprise lodging member 2013. Lodging member 2013 also may be a tube-like member, with a proximal end 2015 affixed to the distal end of outer tube 2012, and a distal end 2014 affixed to the distal end of inner tube 2011. In the present embodiment lodging member 2013 is operable upon deployment to present transversely-extending ribs or other projections that enable it, upon appropriate placement and longitudinal compression, to lodge within the patient's urethra. As shown in FIG. 126, lodging member 2013 may have a series of circumferential, pre-formed folds 2016, which enable lodging member 2013 to longitudinally compress when outer tube 2012 is pushed in a distal direction while inner tube 2011 is held immobile. Thus, upon longitudinal compression, lodging member 2013 can fold in accordion-like fashion to present transversely-extending ribs or other projections that when in position within the patient's urethra, can serve to lodge the instrument in place. Lodging member 2013 may be formed of polyurethane but may also be formed of any other suitable material.

Referring again to FIG. 122, rod 2019 is capped with end cap 2020, which may be rounded and adapted to spread the force exerted by rod 2019 against the inside of positioner 2017 so as to prevent rod 2019 from puncturing positioner 2017. Referring to FIG. 127, end cap 2020 may have thereabout one or more flutes 2021 which can allow urine, fluids or clotted material to flow past end cap 2020 when rod 2019 is retracted. As affixed to rod 2019, end cap 2020 is substantially integral therewith.

It will be appreciated that hollow tubes may be used in the instrument for inner tube 2011 and outer tube 2012 when a coaxial arrangement is desirable, or when one or more of these members is to serve as a catheter, such as will be further described below, but that one or more rods may be substituted for tubes and be used to provide substantially the same mechanical functions, i.e., transmission of forces to actuate the positioner and the lodging member, and thus, may be used when a catheter function, or a coaxial arrangement, and thus a tube, is not required. Thus, for purposes of the claims that may be set forth, unless otherwise specified in a claim, the term "tube" is intended to include and cover a rod.

A method for performing anastomosis of a patient's bladder and urethra, using the above-described retrograde anastomotic instrument, following a prostatectomy, will now be described. Following a prostatectomy, the patient's bladder 1 and urethra opening 6 are separated by a void formerly occupied by the prostate, as shown in FIG. 2. It is necessary to connect the bladder 1 with the urethra 5, with bladder opening 4 and urethra opening 6 aligned, to restore urinary functions after recovery and healing.

Figure 123:
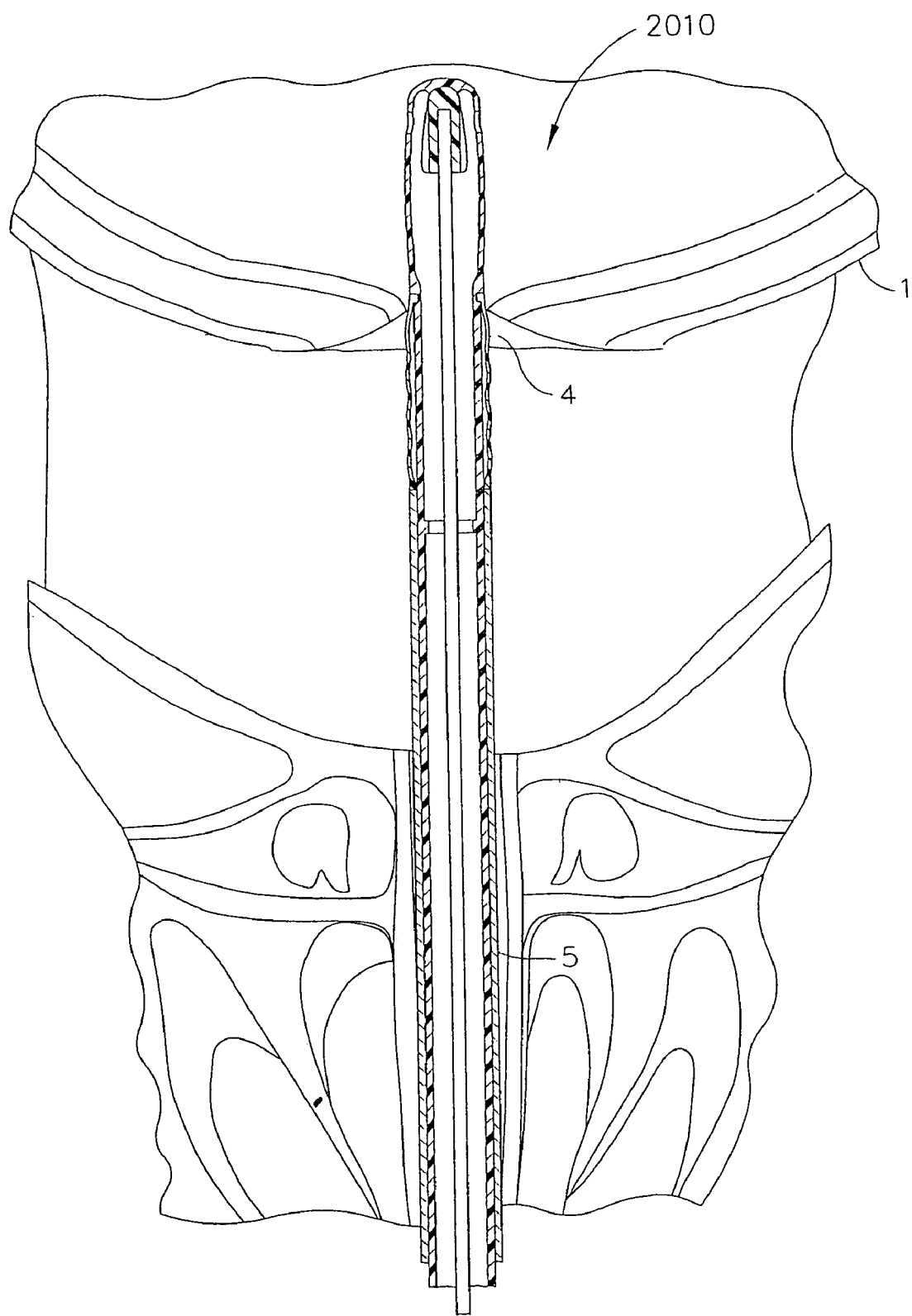

As shown in FIG. 123, anastomotic instrument 2010 may be inserted upwardly into and through the patient's urethra 5 (as can be appreciated from FIG. 127), through the bladder opening 4, and into the bladder 1. The surgeon may then proximally retract rod 2019 with attached end cap 2020, which will allow positioner 2017 to assume its normal shape, which extends transversely to the longitudinal axis of the instrument within the bladder, beyond the diameter of the bladder opening 4, as shown in FIG. 124. The now-transverse orientation of positioner 2017 prevents it from being retracted without pulling bladder wall 2 surrounding bladder opening 4 with it.

Figure 125:
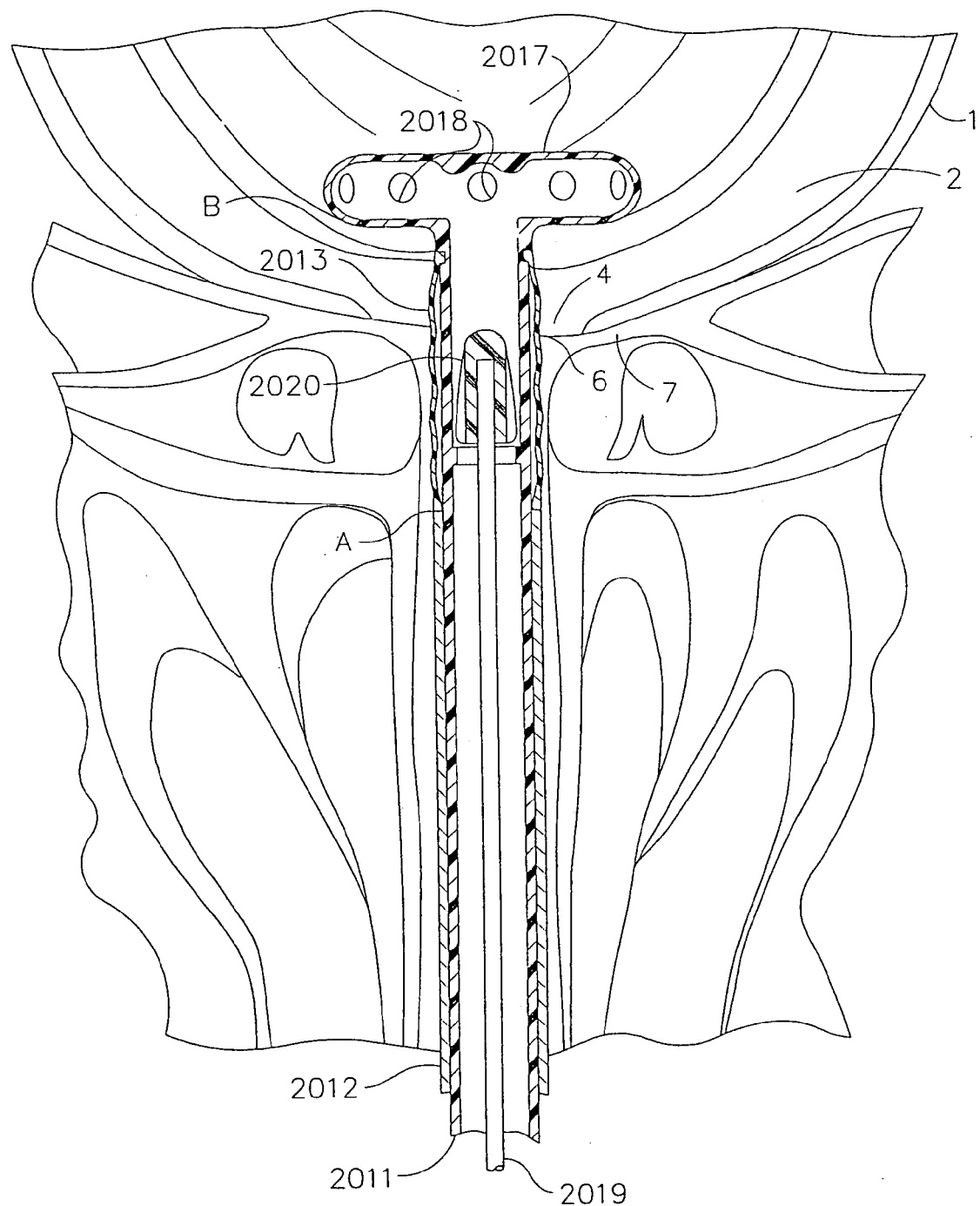

Next, the surgeon may retract the entire instrument downwardly through the urethra, which causes positioner 2017 to pull bladder walls 2 surrounding bladder opening 4 into contact with pelvic floor 7, with bladder opening 4 and urethra opening 6 aligned, in the position shown in FIG. 125.

Next, outer tube 2012 may be moved distally, while inner tube 2011 is held immobile. As can be appreciated from FIG. 126, because the proximal end of lodging member 2013 is affixed to the distal end of outer tube 2012 at point A, and the distal end of lodging member 2013 is affixed to the distal end of inner tube 2011 at point B as shown, this distal movement of outer tube 2012 relative to immobile inner tube 2011 will cause longitudinal compression of lodging member 2013. Pre-formed circumferential folds 2016 in lodging member 2013 cause lodging member 2013 to compress in accordion-like fashion, resulting in the presentation of transversely-extending ribs as shown, which enable the lodging member 2013, and consequently, the entire instrument, to lodge in the urethra in the position shown in FIG. 126.

As shown by way of example but not of limitation in FIGS. 131-133, lodging member 2013 may be configured in various embodiments as shown, such as including perforations which can serve to alleviate radial stresses in the material and thereby facilitate deployment, and also cause lodging member 2013 to present transversely-extending projections 2042, when longitudinally compressed, enhancing its effectiveness in lodging within the urethra. Lodging member 2013 may also be manufactured so as to have a rough outer surface, which can also serve to enhance its effectiveness in lodging within the urethra. It may be desirable to design the lodging member so that any lodging projections that enhance its effectiveness in lodging within the urethra are limited in length so as not to substantially pierce or penetrate surrounding tissues, so as to minimize the possibility of causing permanent damage to sensitive areas in the tissues.

Those skilled in the art of the design of mechanical surgical devices will appreciate that a variety of simple mechanical devices may be configured or adapted to operate and hold inner tube 2011, outer tube 2012 and rod 2019 at the proximal end of the instrument as required by the above steps, and so as to move and hold the instrument in respective retracted, and then deployed and lodged, positions, including the handle assembly depicted in FIGS. 83 and 85 and described above, or a variation thereof.

In the lodged position shown in FIG. 126, the instrument may be used to hold the bladder wall 2 surrounding the bladder opening 4 in contact with the pelvic floor 7 surrounding the urethra opening 6 with bladder opening 4 and urethra opening 6 aligned, during the period of time necessary for these tissues to knit and heal together naturally.

While the instrument is lodged in position shown in FIG. 126 during the time required for healing, urine, fluids and/or clotted material may be drained out of bladder 1 via drainage holes 2018 in positioner 2013, and flow past end cap 2020 of rod 2019 through flutes 2021 in end cap 2020 (shown in enlarged perspective view in FIG. 127), and generally out of the patient via inner tube 2011. As shown in FIG. 128, the instrument may be connected via tubing to a urine collection bag 2023.

It will be appreciated by those skilled in the art of design of mechanical surgical devices that the positioner need not be limited to the embodiment made of flexible and elastic polymeric shape memory material as described herein, but that alternative designs for such positioner are possible, which cause the positioner to alternately assume a retracted position and a deployed position, the deployed position suitable for catching in the bladder opening and urging the bladder into contact with the pelvic floor, in response to forces exerted or transmitted by tubes or other members. The positioner may comprise, for example, any of the positioner assemblies depicted in FIGS. 14, 19, 24 and 57, and described hereinabove. Similarly, it will be appreciated by those skilled in the art of design of mechanical surgical devices that the lodging member need not be limited to the hollow pre-folded polyurethane member described herein, but that alternative designs for such lodging member are possible, which cause the lodging member to alternately assume a retracted position and a deployed position, the deployed position presenting one or more ribs or projections that enable the lodging member to lodge within the urethra, in response to forces exerted or transmitted by tubes or other members.

As previously noted, the combination of tubes, positioner and lodging member may be configured in an instrument adapted for a retrograde anastomosis procedure, as described above, or configured in an instrument adapted for an antegrade procedure, as will now be described. In an antegrade procedure, instead of being inserted upwardly through the urethra, and into the bladder opening proximate the site of excision of the prostate, the instrument is inserted downwardly through a small incision in the patient's abdomen, through a small incision on an upper surface of the patient's bladder, into the bladder, through the bladder opening, and into the urethra opening. The small incisions in the abdomen and upper surface of the bladder may be made with a trocar and cannula assembly (not shown), and held open by the cannula for insertion of the instrument therethrough.

As shown in FIG. 129, an antegrade anastomotic instrument 2030 may comprise outer tube 2031, first inner tube 2032 and second inner tube 2034. Similar to the retrograde anastomotic instrument described previously, these tubes may be sized such that first inner tube 2032 can be placed and be longitudinally movable within outer tube 2031, and second inner tube 2034 can be placed and be longitudinally movable within first inner tube 2032. First inner tube 2032 may have one or more drainage passages 2033 at its distal end. Second inner tube 2034 may have one or more drainage passages 2035 at its distal end.

End cap 2036 may be affixed to the distal end of second inner tube 2034. As shown, end cap 2036 may have a rounded distal end that facilitates insertion of the instrument, and an extended section 2037 that terminates at rim 2038.

As shown in FIG. 129, instrument 2030 may also comprise lodging member 2013, which may be similar to the lodging member of the retrograde anastomotic instrument previously described, and can also be configured as shown by way of example in FIGS. 131-133. Referring again to FIG. 129, lodging member 2013 may be affixed at its proximal end to the distal end of first inner tube 2032 (at point A as shown), and is affixed at its distal end to extended section 2037 of end cap 2036 beneath rim 2038 (at point B as shown). Thus, it can be appreciated that moving second inner tube 2034 longitudinally with respect to first inner tube 2032 will cause either, alternately, longitudinal extension, or longitudinal compression of lodging member 2013, and that extension of lodging member 2013 will cause ribs or projections presented thereby to retract into the pre-deployment position, and compression of lodging member 2013 causes ribs or projections presented thereby to extend to the deployed position (shown in FIG. 129), in a manner substantially similar to that of the lodging member of the retrograde anastomotic instrument previously described.

Antegrade anastomotic instrument 2030 also comprises positioner 2017. Similar to the positioner of the retrograde anastomotic instrument previously described, in its pre-deployment position positioner 2017 may be substantially cylindrical. The pre-deployment shape of positioner 2017 facilitates insertion of the instrument. Positioner 2017 may be made of a suitable elastic and flexible polymeric material having shape memory, manufactured so as to be biased to normally assume a transversely-oriented shape as shown in FIG. 129, upon retraction of first inner tube 2032 relative to outer tube 2031. Positioner 2017 may be affixed at its proximal end to the distal end of outer tube 2031 (at point C as shown in FIG. 129), and may be affixed at its distal end to the distal end of first inner tube 2032 (at point A as shown as FIG. 129).

Thus, it can be appreciated that longitudinal movement of outer tube 2031 with respect to first inner tube 2032 will cause positioner 2017 to assume its retracted, pre-deployment cylindrical position (similar to that shown in FIG. 122), or its deployed position as shown in FIG. 129.

As shown in FIG. 129, positioner 2017 may have, situated thereabout, one or more drainage holes 2018 which can permit urine, fluids or clotted material to drain, through drainage passages 2033 in first inner tube 2032, though drainage passages 2035 in second inner tube 2034, and into second inner tube 2034.

A method for performing anastomosis of a patient's bladder and urethra using the above-described antegrade anastomotic instrument, following a prostatectomy, will now be described, with reference to FIG. 2 for identification of parts of the patient's anatomy and FIG. 129 for identification of parts of the instrument. Following a prostatectomy, the patient's bladder 1 and urethra opening 6 are separated by a void formerly occupied by the prostate, as shown in FIG. 2. It is necessary to connect the bladder 1 with the urethra 5 with bladder opening 4 and urethra opening 6 aligned, to restore urinary functions after recovery and healing.

A cannula with a trocar (not shown) is inserted into the patient's abdomen, and through an upper surface of the patient's bladder. The trocar is then removed and the cannula is left in place. The antegrade anastomotic instrument in its pre-deployment position is inserted into the cannula, until the entire positioner 2017 is within the bladder lumen. The surgeon then may move outer tube 2031 in a distal direction with respect to first inner tube 2032, or alternatively or simultaneously, move first inner tube 2032 in a proximal longitudinal direction with respect to outer tube 2031. This relative movement of the outer tube 2031 and first inner tube 2032 will permit positioner 2017 to assume its transversely-oriented position, shown in FIG. 129. The surgeon then may manipulate the instrument to locate the bladder opening 4 with end cap 2036, and insert end cap 2036 through bladder opening 4. Positioner 2017 in its deployed position will contact bladder wall 2 and catch in bladder opening 4, and cannot pass therethrough. The surgeon then may manipulate the instrument to urge bladder wall 2 surrounding bladder opening 4 downward toward pelvic floor 7, and further manipulate the instrument to locate urethra opening 6, and insert end cap 2036 into urethra opening 6. Thus, bladder wall 2 surrounding bladder opening 4 may be urged into contact with pelvic floor 7 surrounding urethra opening 6, with bladder opening 4 and urethra opening 6 aligned. Next, holding outer tube 2031 and first inner tube 2032 immobile, the surgeon may retract second inner tube 2034 proximally. This will cause longitudinal compression of lodging member 2013, so that it will assume the position shown in FIG. 129, and lodge within the urethra.

Those skilled in the art of design of mechanical surgical devices will appreciate that a variety of simple mechanical devices may be configured to operate and hold outer tube 2031, first inner tube 2032 and second inner tube 2034 by actuation and manipulation at the proximal end of the instrument as required by the above steps, and so as to operate the instrument and hold it in the lodged position, including the handle assembly depicted in FIGS. 83 and 85 and described above, or a variation thereof.

In the lodged position, the instrument may be used to hold the bladder wall 2 surrounding the bladder opening 4 in contact with the pelvic floor 7 surrounding the urethra opening 6 with bladder opening 4 and urethra opening 6 aligned, during the period of time necessary for these tissues to knit and heal together naturally.

While the instrument is lodged in position during the time required for healing, urine and other fluids may be drained out of bladder 1 via drainage holes 2018 in positioner 2017, through drainage passages 2033 and 2035, and generally out of the patient via second inner tube 2034. As shown in FIG. 129, the instrument may be connected via tubing to a urine collection bag 2023.

FIG. 130 depicts an alternative embodiment of instrument 2030. As compared with the embodiment depicted in FIG. 129, first inner tube 2032 may be reduced in radius and second inner tube 2039 may be a rod. Second inner tube 2039 may terminate at its distal end with end cap 2036, having rim 2038 and extended section 2037. Use and function of the instrument depicted in FIG. 130 may be substantially similar to use and function of the instrument depicted in FIG. 129, except that following deployment and lodging of the instrument, urine and other fluids can be drained from the bladder through drainage holes 2018 in positioner 2017, and directly into outer tube 2031, which is connected to urine collection bag 2023, eliminating the necessity for additional drainage passages 2033, 2035 in internal tubes within the instrument as shown in FIG. 129.

Other Refinements

The exemplary embodiments described herein for an instrument in accordance with the present invention comprise one or more tubes and/or rods, used for the translation of forces and movement from a proximal handle assembly to an assembly or assemblies proximate to a distal end of an instrument, and also, potentially, used as catheters for, among other purposes, the transmission of gas or fluid pressure, and the draining of urine or other fluids during recovery and healing. The inventors have determined that nitinol, which when suitably treated and formed, has combined properties of strength, flexibility, elasticity, stiffness, hardness and biocompatibility that make it suitable as a material for such members, by way of example. Other materials may suffice, particularly when one or more of the above-mentioned properties may not be so stringently required. Thus, for example, a polymer such as styrene might be used where it is not necessary, for example, to translate force and movement (such as, for example, when the tube functions only as a catheter). Of course, any other materials having the necessary properties for the particular application may be used.

With respect to instruments designed for a retrograde post-prostatectomy bladder-urethra anastomosis procedure such as described herein, it may be desirable to have a bend angle in the tube assembly, such as in tube assembly 500 (FIG. 3), tube assembly 3200 (FIG. 134), or other tube assembly supporting an end effector. A bend proximate to the end effector assembly, of about 80 to about 90 degrees (expressed as the angle at which a distal portion of the tube assembly is bent away from a straight axis projected distally from a proximal portion of the tube assembly), and preferably about 85 degrees (wherein the tube assembly defines an obtuse angle of about 95 degrees), may be desirable. Such a bend angle may serve to better facilitate manipulation of the instrument within the anatomical architecture involved in the procedure, and facilitate control of the positioning of the end effector assembly within the bladder lumen to enable driving anchors at a desired or selected angle with respect to the pelvic floor.

In order to be most effective at operating within the limited space provided by the anatomical architecture involved in a procedure to effect anastomosis of the bladder and urethra following a prostatectomy, it is desirable that the end effector assembly, including any positioner assembly, anchor driver assembly and/or end cap or harness assembly, be limited in length. Preferably, but not by way of limitation, the length of the end effector assembly, following opening of the positioner, will be less than about 2 inches, and more preferably, less than about 1½ inches, from the proximal surfaces of the positioner when opened to the distal end of the instrument. For similar reasons, for an instrument of the present invention designed for use in a retrograde procedure (involving insertion upwardly through the urethra), the size of the urethra and other anatomical features make it preferable that the end effector and the tube assembly be limited to a diameter of about 28 french, or about 9.3 millimeters.

The inventors also have determined that it may be advantageous for an instrument configured for retrograde insertion (upwardly into and through the urethra) to have a detachable and reattachable, or detached and attachable, end effector assembly. For example, if the end effector assembly (comprising a positioner assembly and an anchor driver assembly such as positioner 400 and anchor driver 300 shown in FIG. 3, shuttlecock assembly 800 shown in FIG. 17, umbrella assembly 900 shown in FIG. 22, or end effector assembly 3400 shown in FIG. 134) is detached from and attachable to the supporting tube assembly or other supporting longitudinal member assembly, the end effector assembly may be separate or detached from the supporting assembly prior to insertion. The supporting assembly may then be inserted through the urethra without the end effector assembly, which may ease insertion and eliminate the possibility for components of the end effector assembly, otherwise attached, to catch or cause tissue damage within the urethra during insertion. Upon insertion, and after the distal end of the supporting assembly is past the urethra and/or above the pelvic floor, the end effector assembly may be introduced into the patient's abdomen via a cannula through the abdominal wall, and attached to the supporting assembly for use in the anastomosis procedure, using any suitable means of guidance such as an endoscope, external imaging techniques and/or tactile feel. It can be appreciated that the supporting assembly and the end effector assembly can have a variety of designs that enable operable connection of their respective structural and operational members to effect attachment and operability of the end effector assembly.

Tubes, rods or other members that are to be inserted and/or remain inside the patient for a substantial period of time during the anastomosis procedure, such as but not limited to central rod or guide wire 3230, catheter tube 3510 (FIGS. 141-144) and/or other components may be provided with an antimicrobial coating, such as that described in copending U.S. Patent Application Publication No. 2004/0220614. Additionally or alternatively, such components may be provided with a hydrophilic or other friction-reducing coating.

Several embodiments of a method for effecting anastomosis of the bladder and urethra following a prostatectomy, as depicted and described herein, involve the driving of anchors into the pelvic floor. In such a procedure it may be desirable for anchors to be driven into the pelvic floor in locations that avoid sensitive areas and thus reduce the potential for complications. For example, referring to FIG. 147, it may be desirable to avoid driving anchors into areas proximate to the dorsal veins D of the penis, other neurovascular bundles N, the rectum R, or other sensitive anatomical features. Accordingly, referring to FIG. 147, the inventors have determined that anchors are preferably driven into the pelvic floor at locations within the zones of about 8 to about 10 o'clock, and about 2 to about 4 o'clock, about the urethra U, as shown at "A" and "B" respectively in FIG. 147. More preferably, as may be the case, for example, with use of the balloon and harness systems depicted and described herein, two anchors are driven into the pelvic floor at locations at about 9 and about 3 o'clock about the urethra.

It also is important, when using an instrument of the present invention to install anchors, to avoid driving anchors into, through or across the ureteric orifices of the bladder. The various embodiments of an instrument described herein facilitate avoidance of this event.

Anchors

As described herein, anchors 700 or other suitable fasteners perform a holding function, holding the bladder wall to the pelvic floor and/or holding a harness to the bladder wall and/or pelvic floor. Each of the anchoring and/or fastening features discussed herein is only exemplary of a large number of designs and configurations possible within the scope of the invention.

An anchor 700 or other fastener may have one or more suitable lodging structures that function to cause the anchor to lodge in tissues after being driven thereinto, so as to resist withdrawal from the tissues. Such lodging structures may comprise barbs, circumferential ridges, projections or any other features effective to cause the anchor to lodge in the tissues when driven into them. The size, shape and number of suitable lodging structures may vary. Additionally, the inventors have determined that, whenever barbs are included on an anchor it may be desirable when manufacturing such an anchor, to round off, or radius, the protruding ends of the barbs (as viewed from the anchor forward end), in order to reduce the possibility that the barbs will snag on loose bladder wall tissue during insertion and opening of an anchor driver assembly, on which the anchor is loaded, inside the bladder.

An anchor or other fastener may also have a head or other suitable penetration-limiting structure that may function to limit the depth to which the anchor or other fastener may be driven and may also function to assist in securing proximal tissues to underlying, distal tissues. It will be appreciated that such a penetration-limiting structure need not necessarily be located at the rearward end of an anchor shaft to be effective.

It may be desirable that the forward end of an anchor be pointed or have a chisel-like shape, to facilitate more effective and/or less damaging penetration of tissues. Additionally, the inventors have determined that a point formed on the forward end of a cylindrical anchor shaft comprising three sloping flat faces in planes intersecting each other at equal angles, facilitates penetration of the anchor into tissues in a manner that minimizes the potential for the anchor to veer off-target or off-direction during driving.

When used to secure the walls of the bladder to the pelvic floor, it may be desirable for anchors to be of a length sufficient to penetrate through the bladder walls and the fascia layer of the pelvic floor. For example but not by way of limitation, such anchors are preferably about ½-inch to 2½-inches in length. For anchors that are to be installed near the rectum, it may be desirable for them to be at the shorter end of the preferred range of length.

Anchors 700 or other suitable fasteners may be formed from a substantially biocompatible polymer or metal. Where shape memory and elasticity may be desired, anchors may be manufactured using elements made of an elastic material, such as an elastic metal alloy or a thermally activated or activatable alloy, such as a nickel-titanium alloy (for example nitinol) or stainless steel alloy, so that the anchors or other fasteners may be preformed and biased with shaped ends or barbs along the shaft, which can be deployed by pushing them out of an instrument so that when they pass into the target tissue, they resume their shape within the target tissue.

If bioabsorbability is desired, anchors 700 or other suitable fasteners may be formed of a suitably substantially biocompatible and bioabsorbable material. The inventors have determined that flexible absorbable polymers (e.g., polydioxanone polymers, or polymers containing lactides, glycolides, polyglactin, etc., such as the polymers marketed by Johnson & Johnson and/or Ethicon, Inc. under the trademarks "Vicryl" and "PDS II") are potentially suitable materials. Other bioabsorbable materials having the necessary physical properties may be used.

When used to anchor harness straps for a balloon and harness system such as depicted and described herein, bioabsorbable anchors may be used to provide a bioabsorbable harness release mechanism that avoids the necessity for, or reduces the importance of, a structure or device capable of attaching a harness to, and then releasing a harness from, an anchor by mechanical means. By way of example but not of limitation, referring to FIG. 145, it can be appreciated that if a structure such as harness hook 760 on anchor 700 is bioabsorbable, with a time degradation characteristic that corresponds to the time required for the anastomosis procedure, the degradation and dissolution of harness hook 760 through bioabsorption will serve to release harness 3430, facilitating removal from the patient.

Additionally, there may be situations when the control of the degradation and absorption profile and/or particle breakup size of a bioabsorbable anchor or other suitable fastener may be desirable. For example, should one or more pieces of a bioabsorbable anchor, such as, for example, the head of an anchor, break away in a large piece as the anchor material is degrading after deployment, it could cause a blockage. Accordingly, bioabsorbable anchors or other suitable fasteners may be designed and manufactured in a manner in which degradation rates and particle breakup size may be controlled. For example, a bioabsorbable anchor or other fastener may be formed with a cast, molded, embossed or machined-in arrangement of scoring, perforation, or grooving that creates areas of reduced thickness and increased stress of the part in selected locations, encouraging earlier fracture proximate to such areas for the purpose of reducing the size of portions that may break away as the material degrades. Alternatively, or additionally, a bioabsorbable anchor or other fastener may be formed of joined materials, or comprise joined components, having differing degradation/absorption profiles such that zones of faster and slower degradation within the part may be created, such that the possibility of breakaway and release within a body lumen of pieces that are large enough to create a possibility of blockage or other adverse effect is reduced.

An anchor shaft may be hollow so as to slidably fit over a driver pin, and be substantially releasably held thereon by friction fit or any other suitable means. Alternatively, an anchor may have a solid shaft wherein a driver pin pushes against the proximal end of the anchor or alternatively, fits over the proximal end of the anchor and releasably grips it by friction fit or any other suitable means.

It would be apparent to a person having skill in the art field that there are various designs for anchors that would be effective for anchoring the bladder to the pelvic floor over the urethra opening. Anchors may be provided that have a plurality of shafts, barbs and tips operatively linked to a driver assembly. It is not necessary that the anchors are individual anchors, only that each anchor's size and shape, alone or in combination, are sufficient to effect and maintain contact between proximal and underlying, distal target tissues for an appropriate period of time.

In still a further embodiment, an anchor may be formed of a bi-metallic or other combination of at least two materials having differing expansion properties, that will cause the part formed therefrom to take a desired shape after heating, for example, by the patient's body. In such a case, the anchor would be supplied in a cold or room-temperature state and then allowed to attain the final desired shape after installation, when heated by the patient's body.

Although nitinol may be used in this service because of its physical properties and its significant history in implantable medical devices, it may also be suitable for use as an anchor because of its overall suitability for use in conjunction with or contemplation of use of magnetic resonance imaging (MRI) technology.

In summary, numerous benefits are apparent which result from employing the concepts of the invention. The foregoing description of one or more embodiments of the invention has been presented for purposes of illustration and description. It is not intended to be exhaustive or to limit the invention to the precise form disclosed. Obvious modifications or variations are possible in light of the above teachings. The embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be limited only by the claims appended hereto.

We claim:

1. A method for effecting the anastomosis of a patient's bladder comprising a bladder wall defining a bladder lumen and a bladder opening, and the patient's urethra, surrounded by the patient's pelvic floor, following a prostatectomy, comprising the steps of:

inserting an instrument, having a longitudinal axis and comprising a positioner, an anchor driver and a balloon harness, in a retrograde direction into and through the patient's urethra, through the bladder opening, and into the bladder lumen, until said positioner and said anchor driver are inside the bladder lumen;

causing said positioner to extend a positioner member transversely with respect to said longitudinal axis, within the bladder lumen;

bringing said positioner member into contact with the bladder wall inside the bladder lumen, and causing said positioner member to urge the bladder wall into proximity with the pelvic floor;

causing said anchor driver to drive an anchor, having thereon a lodging structure, from inside the bladder lumen, through the bladder wall and into the pelvic floor, lodging said anchor in the pelvic floor, and releasing said anchor from said anchor driver, wherein said anchor driving step includes connecting said balloon harness to the pelvic floor, proximate to the bladder opening, with said anchor;

causing said positioner to retract said positioner member transversely with respect to said longitudinal axis;

withdrawing said positioner and said anchor driver from the patient;

following said positioner and anchor driver withdrawing step, inserting a balloon catheter having a balloon into the patient's bladder lumen and into said balloon harness;

inflating said balloon inside the bladder lumen and inside said balloon harness, substantially sealing the bladder opening with said balloon and pressing the tissues of the bladder wall proximate to the bladder opening against the tissues of the pelvic floor;

draining urine from the bladder lumen with said balloon catheter;

maintaining said balloon harness and said balloon catheter in position during a period of time required for tissues of the bladder wall and pelvic floor to effectively knit together; and deflating said balloon, withdrawing said balloon catheter from the patient, disconnecting said balloon harness from said anchor, and withdrawing said balloon harness from the patient.

2. The method of claim 1 wherein said anchor has a bioabsorbable portion that holds said balloon harness to said anchor, and said bioabsorbable portion dissolves within the patient during said period of time, thereby effecting said balloon harness disconnecting step.

* * * * *